(12) United States Patent
Simon et al.

(10) Patent No.: US 11,053,249 B2
(45) Date of Patent: Jul. 6, 2021

(54) PROTEASOME INHIBITING β-LACTAM PRODRUGS USEFUL FOR THE TREATMENT OF CANCER AND NEURODEGENERATIVE DISORDERS

(71) Applicants: Vita Api, La Seyne sur Mer (FR); Etat Français Représenté Par le Directeur Central du Service de Santé des Armées, Armees (FR); Université D'Aix-Marseille, Marseilles (FR); Centre National de la Recherche Scientifique, Paris (FR)

(72) Inventors: Philippe Yves-Rémy Simon, Cuers (FR); Henri Oreal, Le Revest-les-Eaux (FR); Gérard Audran, Marseilles (FR); Marvin Schulz, Marseilles (FR); Jean-Patrick Joly, Marseilles (FR); Didier Siri, Marseilles (FR); Anouk Siri, Marseilles (FR)

(73) Assignees: Philippe Yves-Remy Simon, Cuers (FR); VITA API, La Seyne sur Mer (FR)

( * ) Notice: Subject to any disclaimer, the term of this patent is extended or adjusted under 35 U.S.C. 154(b) by 13 days.

(21) Appl. No.: 16/468,940

(22) PCT Filed: Dec. 22, 2017

(86) PCT No.: PCT/EP2017/084506
§ 371 (c)(1),
(2) Date: Jun. 12, 2019

(87) PCT Pub. No.: WO2018/115497
PCT Pub. Date: Jun. 28, 2018

(65) Prior Publication Data
US 2020/0216455 A1   Jul. 9, 2020

(30) Foreign Application Priority Data

Dec. 22, 2016   (EP) .................................. 16306801

(51) Int. Cl.
*C07D 487/04*    (2006.01)
*C07D 517/04*    (2006.01)
*C07D 205/12*    (2006.01)
*C07D 495/04*    (2006.01)

(52) U.S. Cl.
CPC ......... *C07D 487/04* (2013.01); *C07D 495/04* (2013.01); *C07D 517/04* (2013.01)

(58) Field of Classification Search
CPC .. C07D 487/04; C07D 517/04; C07D 205/12; C07D 495/04
See application file for complete search history.

(56) References Cited

FOREIGN PATENT DOCUMENTS

| WO | 96/32105 A1 | 10/1996 |
|---|---|---|
| WO | 2004/071382 A2 | 8/2004 |
| WO | 2007/033039 A2 | 3/2007 |

OTHER PUBLICATIONS

Hogan et al., "Proteasome Inhibition by a Totally Synthetic beta-Lactam Related to Salinosporamide A and Omuralide," Journal of the American Chemical Society, 127: 15386-15387 (2005).
Ren et al., "Synthesis of Novel beta-Lactam Core Structures Related to the Penam and Penem Antibiotics," Journal of Organic Chemistry, 59: 5858-5861 (1994).
Ren et al., "Studies on Nonconventionally Fused Bicyclic beta-Lactams," Journal of Organic Chemistry, 63: 8898-8917 (1998).
International Search Report issued in corresponding International Patent Application No. PCT/EP2017/084506 dated Mar. 9, 2018.
Written Opinion issued in corresponding International Patent Application No. PCT/EP2017/084506 dated Mar. 9, 2018.

*Primary Examiner* — Sun Jae Yoo
(74) *Attorney, Agent, or Firm* — Morgan, Lewis & Bockius LLP

(57) ABSTRACT

The present invention relates generally to proteasome inhibiting β-lactam compounds useful for the treatment of cancer and neurodegenerative disorders. The invention also provides pharmaceutical compositions and extended release formulations of said compounds, and medical uses of said compounds and/or pharmaceutical compositions to treat cancer and neurodegenerative disorders.

19 Claims, 5 Drawing Sheets

Specification includes a Sequence Listing.

A: 3-iodo-α-methyl-L-tyrosine (IMT)
B: 3-fluoro-α-methyl-L-tyrosine (FMT)
C: 3-iodo-*O*-methyl-L-tyrosine (OMIT)
D: 3-iodo-*O*-methyl-α-methyl-L-tyrosine (OMIMT)
E: 4-iodo-L-*meta*-tyrosine (4-I-*m*Tyr)
F: 6-iodo-L-*meta*-tyrosine (6-I-*m*Tyr)
G: *O*-(2-fluoroethyl)-L-tyrosine (FET)
H: 3-*O*-methyl-6-fluoro-L-dopa (OMFD)
I: 2-iodo-L- tyrosine (2IT)
J: 2-fluoro-L-tyrosine (2FT)

PROTEASOME INHIBITING β-LACTAM PRODRUGS USEFUL FOR THE TREATMENT OF CANCER AND NEURODEGENERATIVE DISORDERS

SEQUENCE LISTING SUBMISSION VIA EFS-WEB

A computer readable text file, entitled "SequenceListing.txt," created on or about Oct. 1, 2019 with a file size of about 8 kb contains the sequence listing for this application and is hereby incorporated by reference in its entirety.

INTRODUCTION

The present invention relates generally to proteasome inhibiting β-lactam compounds useful for the treatment of cancer and neurodegenerative disorders. The invention also provides pharmaceutical compositions and extended release formulations of said compounds, and medical uses of said compounds and/or pharmaceutical compositions to treat cancer and neurodegenerative disorders.

The ubiquitin-proteasome pathway plays a central role in the targeted destruction of key regulatory proteins involved in various essential cellular functions (e.g. cell cycle, apoptosis or inflammatory response). Proteasome inhibiting β-lactams are of most utility in strategies designed to provide antiproliferative and anti-inflammatory effects. However, these inhibitors potentially useful in the treatment of malignant, inflammatory and degenerative diseases must be selectively delivered to specific sites of action. The present invention pertains to the use of carrier-linked prodrugs for site-directed and efficient drug delivery.

FIELD OF THE INVENTION

The invention relates to compounds that can be used in the treatment of cancer and neurodegenerative disorders. More particularly, the invention relates to proteasome inhibitors useful for the treatment of:

hematologic and solid tumor malignancies, central nervous system tumors, including glioma, glioblastoma, astrocytoma, oligodendroglioma, ependymoma, medulloblastoma, pineocytoma, meningioma, and choroid plexus papilloma, peripheral nervous system tumors, including neuroblastoma, ganglioneuroma and paraganglioma, brain and spinal cord injuries, neurodegenerative disorders, including Wallerian degeneration and Alzheimer's disease, neuroinflammatory disorders, including multiple sclerosis and Guillain-Barre syndrome, angiogenesis-dependent diseases and angiogenic disorders, including cancer metastases, diabetic retinopathy, and rheumatoid arthritis, infectious neurological disorders caused by bacteria of the order of Actinomycetales (species from the genera *Mycobacterium, Rhodococcus, Streptomyces* and *Frankia*), protozoan parasites (species from the genera *Giardia, Entamoeba, Leishmania, Trypanosoma, Plasmodium*, and *Toxoplasma*), or other proteasome-containing organisms, and a variety of malignant, infectious, inflammatory, vascular, and degenerative diseases.

STATE OF THE ART

1. The Ubiquitin-Proteasome Pathway

The ubiquitin-proteasome pathway (UPP) mediates the ubiquitin-dependent degradation of damaged or misfolded cellular proteins and various short-lived regulatory proteins that govern a wide array of cellular functions (e.g. mitotic cycle, cell growth and viability, antigen presentation and inflammatory response) [Ciechanover, 1994, 1998; Chondrogianni & Gonos, 2008].

The UPP involves the labeling of target proteins with a polyubiquitin chain. Polyubiquitination occurs via the sequential action of three enzymes of the ubiquitin conjugation system [Adams, 2003]. FIG. 1 shows the ubiquitin-proteasome pathway. Proteins targeted for degradation are covalently modified by multiple ubiquitin molecules in a three-stepped enzymatic process involving an ATP-dependent ubiquitin-activating enzyme (E1), an ubiquitin-conjugating enzyme (E2), and an ubiquitin-protein ligase (E3). E1 activates and transfers ubiquitin to the carrier protein E2. E2 presents ubiquitin to E3. E3 interacts with E2 to covalently attach ubiquitin to the target protein. The hierarchical structure (i.e., a limited number of E2s and a larger number of E3s with limited substrate specificity) allows for highly specific interactions. Polyubiquitinated proteins are recognized by the 19S proteasome regulatory particles, denaturated, deubiquitinated and degraded by the catalytic 20S core into oligopeptides. The ubiquitin molecules are released and recycled for further proteolysis. The cascade covalently links the C-terminus of ubiquitin to a free amino group on the target protein, usually the ε-amino of a lysine residue. The ubiquitination reaction is processive, and additional ubiquitin molecules are conjugated to the preceding ubiquitin [DeMartino & Slaughter, 1999]. Substrate ubiquitination can be reversed by deubiquitinating proteases [Amerik & Hochstrasser, 2004]. Polyubiquitinated proteins are then degraded by the proteasome complex in the nucleus and cytosol. The proteasome is a large multiprotein complex composed of a 20S core particle and two 19S regulatory particles. Each 19S particle contains an isopeptidase that disassembles polyubiquitin-chains [DeMartino & Slaughter, 1999; Adams, 2003]. The deubiquitinated substrates are then denaturated and fed into the proteolytic core [Adams, 2003]. The 20S core particle is a cylindrical-shaped structure composed of four axially stacked heptameric rings [DeMartino & Slaughter, 1999; Adams, 2003]. FIG. 2 shows the structural organization of the 26S proteasome. The 26S proteasome is composed of a 20S core particle and two 19S regulatory particles. The 20S core particle is a barrel-shaped structure composed of four heptameric stacked rings: two outer α rings and two inner β rings. The α rings complex with the 19S regulatory particles, forming a narrow channel through which denaturated proteins may pass. Each β ring contains three proteolytic sites on the inner, central channel-facing surfaces. The catalytic sites differ in their substrate specificity and activity. Proteins are degraded by the core particle in a progressive manner, generating peptides. The proteolytic activities occur within a hollow cavity of the cylinder [DeMartino & Slaughter, 1999]. The proteasome is characterized by three activities. Each catalytic activity is linked with a specific β subunit. FIG. 3 shows a cross-sectional view of β rings. Each β ring contains three proteolytic sites named for their trypsin-like (cleavage after basic side chains, mediated by the β2s subunit), chymotrypsin-like (cleavage after hydrophobic side chains, mediated by the β5s subunit), or peptidylglutamyl peptide hydrolyzing-like (cleavage after acidic side chains, mediated by the β1s subunit) activity. The N-terminal threonine (T) present in all three catalytically active β subunits is responsible for catalysis and does so through nucleophilic attack [DeMartino & Slaughter, 1999]. In higher eukaryotes, each of the three catalytic subunits (termed β1s or Y or δ; β2s or Z, and β5s or X or ε) has a cytokine-inducible close homolog (immunosubunits LMP2 (β1i), LMP10 (MECL-1; β2i), and LMP7 (β5i), respectively). All six subunits have N-terminal threonines.

The UPP intervenes in numerous pathological processes, including cancer, inflammatory and neurodegenerative disorders, such as Alzheimer's, Parkinson's and Huntington's diseases, amyotrophic lateral sclerosis and Creutzfeld-Jakob disease [Ciechanover, 1998; Elliott & Ross, 2001; Ciechanover & Brundin, 2003].

2. The Therapeutic Applications of Proteasome Inhibitors in Cancer Treatment

The UPP modulates many important processes including cell-cycle progression, apoptosis and gene expression, and is therefore a target for anticancer therapy [Adams, 2003, 2004].

Rapidly dividing cells, such as cancer cells, are more sensitive to the inhibition than non-dividing cells, such as non-malignant, quiescent cells [Adams, 2003; 2004]. A partial inhibition (around 20-30%) of the tumor cell proteasome activity suffices to block the tumoral processes and induce the death of cancer cells, whereas the normal (quiescent) cells are not affected [Elliott & Ross, 2001; Adams, 2003; 2004]. Tumor cells strongly solicit their proteasomes, particularly during their cell cycles. These last are constantly at the maximum of their capacity and are therefore limiting.

Proteasome inhibition can also prevent tumor angiogenesis and invasiveness, thus limiting tumor progression particularly in the case of nervous system tumors (e.g., gliomas, glioblastomas, etc.) [Elliott & Ross, 2001; Adams, 2003, 2004; Ho et al., 2007].

Inhibitors with relative specificity for the proteasome catalytic subunits have been identified. However, the inhibitors already commercialized or in clinical trials do not allow a selective therapeutic targeting.

3. The Therapeutic Applications of Proteostasis Modulators in Age-Related Neurodegenerative Diseases Protein homeostasis (or proteostasis) influences the rate of aging (cellular lifespan). Senescence and aging are accelerated by exposure of cells to oxidative stresses that contribute, among other effects, to the accumulation of damaged proteins. Proteasome activity declines during aging, as the multicatalytic protease is progressively inhibited by binding to ever increasing levels of oxidized and cross-linked protein aggregates. Noteworthy, proteasome increased expression delays senescence.

The age-related standard proteasome activity decrease weakens the capacity of cells to remove oxidatively damaged proteins and favors the development of neurodegenerative diseases. During ageing, intermediate-type proteasomes (hybrids) and immunoproteasomes accumulate in brain, a tissue that normally predominantly contains standard proteasomes [Dahlmann, 2007]. The exposure of cells to inflammatory cytokines, such as interferon (IFN)-γ or tumor necrosis factor (TNF)-α, induces the synthesis of alternative catalytic subunits (β1i/LMP2, β2i/MECL-1 and β5i/LMP7; i for inducible), which replace the constitutive catalytic subunits (β1s, β2s and β5s; s for standard), and form alternative proteasome forms [Kloetzel, 2001; Ho et al., 2007; Aiken et al., 2011]. The IFN-γ-inducible proteasome subunits β1i/LMP2 and β5i/LMP7 are highly expressed in neurons, astrocytes and endothelial cells of the hippocampus region of elderly humans, but only scarcely in that of young humans [Mishto et al., 2006; Dahlmann, 2007].

As shown in Table 1, the variation generated by the inducible proteasome complex originates from enhanced cleavage after basic and hydrophobic residues (trypsin-like activity and chymotrypsin-like activities, respectively), while the degradation after acidic amino acids is reduced (caspase-like activity) [Huber et al., 2012; Schröter & Adjaye, 2014].

TABLE 1

| 20S subunit | Activity |
|---|---|
| β1s | Caspase-like |
| β2s | Trypsin-like |
| β5s | Chymotrypsin-like |
| β1i | Chymotrypsin-like |
| β2i | Trypsin-like |
| β5i | Chymotrypsin-like |

As a consequence, the immunoproteasome, as compared to the constitutive proteasome has an enhanced capacity to generate peptides bearing C-terminal hydrophobic and basic amino acids and a reduced capacity to produce peptides bearing C-terminal acidic residues [Rock & Goldberg, 1999; Ho et al., 2007]. The resultant peptides associate with MHC class I molecules with increased affinity [Fruh et al., 1994; Ho et al., 2007]. The immunoproteasome plays therefore a major role in MHC class I antigen presentation [Ho et al., 2007; Aiken et al., 2011]. The enhanced presence of immunoproteasomes in the central nervous system of elderly persons would reflect a persistent inflammatory reaction [Dahlmann, 2007]. Ubiquitin-positive intraneuronal inclusions are consistent features of the major human neurodegenerative diseases (e.g., Alzheimer's, Parkinson's and Huntington's diseases and amyotrophic lateral sclerosis), suggesting that dysfunctions of the UPP are central to disease etiology [Bedford et al., 2008; Dahlmann, 2007].

Very high levels of immunoproteasome catalytic subunits are detected in neurodegenerative human brains [Diaz-Hernandez et al., 2003; Piccinini et al., 2003; Ho et al., 2007]. The β1i/LMP2 catalytic subunit is more highly expressed in the brains of Alzheimer's disease (AD) patients than in the brains of nondemented elderly [Mishto et al., 2006; Ho et al., 2007]. Noteworthy, neurons die in AD because of faulty cell cycle control before plaques and tangles appear [Bloom, 2012].

Ubiquitylated inclusion bodies found in Huntington's disease (HD) suggest that alterations in the UPP might also contribute to HD pathogenesis [Diaz-Hernandez et al., 2003, 2004]. In the affected and aggregate-containing brain regions, striatum and cortex, a neuronal increase in the IFN-γ-inducible subunits of the immunoproteasome β1i/LMP2 and β5i/LMP7 is observed [Diaz-Hernandez et al., 2004]. These immunoproteasome catalytic subunits might therefore be involved in HD neurodegeneration [Diaz-Hernandez et al., 2003; Ho et al., 2007].

The use of proteasome-activating and/or -modulating compounds could be effective in the treatment of age-related neurodegenerative diseases [Dahlmann, 2007].

As proteasome has an impaired function during aging, emphasis has been given recently in identifying ways of its activation [Chondrogianni & Gonos, 2008]. Various factors are involved in proteasome biosynthesis and assembly, and contribute to its activation. Natural and synthetic compounds (e.g., oleuropein, betulinic acid derivatives, etc.) have proteasome activation, anti-oxidative and anti-aging properties [Katsiki et al., 2007; Huang & Chen, 2009]. Furthermore, proteasome activated cell lines exhibit an extended lifespan [Chondrogianni & Gonos, 2008; Katsiki et al., 2007]. The beneficial effect of these compounds provides new insights toward a therapeutic enhancement of cellular proteasome activity [Katsiki et al., 2007].

A distinct, complementary approach consists in targeted inhibiting of the immunoproteasome. Several immunoproteasome-specific inhibitors with relative specificity for the immunoproteasome have been identified [Kuhn et al., 2009]. They provide anti-immunoproteasome activity with greater specificity and lesser toxicity than current inhibitors. However, the potency of these inhibitors is not sufficient to warrant in vivo testing or translation into the clinic. Further efforts are needed to ameliorate their tissue distribution and their selectivity.

5. β-lactone and β-lactam Proteasome Inhibitors

The most important proteasome inhibitors fall into five classes: peptide aldehydes, peptide vinyl sulfones, peptide boronates, peptide epoxyketones, and β-lactones. Almost all these compounds exhibit properties unsuitable for drug development [Adams et al. 2004]. The biological activities of the β-lactones have been extensively studied. Unfortunately, many of these compounds are unstable. However, β-lactam analogues of these proteasome inhibitors exhibit favorable properties.

Lactacystin, (2R)-2-(acetylamino)-3-[({(2R,3S,4R)-3-hydroxy-2-[(1S)-1-hydroxy-2-methylpropyl]-4-methyl-5-oxopyrrolidin-2-yl}carbonyl)sulfanyl]-propanoic acid, is a microbial product isolated from *Streptomyces lactacystinaeus* [Omura et al., 1991a,b]. As shown below, the structure consists of two α-amino acids, namely (R)—N-acetylcysteine and an α-substituted pyroglutamic acid which are joined through a thioester linkage [Tomoda & Omura, 2000].

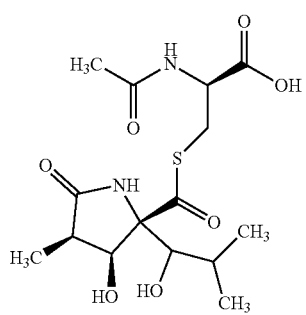 [SMILES: CC(=O)N[C@H](CSC(=O)[C@]1(C(O)C(C)C)NC(=O)[C@H](C)[C@@H]1O)C(=O)O]

Lactacystin per se is not a proteasome inhibitor. Lactacystin inhibits proteasome via a cell-permeable β-lactone-γ-lactam intermediate, the clasto-lactacystin β-lactone (omuralide or (1R,4R,5S)-1-[(1S)-1-hydroxy-2-methylpropyl]-4-methyl-6-oxa-2-azabicyclo[3.2.0]heptane-3,7-dione) [Dick et al., 1996, 1997] shown below.

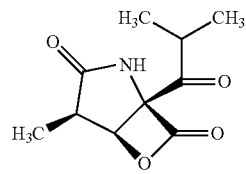

In aqueous solution, lactacystin spontaneously hydrolyzes into clasto-lactacystin β-lactone via intramolecular lactonization. The clasto-lactacystin β-lactone is unstable and hydrolyzes to the inactive clasto-lactacystin dihydroxy acid, as shown below, at a considerable rate [Dick et al., 1996, 1997].

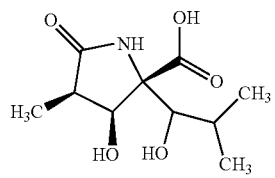 [SMILES: CC(C)C(O)[C@@]1(C(=O)O)NC(=O)[C@H](C)[C@@H]1O]

In cells, the clasto-lactacystin β-lactone reacts with the sulfhydryl of glutathione to form an inactive thioester adduct called lactathione shown below.

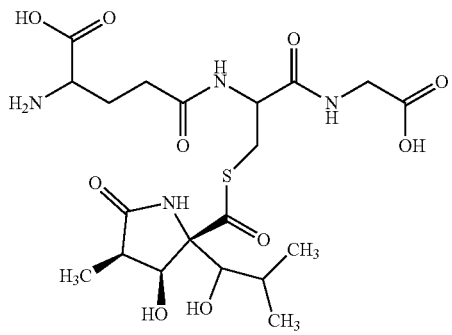 [SMILES: CC(C)C(O)[C@@]1(C(=O)SCC(NC(=O)CCC(N)C(=O)O)C(=O)NCC(=O)O)NC(=O)[C@H](C)[C@@H]1O]

Like lactacystin, lactathione can undergo lactonization to yield back the active β-lactone [Dick et al., 1997]. FIG. 4 shows the mechanism of proteasome inhibition by lactacystin in cells. In aqueous solution, lactacystin spontaneously hydrolyzes into clasto-lactacystin β-lactone via intramolecular lactonization. The β-lactone readily react with N-acetyl-L-cysteine (NAC) to yield back the thioester adduct that is lactacystin. The β-lactone can hydrolyze to the inactive clasto-lactacystin dihydroxy acid. Only β-lactone can enter cells. Once inside the cell, the β-lactone reacts with the sulfhydryl of glutathione (GSH) to form an inactive GSH conjugate called lactathione. Like lactacystin, lactathione can spontaneously regenerate the active β-lactone, via intramolecular lactonization.

The clasto-lactacystin β-lactone irreversibly inhibits the chymotryptic, tryptic and peptidylglutamyl activities of the 20S proteasome at different rates by forming a covalent bond with the side chain of the catalytic N-terminal threonine residues [Craiu et al., 1997]. The clasto-lactacystin β-lactone acylates the N-terminal threonine hydroxy group of the β subunits as a result of β-lactone ring opening [Tomoda & Omura, 2000]. FIG. 5 shows the covalent modification of the active sites. The mechanism involves a nucleophilic attack of the clasto-lactacystin β-lactone by the hydroxy group of the N-terminal threonine (Thr) and subsequent opening of the β-lactone ring.

Lactacystin and its active metabolite clasto-lactacystin β-lactone exert antiproliferative, antineoplastic, anti-inflammatory and antiangiogenic activities [Fenteany et al., 1995; Oikawa et al. 1998; Masdehors et al., 1999; 2000]. Lactacystin enhances the activity of anticancer agents and triggers apoptotic cell death in tumor cells including several human glioma cell lines [Kitagawa et al., 1999; Tani et al., 2001; Legnani et al., 2006].

By preventing the degradation of the inhibitory protein IκB, lactacystin blocks the activation of the nuclear factor NF-κB, a transcriptional activator involved in inflammatory response and in tumor development [Palombella et al., 1994; Tomoda & Omura, 2000; Karin et al., 2002]. Under normal conditions, NF-κB is bound to its inhibitor IκB. In response to cellular stresses, NF-κB is released from its inhibitory complex through proteasome degradation of IκB, inducing the activation of numerous cytokines and cell adhesion molecules that orchestrate the inflammatory and immune responses. In addition, NF-kB controls the expression of anti-apoptotic genes and functions as an endogenous apoptosis inhibitor [Beg & Baltimore, 1996]. Activation of NF-κB occurs in response to chemotherapy and radiotherapy and confers tumor cell resistance [Wang et al., 1999]. Lactacystin provides anti-inflammatory effects, induces apoptotic death in tumor vs normal cells and sensitizes chemo- and radio-resistant tumor cells to apoptosis [Imajoh-Ohmi et al., 1995; Delic et al., 1998].

By preventing production of plasminogen activator, a protease responsible for induction of angiogenesis, lactacystin significantly reduces angiogenesis, a phenomenon critical for the progression of many diseases, including cancer, rheumatoid arthritis and diabetic retinopathy [Oikawa et al., 1998]. Due to their high angiogenic activity, malignant gliomas are ideal targets [Legnani et al., 2006].

Interestingly, lactacystin induces neurite outgrowth and enhances oligodendroglial cell differentiation [Omura et al., 1991a,b; Obin et al., 1999; Pasquini et al., 2003]. Oligodendroglial cells are the myelin-producing cells in the CNS. Addition of lactacystin to oligodendroglial cell primary cultures induces the appearance of extensive myelin-like sheets.

Moreover, lactacystin delays Wallerian degeneration (i.e. lesion-induced or neurotrophin deprivation-triggered anteretrograde axon degeneration) by stabilizing microtubule skeleton [Zhai et al., 2003; He et al., 2005].

Systemic administration of lactacystin, however, requires very high doses to achieve penetration through the blood brain barrier (BBB), an approach likely to generate severe toxicity [Legnani et al., 2006].

Salinosporamide A, (1R,4R,5S)-4-(2-chloroethyl)-1-[(S)-(1S)-cyclohex-2-en-1-yl(hydroxyl)methyl]-5-methyl-6-oxa-2-azabicyclo[3,2,0]heptane-3,7-dione (NPI-0052; ML858), is a bioactive metabolite isolated from the marine actinomycete Salinospora tropicana [Feling et al., 2003]. Structurally, salinosporamide A comprises a β-lactone-γ-lactam bicyclic ring system substituted with methyl, cyclohex-2-enylcarbinol, and chloroethyl substituents as shown below [Manam et al., 2007].

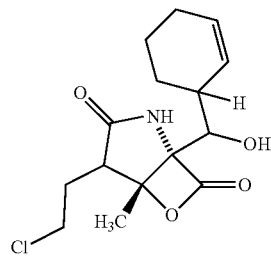

Open analogs, such as 2-pyrrolidone derivatives from microorganisms (Streptomyces), have been also described [Stadler et al., 2004; Guedat & Colland, 2007].

Salinosporamide A is a highly potent and selective 20S proteasome inhibitor with irreversible activity against all three catalytic sites [Williams et al., 2005a]. Salinosporamide A is more potent than the structurally related clasto-lactacystin β-lactone, and displays high cytotoxicity towards many tumor cell lines [Reddy et al., 2004; Caubert & Langlois, 2006]. Salinosporamide A also inhibits the proteasome-catalyzed IκB degradation [Williamson et al., 2006].

Interestingly, salinosporamide A inhibits the human malaria parasite, Plasmodium falciparum, and represents a new class of antimalarial drugs [Prudhomme et al., 2008].

However, salinosporamide A, like other members of the β-lactone family, is hydrolytically unstable and fails to maintain high levels of proteasome inhibition over time [Williamson et al., 2006]. Its hydrolysis product is devoid of inhibitory activity [Williamson et al., 2006].

The proteasome inhibitor PS-519, 1R-[1S,4R,5S]-1-(1-hydroxy-2-methylpropyl)-4-propyl-6-oxa-2-azabicyclo [3.2.1.]heptane-3,7-dione (MLN-519), is a synthetic analogue of clasto-lactacystin β-lactone in which the methyl group is substituted to n-propyl one as shown below.

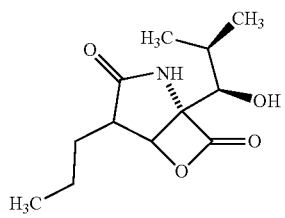

PS-519 exerts anti-inflammatory and anti-ischemic activities, and elicits neuroprotective and cardioprotective effects [Campbell et al., 1999; Phillips et al., 2000; Shah et al., 2002; Williams et al., 2003, 2004; Wojcik & Di Napoli, 2004; Shah & Di Napoli, 2007].

PS-519 blocks activation of NF-kB and exhibits notable effects in many ailments involving an inflammatory response, such as cerebral ischemia (i.e. stroke), CNS injuries, cerebral and myocardial infarctions [Phillips et al., 2000; Shah et al., 2002; Berti et al., 2003; Williams et al., 2003, 2004, 2006; Wojcik & Di Napoli, 2004]. PS-519 prevents the inflammatory response by inhibiting the expression of cytokines and cell adhesion molecules, and the subsequent diapedesis of infiltrating cells [Phillips et al., 2000; Shah et al., 2002; Berti et al., 2003; Williams et al., 2003, 2004, 2006; Wojcik & Di Napoli, 2004]. The anti-ischemic effect of PS-519 is mediated through a reduction in the number of invading cells [Phillips et al., 2000; Williams et al., 2003, 2004, 2006; Wojcik & Di Napoli, 2004].

PS-519 shows no brain tissue penetration [Phillips et al., 2000; Shah et al., 2002; Wiliams et al., 2004]. Neuroprotective effects of PS-519 involve nonneuronal mechanisms, primarily in the vasculature within the injured tissues [Phillips et al., 2000; Shah et al., 2002; Williams et al., 2004]. Administration of PS-519 improves neurological recovery and did not induce further damage [Phillips et al., 2000; Elliott & Ross, 2001; Zhang et al., 2001; Williams et al., 2003, 2005b]. Proteasome inhibition by PS-519 is well tolerated at levels that are maximally neuroprotective [Elliott & Ross, 2001; Shah et al., 2002].

PS-519 has also been tested in other inflammatory conditions (e.g. asthma, autoimmune encephalomyelitis, etc.) and found to elicit positive outcomes [Elliott et al., 1999; Vanderlugt et al., 2000; Elliott & Ross, 2001; Shah et al., 2002].

However, PS-519 is unstable [Williamson et al., 2006] As PS-519-induced inhibition of the proteasome rapidly returns to baseline, then repeated dosing must be performed to maintain therapeutical levels [Elliott & Ross, 2001; Shah et al., 2002].

A cell-permeable proteasome inhibiting β-lactone structurally related to clasto-lactacystin β-lactone and salinosporamide A (Omuralide-salinosporamide hybrid) irreversibly inactivates the β5-subunit of the human 20S proteasome. The β-lactone compound is more potent than clasto-lactacystin β-lactone and exhibits comparable whole cell potency as Salinosporamide A [Reddy, et al. 2005]. Its structure is shown below.

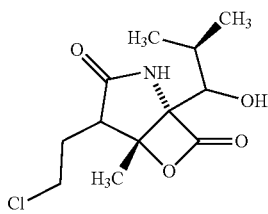

A proteasome inhibiting β-lactam structurally related to clasto-lactacystin β-lactone and salinosporamide A is much more stable than the corresponding β-lactones [Hogan & Corey, 2005; Corey & Hogan, 2007]. Although slower, the rate of proteasome inhibition is more than compensated for by the greatly increased aqueous stability of the β-lactam under physiological conditions [Hogan & Corey, 2005]. Its structure is shown below.

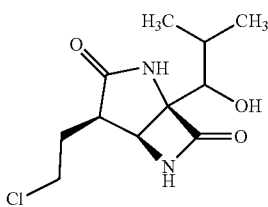 [SMILES: CC(C)C(O)[C@@]12NC(=O)[C@H](CCCl)[C@@H]1NC2=O]

The pathway of proteasome inhibition by the β-lactam follows that of the structurally related β-lactones clasto-lactacystin β-lactone and salinosporamide A, i.e., selective and irreversible acylation of the catalytically active threonines of the proteolytic β-subunits of the 20S proteasome [Hogan & Corey, 2005; Corey & Hogan, 2007]. Acylation is rendered irreversible by ring closure involving the chloroethyl group as an electrophile [Hogan & Corey, 2005; Corey & Hogan, 2007].

The proteasome inhibiting β-lactam exhibits properties that render it suitable for further drug development.

6. Carrier-Linked Prodrugs

Prodrugs are pharmacologically inert derivatives of drug molecules that must undergo an enzymatic and/or chemical transformation in vivo to release the active parent drugs and exert a therapeutic effect. Prodrugs are usually designed to mask undesirable drug properties such as limited bioavailability, lack of specificity, chemical instability and/or systemic toxicity, as well as to achieve site-specific delivery. Site selectivity may be achieved through transporter mediated delivery (e.g. carrier-mediated prodrug transport) and/or by selective activation (e.g. enzymatic activation). Carrier-linked prodrugs (or carrier prodrugs) refer to transporter targeted prodrugs containing a bioreversible carrier group removed after absorption. Functional groups amenable to prodrug design include carboxylic, hydroxyl, amine, phosphate/phosphonate and carbonyl groups. Prodrugs typically produced via the modification of these groups include esters, carbonates, carbamates, anhydrides, amides, phosphates and oximes.

The conjugation of a carrier group via a hydrotically labile anhydride bond is an effective prodrug approach for β-lactams. The anhydrides degrade in a predictable fashion and are biocompatible with the human body tissues, including the brain [Laurencin et al., 1990]. Anhydride prodrugs require an enzyme-mediated hydrolytic activation to release the parent drug. The scheme below shows the activation of anhydride prodrugs.

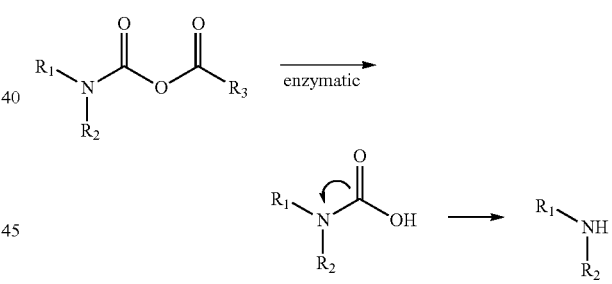

The (acyloxy)alkyl carbamylation of amine functional groups is another effective prodrug approach for β-lactams. (Acyloxy)alkyl carbamate prodrugs (or N-acyloxy-alkoxycarbonyl derivatives) require an enzymatic activation (e.g. esterase) to liberate the active parent drug [Cundy et al., 2004a,b; Rautio et al., 2008; Simplicio et al., 2008]. The scheme below shows the activation of (acyloxy)alkyl carbamate prodrugs. Enzymatic hydrolysis of the terminal group triggers a subsequent spontaneous decomposition of the intermediate (hydroxyalkoxy)carbonyl derivative liberating the parent amine.

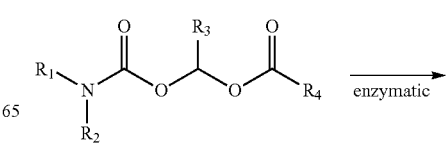

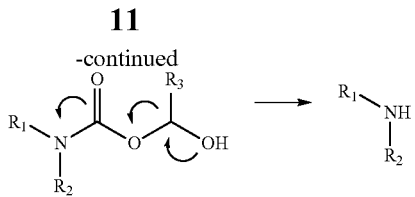

(Acyloxy)alkyl carbamate prodrugs are efficiently absorbed and converted to the parent drug after oral dosing. These compounds take advantage of both a monocarboxylate transporter type 1 (MCT1), which is highly expressed in the gastrointestinal tract, and a sodium-dependent multivitamin transporter (SMVT), responsible for absorption of multiple essential nutrients [Cundy et al., 2004a,b; Rautio et al., 2008; Simplicio et al., 2008]. The oral bioavailability is improved with carbamate prodrugs [Cundy et al., 2004a,b; Rautio et al., 2008; Simplicio et al., 2008].

Interestingly, the monocarboxylate transporter MCT1 is also expressed at high levels in brain microvessel endothelial cells (BMEC) that form the BBB [Gerhart et al., 1997; Roberts et al., 2008]. In addition, MCT1 is highly expressed in ependymomas and high grade glial neoplasms [Froberg et al., 2001]. (Acyloxy)alkyl carbamate prodrugs are consequently candidate substrates for crossing the BBB and treating CNS tumors. The BBB is a major barrier to the passage of active molecules from the blood compartment to the brain. The brain microvessel endothelial cells (BMEC) that form the BBB, restricts the passage of compounds from the blood into the extracellular environment of the brain. However, circulating molecules can penetrate into the CNS by interaction with endogenous transport systems located within the brain capillary endothelium or the neuroepithelial cells of the choroid plexus [Pavan et al., 2008].

The transporters of neutral amino acids (LAT1), hexose (GLUT1), monocarboxylic acids (MCT1), cationic aminoacids (CAT1) and nucleosides (CNT2) are widely expressed at the BBB level, whereas the ascorbic acid transporter (SVCT2) is mainly expressed in the choroids plexus [Pavan et al., 2008]. LAT1, in particular, is able to transport drug conjugates [Pavan et al., 2008].

LAT1 (sodium-independent L-type amino acid transporter 1) is essential for the transport of large, neutral amino acids, such as leucine, isoleucine, valine, phenylalanine, tyrosine, tryptophan, histidine, and methionine [Kanai et al., 1998]. L-dopa, 3-O-methyldopa, α-methylphenylalanine, α-methyltyrosine, α-methyldopa and gabapentin are also transported by LAT1 [Uchino et al., 2002]. A second transporter, designated LAT2, has been identified [Pineda et al., 1999; Segawa et al., 1999]. LAT1, but not LAT2, is selective for the large neutral amino acids [Kanai et al., 1998; Boado et al., 1999; Segawa et al., 1999; Pineda et al., 1999]. Co-expression of the 4F2 heavy chain (4F2hc) is essential for LAT1 and LAT2 to be functional [Kanai et al., 1998; Segawa et al., 1999]. The 4F2hc heavy chain and either the LAT1 or LAT2 light chains form a heterodimeric functional complex via a disulfide bond. LAT1-4F2hc and LAT2-4F2hc complexes function as amino acid exchangers, and can transport against a concentration gradient [Simmons-Willis et al., 2002].

LAT1 expression is up-regulated in rapidly-growing tumor cell lines of various organs to support their proliferation [Kanai et al., 1998; Yanagida et al., 2001; Nawashiro et al., 2005; Asano et al., 2007; Kobayashi et al., 2007]. High levels expression of LAT1 enhances the rates of tumor cell proliferation and growth in vivo [Kobayashi et al., 2007].

LAT1 is selectively expressed at high levels on both the luminal and abluminal membranes of the endothelial cells that form the BBB, and contributes to the transendothelial transport of large neutral amino acids into brain [Boado et al., 1999; Matsuo et al., 2000; Duelli et al., 2000; Kageyama et al., 2000b; Kido et al., 2001; Killian & Chikhale, 2001]. However, LAT1 is far less expressed in brain tissues than at the BBB [Boado et al., 1999; Kageyama et al., 2000a,b; Matsuo et al., 2000; Kobayashi et al., 2007].

Gliomas have a high proliferative activity and infiltrative tendency to the surrounding normal brain parenchyma. Malignant gliomas remain largely incurable despite intensive treatments, including surgical resection, irradiation, and chemotherapy. LAT1 is highly expressed in infiltrating glioma and glioblastoma cells [Nawashiro et al., 2005; Kobayashi et al., 2007]. High LAT1 expression correlated with poor survival of glioma patients [Nawashiro et al., 2005; Kobayashi et al., 2007]. Glioma cells with high LAT1 expression levels are distinghishable from surrounding quiescent, mature neurons and astrocytes [Kobayashi et al., 2007].

Radiolabeled amino acids are used in nuclear medicine as tracers for the delineation of tumors, particularly cerebral gliomas. So far, the most commonly used amino acid tracers are α-methylated iodo- and fluoro-tyrosines, such as 3-iodo-α-methyl-L-tyrosine and 3-fluoro-α-methyl-L-tyrosine.

The tracer 3-[$^{123}$I]iodo-α-methyl-L-tyrosine (IMT; FIG. 6A) is an imaging agent of brain tumors and extracranial malignancies [Kawai et al., 1991; Langen et al., 1998, 2002; Riemann et al., 2001]. IMT is selectively transported by LAT1 [Shikano et al., 2003a,b; Nawashiro et al., 2005]. IMT rapidly crosses the BBB and exhibits high uptake in brain tumors, especially in cerebral gliomas [Kawai et al., 1991; Langen et al., 1990, 1991, 2002; Riemann et al., 2001]. IMT uptake in gliomas is dependent on cell proliferation [Kuwert et al., 1997; Langen et al., 2001; Nawashiro et al., 2005]. IMT is metabolically stable in vivo and not incorporated into proteins [Kawai et al., 1991; Langen et al., 1990, 1998, 2002; Riemann et al., 2001]. α-methylation increases the in vivo stability of IMT towards deiodination [Kawai et al., 1991; Krummeich et al., 1994]. IMT is non-toxic and well tolerated [Langen et al., 2002]. IMT is an inhibitor of tyrosine hydroxylase [Langen et al., 2002]. A fluorinated variant of IMT, the tracer 3-[$^{18}$F]fluoro-α-methyl-L-tyrosine (FMT, FIG. 6B) exhibits similar properties [Inoue et al., 2001].

O-methylated iodotyrosines, such as 3-[$^{123}$I]iodo-O-methyl-L-tyrosine (OMIT; FIG. 6C) and 3-[$^{123}$I]iodo-O-methyl-α-methyl-L-tyrosine (OMIMT; FIG. 6D) exhibit great in vivo stability and higher brain uptakes than IMT [Krummeich et al., 1994; Langen et al., 1998]. O-methylation not only increases brain uptake, but significantly prevents in vivo deiodination [Krummeich et al., 1994]. However, the tumor-to-brain (T/B) ratios are low [Langen et al., 1998].

Geometric isomers of radioiodinated L-meta-tyrosine, 4-[$^{125}$I]iodo-L-meta-tyrosine (4-I-mTyr; FIG. 6E) and 6-[$^{125}$I]iodo-L-meta-tyrosine (6-I-mTyr; FIG. 6F), rapidly enters the brain through stereospecific amino acid active transport [Flores et al., 2000]. Brain uptakes of 4-I-mTyr and 6-I-mTyr are comparable to that of IMT [Flores et al., 2000; Shikano et al., 2003c]. 4-I-mTyr and 6-I-mTyr exhibit high metabolic stability and similar biodistributions to other radiolabeled L-Tyr analogs [Flores et al., 2000; Shikano et al., 2003c]. In contrast to mTyr, 4-I-mTyr and 6-I-mTyr are not incorporated into proteins and have no significant cytotoxic effects [Shikano et al., 2003c; Gurer-Orhan et al., 2006]. Both isomers display high stability against deiodination [Flores et al., 2000; Shikano et al., 2003c].

The tracer O-(2-[$^{18}$F]fluoroethyl)-L-tyrosine (FET; FIG. 6G), a nonmetabolized L-tyrosine analog carrying a fluoroethyl group in the para position, is an imaging agent for brain tumors [Langen et al., 2006]. FET is not metabolized in vivo and not incorporated into proteins [Langen et al., 2006]. No side effects have been reported [Langen et al., 2006]. The tracer is poorly transported by LAT1 and seems to be selectively transported by LAT2 [Langen et al., 2006]. FET shows high uptake in cerebral gliomas [Langen et al., 2006]. Nevertheless, increased regional uptake of FET in the brain is not absolutely specific for glioma tissue [Langen et al., 2006].

The tracer 3-O-methyl-6-[$^{18}$F]-fluoro-L-dopa (OMFD; FIG. 6H) also accumulates in tumors via LAT1 and represents an important class of imaging agents for visualization of tumors in vivo [Haase et al., 2007; Bergmann et al., 2004]. OMFD enables the visualization of brain tumors [Beuthien-Baumann et al., 2003; Alheit et al., 2008]. OMFD is metabolically stable and not incorporated into proteins [Bergmann et al., 2004]. The distribution of OMFD is comparable to that of FET [Beuthien-Baumann et al., 2003].

Radiolabeled tyrosine analogues, such as 2-[$^{123}$I]iodo-L-tyrosine (2IT; FIG. 6I) and 2-fluoro-L-tyrosine (2FT; FIG. 6J), are also used to detect tumors expressing LAT1 [Lahoutte et al., 2004]. 2IT shows high and fast tumor accumulation, and demonstrates high tumor specificity [Kersemans et al., 2006]. However, 2IT is transported by LAT1 at a lower rate than 2FT [Lahoutte et al., 2004].

These results suggest the potential use of such amino acid analogues as drug delivery systems.

Problem Solved

Figure 1:
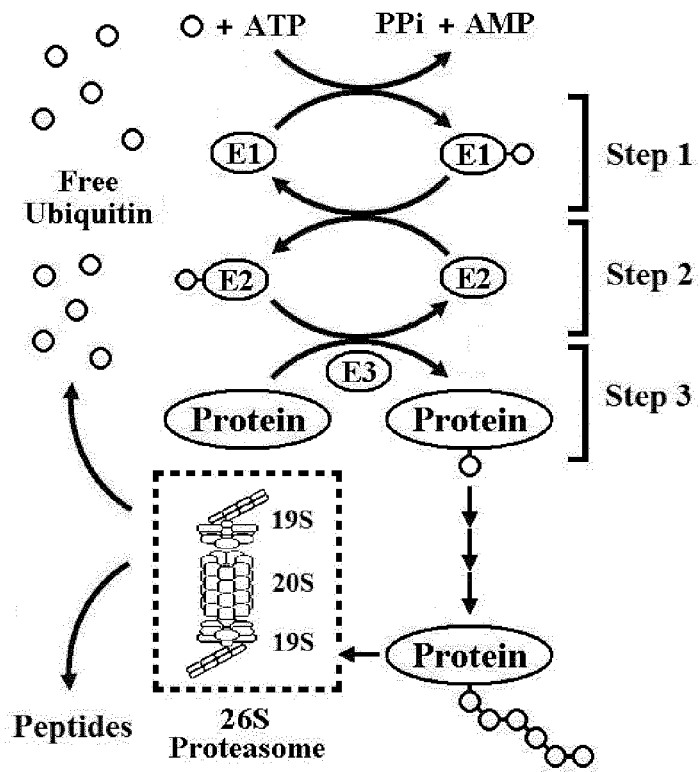
FIG. 1 shows the ubiquitin-proteasome pathway.
Figure 2:
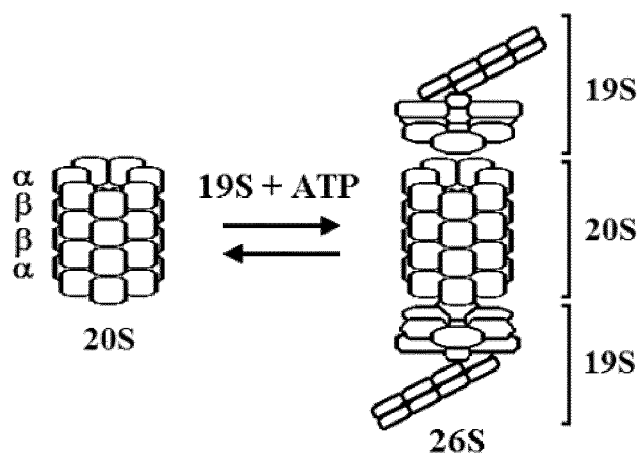
FIG. 2 shows the structural organization of the 26S proteasome.
Figure 3:
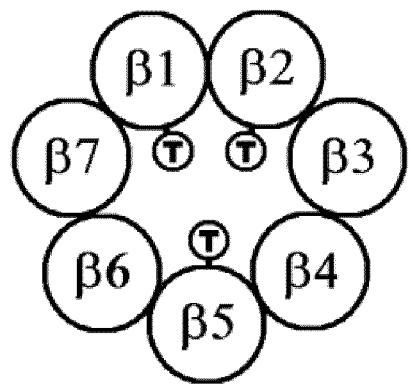
FIG. 3 shows a cross-sectional view of β rings.
Figure 4:
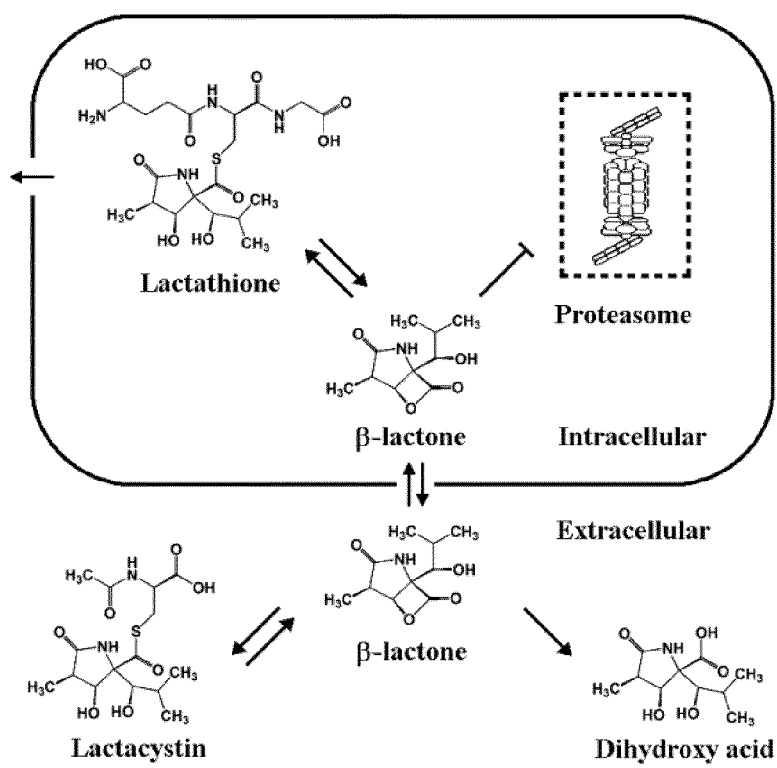
FIG. 4 shows the mechanism of proteasome inhibition by lactacystin in cells.
Figure 5:
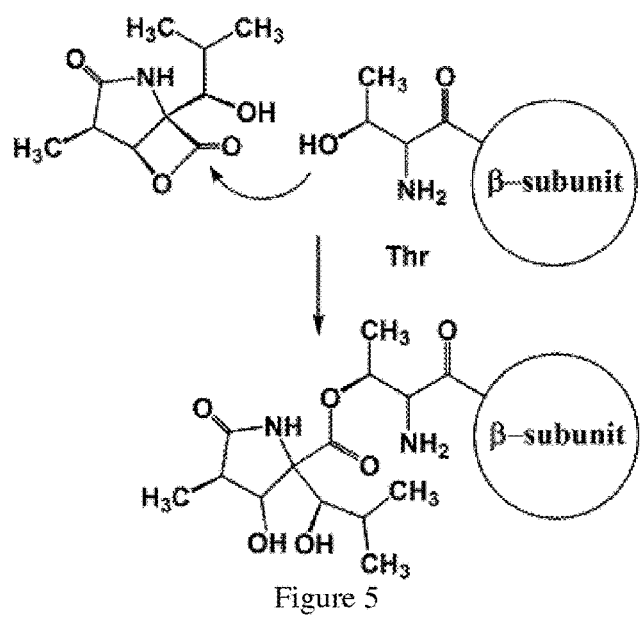
FIG. 5 shows the covalent modification of the active sites.
Figure 6:
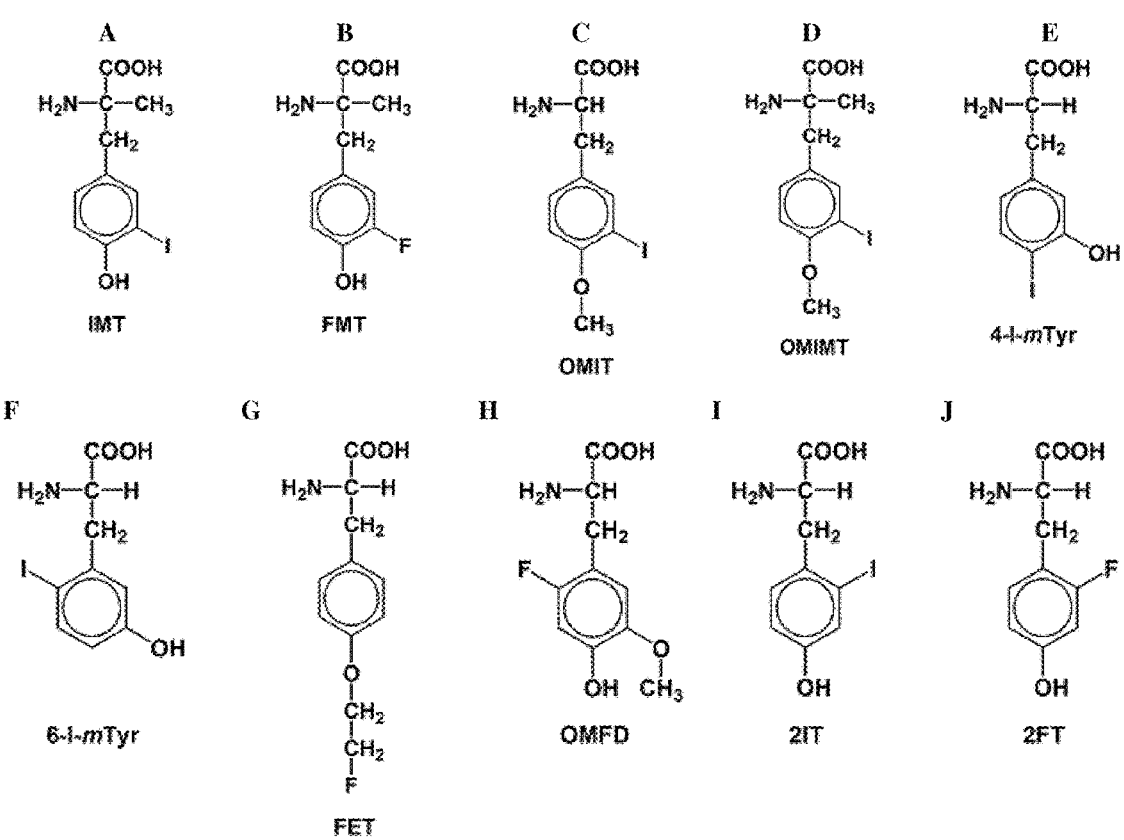
FIG. 6 shows the structure of the labelled tracers (A-J).

The compounds object of the invention exhibit proteasome inhibiting activity and thus offer a promising approach for the treatment of cancer and neurodegenerative disorders.

In particular, the carbamate prodrugs of the invention advantageously exhibit enhanced penetration of the blood-brain barrier and the blood-cerebrospinal fluid barrier. As a consequence, said carbamate prodrugs are especially effective for use in the treatment of many diseases affecting the central nervous system.

Another advantage of the carbamate prodrugs of the present invention is that they can be transported and activated within the target. This advantage overcomes the major drawbacks of surgical-based approaches, such as local delivery of proteasome-inhibitors using controlled-release polymers.

Still another advantage of the present invention is that the carbamate prodrugs of the invention greatly reduce systemic toxicity.

A consequential advantage of the present invention is that the carbamate prodrugs of the invention will have a higher efficacy than state-of-the-art methods.

A first object of the present invention is a simonorealide compound general formula (1a) or (1b):

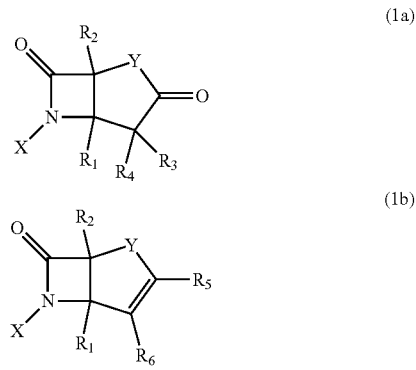

wherein X, Y, $R_1$, $R_2$, $R_3$, $R_4$, $R_5$, $R_6$, are as defined herein.

Yet another object of the present invention is a composition comprising a therapeutically effective amount of a compound of the present invention, and a pharmaceutically acceptable vehicle, carrier or diluent.

Another object of the present invention is a compound or a composition according to the invention, for use in the treatment of cancer, brain and spinal cord injuries, neurodegenerative disorders, neuroinflammatory disorders, angiogenesis-dependent diseases, angiogenic disorders, and infectious neurological disorders.

DETAILED DESCRIPTION OF THE INVENTION

Abbreviations and Definitions

In the application, the following abbreviations and definitions are used.
BBB Blood brain barrier
BMEC Brain microvessel endothelial cell
CA Crotonic acid
CMC Carboxymethyl cellulose
CNS Central nervous system
GSH Glutathione
HEC Hydroxyethyl cellulose
HPC Hydroxypropyl cellulose
HPMC Hydroxypropyl methyl-cellulose
LAT L-type amino acid transporter 1
MA Maleic anhydride
MAA Methacrylic acid
MC Methyl cellulose
MCT1 Monocarboxylate transporter 1
MVE Methyl vinyl ether
NAC N-acetyl-L-cysteine
NF-κB Nuclear factor-kappaB
PEO Polyethylene oxide
PNS Peripheral nervous system
PVA Polyvinyl alcohol
PVP Polyvinylpyrrolidone
SMVT Sodium-dependent multivitamin transporter
UPP Ubiquitin proteasome pathway
VA Vinyl acetate As used herein, the term "C-fused penem" refers to C-fused β-lactam core structures corresponding to the penem class of compounds whose lactam group is removed from the centers of the ring fusion.

As used herein, the term "β-lactone" refers to a compound having the group —CO—O— as part of a four-membered heteroatomic ring structure consisting of three carbon atoms and one oxygen atom.

As used herein, the term "β-lactam" refers to a nitrogen analogue of β-lactones having the group —CO—NH— as part of a four-membered heteroatomic ring structure consisting of three carbon atoms and one nitrogen atom.

As used herein, the term "γ-lactone" refers to a compound having the group —CO—O— as part of a five-membered heteroatomic ring structure consisting of four carbon atoms and one oxygen atom.

As used herein, the term "γ-lactam" refers to a nitrogen analogue of γ-lactones having the group —CO—NH— as part of a five-membered heteroatomic ring structure consisting of four carbon atoms and one nitrogen atom.

As used herein, the term "γ-thiolactone" refers to a sulfur analogue of γ-lactones having the group —CO—S— as part of a five-membered heteroatomic ring structure consisting of four carbon atoms and one sulfur atom.

As used herein, the term "γ-selenolactone" refers to a selenium analogue of γ-lactones having the group —CO—Se— as part of a five-membered heteroatomic ring structure consisting of four carbon atoms and one selenium atom.

As used herein, the term "γ-tellurolactone" refers to a tellurium analogue of γ-lactones having the group —CO—Te— as part of a five-membered heteroatomic ring structure consisting of four carbon atoms and one tellurium atom.

As used herein, the term "substituted derivatives thereof" means a group substituted by one or more substituents selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkenyl, heteroarylalkynyl, cycloheteroalkyl, cycloheteroalkenyl, cycloheteroalkynyl, acyl, alkoxy, alkoxycarbonyl, carbamoyl, halogen, haloalkyl, haloalkenyl, haloalkynyl, etc.

As used herein, the term "alkyl" refers to a branched or unbranched, saturated aliphatic hydrocarbon radical. Examples include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like.

As used herein, the term "alkenyl" refers to an alkyl radical containing at least one carbon-carbon double bond. Examples include ethenyl, propenyls, butenyls, and the like.

As used herein, the term "alkynyl" refers to an alkyl radical containing at least one carbon-carbon triple bond. Examples include ethynyl, propynyls, butynyls, and the like.

As used herein, the term "aryl" refers to a monocyclic or polycyclic aromatic radical. Examples include phenyl, naphtyl, biphenyl, phenanthrenyl, naphthacenyl, and the like.

As used herein, the term "arylalkyl" refers to at least one aryl group appended to an alkyl radical. Examples include benzyl, naphthylmethyl, phenethyl, and the like.

As used herein, the term "arylalkenyl" refers to at least one aryl group appended to an alkenyl radical.

As used herein, the term "arylalkynyl" refers to at least one aryl group appended to an alkynyl radical.

As used herein, the term "cycloalkyl" refers to a saturated cyclic alkyl radical. Examples include cyclopropyl, cyclobutyl, cyclopentyl, cyclohexyl, and the like.

As used herein, the term "cycloalkenyl" refers to a cyclic alkyl radical containing at least one carbon-carbon double bond.

As used herein, the term "cycloalkynyl" refers to a cyclic alkyl radical containing at least one carbon-carbon triple bond.

As used herein, the term "heteroalkyl" refers to an alkyl radical containing at least one heteroatom (N, P, O, S, etc.).

As used herein, the term "heteroalkenyl" refers to an alkenyl radical containing at least one heteroatom (N, P, O, S, etc.).

As used herein, the term "heteroalkynyl" refers to an alkynyl radical containing at least one heteroatom (N, P, O, S, etc.).

As used herein, the term "heteroaryl" refers to an aryl radical containing at least one heteroatom (N, P, O, S, etc.). Examples include groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

As used herein, the term "heteroarylalkyl" refers to at least one heteroaryl group appended to an alkyl radical.

As used herein, the term "heteroarylalkenyl" refers to at least one heteroaryl group appended to an alkenyl radical.

As used herein, the term "heteroarylalkynyl" refers to at least one heteroaryl group appended to an alkynyl radical.

As used herein, the term "cycloheteroalkyl" refers to a cycloalkyl radical containing at least one heteroatom (N, P, O, S, etc.). Examples include groups derived from epoxides, azirines, thiiranes, imidazolidine, morpholine, piperazine, piperidine, pyrazolidine, pyrrolidine, quinuclidine, and the like.

As used herein, the term "cycloheteroalkenyl" refers to a cycloalkenyl radical containing at least one heteroatom.

As used herein, the term "cycloheteroalkynyl" refers to a cycloalkynyl radical containing at least one heteroatom.

As used herein, the term "acyl" refers to a radical —C(O)R, where R is hydrogen, alkyl, cycloalkyl, cycloheteroalkyl, aryl, arylalkyl, heteroalkyl, heteroaryl, or heteroarylalkyl. Examples include formyl, acetyl, cyclohexylcarbonyl, cyclohexylmethylcarbonyl, benzoyl, benzylcarbonyl, and the like.

As used herein, the term "alkoxy" refers to a radical —OR, where R represents an alkyl, cycloalkyl, aryl or arylalkyl group. Examples include methoxy, ethoxy, propoxy, butoxy, cyclohexyloxy, and the like.

As used herein, the term "alkoxycarbonyl" refers to a radical —C(O)OR, where R represents an alkyl, cycloalkyl, aryl or arylalkyl group. Examples include methoxycarbonyl, ethoxycarbonyl, propoxycarbonyl, butoxycarbonyl, and the like.

As used herein, the term "carbamoyl" refers to the radical —C(O)NR'R", where R' and R" are independently selected from hydrogen, alkyl, cycloalkyl, or aryl.

As used herein, the term "halogen" refers to chlorine, bromine, fluorine and iodine.

As used herein, the term "haloalkyl" refers to an alkyl radical substituted by halogen. Examples include fluoro-, chloro-, bromo-, or iodo-methyl, ethyl, propyl, isopropyl, butyl, isobutyl, tert-butyl, and the like.

As used herein, the term "haloalkenyl" refers to an alkenyl radical substituted by halogen.

As used herein, the term "haloalkynyl" refers to an alkynyl radical substituted by halogen.

As used herein, the term "vinyl acetate/crotonic acid copolymer" refers to a polymer formed from vinyl acetate and crotonic acid monomers.

As used herein, the term "methacrylic acid copolymer" refers to a fully polymerized copolymer of methacrylic acid and an acrylic or methacrylic ester.

As used herein, the term "maleic anhydride/methyl vinyl ether copolymer" refers to a polymer formed from maleic anhydride and methyl vinyl ether monomers.

As used herein, the term "transport substrate of GLUT1" refers to a residue that is transported by GLUT1 protein, such as glucose and other hexoses.

As used herein, the term "transport substrate of MCT1" refers to a residue that is transported by MCT1 protein, such as simple organic carboxylates, for example lactate, pyruvate and short-chain fatty acids, such as butyrate, γ-hydroxybutyrate.

As used herein, the term "transport substrate of CAT-1" refers to a residue that is transported by CAT-1 protein, such as a cationic amino-acid.

As used herein, the term "transport substrate of CNT2" refers to a residue that is transported by CNT2 protein, such as adenosine.

As used herein, the term "transport substrate of SVCT2" refers to a residue that is transported by SVCT2 protein, such as ascorbic acid.

As used herein, the term "transport substrate of SMVT" refers to a residue that is transported by SMVT protein, such as vitamins and essential cofactors, for example biotin, lipoate and pantothenate.

As used herein the term "peptide" refers to small proteins with or without structure containing up to 50 amino acid residues.

As used herein, the term "peptide substrate" refers to a peptide, for example a peptide that is specific towards proteasome and immunoproteasome catalytic sub-units.

As used herein, the term "peptide vector" refers to a peptide, for example a blood-brain barrier translocating peptide, also known as a blood-brain barrier shuttle, that is specific towards proteasome and immunoproteasome catalytic sub-units.

Compounds

The compounds of the invention are proteasome inhibitors, also known under the trade name Simonorealide®, comprising a β-lactam cycle fused with 5-membered heterocycle comprising a heteroatom selected from N, S, Se, or Te. The compounds of the invention are advantageously more stable than the corresponding β-lactam-γ-lactone derivatives.

The compounds of the invention correspond to general formula (1a) or (1b):

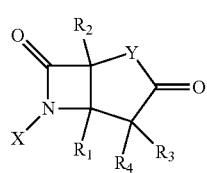

(1a)

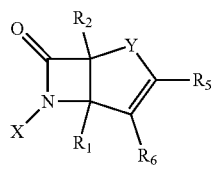

(1b)

wherein
X is H or —CO—O—$R_7$;
Y is $NR_8$, $S(O)_n$, $Se(O)_n$ or $Te(O)_n$;
$R_1$ is selected from hydrogen, alkyl, alkenyl, alkynyl, aryl, arylalkyl, arylalkenyl, arylalkynyl, cycloalkyl, cycloalkenyl, cycloalkynyl, and substituted derivatives thereof;
$R_2$ is —CH(OH)$R_9$, —$SO_2$—R, —$SeO_2$—R or —$TeO_2$—R with R is an alkyl such as methyl or ethyl, and substituted derivatives thereof;
$R_3$ and $R_4$ are independently selected from hydrogen, alkyl, halogen, haloalkyl, haloalkenyl, haloalkynyl, hydroxyalkyl, alkyl substituted by group selected from —O—$SO_2$—R', —O—$SeO_2$—R' or —O—$TeO_2$—R' with R' is an alkyl such as methyl or ethyl, or an aryl such as tolyl, and substituted derivatives thereof;
$R_5$ is selected from hydrogen, hydroxyl, sulfhydryl, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof;
$R_6$ is selected from hydrogen, alkyl, halogen, haloalkyl, haloalkenyl, haloalkynyl, hydroxyalkyl, alkyl substituted by group selected from —O—$SO_2$—R', —O—$SeO_2$—R' or —O—$TeO_2$—R' with R' is an alkyl such as methyl or ethyl, or an aryl such as tolyl, and substituted derivatives thereof;
$R_7$ is —[C($R_{10}$)($R_{11}$)—O—CO]$_m$—$R_{12}$;
$R_8$ is hydrogen, alkyl, and substituted derivatives thereof;
$R_9$ is selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof;
$R_{10}$ and $R_{11}$ are independently selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, alkoxy, alkoxycarbonyl, carbamoyl, and substituted derivatives thereof;
$R_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof; or $R_{12}$ is transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector;

n is 0, 1 or 2;

m is 0 or 1;

with the proviso that when Y is NH then X is not H.

In particular, the Y group of the compounds of the invention is selected from $NR_8$, $S(O)_n$, $Se(O)_n$ or $Te(O)_n$.

As such, the compounds of the present invention correspond to general formula (2a), (2b), (3a), (3b), (4a), (4b), (5a) or (5b):

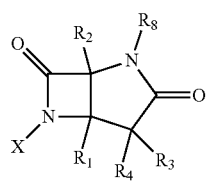
(2a)

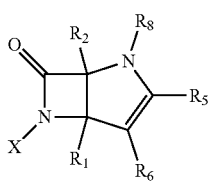
(2b)

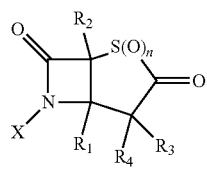
(3a)

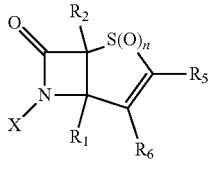
(3b)

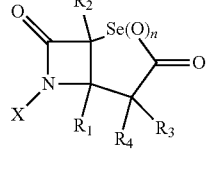
(4a)

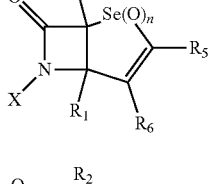
(4b)

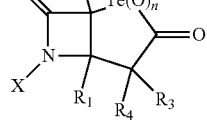
(5a)

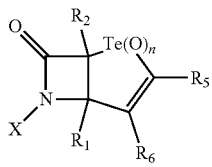
(5b)

wherein X, $R_1$, $R_2$, $R_3$, $R_4$, $R_5$, $R_6$, $R_7$, $R_8$, $R_9$, $R_{10}$, $R_{11}$, $R_{12}$, n and m are as defined herein.

Particularly preferred are compounds of general formula (3a), (3b), (4a), (4b), (5a) or (5b); more preferably compounds of general formula (4a), (4b), (5a) or (5b); and more preferably still compounds of general formula (5a) or (5b).

In particular, the X group of the compounds of the invention is selected from H or —CO—O—$R_7$.

Compounds having X is H are therapeutically active proteasome inhibitors. Compounds with X is H can also be used to prepare carrier-linked prodrugs.

Compounds having X is —CO—O—$R_7$ are referred to as carbamate prodrugs. The carbamate prodrugs are converted in vivo to the corresponding compound with X is H which is the active form of the proteasome inhibitor.

Figure 7:
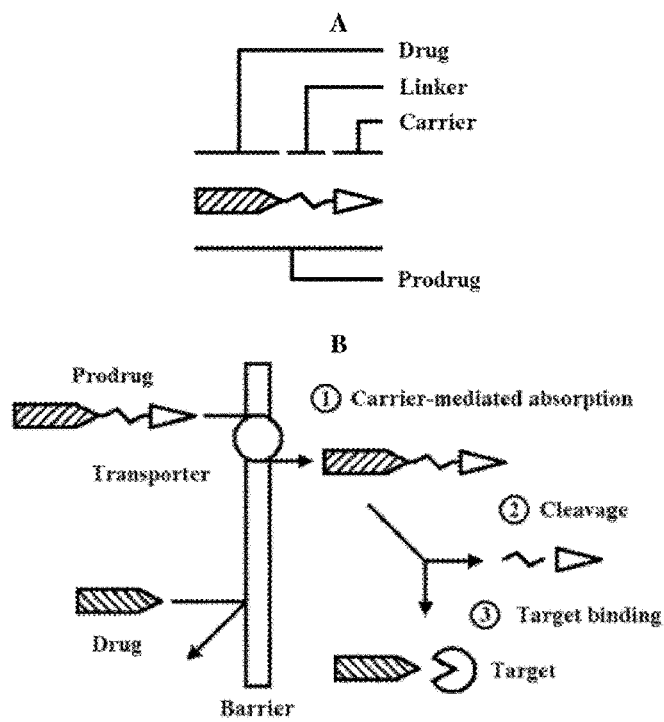
FIG. 7 shows the carrier-mediated absorption of transporter targeted prodrugs.

The term "prodrug" as used herein refers to pharmacologically inert derivatives of drug molecules that undergo an enzymatic and/or chemical transformation in vivo to release the active parent drugs and exert a therapeutic effect. The term "carrier-linked prodrug" (or carrier prodrug) as used herein refers to transporter targeted prodrugs containing a bioreversible carrier group removed after absorption. FIG. 7 shows the carrier-mediated absorption of transporter targeted prodrugs. FIG. 7A shows the structure of transporter targeted prodrugs and FIG. 7B shows the sequential steps for delivery of carrier-linked prodrugs and active drugs through epithelial and endothelial barriers.

Carrier-linked prodrugs are usually designed to overcome problems associated with stability, toxicity, lack of specificity and/or limited bioavailability.

Indeed, compounds wherein X is H may be inefficiently absorbed from the gastro-intestinal tract and poorly active. Moreover, compounds wherein X is H may exhibit inefficient BBB crossing and thus poor delivery in the central nervous system.

Masking the amine functional group with suitable bioreversible carrier groups, such as a carbamate group to result in compound wherein X is —CO—O—$R_7$, may significantly improve the oral bioavailability, dose proportionality, colonic absorption, tissue distribution and BBB crossing of the drug.

Therefore, the group —CO—O—$R_7$ is a bioreversible prodrug moiety for amine functional groups enabling the carrier-mediated absorption of proteasome inhibiting compounds throughout the gastro-intestinal tract and the carrier-mediated crossing of proteasome inhibiting compounds through the BBB.

The term "prodrug moiety" (or promoiety) refers to the functional group used to modify the structure of pharmacologically active agents to improve physicochemical, biopharmaceutical or pharmacokinetic properties. The prodrug moiety —CO—O—$R_7$ is particularly advantageous because it is safe and rapidly excreted from the body.

According to a preferred embodiment, X is —CO—O—$R_{12}$ or —CO—O—C($R_{10}$)($R_{11}$)—O—CO—$R_{12}$; wherein $R_{10}$ and $R_{11}$ are independently selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, alkoxy, alkoxycarbonyl, carbamoyl, and substituted derivatives thereof; preferably $R_{10}$ and $R_{11}$ are selected from H and alkyl; more preferably $R_{10}$ and $R_{11}$ are H and methyl; and $R_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof, or $R_{12}$ is transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof, or $R_{12}$ is a transport substrate of GLUT1, MCT1, CAT1, CNT2 or SVCT2; or $R_{12}$ is a peptide substrate; or $R_{12}$ is a peptide vector.

According to a particular embodiment, X is —COO—C($R_{10}$)($R_{11}$)—O—CO—$R_{12}$, wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof.

According to a particular embodiment, X is —COO—C($R_{10}$)($R_{11}$)—O—CO—$R_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is an alkyl having 1-6 carbon atoms or aryl having 6-12 carbon atoms; preferably $R_{12}$ is methyl, ethyl, propyl, isopropyl, butyl, isobutyl, tert-butyl, pentyl, hexyl, phenyl, naphthyl; more preferably $R_{12}$ is isopropyl.

The (acyloxy)alkyl or (acyloxy)aryl carbamylation of amine functional groups is an effective prodrug approach. (Acyloxy)alkyl or (acyloxy)aryl carbamate prodrugs (or N-acyloxyalkoxycarbonyl or N-acyloxyaryloxycarbonyl derivatives) are efficiently absorbed and converted to active drugs after oral dosing. As such, compounds wherein X is —COO—C($R_{10}$)($R_{11}$)—O—CO—$R_{12}$ and $R_{12}$ is an alkyl having 1-6 carbon atoms or aryl having 6-12 carbon atoms, more preferably isopropyl, are compounds that exhibit several high-capacity absorption pathways present throughout the intestine.

Figure 8:
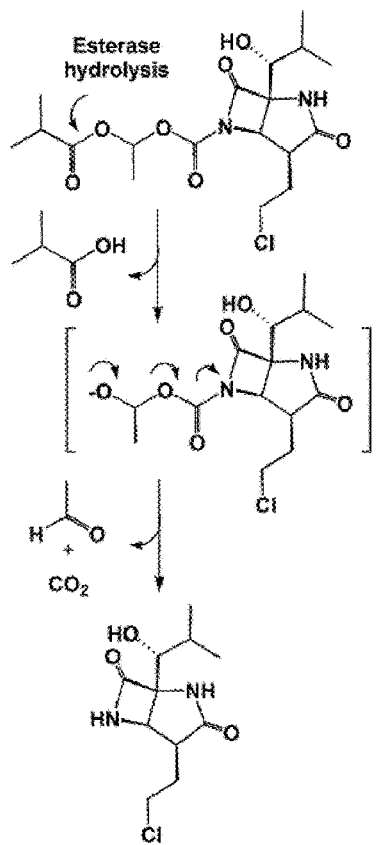
FIG. 8 shows the mechanism of prodrug activation.

Indeed, when X is —COO—C($R_{10}$)($R_{11}$)—O—CO—$R_{12}$ and $R_{12}$ is alkyl having 1-6 carbon atoms or aryl having 6-12 carbon atoms, more preferably isopropyl, group X is advantageously a substrate of monocarboxylate transporter type 1 (MCT1), which is highly expressed in all segments of the colon and upper gastro-intestinal tract, and a substrate of sodium-dependent multivitamin transporter (SMVT), responsible for absorption of multiple essential nutrients. The carrier-linked prodrug exhibits an esterase sensitive terminal group, whose hydrolysis triggers the spontaneous decomposition of an intermediate (hydroxyalkoxy) carbonyl derivative liberating the parent amine compound where X is H. FIG. 8 shows the mechanism of prodrug activation. The activation mechanism involves the initial hydrolysis of a terminal ester by an unspecific esterase. After enzymatic hydrolysis, the next step of decomposition for release of the drug takes place spontaneously. The (hydroxyalkoxy)carbonyl derivative in brackets is unstable.

The high transport capacity of MCT1 and SMVT allows higher prodrug doses to be absorbed without saturation of uptake, providing dose-proportional exposure to the active parent drug. Oral administration of the carrier-linked prodrug results in improved drug bioavailability, dose proportionality and colonic absorption compared with oral administration of the parental drug. Therefore, the present invention provides an efficient carrier-linked prodrug for oral delivery.

In addition, the high expression of MCT1 in brain microvessel endothelial cells (BMEC) that form the BBB suggests that the carrier-linked prodrug can be used in the treatment of neurological diseases. Therefore, the present invention also provides an efficient carrier-linked prodrug for brain delivery.

According to another particular embodiment, X is —COO—C($R_{10}$)($R_{11}$)—O—CO—$R_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is an alkyl or alkenyl having 8-22 carbon atoms; more preferably $R_{12}$ is a long chain alkyl group selected from n-octyl, n-decyl, n-dodecyl, n-tetradecyl, n-hexadecyl, n-octadecyl and n-eicosyl or $R_{12}$ is an long chain unsaturated alkyl group selected from tetradecaenyl, oleyl, linoleyl, octadecadienyl octadecatrienyl and arachidonyl. Indeed, when group X comprises a long-chain aliphatic ester, the resulting prodrug exhibits slow and prolonged release of the active proteasome inhibiting compound due to a higher enzymatic stability of the carbamate prodrug in plasma.

According to a specific embodiment, the compound of the present invention is a carbamate prodrug that corresponds to general formula (2c), (2d), (3c), (3d), (4c), (4d), (5c) or (5d)

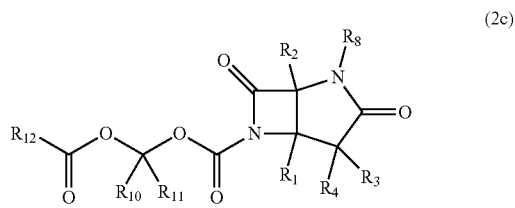

(2c)

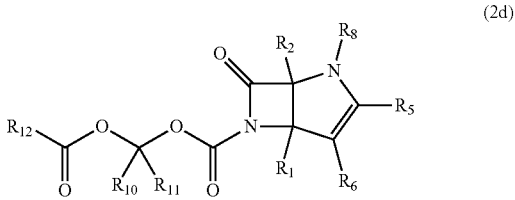

(2d)

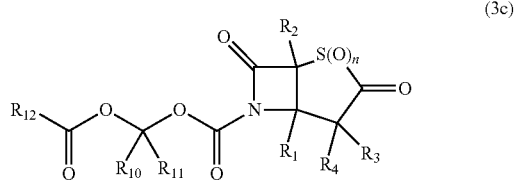

(3c)

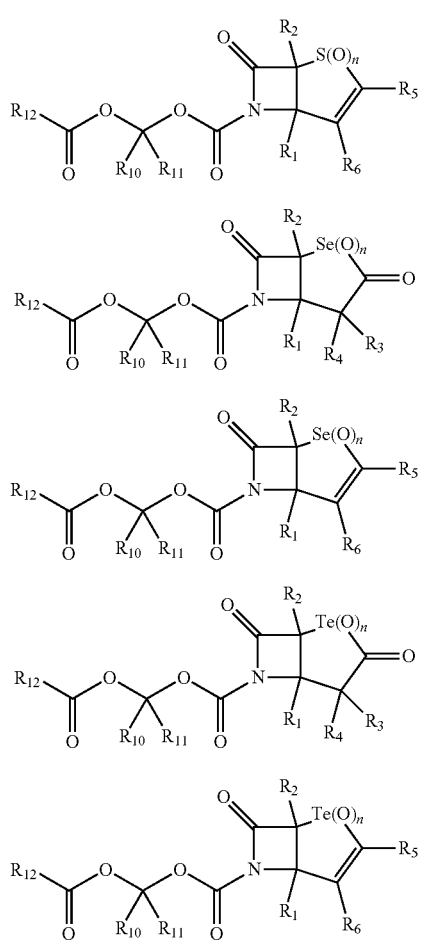

(3d)
(4c)
(4d)
(5c)
(5d)

wherein $R_1$, $R_2$, $R_3$, $R_4$, $R_5$, $R_6$, $R_8$, $R_9$, $R_{10}$, $R_{11}$, and n are as defined herein; and $R_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl heteroarylalkyl, heteroarylalkenyl, heteroarylalkynyl, cycloheteroalkyl, cycloheteroalkenyl, cycloheteroalkynyl, acyl, and substituted derivatives thereof.

Particularly preferred are compounds of general formula (3c), (3d), (4c), (4d), (5c) or (5d); more preferably compounds of general formula (4c), (4d), (5c) or (5d); and more preferably still compounds of general formula (5c) or (5d).

According to another particular embodiment, X is —COO—C($R_{10}$)($R_{11}$)—O—CO—$R_{12}$ or X is —COOR$_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is a transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector.

According to a particular embodiment, X is —COO—C($R_{10}$)($R_{11}$)—O—CO—$R_{12}$ or X is —COOR$_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is a transport substrate of LAT1; preferably $R_{12}$ is tyrosine, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, or 2-fluoro-L-tyrosine, more preferably $R_{12}$ is tyrosine.

Indeed, such compounds comprise a bioreversible prodrug moiety enabling the carrier-mediated transport of proteasome inhibitors through the BBB.

An approach to utilize LAT1 for BBB transport is to conjugate the β-lactam with a LAT1 substrate. Any substrate transported by LAT1, such as leucine, isoleucine, valine, phenylalanine, tyrosine, tryptophan, histidine, methionine, L-dopa, 3-O-methyldopa, α-methylphenylalanine, α-methyltyrosine, α-methyldopa, gabapentin, and derivatives thereof, can be used as drug carrier.

In particular, L-tyrosine has a phenolic hydroxyl group suitable for the conjugation of drug molecules with a biodegradable linkage, leaving both carboxyl and α-amino groups unsubstituted—a necessary feature for LAT1 recognition. These carrier-linked prodrugs can cross the BBB, penetrate the brain parenchyma, and undergo a rapid bioconversion to active β-lactam (X is H) in the brain tissue. Iodinated and fluorinated tyrosine analogues, such as:
3-iodo-α-methyl-L-tyrosine,
3-fluoro-α-methyl-L-tyrosine,
3-iodo-O-methyl-L-tyrosine,
3-iodo-O-methyl-α-methyl-L-tyrosine,
4-iodo-L-meta-tyrosine,
6-iodo-L-meta-tyrosine,
O-(2-fluoroethyl)-L-tyrosine,
3-O-methyl-6-fluoro-L-dopa,
2-iodo-L-tyrosine,
2-fluoro-L-tyrosine,
can advantageously be used as carriers to achieve efficient BBB crossing and selective drug delivery to brain tumors. Similar compounds designed for selective recognition by LAT1 at the cerebro-vasculature, can also be used as carriers for intravenous delivery.

According to a particular embodiment, X is —COO—C($R_{10}$)($R_{11}$)—O—CO—$R_{12}$ or X is —COOR$_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is a transport substrate of GLUT1, MCT1, CAT1, CNT2 or SVCT2.

According to a particular embodiment, X is —COO—C($R_{10}$)($R_{11}$)—O—CO—$R_{12}$ or X is —COOR$_{12}$ wherein $R_{10}$ and $R_{11}$ are as defined above; preferably $R_{10}$ and $R_{11}$ are selected from H and alkyl; more preferably $R_{10}$ and $R_{11}$ are H and methyl; and $R_{12}$ is a peptide substrate.

In particular, said peptide substrate is a peptide of general sequence $NH_2$—$X_n$—$X_{x-1}$— ... —$X_3$—$X_2$—$X_1$—COOH selective/specific for caspase-like β1s subunits that preferentially cleave peptides at the carboxyl side of acidic side chains, wherein X$_1$ is aspartic acid (Asp, D), glutamic acid (Glu, E);

X$_2$, X$_3$, ..., X$_{n-1}$ and X$_n$ are identical or different groups representing natural or non-natural (including D-configuration) aliphatic or aromatic amino acids, such as glycine, alanine, valine, norleucine, isoleucine, leucine, cysteine, cysteine(Acm), penicillamine, methionine, serine, threonine, asparagine, glutamine, phenylalanine, histidine, tryptophan, tyrosine, proline, aminobutyric acid, 1-aminocyclohexanecarboxylic acid, aminoisobutyric acid, 2-aminotetraline-2-carboxylic, 4-bromophenylalanine, tert-leucine, 4-chlorophenylalanine, beta-cyclohexylalanine, 3,4-dichlorophenylalanine, 4-fluorophenylalanine, homoleucine, beta-homoleucine, homophenylalanine, 4-methylphenylalanine, 1-naphtylalanine, 2-naphtylalanine, 4-nitrophenylalanine, 3-nitrotyrosine, norvaline, phenylglycine, 3-pyridylalanine and 2-thienylalanine.

In particular, said peptide substrate selective/specific for caspase-like β1s subunit is a tripeptide, such as for example LLE (SEQ ID NO:1).

Another type of suitable peptide substrate is a peptide of general sequence NH$_2$—X$_n$—X$_{n-1}$— ... —X$_3$—X$_2$—X$_1$—COOH selective/specific for trypsin-like β2s or β2i subunits that cleave peptides at the carboxyl side of basic side-chains, wherein X$_1$ is a basic aminoacid, such as asparagine (Asn, N), glutamine (Gln, Q), histidine (His, H), lysine (Lys, K), arginine (Arg, R);

X$_2$, X$_3$, ..., X$_{n-1}$ and X$_n$ are identical or different groups representing natural or non-natural (including D-configuration) aliphatic or aromatic amino acids, such as glycine, alanine, valine, norleucine, isoleucine, leucine, cysteine, cysteine(Acm), penicillamine, methionine, serine, threonine, asparagine, glutamine, phenylalanine, histidine, tryptophan, tyrosine, proline, aminobutyric acid, 1-aminocyclohexanecarboxylic acid, aminoisobutyric acid, 2-aminotetraline-2-carboxylic acid, 4-bromophenylalanine, tert-leucine, 4-chlorophenylalanine, beta-cyclohexylalanine, 3,4-dichlorophenylalanine, 4-fluorophenylalanine, homoleucine, beta-homoleucine, homophenylalanine, 4-methylphenylalanine, 1-naphtylalanine, 2-naphtylalanine, 4-nitrophenylalanine, 3-nitrotyrosine, norvaline, phenylglycine, 3-pyridylalanine and 2-thienylalanine.

In particular, said peptide substrate selective/specific for trypsin-like β2 subunit is a tripeptide, such as for example VGR (SEQ ID NO:2), LRR (SEQ ID NO:3), a dipeptide, or a single aminoacid, such as arginine (Arg, R).

Another type of suitable peptide substrate is a peptide of general sequence NH$_2$—X$_n$—X$_{n-1}$— ... —X$_3$—X$_2$—X$_1$—COOH selective/specific for chymotrypsin-like β5s subunits that predominantly cleave peptides at the carboxyl side of tiny hydrophobic side-chains such as Ala or Val, for chymotrypsin-like β5i subunits that preferentially cleave peptides at the carboxyl side of large nonpolar side chains like Tyr, Trp, and Phe, both activities displaying a certain degree of overlapping substrate specificities, especially with respect to Leu, Ile, and Tyr, or for chymotrypsin-like β1i subunits that preferentially cleave peptides at the carboxyl side of small, hydrophobic, and branched side-chains, such as Ile, Leu or Val;

wherein

X$_1$ is an aminoacid, such as methionine (Met, M), alanine (Ala, A), valine (Val, V), leucine (Leu, L), isoleucine (Ile, I), tyrosine (Tyr, Y), tryptophan (Trp, W), Phenylalanine (Phe, F);

X$_2$, X$_3$, ..., X$_{n-1}$ and X$_n$ are identical or different groups representing natural or non-natural (including D-configuration) aliphatic or aromatic amino acids, such as glycine, alanine, valine, norleucine, isoleucine, leucine, cysteine, cysteine(Acm), penicillamine, methionine, serine, threonine, asparagine, glutamine, phenylalanine, histidine, tryptophan, tyrosine, proline, aminobutyric acid, 1-aminocyclohexanecarboxylic acid, aminoisobutyric acid, 2-aminotetraline-2-carboxylic acid, 4-bromophenylalanine, tert-leucine, 4-chlorophenylalanine, beta-cyclohexylalanine, 3,4-dichlorophenylalanine, 4-fluorophenylalanine, homoleucine, beta-homoleucine, homophenylalanine, 4-methylphenylalanine, 1-naphtylalanine, 2-naphtylalanine, 4-nitrophenylalanine, 3-nitrotyrosine, norvaline, phenylglycine, 3-pyridylalanine and 2-thienylalanine.

In particular, said peptide substrate selective/specific for chymotrypsin-like β5s, β5i and/or β1i subunits is a tetrapeptide, such as for example LLVY (SEQ ID NO:4), a tripeptide, such as LLL (SEQ ID NO:5), GGL (SEQ ID NO:6), WLA (SEQ ID NO:7; β5s-specific), ANW (SEQ ID NO:8; β5i-specific), PAL (SEQ ID NO:9; β1i-specific), or a dipeptide such as AL (SEQ ID NO:10).

According to a particular embodiment, X is —COO—C(R$_{10}$)(R$_{11}$)—O—CO—R$_{12}$ or X is —COOR$_{12}$ wherein R$_{10}$ and R$_{11}$ are as defined above; preferably R$_{10}$ and R$_{11}$ are selected from H and alkyl; more preferably R$_{10}$ and R$_{11}$ are H and methyl; and R$_{12}$ is a peptide vector.

In particular, said peptide vector is a linear peptide derived from the protegrin or tachyplesin families having one of the following amino acid sequences:

(SEQ ID NO: 11)
RX$_1$X$_1$RX$_1$X$_2$X$_1$X$_2$RRRX$_1$X$_2$X$_1$X$_2$X$_1$X$_1$R (SEQ ID NO: 12)
RX$_1$X$_2$X$_1$RX$_1$X$_2$X$_1$RX$_1$X$_1$X$_2$X$_1$RRX$_2$R wherein R is arginine, the X$_1$ groups are identical or different groups representing natural or non-natural (including D-configuration) aliphatic or aromatic amino acids, such as glycine, alanine, valine, norleucine, isoleucine, leucine, cysteine, cysteine (Acm), penicillamine, methionine, serine, threonine, asparagine, glutamine, phenylalanine, histidine, tryptophan, tyrosine, proline, aminobutyric acid, 1-aminocyclohexanecarboxylic acid, aminoisobutyric acid, 2-aminotetraline-2-carboxylic, 4-bromophenylalanine, tert-leucine, 4-chlorophenylalanine, beta-cyclohexylalanine, 3,4-dichlorophenylalanine, 4-fluorophenylalanine, homoleucine, beta-homoleucine, homophenylalanine, 4-methylphenylalanine, 1-naphtylalanine, 2-naphtylalanine, 4-nitrophenylalanine, 3-nitrotyrosine, norvaline, phenylglycine, 3-pyridylalanine and 2-thienylalanine.

and X$_2$ is serine or threonine.

In the vertebrates, the central nervous system lies behind the protective blood-brain and blood-cerebrospinal fluid barriers, two membranes preventing transport of most drugs from the blood circulation to the cerebrospinal fluid.

Peptide-vector-mediated strategies have been developed to deliver therapeutic compounds to the central nervous system across the blood-brain and blood-cerebrospinal barriers. The SynB peptide vectors derived from the antimicrobial protegrin-1 or tachyplesin-1 peptides are of major interest.

In its native form, the protegrin-1 peptide has a structure constrained by two disulfide bridges. This peptide disrupts the bacterial membranes by forming pores. Various linear analogues of protegin-1 peptide devoid of disulfide bridges have been described. These linear peptides cross membranes via an energy-dependent endocytosis mechanism without any cytolytic effect [Drin et al., 2002. *AAPS Pharm. Sci.* 4(4), art. 26]. Injected intravenously, the SynB1 and SynB3 translocating vectors are able to deliver therapeutic molecules across the blood-brain barrier. The conjugation of drugs to SynB vectors leads to a considerable enhancement of central nervous system uptake immediately after intravenous injection. The SynB1 and SynB3 peptides have no significant lytic activity even at high concentrations. Nevertheless, high concentrations of SynB5 can perturb the integrity of membranes. D-enantiomer forms, wherein all amino acids are in the D-configuration, and retro-inverso sequences exhibit identical penetrating activity. D-enantiomer forms confer resistance to protease activity. Linear analogues with amino acid substitutions and/or permutations have been described. Linear analogues of tachyplesin-1 peptide devoid of disulfide bridges have been described. The SynB4 peptide presents similar properties.

According to a preferential embodiment, said peptide vector is a peptide having one of the following amino acid sequences: RGGRLSYSRRRFSTSTGR (SEQ ID NO:13), RRLSYSRRRF (SEQ ID NO:14), RGGRLAYLRRR-WAVLGR (SEQ ID NO:15), AWSFRVSYRGISYRRSR (SEQ ID NO:16) or their retroinverted sequences: RGTST-SFRRRSYSLRGGR (SEQ ID NO:17), FRRRSYSLRR (SEQ ID NO:18), RGLVAWRRRLYALRGGR (SEQ ID NO:19), RSRRYSIGRYSVRFSWA (SEQ ID NO:20).

According to another embodiment, the sequences RGGRLSYSRRRFSTSTGR (SEQ ID NO:21), RRLSYS-RRRF (SEQ ID NO:22), RGGRLAYLRRRWAVLGR (SEQ ID NO:23) are in a D-enantiomer form.

According to a specific embodiment, said peptide vector exhibits at least 70%, preferably at least 75%, 80%, 85%, 90% or even 95% of sequence identity with the original peptide sequence. The sequence identity is defined as the percentage of amino acids in the variant sequence with those in the original sequence, after alignment and introduction of empty spaces, if necessary, to obtain a maximum sequence identity, without considering conservative substitutions as part of sequence identity.

Suitable peptide substrates and peptide vectors in the context of the present invention are also variants of amino acid sequences SEQ ID NO 1 to 23. Variants of said amino acid sequences comprise, for example, deletions, insertions and/or substitutions. To analyse the impact of a mutation, variants must be tested for each desired activity. Generally, variant amino acid sequences of the present invention have at least 70% identity, preferably at least 75%, 80%, 85% or even 95% sequence identity with the original sequence. The sequence identity is defined as the percentage of amino acids in the variant sequence with those in the original sequence, after alignment and introduction of empty spaces, if necessary, to obtain a maximum sequence identity, without considering conservative substitutions as part of sequence identity.

Conservative substitutions are shown in table 2:

| Original amino acid | Possible substitutions | Prefered substitution |
|---|---|---|
| Ala (A) | val; leu; ile | val |
| Arg (R) | lys; gln; asn | lys |
| Asn (N) | gln; his; asp; lys; arg | arg |
| Asp (D) | glu; asn | glu |

-continued

| Original amino acid | Possible substitutions | Prefered substitution |
|---|---|---|
| Cys (C) | ser; ala | ser |
| Gln (Q) | asn; ala; ser | ser |
| Glu (E) | asp; gln | asp |
| Gly (G) | ala | |
| His (H) | asn; gln; lys; arg | |
| Ile (I) | leu; val; met; ala; phe; norleucine | leu; norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

The natural residues can be divided in different groups according to their properties:
(1) hydrophobic residues: norleucine, met, ala val, leu, ile;
(2) neutral polar residues: cys, ser, thr;
(3) acidic residues: asp, glu;
(4) basic residues: asn, gln, his, lys, arg;
(5) residues influencing the chain orientation: gly, pro; and
(6) aromatic residues: trp, tyr, phe.

The conservative substitutions implicate the replacement of an amino acid with one of the same group, while the nonconservative substitutions implicate the replacement of an amino acid with one of an another group.

According to a specific embodiment, the compound of the present invention is a carbamate prodrug that corresponds to general formula (2c), (2d), (3c), (3d), (4c), (4d), (5c) or (5d)

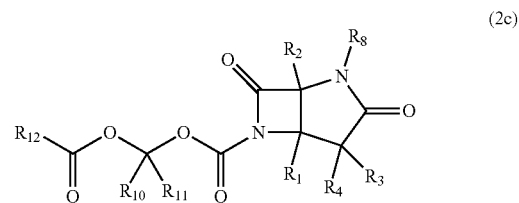

(2c)

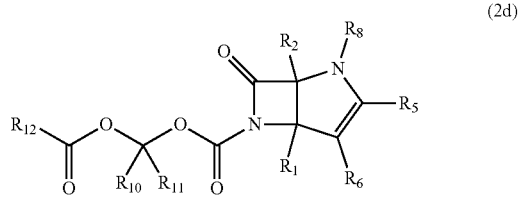

(2d)

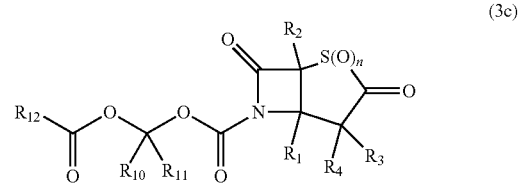

(3c)

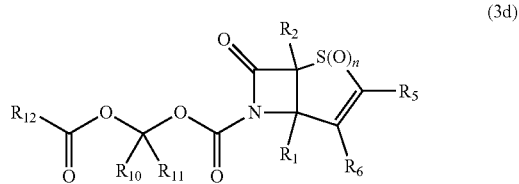

(3d)

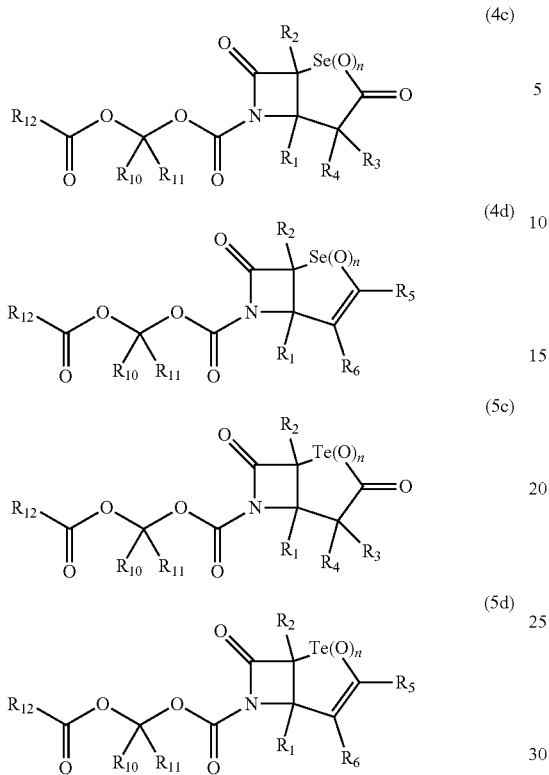

(4c)

(4d)

(5c)

(5d)

wherein $R_1$, $R_2$, $R_3$, $R_4$, $R_5$, $R_6$, $R_8$, $R_9$, $R_{10}$, $R_{11}$, and n are as defined herein; and $R_{12}$ is a transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector; preferably $R_{12}$ is tyrosine, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 2-iodo-L-tyrosine, 2-fluoro-L-tyrosine, or a peptide substrate or peptide vector having a SEQ ID NO 1 to 23; more preferably $R_{12}$ is tyrosine.

Particularly preferred are compounds of general formula (3c), (3d), (4c), (4d), (5c) or (5d); more preferably compounds of general formula (4c), (4d), (5c) or (5d); and more preferably still compounds of general formula (5c) or (5d).

According to another specific embodiment, the compound of the present invention is a carbamate prodrug that corresponds to general formula (2e), (2f), (3e), (3f), (4e), (4f), (5e) or (5f)

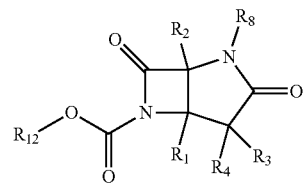

(2e)

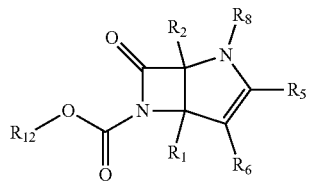

(2f)

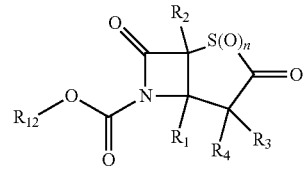

(3e)

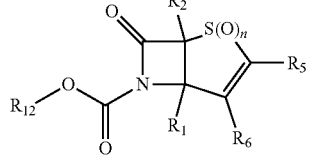

(3f)

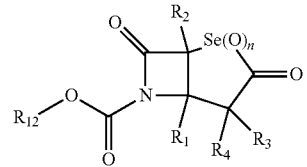

(4e)

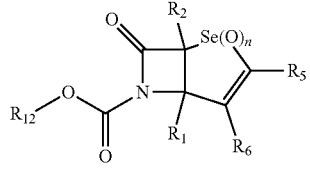

(4f)

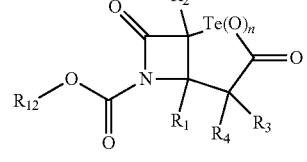

(5e)

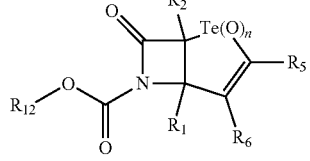

(5f)

wherein $R_1$, $R_2$, $R_3$, $R_4$, $R_5$, $R_6$, $R_8$, $R_9$, and n are as defined herein; and $R_{12}$ is a transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector; preferably $R_{12}$ is tyrosine, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 2-iodo-L-tyrosine, 2-fluoro-L-tyrosine, or a peptide substrate or peptide vector having a SEQ ID NO 1 to 23; more preferably $R_{12}$ is tyrosine.

Particularly preferred are compounds of general formula (3e), (3f), (4e), (4f), (5e) or (5f); more preferably compounds of general formula (4e), (4f), (5e) or (5f); and more preferably still compounds of general formula (5e) or (5f).

In particular, the compound of the present invention may be a compound of formula (1a), (1b), (2a), (2b), (2c), (2d), (2e), (2f), (3a), (3b), (3c), (3d), (3e), (3f), (4a), (4b), (4c), (4d), (4e), (4f), (5a), (5b), (5c), (5d), (5e) or (5f) wherein X, Y, $R_2$, $R_3$, $R_4$, $R_5$, $R_6$, $R_7$, $R_8$, $R_9$, $R_{10}$, $R_{11}$, $R_{12}$, n and m, when present, are as defined herein; and $R_1$ is H.

In particular, the compound of the present invention may be a compound of formula (1a), (1b), (2a), (2b), (2c), (2d), (2e), (2f), (3a), (3b), (3c), (3d), (3e), (3f), (4a), (4b), (4c), (4d), (4e), (4f), (5a), (5b), (5c), (5d), (5e) or (5f) wherein X, Y, $R_1$, $R_3$, $R_4$, $R_5$, $R_6$, $R_7$, $R_8$, $R_{10}$, $R_{11}$, $R_{12}$, n and m, when present, are as defined herein;

$R_2$ is —CH(OH)$R_9$, —SO$_2$—R, —SeO$_2$—R or —TeO$_2$—R; preferably —CH(OH)$R_9$ or —SO$_2$—R; more preferably —CH(OH)$R_9$;

R is an alkyl such as methyl or ethyl, and substituted derivatives thereof; and $R_9$ is selected from alkyl and cycloalkenyl; preferably isopropyl and cyclohexenyl; more preferably isopropyl.

In particular, the compound of the present invention may be a compound of formula (1a), (2a), (2c), (2e), (3a), (3c), (3e), (4a), (4c), (4e), (5a), (5c) or (5e) wherein X, Y, $R_1$, $R_2$, $R_5$, $R_6$, $R_7$, $R_8$, $R_9$, $R_{10}$, $R_{11}$, $R_{12}$, n and m, when present, are as defined herein; and $R_3$ and $R_4$ are independently selected from hydrogen, alkyl and haloalkyl; preferably $R_3$ and $R_4$ are independently selected from H, methyl and 2-chloroethyl; more preferably $R_3$ is H and $R_4$ is alkyl or haloalkyl; even more preferably $R_3$ is H and $R_4$ is methyl or 2-chloroethyl.

In particular, the compound of the present invention may be a compound of formula (1b), (2b), (2d), (2f), (3b), (3d), (3f), (4b), (4d), (4f), (5b), (5d) or (5f) wherein X, Y, $R_1$, $R_2$, $R_6$, $R_7$, $R_8$, $R_9$, $R_{10}$, $R_{11}$, $R_{12}$, n and m, when present, are as defined herein; and $R_5$ is selected from H or alkyl, preferably $R_5$ is selected from H or methyl.

In particular, the compound of the present invention may be a compound of formula (1b), (2b), (2d), (2f), (3b), (3d), (3f), (4b), (4d), (4f), (5b), (5d) or (5f) wherein X, Y, $R_1$, $R_2$, $R_5$, $R_7$, $R_8$, $R_9$, $R_{10}$, $R_{11}$, $R_{12}$, n and m, when present, are as defined herein; and $R_6$ is selected from alkyl or haloalkyl, more preferably $R_6$ is selected from methyl or 2-chloroethyl.

In particular, the compound of the present invention may be a compound of formula (2a), (2b), (2c), (2d), (2e) or (2f), wherein X, $R_1$, $R_2$, $R_3$, $R_4$, $R_5$, $R_6$, $R_7$, $R_9$, $R_{10}$, $R_{11}$, $R_{12}$, n and m, when present, are as defined herein; and $R_8$ is H.

In particular, the compound of the present invention may be a compound of formula (2c), (2d), (3c), (3d), (4c), (4d), (5c), or (5d) wherein $R_1$, $R_2$, $R_3$, $R_4$, $R_5$, $R_6$, $R_8$, $R_9$, $R_{12}$ and n, when present, are as defined herein; and $R_{10}$ and $R_{11}$ are independently selected from hydrogen and alkyl; preferably $R_{10}$ and $R_{11}$ are independently selected from hydrogen and methyl.

In particular, the compound of the present invention may be a compound of formula ((3a), (3b), (3c), (3d), (3e), (3f), (4a), (4b), (4c), (4d), (4e), (4f), (5a), (5b), (5c), (5d), (5e) or (5f) wherein $R_1$, $R_2$, $R_3$, $R_4$, $R_5$, $R_6$, $R_8$, $R_9$, $R_{10}$, $R_{11}$ and $R_{12}$, when present, are as defined herein; and n is 1 or 2, preferably n is 2.

According to a preferential embodiment, the compounds of the invention correspond to general formula (1a), (1b), (2a), (2b), (2c), (2d), (2e), (2f), (3a), (3b), (3c), (3d), (3e), (3f), (4a), (4b), (4c), (4d), (4e), (4f), (5a), (5b), (5c), (5d), (5e) or (5f) wherein X, Y, $R_2$, $R_7$, $R_{12}$, n and m, when present, are as defined herein; and $R_1$ is H;

$R_3$ and $R_4$ are independently selected from hydrogen, alkyl and haloalkyl; preferably $R_3$ is H and $R_4$ is alkyl or haloalkyl;

$R_5$ is selected from hydrogen or alkyl;

$R_6$ is selected from alkyl or haloalkyl;

$R_8$ is hydrogen;

$R_9$ is selected from alkyl and cycloalkenyl;

$R_{10}$ and $R_{11}$ are independently selected from hydrogen and alkyl.

According to an even more preferred embodiment, the compounds of the invention correspond to general formula (1a), (1b), (2a), (2b), (2c), (2d), (2e), (2f), (3a), (3b), (3c), (3d), (3e), (3f), (4a), (4b), (4c), (4d), (4e), (4f), (5a), (5b), (5c), (5d), (5e) or (5f) wherein X, Y, $R_2$, $R_7$, $R_{12}$, n and m, when present, are as defined herein; and $R_1$ is H;

$R_3$ is H;

$R_4$ is methyl or 2-chloroethyl;

$R_5$ is selected from hydrogen or methyl;

$R_6$ is selected from methyl or 2-chloroethyl;

$R_8$ is hydrogen;

$R_9$ is selected from isopropyl and cyclohex-2-enyl;

$R_{10}$ and $R_{11}$ are independently selected from hydrogen and methyl.

According to a particular embodiment of the present invention, the compounds are selected from:

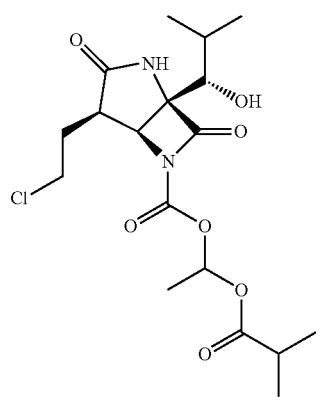

2

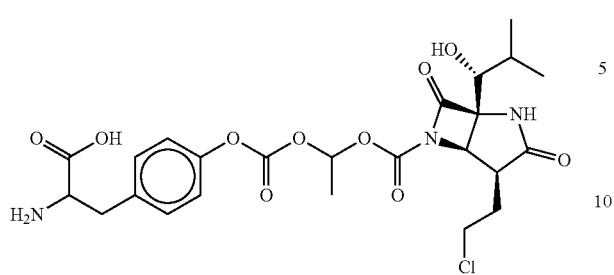
(8)
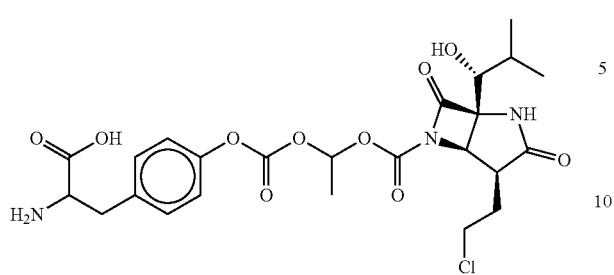
(9)
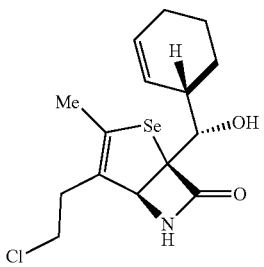
(6a)
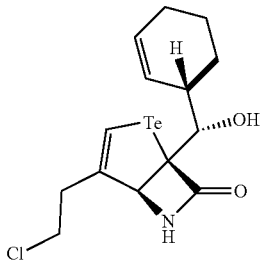
(6b)
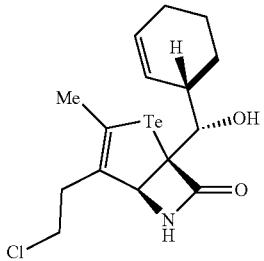
(6c)
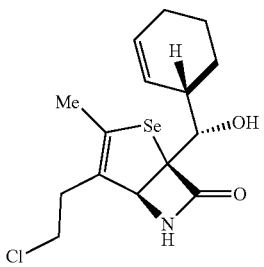
(6d)
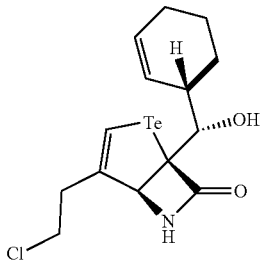
(6e)
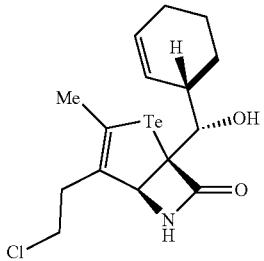
(6f)
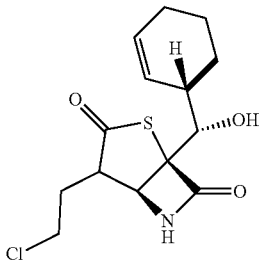
(6g)
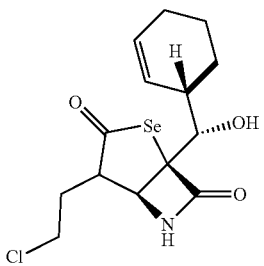
(6h)
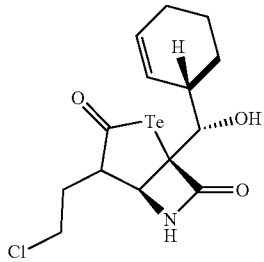
(6i)

(6j)
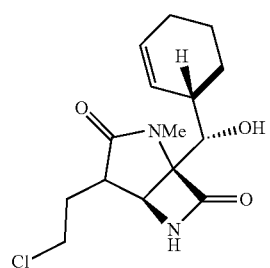
(7a)
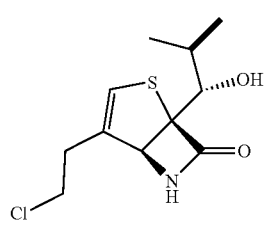
(7b)
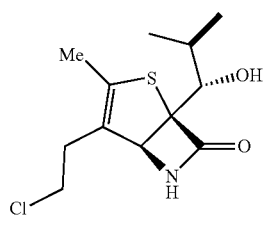
(7c)
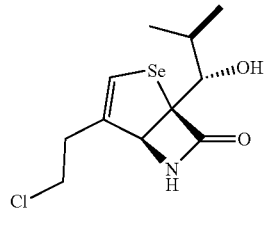
(7d)
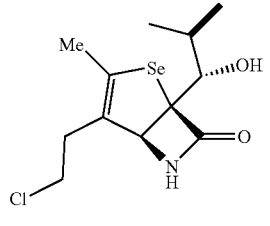
(7e)
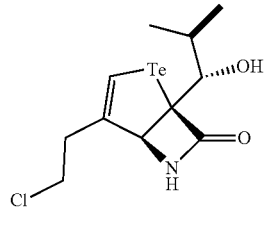
(7f)
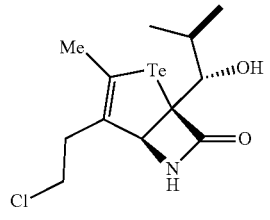
(7g)
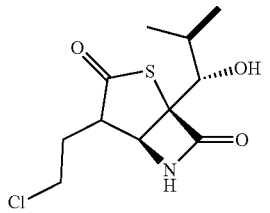
(7h)
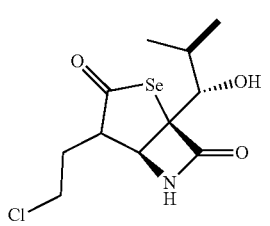
(7i)
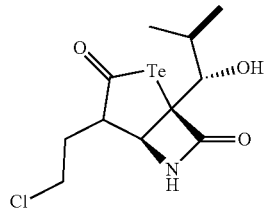
(7j)
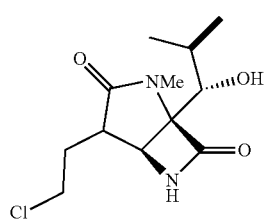
(8a)
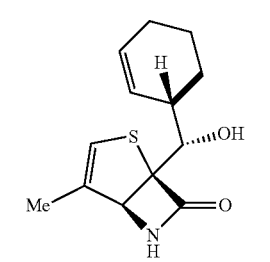
(8b)
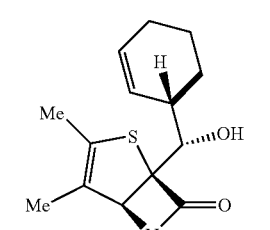
(8c)
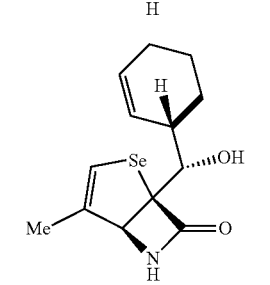

-continued (8d)
(8e)
(8f)
(8g)
(8h)
(8i)
(8j)
(9a)
(9b)
(9c)
(9d)
(9e)
(9f)

-continued (9g)

(9h)

(9i)

(9j)

(10a)

(10b)

(10c)

(10d)

(10e)

(10f)

(10g)

(10h)

(10i)

(11a) 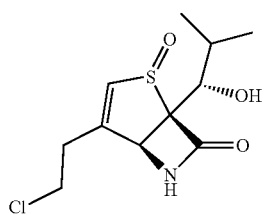
(11b) 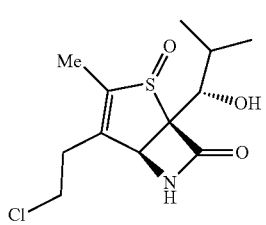
(11c) 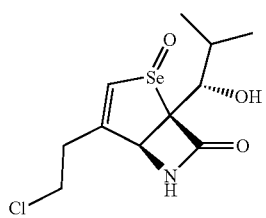
(11d) 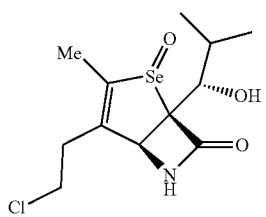
(11e) 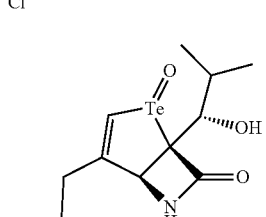
(11f) 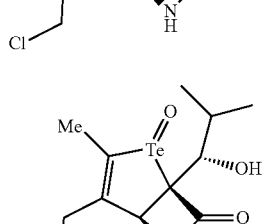
(11g) 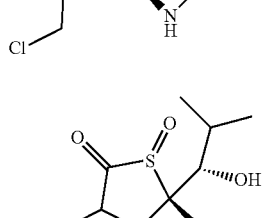
(11h) 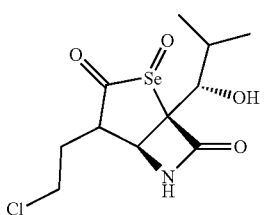
(11i) 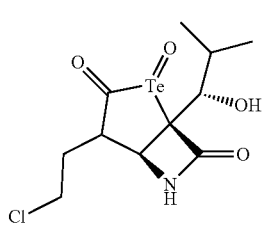
(12a) 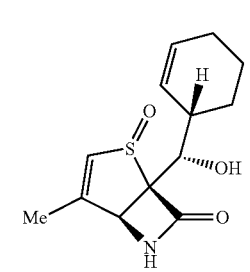
(12b) 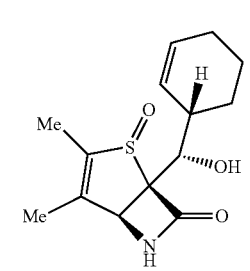
(12c) 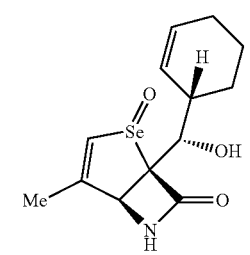
(12d) 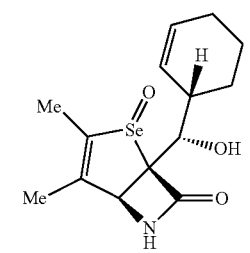

(12e)
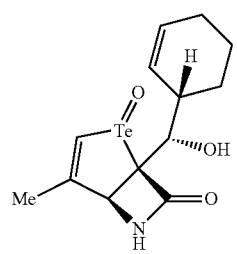
(12f)
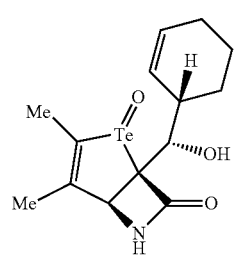
(12g)
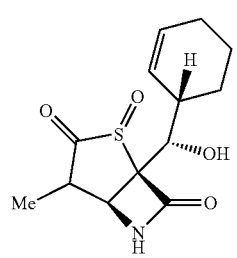
(12h)
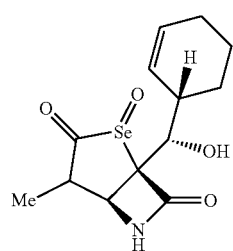
(12i)
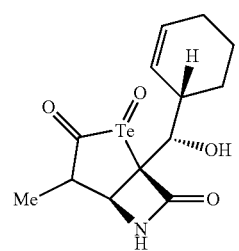
(13a)
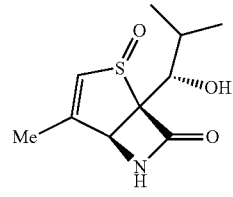
(13b)
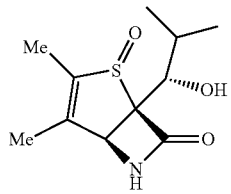
(13c)
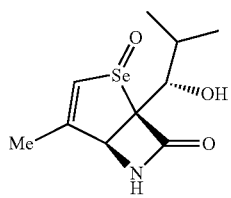
(13d)
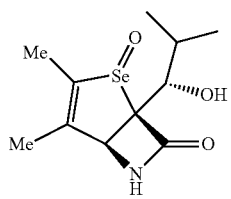
(13e)
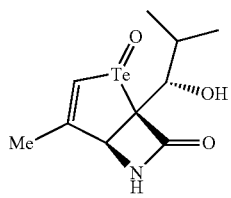
(13f)
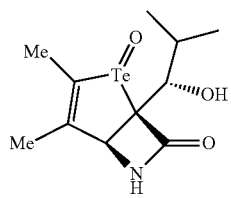
(13g)
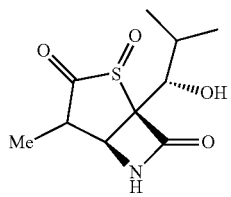
(13h)
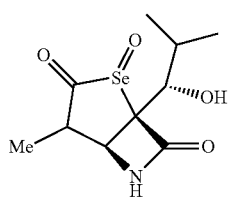
(13i)
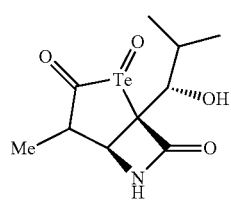

(14a)
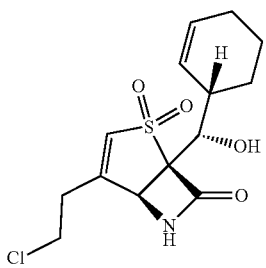
(14b)
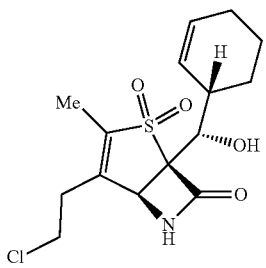
(14c)
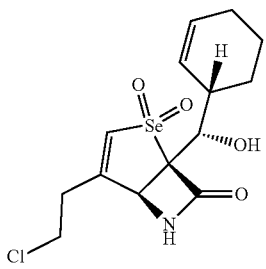
(14d)
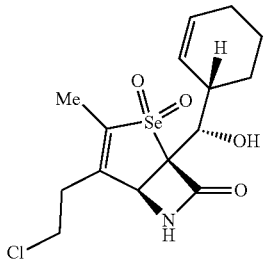
(14e)
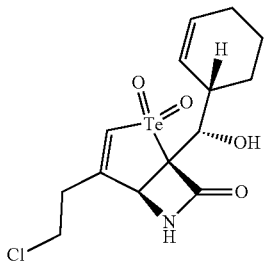
(14f)
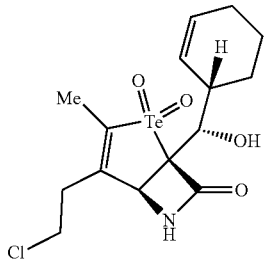
(14g)
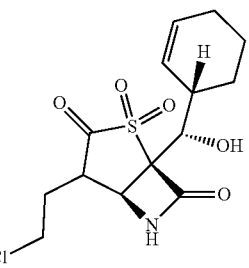
(14h)
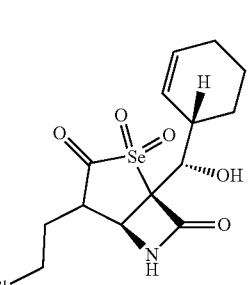
(14i)
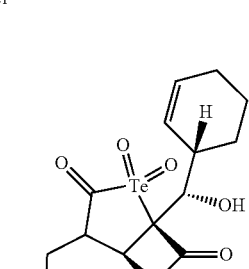
(15a)
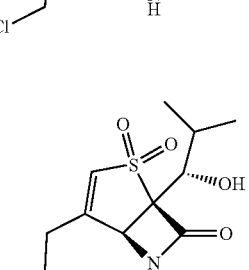
(15b)
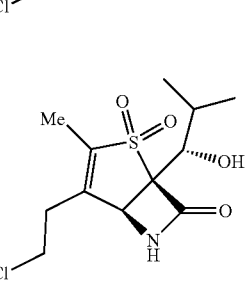
(15c)
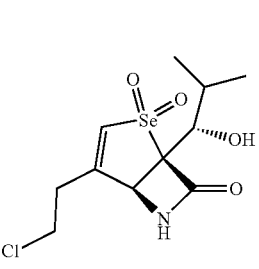

-continued
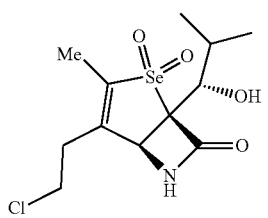
(15d)
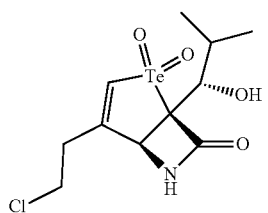
(15e)
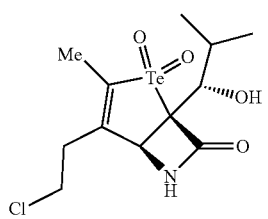
(15f)
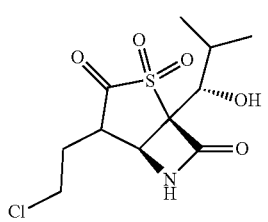
(15g)
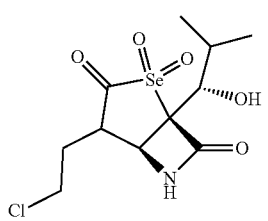
(15h)
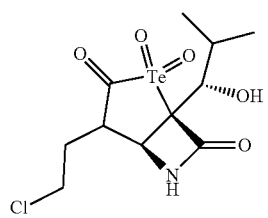
(15i)
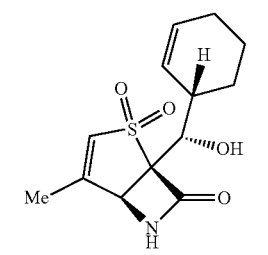
(16a)
-continued
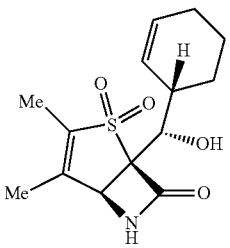
(16b)
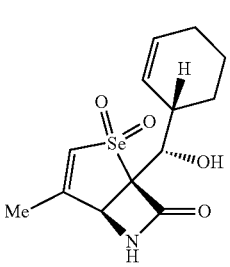
(16c)
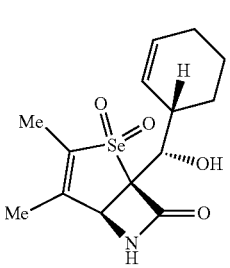
(16d)
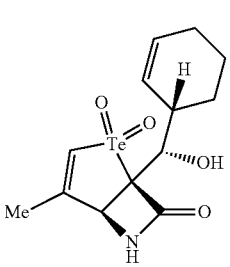
(16e)
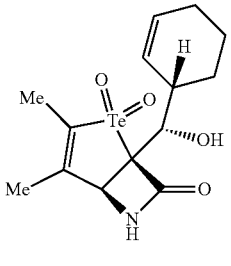
(16f)
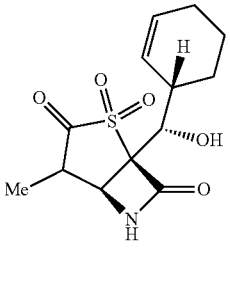
(16g)

-continued
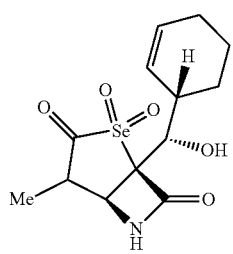
(16h)
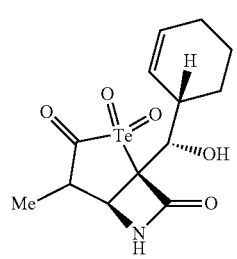
(16i)
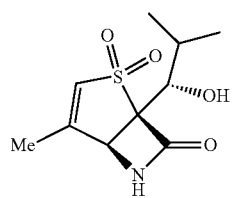
(17a)
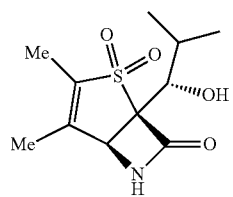
(17b)
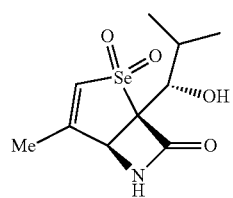
(17c)
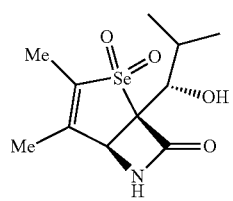
(17d)
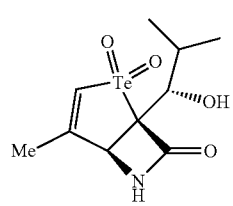
(17e)
-continued
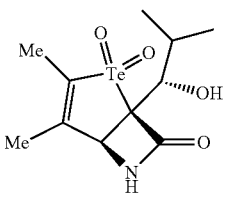
(17f)
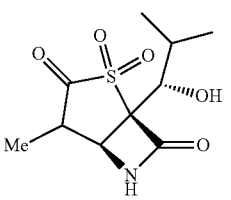
(17g)
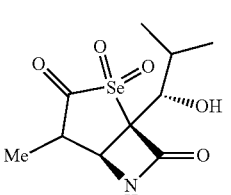
(17h)
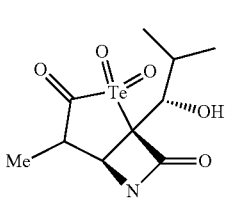
(17i)
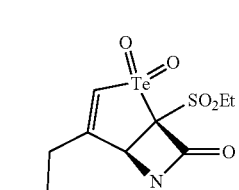
(14j)
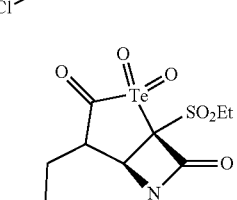
(14k)
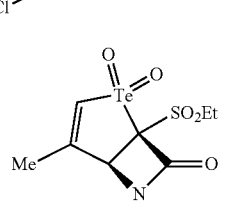
(16j)
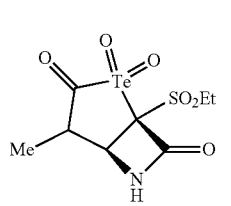
(16k)

-continued

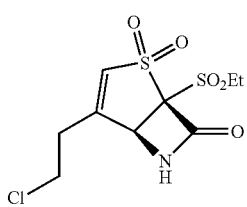
(14l)

Process for the Preparation of the Compounds of the Invention

Compounds of general formula (1b) wherein Y is S, Se or Te and n is 0, according to the invention, for example compounds (6a)-(6f), (7a)-(7f), (8a)-(8f) and (9a)-(9f), and the corresponding carbamate prodrugs thereof, can be prepared according to the process described in the following scheme:

the formation of an alkenyl azetidinone (20) by a Staudinger reaction between acyl chloride (18) and imine (19);

optionally the conversion of alkenyl azetidinone (20) of trans configuration into alkenyl azetidinone (20) of cis configuration;

the iodine-promoted cyclization of (20) to form iodopenem adduct (21);

the Stille cross-coupling between iodopenem adduct (21) and $R_6$—$SnBu_3$ to form compound (22) or (23);

the ozonolysis of the carbon-carbon double bond of compound (22) or (23) to form aldehyde (24) or (25);

the addition of $R_9$—ZnCl on the aldehyde (24) or (25) to form alcohol (26), (27), (28) or (29);

the deprotection of the nitrogen of the β-lactam ring of compounds (26), (27), (28) or (29) to form proteasome inhibitors (6), (7), (8) or (9) according to the invention:

optionally the carbamylation of proteasome inhibitors (6), (7), (8) or (9) to form the corresponding carbamate

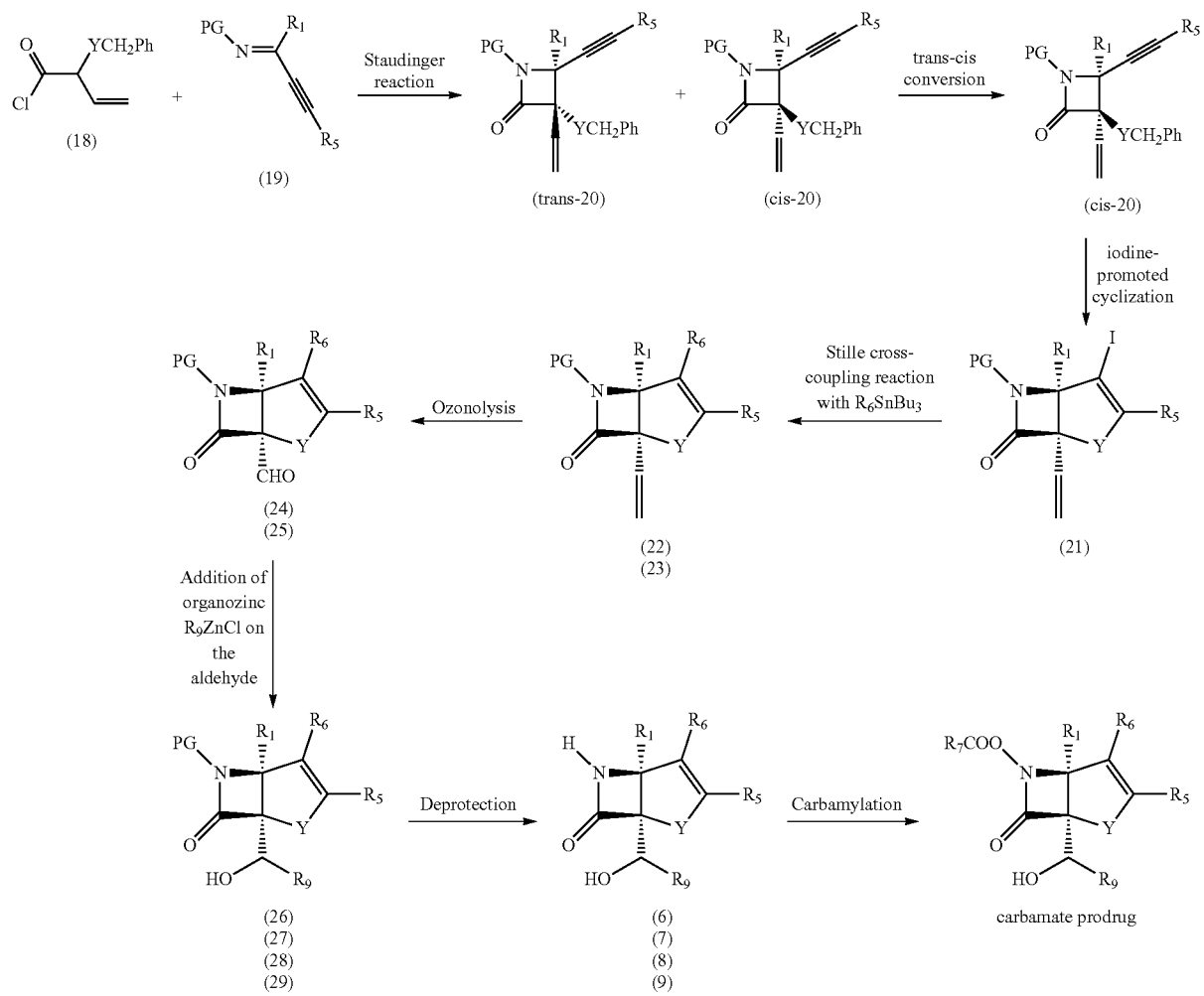

Y is S, Se or Te
PG is an amino-protecting group

The process of preparation of compounds of general formula (1b) wherein Y is S, Se or Te and n is 0, according to the invention, for example compounds (6a)-(6f), (7a)-(7f), (8a)-(8f) and (9a)-(9f), and the corresponding carbamate prodrugs thereof, comprises the following steps:

prodrugs of general formula (1b) wherein Y is S, Se or Te, n is 0 and X is —$COOR_7$.

The process for the preparation of carbamate prodrugs is further detailed below.

Compounds of general formula (1b) wherein Y is S, Se, or Te and n is 1, according to the invention, for example compounds (10a)-(10f), (11a)-(11f), (12a)-(12f) and (13a)-(13f), and the corresponding carbamate prodrugs thereof, can be prepared according to the process described in the following scheme:

- the formation of an alkenyl azetidinone (20) by a Staudinger reaction between acyl chloride (18) and imine (19);
- optionally the conversion of alkenyl azetidinone (20) of trans configuration into alkenyl azetidinone (20) of cis configuration;
- the iodine-promoted cyclization of (20) to form iodopenem adduct (21);

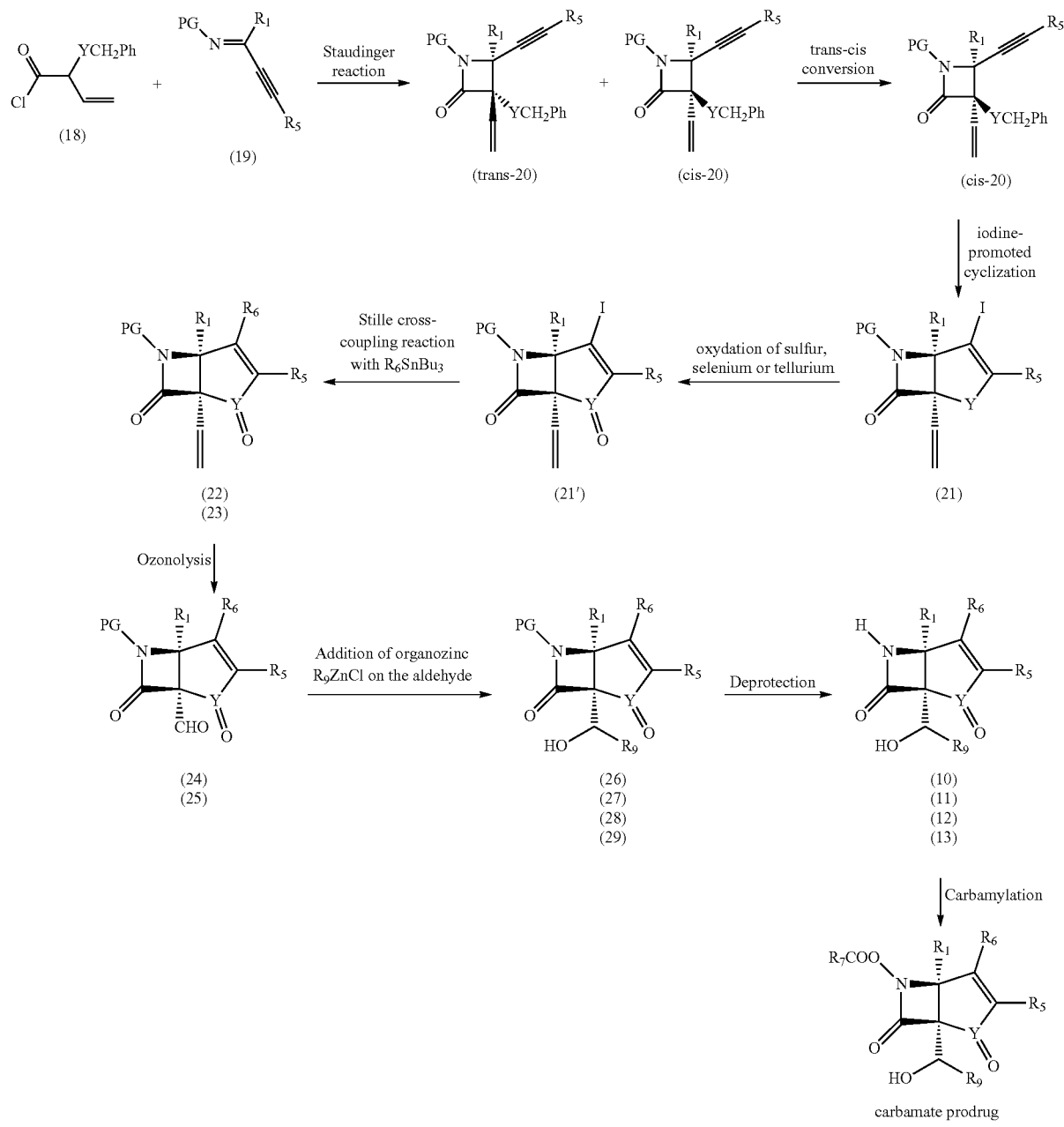

Y is S, Se or Te
PG is an amino-protecting group

The process of preparation of compounds of general formula (1b) wherein Y is S, Se, or Te and n is 1, according to the invention, for example compounds (10a)-(10f), (11a)-(11f), (12a)-(12f) and (13a)-(13f), and the corresponding carbamate prodrugs thereof, comprises the following steps:

- the oxidation of iodopenem adduct (21) to form sulfoxide, -selenoxide or telluroxide (21');
- the Stille cross-coupling between sulfoxide, selenoxide or telluroxide (21') and $R_6$—$SnBu_3$ to form compound (22) or (23);

the ozonolysis of the carbon-carbon double bond of compound (22) or (23) to form aldehyde (24) or (25);

the addition of R$_9$—ZnCl on the aldehyde (24) or (25) to form alcohol (26), (27), (28) or (29);

the deprotection of the nitrogen of the β-lactam ring of compounds (26), (27), (28) or (29) to form proteasome inhibitors (10), (11), (12) or (13) according to the invention;

optionally the carbamylation of proteasome inhibitors (10), (11), (12) or (13) to form the corresponding carbamate prodrugs of general formula (1b) wherein Y is S, Se or Te, n is 1 and X is —COOR$_7$.

The process for the preparation of carbamate prodrugs is further detailed below.

Compounds of general formula (1b) wherein Y is S, Se, or Te and n is 2, according to the invention, for example compounds (14a)-(14f), (15a)-(15f), (16a)-(16f) and (17a)-(17f), and the corresponding carbamate prodrugs thereof, can be prepared according to the process described in the following scheme:

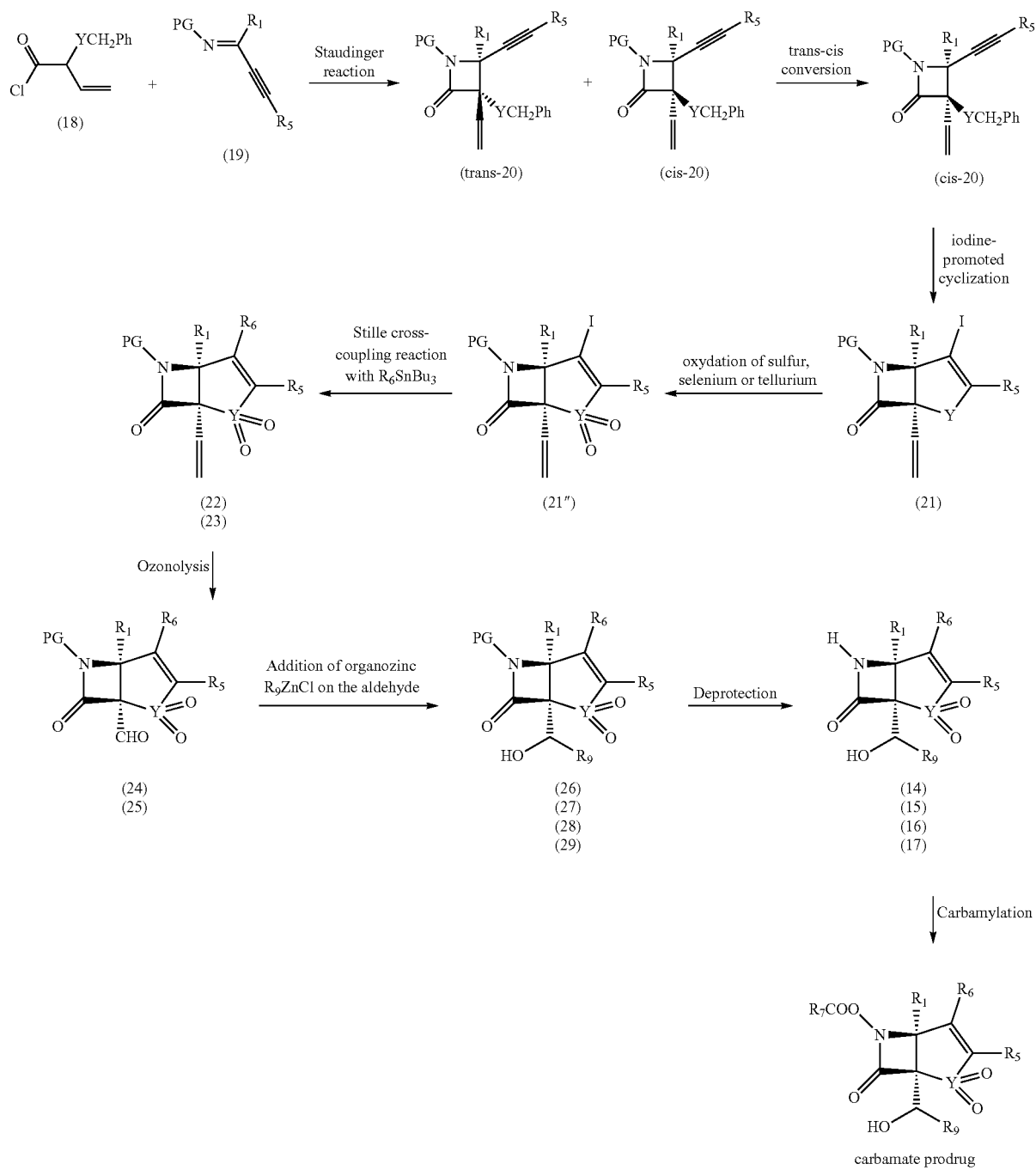

Y is S, Se or Te
PG is an amino-protecting group

The process of preparation of compounds of general formula (1b) wherein Y is S, Se, or Te and n is 2, according to the invention, for example compounds (14a)-(14f), (15a)-(15f), (16a)-(16f) and (17a)-(17f), and the corresponding carbamate prodrugs thereof, comprises the following steps:

- the formation of an alkenyl azetidinone (20) by a Staudinger reaction between acyl chloride (18) and imine (19);
- optionally the conversion of alkenyl azetidinone (20) of trans configuration into alkenyl azetidinone (20) of cis configuration;
- the iodine-promoted cyclization of (20) to form iodopenem adduct (21);
- the oxidation of iodopenem adduct (21) to form sulfone, selenone or tellurone (21″);
- the Stille cross-coupling between sulfone, selenone or tellurone (21″) and $R_6$—$SnBu_3$ to form compound (22) or (23);
- the ozonolysis of the carbon-carbon double bond of compound (22) or (23) to form aldehyde (24) or (25);
- the addition of $R_9$—ZnCl on the aldehyde (24) or (25) to form alcohol (26), (27), (28) or (29);
- the deprotection of the nitrogen of the β-lactam ring of compounds (26), (27), (28) or (29) to form proteasome inhibitors (14), (15), (16) or (17) according to the invention;
- optionally the carbamylation of proteasome inhibitors (14), (15), (16) or (17) to form the corresponding carbamate prodrugs of general formula (1b) wherein Y is S, Se or Te, n is 2 and X is —$COOR_7$.

The process for the preparation of carbamate prodrugs is further detailed below.

Compounds of general formula (1b) wherein $R_2$ is —$Y(O)_n$—R; $R_6$ is chloroethyl; R is alkyl; each Y is independently S, Se, or Te and n is 0, 1 or 2, according to the invention, for example compounds (14j), (14k) and (14l), and the corresponding carbamate prodrugs thereof, can be prepared according to the process described in the following scheme:

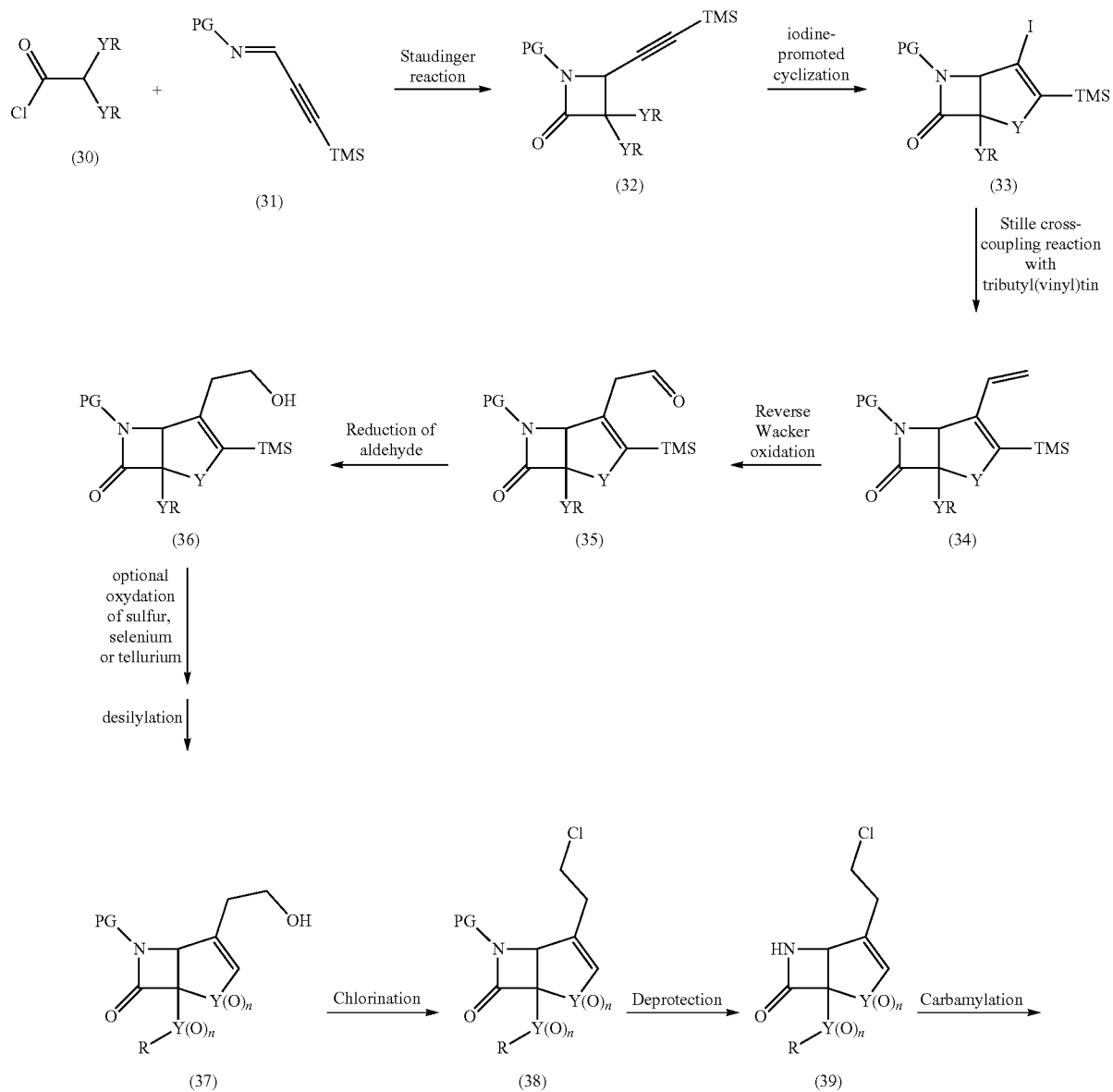

-continued

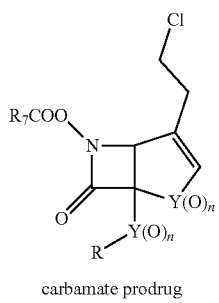

carbamate prodrug

Y is independently S, Se or Te
R is alkyl
PG is an amino-protecting group
n is 0, 1 or 2

The process of preparation of compounds of general formula (1b) wherein $R_2$ is —Y(O)$_n$—R; $R_6$ is chloroethyl; R is alkyl; each Y is independently S, Se, or Te and n is 0, 1 or 2, according to the invention, for example compounds (14j), (14k) and (14l), and the corresponding carbamate prodrugs thereof, comprises the following steps:
the formation of alkenyl azetidinone (32) by a Staudinger reaction between acyl chloride (30) and imine (31);
the iodine-promoted cyclization of (32) to form iodopenem adduct (33);
the Stille cross-coupling between (33) and tributyl(vinyl) tin to form compound (34);
the reverse Wacker oxidation of the carbon-carbon double bond of compound (34) to form aldehyde (35);
the reduction of aldehyde (35) to form alcohol (36);
optionally the oxidation of alcohol (36) to form the corresponding sulfoxyde, sulfone, selenoxide, selenone, telluroxide or tellurone;
the desilylation to form compound (37);
the chlorination of compound (37) to form chloride (38);
the deprotection of the nitrogen of the β-lactam ring of compound (38) to form proteasome inhibitor (39) according to the invention;
optionally the carbamylation of proteasome inhibitor (39) to form the corresponding carbamate prodrugs of general formula (1b) wherein $R_2$ is —Y(O)$_n$—R; $R_6$ is chloroethyl; R is alkyl; each Y is independently S, Se, or Te; n is 0, 1 or 2; and X is —COOR$_7$.

The formation of alkenyl azetidinone (32) by a Staudinger reaction between acyl chloride (30) and imine (31) can be carried out in the presence of a base, such as triethylamine. The reaction may be conducted in a solvent such as dichloromethane. The mixture can be stirred at a temperature of 20 to 25° C. for several minutes, for example 30 min.

The iodine-promoted cyclization of (32) to form iodopenem adduct (33) can be carried in the presence of iodine. The reaction may be conducted in a solvent such as dichloromethane. The mixture can be stirred at a temperature of 20 to 25° C. for several hours, for example 2 hours.

The Stille cross-coupling between (33) and tributyl(vinyl) tin to form compound (34) can be carried out in the presence of a catalyst, such as tris(dibenzylideneacetone)dipalladium, and a ligand, such as triphenylphosphine. The reaction may be conducted in a solvent such as dimethylformamide. The mixture can be stirred at a temperature of 20 to 25° C. for several hours, for example 12 hours.

The reverse Wacker oxidation of the carbon-carbon double bond of compound (34) to form aldehyde (35) can be carried out in the presence of an oxidant, such as oxygen; a catalyst, such as, bis(benzonitrile)palladium chloride; a copper salt, such as CuCl$_2$; and a nitrite co-catalyst, such as AgNO$_2$. The reaction may be conducted in a mixture of solvents such as tert-butanol and nitromethane. The mixture can be stirred at a temperature of 20 to 25° C. for several hours, for example 6 hours.

The reduction of aldehyde (35) to alcohol (36) can be carried out in the presence of a reducing agent, such as sodium borohydride. The reaction may be conducted in a solvent such as ethanol. The mixture can be stirred at a temperature of 0° C. for several hours, for example 3 hours.

The optional oxidation of alcohol (36) to form sulfoxide, sulfone, selenoxide, selenone, telluroxide or tellurone can be carried out in the presence of an oxidant, such as meta-chloroperoxybenzoic acid. The reaction may be conducted in a mixture of solvents such as dichloromethane and a buffer of pH 7. The mixture can be stirred at a temperature of 20 to 25° C. for several hours, for example 16 hours.

The desilylation to form compound (37) can be carried out in the presence of a fluoride, such as tetrabutylammonium fluoride. The reaction may be conducted in a solvent such as tetrahydrofurane. The mixture can be stirred at a temperature of 20 to 25° C. for several hours, for example 2 hours.

The chlorination of compound (37) to form chloride (38) can be carried out in the presence of a chlorinating agent, such as dichlorotriphenylphosphorane and a base, such as pyridine. The reaction may be conducted in a solvent such as acetonitrile. The mixture can be stirred at a temperature of 20 to 25° C. for several hours, for example 4 hours.

The deprotection of the nitrogen of the β-lactam ring of compound (38) to form proteasome inhibitor (39) depends on the nature of the protecting group. When the protection group is para-methoxyphenyl (PMP), the deprotection can be carried out in the presence of ceric ammonium nitrate. The reaction may be conducted in a mixture of solvents such as acetonitrile and water. The mixture can be stirred at a temperature of 0° C. for several hours, for example 3 hours.

The process for the preparation of carbamate prodrugs is further detailed below.

The process described above is particularly advantageous to obtain proteosome inhibitors according to the invention wherein both Y are different atoms, for example one Y is S and the other is Se or Te or one Y is Se and the other is S or Te or one Y is Te and the other is S or Se. The process described above can also be used to obtain proteosome inhibitors according to the invention wherein both Y are the same.

Compounds of general formula (1b) wherein $R_2$ is —CH(OH)$R_9$; $R_6$ is chloroethyl; Y is S, Se, or Te and n is 0, 1 or 2, according to the invention, for example compounds (6a), (6c), (6e), (7a), (7c), (7e), (10a), (10c), (10e), (11a), (11c), (Ile), (14a), (14c), (14e), (15a), (15c) and (15e), and the corresponding carbamate prodrugs thereof, can be prepared according to the process described in the following scheme:

(15a), (15c) and (15e), and the corresponding carbamate prodrugs thereof, comprises the following steps:
- the formation of alkenyl azetidinone (40) by a Staudinger reaction between acyl chloride (18) and imine (31);
- the iodine-promoted cyclization of (40) to form iodopenem adduct (41);
- the ozonolysis of the carbon-carbon double bond of compound (41) to form aldehyde (42);

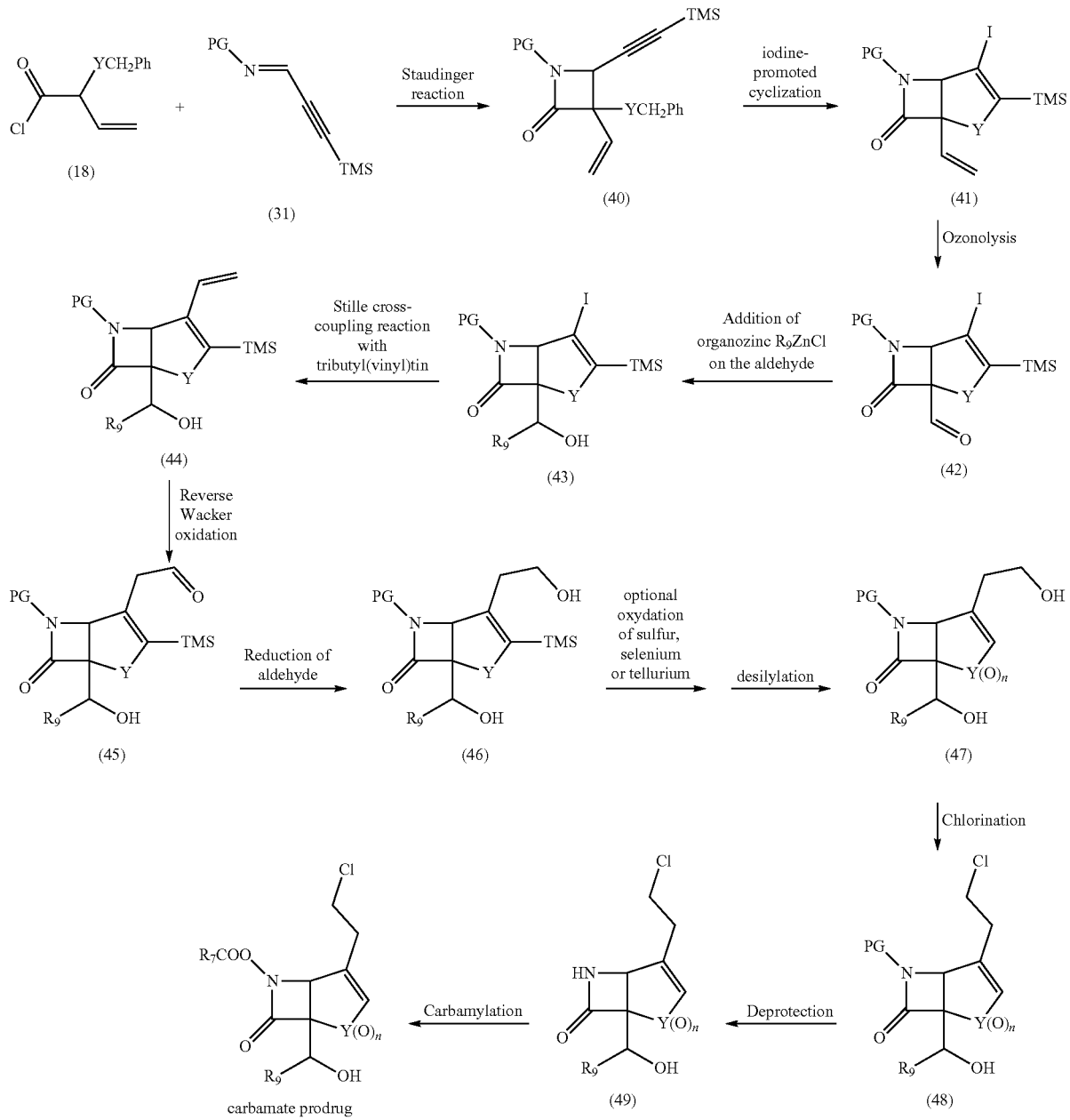

Y is S, Se or Te
PG is an amino-protecting group
n is 0, 1 or 2

The process of preparation of compounds of general formula (1b) wherein $R_2$ is —CH(OH)$R_9$; $R_6$ is chloroethyl; Y is S, Se, or Te and n is 0, 1 or 2, according to the invention, for example compounds (6a), (6c), (6e), (7a), (7c), (7e), (10a), (10c), (10e), (11a), (11c), (Ile), (14a), (14c), (14e),

- the addition of $R_9$—ZnCl on the aldehyde (42) to form alcohol (43);
- the Stille cross-coupling between (43) and tributyl(vinyl)tin to form compound (44);

the reverse Wacker oxidation of the carbon-carbon double bond of compound (44) to form aldehyde (45);

the reduction of aldehyde (45) to form alcohol (46);

optionally the oxidation of alcohol (46) to form the corresponding sulfoxide, sulfone, selenoxide, selenone, telluroxide or tellurone;

the desilylation to form compound (47);

the chlorination of compound (47) to form chloride (48);

the deprotection of the nitrogen of the β-lactam ring of compound (48) to form proteasome inhibitor (49) according to the invention;

optionally the carbamylation of proteasome inhibitor (49) to form the corresponding carbamate prodrug of general formula (1b) wherein $R_2$ is —CH(OH)$R_9$; $R_6$ is chloroethyl; Y is S, Se, or Te; n is 0, 1 or 2; and X is —COO$R_7$.

The formation of alkenyl azetidinone (40) by a Staudinger reaction between acyl chloride (18) and imine (31) can be carried out in the presence of a base, such as triethylamine. The reaction may be conducted in a solvent such as dichloromethane. The mixture can be stirred at a temperature of 20 to 25° C. for several minutes, for example 30 min.

The iodine-promoted cyclization of (40) to form iodopenem adduct (41) can be carried in the presence of iodine. The reaction may be conducted in a solvent such as dichloromethane. The mixture can be stirred at a temperature of 20 to 25° C. for several hours, for example 2 hours.

The ozonolysis of the carbon-carbon double bond of compound (41) to form aldehyde (42) can be carried out in the presence of ozone. The reaction may be conducted in a solvent such as dichloromethane. The mixture can be stirred at a temperature of −78° C.

The addition of $R_9$—ZnCl on the aldehyde (42) to form alcohol (43) can be carried out in the presence of 2-propylzinc chloride or 2-cyclohexenylzinc chloride. The reaction may be conducted in a solvent such as tetrahydrofurane. The mixture can be stirred at a temperature of −78° C. for several hours, for example 5 hours.

The Stille cross-coupling between (43) and tributyl(vinyl)tin to form compound (44) can be carried out in the presence of a catalyst, such as tris(dibenzylideneacetone)dipalladium, and a ligand, such as triphenylphosphine. The reaction may be conducted in a solvent such as dimethylformamide. The mixture can be stirred at a temperature of 20 to 25° C. for several hours, for example 12 hours.

The reverse Wacker oxidation of the carbon-carbon double bond of compound (44) to form aldehyde (45) can be carried out in the presence of an oxidant, such as oxygen; a catalyst, such as, bis(benzonitrile)palladium chloride; a copper salt, such as $CuCl_2$; and a nitrite co-catalyst, such as $AgNO_2$. The reaction may be conducted in a mixture of solvents such as tert-butanol and nitromethane. The mixture can be stirred at a temperature of 20 to 25° C. for several hours, for example 6 hours.

The reduction of aldehyde (45) to alcohol (46) can be carried out in the presence of a reducing agent, such as sodium borohydride. The reaction may be conducted in a solvent such as ethanol. The mixture can be stirred at a temperature of 0° C. for several hours, for example 3 hours.

The optional oxidation of alcohol (46) to form sulfoxide, sulfone, selenoxide, selenone, telluroxide or tellurone can be carried out in the presence of an oxidant, such as meta-chloroperoxybenzoic acid. The reaction may be conducted in a mixture of solvents such as dichloromethane and a buffer of pH 7. The mixture can be stirred at a temperature of 20 to 25° C. for several hours, for example 16 hours.

The desilylation to form compound (47) can be carried out in the presence of a fluoride, such as tetrabutylammonium fluoride. The reaction may be conducted in a solvent such as tetrahydrofurane. The mixture can be stirred at a temperature of 20 to 25° C. for several hours, for example 2 hours.

The chlorination of compound (47) to form chloride (48) can be carried out in the presence of a chlorinating agent, such as dichlorotriphenylphosphorane and a base, such as pyridine. The reaction may be conducted in a solvent such as acetonitrile. The mixture can be stirred at a temperature of 20 to 25° C. for several hours, for example 4 hours.

The deprotection of the nitrogen of the β-lactam ring of compound (48) to form proteasome inhibitor (49) depends on the nature of the protecting group. When the protection group is para-methoxyphenyl (PMP), the deprotection can be carried out in the presence of ceric ammonium nitrate. The reaction may be conducted in a mixture of solvents such as acetonitrile and water. The mixture can be stirred at a temperature of 0° C. for several hours, for example 3 hours.

The process for the preparation of carbamate prodrugs is further detailed below.

Compounds of general formula (1b) wherein $R_2$ is —Y(O)$_n$—R; $R_6$ is methyl; R is alkyl; each Y is independently S, Se, or Te and n is 0, 1 or 2, according to the invention, for example compounds (16j) and (16k), and the corresponding carbamate prodrugs thereof, can be prepared according to the process described in the following scheme:

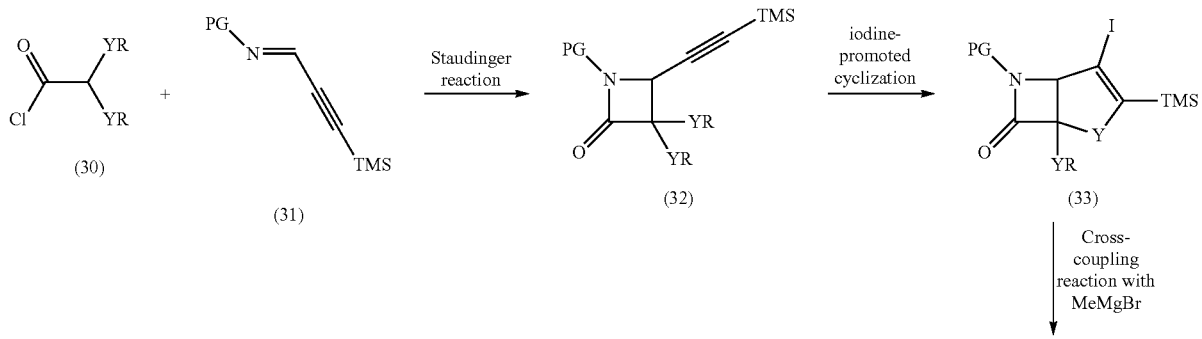

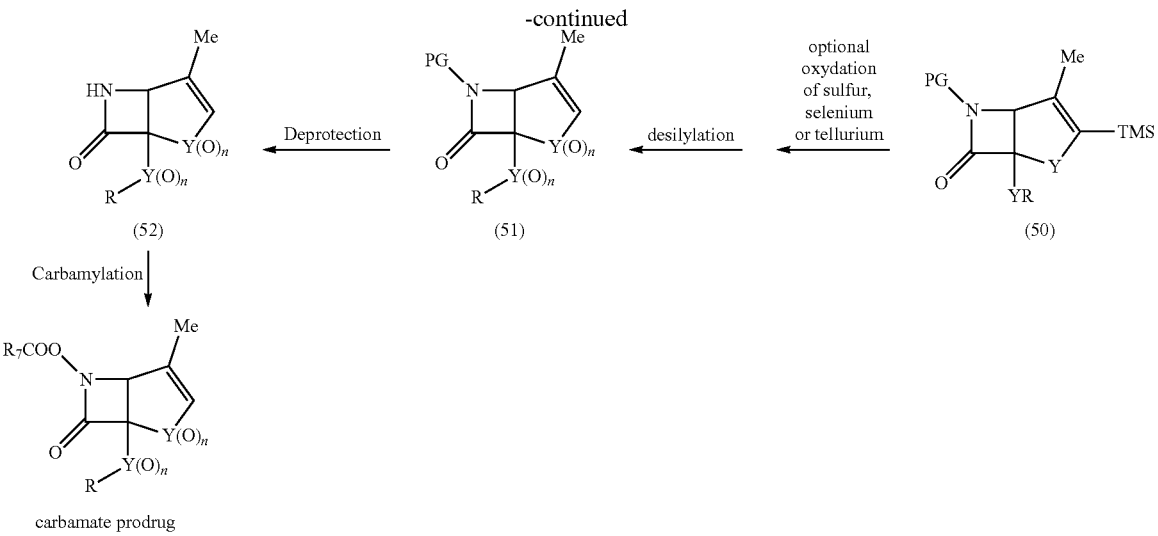

Y is independently S, Se or Te
R is alkyl
PG is an amino-protecting group
n is 0, 1 or 2

The process of preparation of compounds of general formula (1b) wherein $R_2$ is —Y(O)$_n$—R; $R_6$ is methyl; R is alkyl; each Y is independently S, Se, or Te and n is 0, 1 or 2, according to the invention, for example compounds (16j) and (16k), and the corresponding carbamate prodrugs thereof, comprises the following steps:

- the formation of alkenyl azetidinone (32) by a Staudinger reaction between acyl chloride (30) and imine (3¹);
- the iodine-promoted cyclization of (32) to form iodopenem adduct (33);
- the cross-coupling between (33) and methylmagnesium bromide to form compound (50);
- optionally the oxidation of alcohol (50) to form the corresponding sulfoxyde, sulfone, selenoxide, selenone, telluroxide or tellurone;
- the desilylation to form compound (51);
- the deprotection of the nitrogen of the β-lactam ring of compound (51) to form proteasome inhibitor (52) according to the invention;
- optionally the carbamylation of proteasome inhibitor (52) to form the corresponding carbamate prodrugs of general formula (1b) wherein $R_2$ is —Y(O)$_n$—R; $R_6$ is methyl; R is alkyl; each Y is independently S, Se, or Te; n is 0, 1 or 2; and X is —COOR$_7$.

Compounds (32) and (33) can be obtained as described above.

The cross-coupling between (33) and methylmagnesium bromide to form compound (50) can be carried out in the presence of a catalyst, such as such as nickel acetylacetonate (Ni(acac)$_2$).

The optional oxidation of alcohol (50) to form sulfoxide, sulfone, selenoxide, selenone, telluroxide or tellurone can be carried out in the presence of an oxidant, such as meta-chloroperoxybenzoic acid. The reaction may be conducted in a mixture of solvents such as dichloromethane and a buffer of pH 7. The mixture can be stirred at a temperature of 20 to 25° C. for several hours, for example 16 hours.

The desilylation to form compound (51) can be carried out in the presence of a fluoride, such as tetrabutylammonium fluoride. The reaction may be conducted in a solvent such as tetrahydrofurane. The mixture can be stirred at a temperature of 20 to 25° C. for several hours, for example 2 hours.

The deprotection of the nitrogen of the β-lactam ring of compound (51) to form proteasome inhibitor (52) depends on the nature of the protecting group. When the protection group is para-methoxyphenyl (PMP), the deprotection can be carried out in the presence of ceric ammonium nitrate. The reaction may be conducted in a mixture of solvents such as acetonitrile and water. The mixture can be stirred at a temperature of 0° C. for several hours, for example 3 hours.

The process for the preparation of carbamate prodrugs is further detailed below.

The process described above is particularly advantageous to obtain proteosome inhibitors according to the invention wherein both Y are different atoms, for example one Y is S and the other is Se or Te or one Y is Se and the other is S or Te or one Y is Te and the other is S or Se. The process described above can also be used to obtain proteosome inhibitors according to the invention wherein both Y are the same.

Compounds of general formula (1b) wherein $R_2$ is —CH(OH)$R_9$; $R_6$ is methyl; Y is S, Se, or Te and n is 0, 1 or 2, according to the invention, for example compounds (8a), (8c), (8e), (9a), (9c), (9e), (12a), (12c), (12e), (13a), (13c), (13e), (16a), (16c), (16e), (17a), (17c) and (17e), and the corresponding carbamate prodrugs thereof, can be prepared according to the process described in the following scheme:

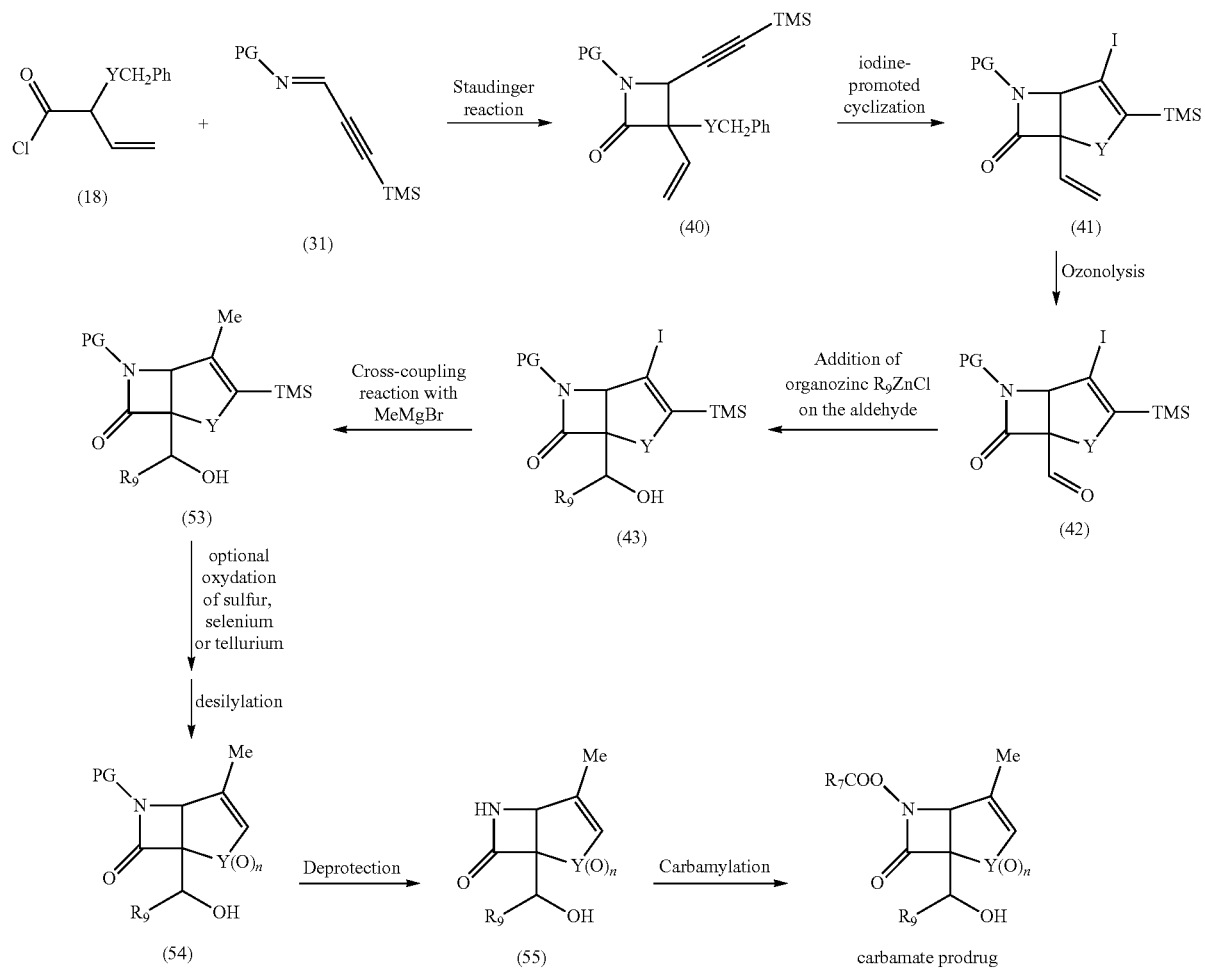

Y is S, Se or Te
PG is an amino-protecting group
n is 0, 1 or 2

The process of preparation of compounds of general formula (1b) wherein $R_2$ is —CH(OH)$R_9$; $R_6$ is methyl; Y is S, Se, or Te and n is 0, 1 or 2, according to the invention, for example compounds (8a), (8c), (8e), (9a), (9c), (9e), (12a), (12c), (12e), (13a), (13c), (13e), (16a), (16c), (16e), (17a), (17c) and (17e), and the corresponding carbamate prodrugs thereof, comprises the following steps:
- the formation of alkenyl azetidinone (40) by a Staudinger reaction between acyl chloride (18) and imine (31);
- the iodine-promoted cyclization of (40) to form iodopenem adduct (41);
- the ozonolysis of the carbon-carbon double bond of compound (41) to form aldehyde (42);
- the addition of $R_9$—ZnCl on the aldehyde (42) to form alcohol (43);
- the cross-coupling between (43) and methylmagnesium bromide to form compound (53);
- optionally the oxidation of alcohol (53) to form the corresponding sulfoxide, sulfone, selenoxide, selenone, telluroxide or tellurone;
- the desilylation to form compound (54);
- the deprotection of the nitrogen of the β-lactam ring of compound (54) to form proteasome inhibitor (55) according to the invention;
- optionally the carbamylation of proteasome inhibitor (55) to form the corresponding carbamate prodrug of general formula (1b) wherein $R_2$ is —CH(OH)$R_9$; $R_6$ is methyl; Y is S, Se, or Te; n is 0, 1 or 2; and X is —COOR$_7$.

Compounds (40), (41), (42) and (43) can be obtained as described above.

The cross-coupling between (43) and methylmagnesium bromide to form compound (53) can be carried out in the presence of a catalyst, such as nickel acetylacetonate (Ni(acac)$_2$).

The optional oxidation of alcohol (53) to form sulfoxide, sulfone, selenoxide, selenone, telluroxide or tellurone can be carried out in the presence of an oxidant, such as meta-chloroperoxybenzoic acid. The reaction may be conducted in a mixture of solvents such as dichloromethane and a buffer of pH 7. The mixture can be stirred at a temperature of 20 to 25° C. for several hours, for example 16 hours.

The desilylation to form compound (54) can be carried out in the presence of a fluoride, such as tetrabutylammonium fluoride. The reaction may be conducted in a solvent such as tetrahydrofurane. The mixture can be stirred at a temperature of 20 to 25° C. for several hours, for example 2 hours.

The deprotection of the nitrogen of the β-lactam ring of compound (54) to form proteasome inhibitor (55) depends on the nature of the protecting group. When the protection group is para-methoxyphenyl (PMP), the deprotection can be carried out in the presence of ceric ammonium nitrate. The reaction may be conducted in a mixture of solvents such as acetonitrile and water. The mixture can be stirred at a temperature of 0° C. for several hours, for example 3 hours.

The process for the preparation of carbamate prodrugs is further detailed below.

Compounds of general formula (1a) wherein Y is NH, according to the invention, can be prepared according to the process described in Hogan & Corey, 2005. J. Am. Chem. Soc. 127(44), 15386-15387 and in Corey and Hogan, 2007. Patent WO 2007/033039.

Compounds of general formula (1a) wherein Y is S, Se or Te, according to the invention, can be prepared according to the process described in Hogan & Corey, 2005. J. Am. Chem. Soc. 127(44), 15386-15387 and in Corey and Hogan, 2007. Patent WO 2007/033039, with modifications, by replacing the oxazolidinone precursor with an equivalent one wherein the N atom is replaced by a S, Se or Te atom and by adapting the next steps.

Compounds of general formula (1a) wherein Y is SO, $SO_2$, SeO, $SeO_2$, TeO or $TeO_2$, according to the invention, can be obtained from the previous compounds according to the processes described in Ren et al., 1998, J. Org. Chem. 63, 8898-8917, and in Coantic et al., 2007, Tetrahedron 63, 3205-3216 (formation of mono- or disulfone derivatives or selenium or tellurium equivalents).

Compounds of general formula (1b) wherein Y is NH, according to the invention, can be prepared according to the process described in Hogan & Corey, 2005.1 Am. Chem. Soc. 127(44), 15386-15387 and in Corey and Hogan, 2007. Patent WO 2007/033039 by bypassing the γ-lactam carbonyl formation step (conversion of 2-trimethylsilylfuran into butenolide) and proceeding directly to the next steps, that is to fuse the five-membered heteroatomic ring structure to the four-membered β-lactam ring structure.

Carbamylation

The carbamate prodrugs can for example be obtained by reacting a compound according to the invention wherein X is H with an amine-specific cross-linker.

One example of an amine-specific cross-linker that can be used to obtain a compound according to the invention wherein X is $-COOR_{12}$ and $R_{12}$ is an alkyl is an N-acyloxy-alkoxycarbonyloxy succinimide cross-linking agent that has the following general formula:

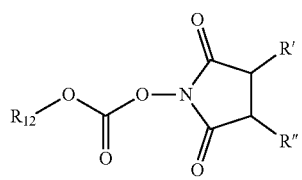

wherein R' and R" are H, $-SO_2$ or $-SO_2-O^-Na^+$.

Another example of an amine-specific cross-linker that can be used to obtain a compound according to the invention wherein X is $-COO-C(R_{10})(R_{11})-O-CO-R_{12}$ and $R_{12}$ is an alkyl is an N-acyloxy-alkoxycarbonyloxy succinimide cross-linking agent that has the following general formula:

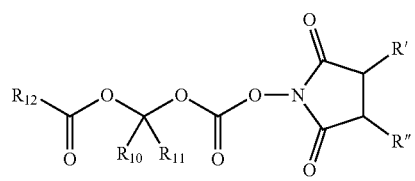

wherein $R_{10}$ and $R_{11}$ are as defined herein, and R' and R" R' and R" are H, $-SO_2$ or $-SO_2-O^-Na^+$.

The method of synthetizing 1-(acyloxy)-alkyl N-hydroxysuccinimidyl carbonate cross-linking agents is well known in the art and comprises, according to the method described by Gallop et al., 2004, PCT application published as WO 2005/066122, contacting a compound of formula (A), wherein C is Cl, Br or I, with a compound of formula $R_4-S^-B_1^+$, wherein $B_1^+$ is for example an alkali metal cation, to provide a compound of formula (B), contacting the compound of formula (B) with a carboxylate compound $R_{12}-COO^-B_2^+$, wherein $B_2^+$ is an alkali metal cation or an alkaline earth metal cation, to provide an acyloxyalkyl thiocarbonate compound of formula (C), contacting the thiocarbonate compound of formula (C) with an oxidant to provide an acylsulfoxide or acylsulfone compound of formula (D), wherein n is 1 or 2, and contacting the compound of formula (D) with an N-hydroxysuccinimide compound of formula, in the presence of a base, to afford a compound of formula (E)

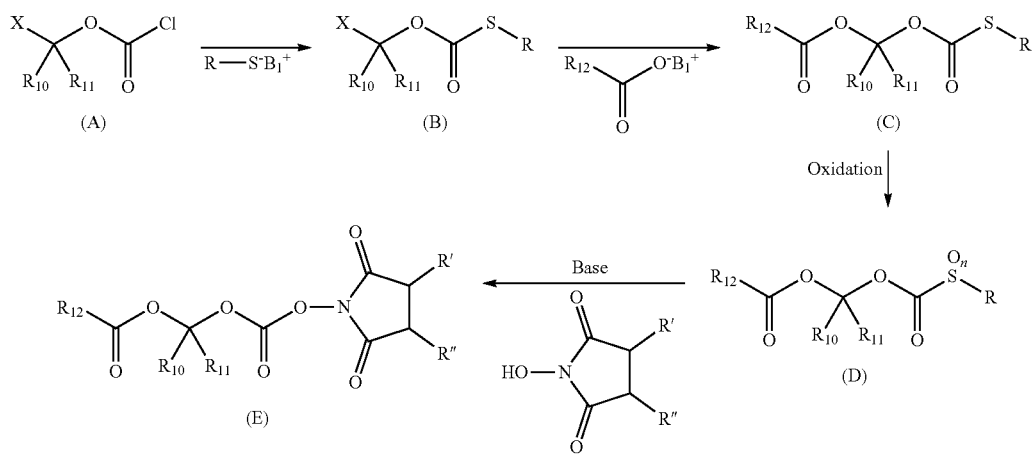

A covalent amine bond is formed when the N-hydroxysuccinimide cross-linking agent reacts with an amine-containing drug releasing N-hydroxysuccinimide.

One example of an amine-specific cross-linker that can be used to obtain a compound according to the invention wherein X is —COO—$R_{12}$ and $R_{12}$ is a peptide substrate is an N-(α-aminoacyl/peptidyl)oxy succimide that has the following general formula:

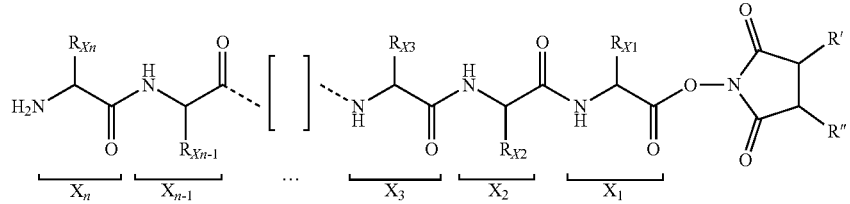

wherein R' and R" are H, —$SO_2$ or —$SO_2$—$O^-Na^+$.

Another example of an amine-specific cross-linker that can be used to obtain a compound according to the invention wherein X is —COO—C($R_{10}$)($R_{11}$)—O—CO—$R_{12}$ and $R_{12}$ is a peptide substrate is an N-(α-aminoacyl/peptidyl)oxyalkoxycarbonyloxy succinimide that has the following general formula:

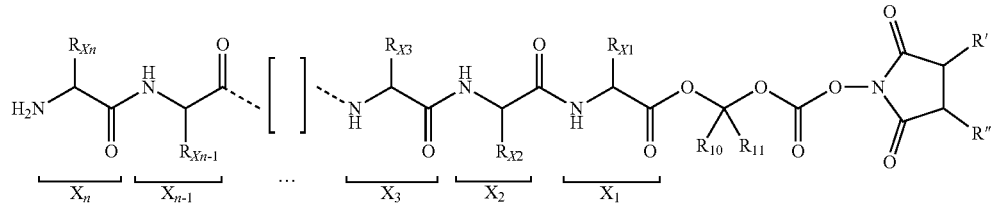

wherein $R_{10}$ and $R_{11}$ are as defined herein, and R' and R" R' and R" are H, —$SO_2$ or —$SO_2$—$O^-Na^+$.

Another example of an amine-specific cross-linker that can be used to obtain a compound according to the invention wherein X is —COO—$R_{12}$ and $R_{12}$ is a peptide substrate is an N-(α-aminoacyl/peptidyl)oxy)carbonyloxy succinimide that has the following general formula:

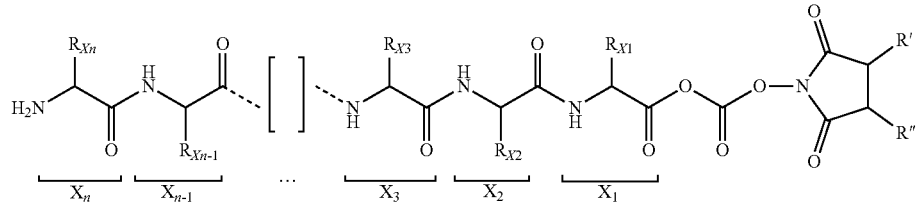

wherein R' and R" are H, —$SO_2$ or —$SO_2$—$O^-Na^+$.

Composition

The composition of the present invention comprises a therapeutically effective amount of a compound according to the invention, and a pharmaceutically acceptable vehicle, carrier or diluent.

The therapeutically effective amount of the compound of the present invention depends on a variety of factors including the condition to be treated, the administration mode, the age and the body weight of the subject. The therapeutically effective amount of the compound is determined by the attending physician or veterinarian.

In particular, the composition of the invention may be an ingestable solid formulation for oral delivery. More particularly, said ingestable solid formulation may be an extended release formulation that contains matrix-forming agents.

The term "extended release formulation" (or sustained release formulation) as used herein refers to a formulation designed to release the compound according to the invention over an extended period of time after ingestion.

Oral extended release formulations advantageously delay the dissolution and prolong the subsequent absorption of the drug. A prolonged, stable exposure to the drug provides several clinical benefits, including greater efficacy, prolonged duration of action, and a reduced incidence of adverse effects related to peak drug levels. When the compound of the invention is a prodrug, stable plasma concentrations of the parent drug can be kept due to prolonged absorption of the prodrug and slow release of the parent drug. Moreover, extended release formulations reduce the frequency of dosing of a drug and improve patient compliance with the treatment.

Methods of preparing extended release formulations for oral delivery are well known in the art. Controlled-release polymers are generally used. Suitable matrix-forming agents that can be introduced in the extended release formulation include cellulosic ethers, such as hydroxypropyl methylcellulose (HPMC), hydroxy-propyl cellulose (HPC), hydroxyethyl cellulose (HEC), methyl cellulose (MC), calcium and sodium carboxymethyl cellulose (CMC), and non-saccharidic polymers, such as polyvinyl alcohol (PVA), polyethylene oxide (PEO), polyvinylpyrrolidone (PVP), vinyl acetate (VA)/crotonic acid (CA) copolymers, methacrylic acid (MAA) copolymers, maleic anhydride (MA)/methyl vinyl ether (MVE) copolymers, derivatives thereof and mixtures thereof. The release process is adjusted by varying the amount of matrix-forming agent in the extended release formulation.

According to a specific embodiment, the extended release formulation may comprise a delayed release coating, such as an enteric coating that promotes dissolution and release in the intestine. Methacrylic acid (MAA) copolymers are generally used for enteric coating purposes.

When the compound of the invention that is introduced in the extended release formulation is a prodrug, the enteric coating enables the prolonged absorption of the prodrug in the gastro-intestinal tract. However these formulations that prolong absorption of the prodrug do not slow release of the parent drug. To obtain a slow and prolonged release of the parent drug, prodrugs according to the invention wherein group X comprises a long chain aliphatic ester, i.e. X is —COO—C($R_{10}$)($R_{11}$)—O—CO—$R_{12}$ and $R_{12}$ is an alkyl having 7-20 carbon atoms can be used.

The composition of the invention may further comprise an additional pharmaceutical active, such as an anti-cancer agent or an anti-inflammatory agent.

The composition according to the invention can be formulated as granules, powder, a capsule, a tablet, a pill.

Medical Uses

The compounds and compositions according to the invention are useful in the treatment of cancer, brain and spinal cord injuries, neuro-degenerative disorders, neuroinflammatory disorders, angiogenesis-dependent diseases and angiogenic disorders.

In particular, the compounds and compositions according to the invention are useful in the treatment of
  hematologic and solid tumor malignancies,
  central nervous system tumors, including glioma, glioblastoma, astrocytoma, oligodendroglioma, ependymoma, medulloblastoma, pineocytoma, meningioma, and choroid plexus papilloma,
  peripheral nervous system tumors, including neuroblastoma, ganglioneuroma and paraganglioma,
  brain and spinal cord injuries,
  neurodegenerative disorders, including Wallerian degeneration and Alzheimer's disease,
  neuroinflammatory disorders, including multiple sclerosis and Guillain-Barre syndrome,
  angiogenesis-dependent diseases and angiogenic disorders, including cancer metastases, diabetic retinopathy, and rheumatoid arthritis,
  infectious neurological disorders caused by bacteria of the order of Actinomycetales (species from the genera *Mycobacterium, Rhodococcus, Streptomyces* and *Frankia*), protozoan parasites (species from the genera *Giardia, Entamoeba, Leishmania, Trypanosoma, Plasmodium,* and *Toxoplasma*), or other proteasome-containing organisms,
  and a variety of malignant, infectious, inflammatory, vascular, and degenerative diseases.

As such, the present invention also provides a method of treatment of cancer, brain and spinal cord injuries, neurodegenerative disorders, neuroinflammatory disorders, angiogenesis-dependent diseases and angiogenic disorders comprising the administration of a compound or a composition according to the invention.

While, there have been shown and described what are at present believed to be the preferred embodiments of the present invention, it will be obvious to one of ordinary skill in the art to which the invention relates that various changes and modifications may be made therein without departing from the scope of the invention as defined by the appended claims.

7. References

Adams J., 2003. The proteasome: structure, function, and role in the cell. *Cancer Treat. Rev.* 29 (Suppl. 1), 3-9.

Adams J., 2004. The development of proteasome inhibitors as anticancer drugs. *Cancer Cell* 5, 417-421.

Aiken C. T., Kaake R. M., Wang X. and Huang L., 2011. Oxidative stress-mediated regulation of proteasome complexes. Mol. Cell. Proteomics 10:10.1074/mcp.R110.006924, 1-11.

Alheit H., Oehme L., Winkler C., Füchtner F., Hoepping A., Grabowski J., Kotzerke J. and Beuthien-Baumann B., 2008. Radiation treatment planning in brain tumours. Potential impact of 3-O-methyl-6-[$^{18}$F]fluoro-L-DOPA and PET. *Nuklearmedizin* 47, 200-204.

Amerik A. Y. & Hochstrasser M., 2004. Mechanism and function of deubiquitinating enzymes. *Biochim. Biophys. Acta* 1695, 189-207.

Asano S., Kameyama M., Oura A., Morisato A., Sakai H., Tabuchi Y., Chairoungdua A., Endou H. and Kanai Y., 2007. L-type amino acid transporter-1 expressed in human asrocytomas, U343MGa. *Biol. Pharm. Bull.* 30(3), 415-422.

Bedford L., Hay D., Devoy A., Paine S., Powe D. G., Seth R., Gray T., Topham I., Fone K., Rezvani N., Mee M., Soane T., Layfield R., Sheppard P. W., Ebendal T., Usoskin D., Lowe J. and Mayer R. J., 2008. Depletion of 26S proteasomes in mouse brain neurons causes neurodegeneration and Lewy-like inclusions resembling human pale bodies. J. Neurosci. 28(33), 8189-8198.

Beg A. A. and Baltimore D., 1996. An essential role for NF-κB in preventing TNF-α-induced cell death. *Science* 274, 782-784.

Bergmann R., Pietzsch J., Fuechtner F., Pawelke B., Beuthien-Baumann B., Johannsen B. and Kotzerke J., 2004. 3-O-methyl-6-18F-fluoro-L-dopa, a new tumor imaging agent: investigation of transport mechanism in vitro. *J. Nucl. Med.* 45, 2116-2122.

Berti R., Williams A T., Verlade L. C., Moffett J. R., Elliot P. J., Adams J., Yao C., Dave J. R. and Tortella F. C., 2003. Effect of the proteasome inhibitor MLN519 on the expression of inflammatory molecules following middle cerebral artery occlusion and reperfusion in the rat. *Neurotox. Res.* 5(7), 505-514.

Beuthien-Baumann B., Bredow J., Burchert W., Füchtner F., Bergmann R., Alheit H. D., Reiss G., Hliscs R., Steinmeier R., Franke W. G., Johannsen B. and Kotzerke J., 2003. 3-O-methyl-6-[$^{18}$F]fluoro-L-DOPA and its evaluation in brain tumor imaging. *Eur. J. Nucl. Med. Mol. Imaging* 30, 1004-1008.

Bloom G., 2012. Amyloid-β signals through tau to drive ectopic neuronal cell cycle re-entry in Alzheimer's disease. Annual meeting of the American Society for Cell Biology (ASCB), December 15-19, San Francisco.

Boado R. J., Li J. Y., Nagaya M., Zhang C. and Pardridge W. M., 1999. Selective expression of the large neutral amino acid transporter at the blood-brain barrier. *PNAS* 96(21), 12079-12084.

Campbell B., Adams J., Shin Y. K. and Lefer A. M., 1999. Cardioprotective effects of a novel proteasome inhibitor following ischemia and reperfusion in the isolated perfused rat heart. *J. Mol. Cell. Cardiol.* 31, 467-476.

Caubert V. and Langlois N., 2006. Studies toward the synthesis of salinosporamide A, a potent proteasome inhibitor. *Tetrahedron Lett.* 47, 4473-4475.

Chondrogianni N. and Gonos E. S., 2008. Proteasome activation as a novel antiaging strategy. IUBMB Life 60(10), 651-655.

Ciechanover A., 1994. The ubiquitin-proteasome proteolytic pathway. *Cell.* 79, 13-21.

Ciechanover A., 1998. The ubiquitin-proteasome pathway: on protein death and cell life. *EMBO J.,* 17(24), 7151-7160.

Ciechanover A. and Brundin P., 2003. The ubiquitin proteasome system in neurodegenerative diseases: sometimes the chicken, sometimes the egg. *Neuron* 40, 427-446.

Coantic S., Mouysset D., Mignani S., Tabart M. and Stella L., 2007, The use of N-sulfenylimines in the β-lactam synthon method: Staudinger reaction, oxidation of the cycloadducts and ring opening of β-lactams. *Tetrahedron* 63, 3205-3216

Corey E. J. and Hogan P. C., 2007. Proteasome inhibiting β-lactam compounds. Patent WO 2007/033039.

Craiu A., Gaczynska M., Akopian T., Gramm C. F., Fenteany G., Goldberg A. L. and Rock K. L., 1997. Lactacystin and clasto-lactacystin β-lactone modify multiple proteasome β-subunits and inhibit intracellular protein degradation and major histocompatibility complex class I antigen presentation. *J. Biol. Chem.* 272(20), 13437-13445.

Cundy K. C., Branch R., Chernov-Rogan T., Dias T., Estrada T., Hold K., Koller K., Liu X., Mann A., Panuwat M., Raillard S. P., Upadhyay S., Wu Q. Q., Xiang J. N., Yan H., Zerangue N., Zhou C. X., Barrett R. W. and Gallop M. A., 2004a. XP13512 [(±)-1-([(α-isobutanoyloxyethoxy) carbonyl]aminomethyl)-1-cyclo-hexane acetic acid, a novel gabapentin prodrug: I. Design, synthesis, enzymatic conversion to gabapentin, and transport by intestinal solute transporters. *J. Pharmacol. Exp. Ther.* 311(1), 315-323.

Cundy K. C., Annamalai T, Bu L., De Verra J., Estrela J., Luo W., Shirsat P., Tomeros A., Yao F., Zou J., Barrett R. W. and Gallop M. A., 2004b. XP13512 [(±)-1-([(α-isobutanoyloxyethoxy)carbonyl]aminomethyl)-1-cyclohexane acetic acid, a novel gabapentin prodrug: II. Improved oral bioavailability, dose proportionality and colonic absorption compared with gabapentin in rats and monkeys. *J. Pharmacol. Exp. Ther.* 311(1), 324-333.

Dahlmann B., 2007. Role of proteasomes in disease. BMC Biochem. 8(Suppl. 1):53.

Delic J., Masdehors P., Omura S., Cosset J. M., Dumont J., Binet J. L. and Magdelenat H., 1998. The proteasome inhibitor lactacystin induces apoptosis and sensitizes chemo- and radioresistant human chronic lymphocytic leukaemia lymphocytes to TNF-alpha-initiated apoptosis. *Br. J. Cancer* 77, 1103-1107.

DeMartino G. N. and Slaughter C. A., 1999. The proteasome, a novel protease regulated by multiple mechanisms. *J. Biol. Chem.* 274(32), 22123-22126.

Diaz-Hernandez M., Hernandez F., Martin-Aparicio E., Gomez-Ramos P., Moran M. A., Castano J. G., Ferrer I., Avila J. and Lucas J. J., 2003. Neuronal induction of the immunoproteasome in Huntington's disease. J. Neurosci. 23(37), 11653-11661.

Diaz-Hernandez M., Martin-Aparicio E., Avila J., Hernandez F. and Lucas J. J., 2004. Enhanced induction of the immunoproteasome by interferon gamma in neurons expressing mutant Huntingtin. Neurotox. Res. 6(6), 463-468.

Dick L. R., Cruikshank A. A., Grenier L., Melandri F. D., Nunes S. L. and Stein R. L., 1996. Mechanistic studies on the inactivation of the proteasome by lactacystin: a central role for clastolactacystin β-lactone. *J. Biol. Chem.* 271 (13), 7273-7276.

Dick L. R., Cruikshank A. A., Destree A. T., Grenier L., McCormack T. A., Melandri F. D., Nunes S. L., Palombella V. J., Parent L. A., Plamondon L. and Stein R. L., 1997. Mechanistic studies on the inactivation of the proteasome by lactacystin in cultured cells. *J. Biol. Chem.* 272(1), 182-188.

Duelli R., Enerson B. E., Gerhart D. Z. and Drewes L. R., 2000. Expression of large amino acid transporter LAT1 in rat brain endothelium. *J. Cereb. Blood Flow Metab.* 20, 1557-1562.

Elliott P. J., Pien C. S., McCormack T. A., Chapman I. D. and Adams J., 1999. Proteasome inhibition. A novel mechanism to combat asthma. *J. Allergy Clin. Immunol.* 104, 294-300.

Elliott P. J. and Ross J. S., 2001. The proteasome: a new target for novel drug therapies. *Am. J. Clin. Pathol.* 116, 637-646.

Feling R. H., Buchanan G. O., Mincer T. J., Kauffman C. A., Jensen P. R. and Fenical W., 2003. Salinosporamide A: a highly cytotoxic proteasome inhibitor from a novel microbial source, a marine bacterium of the new genus *Salinospora. Angew Chem. Int. Ed. Engl.* 42, 355-357.

Fenteany G., Standaert R. F., Lane W. S., Choi S., Corey E. J. and Schreiber S. L., 1995. Inhibition of proteasome activities and subunit-specific amino-terminal threonine modification by lactacystin. *Science* 268, 726-731.

Flores L. G., Kawai K., Nakagawa M., Shikano N., Jinnouchi S., Tamura S., Watanabe K. and Kubodera A., 2000. A new radiopharmaceutical for the cerebral dopaminergic presynaptic function: 6-radioiodinated L-metatyrosine. *J. Cereb. Blood Flow Metab.* 20(1), 207-212.

Froberg M. K., Gerhart D. Z., Enerson B. E., Manivel C., Guzman-Paz M., Seacotte N. and Drewes L. R., 2001. Expression of monocarboxylate transporter MCT1 in normal and neoplastic human CNS tissues. *Neuroreport* 12(4), 761-765.

Fruh K., Gossen M., Wang K., Bujard H., Peterson P. A. and Yang Y., 1994. Displacement of housekeeping proteasome subunits by MHC-encoded LMPs: a newly discovered mechanism for modulating the multicatalytic proteinase complex. EMBO J. 13, 3236-3244.

Gerhart D. Z., Enerson B. E., Zhdankina O. Y., Leino R. L. and Drewes L. R., 1997. Expression of monocarboxylate transporter MCT1 by brain endothelium and glia in adult and suckling rats. *Am. J. Physiol.* 273(1), 207-213.

Guedat P. and Colland F., 2007. Patented small molecule inhibitors in the ubiquitin proteasome system. *BMC Biochemistry* 8(Suppl. 1), S14(1-12).

Gurer-Orhan H., Ercal N., Mare S., Pennathur S., Orhan H. and Heinecke J. W., 2006. Misincorporation of free m-tyrosine into cellular proteins: a potential cytotoxic mechanism for oxidized amino acids. *Biochem. J.* 395, 277-284.

Haase C., Bergmann R., Fuechtner F., Hoepping A. and Pietzsch J., 2007. L-type amino acid transporters LAT1 and LAT4 in cancer: uptake of 3-O-methyl-6-$^{18}$F-fluoro-L-dopa in human adenocarcinoma and squamous cell carcinoma in vitro and in vivo. *J. Nucl. Med.* 48, 2063-2071.

He Z., Zhai Q., Wang J., Watts R., Hoopfer E. and Luo L., 2005. Reducing axon degeneration with proteasome inhibitors. Patent WO2005/014783.

Ho Y. K. A., Bargagna-Mohan P., Wehenkel M., Mohan R. and Kim K. B., 2007. LMP2-specific inhibitors: chemical genetic tools for proteasome biology. Chem. Biol. 14, 419-430.

Hogan P. C. and Corey E. J., 2005. Proteasome inhibition by a totally synthetic β-lactam related to salinosporamide A and omuralide. J. Am. Chem. Soc. 127(44), 15386-15387.

Huang L. and Chen C. H., 2009. Proteasome regulators: activators and inhibitors. Curr. Medicinal Chem. 16(8), 931-939.

Huber E. M., Basler M., Schwab R. Heinemeyer W., Kirk C. J., Groettrup M. and Groll M., 2012. Immuno- and constitutive proteasome crystal structures reveal differences in substrate and inhibitor specificity. Cell 148, 727-738.

Imajoh-Ohmi S., Kawaguchi T., Sugiyama S., Tanaka K., Omura S. and Kikuchi H., 1995. Lactacystin, a specific inhibitor of the proteasome, induces apoptosis in human monoblast U937 cells. Biochem. Biophys. Res. Commun. 217(3), 1070-1077.

Inoue T., Koyama K., Oriuchi N., Alyafei S., Yuan Z., Suzuki H., Takeuchi K., Tomaru Y., Tomiyoshi K., Aoki J. and Endo K., 2001. Detection of malignant tumors: whole-body PET with fluorine 18 α-methyl tyrosine versus FDG—preliminary study. Radiol. 220, 54-62.

Kageyama T., Imura T., Matsuo A., Minato N. and Shimohama S., 2000a. Distribution of the 4F2 light chain, LAT1, in the mouse brain. Neuroreport 11(17), 3663-3666.

Kageyama T., Nakamura M., Matsuo A., Yamasaki Y., Takakura Y., Hashida M., Kanai Y., Naito M., Tsuruo T., Minato N. and Shimohama S., 2000b. The 4F2hc/LAT1 complex transports L-DOPA across the blood-brain barrier. Brain Res. 879, 115-121.

Kanai Y., Segawa H., Miyamoto K., Uchino H., Takeda E. and Endou H., 1998. Expression cloning and characterization of a transporter for large neutral amino acids activated by the heavy chain of 4F2 antigen (CD98). J. Biol. Chem. 273(37), 23629-23632.

Karin M., Cao Y., Greten F. R. and Li Z. W., 2002. NF-κB in cancer: from innocent bystander to major culprit. Nat. Rev. Cancer 2, 301-310.

Katsiki M., Chondrogianni N., Chinon I., Rivett A. J. and Gonos E. S., 2007. The olive constituent oleuropein exhibits proteasome stimulatory properties in vitro and confers life span extension of human embryonic fibroblasts. Rejuvenation Res. 10(2), 157-172.

Kawai K., Fujibayashi Y., Saji H., Yonekura Y., Konishi J., Kubodera A. and Yokoyama A., 1991. A strategy for the study of cerebral amino acid transport using iodine-123-labeled amino acid radiopharmaceutical: 3-iodo-alpha-methyl-L-tyrosine. J. Nucl. Med. 32, 819-824.

Kersemans V., Cornelissen B., Kersemans K., Dierckx R. A., De Spiegeleer B., Mertens J. and Slegers G., 2006. Comparative biodistribution study of the new tumor tracer [$^{123}$I]-2-iodo-L-phenylalanine with [$^{123}$I]-2-iodo-tyrosine. Nucl. Med. Biol. 33, 111-117.

Kido Y., Tamai I., Uchino H., Suzuki F., Sai Y. and Tsuji A., 2001. Molecular and functional identification of large neutral amino acid transporters LAT1 and LAT2 and their pharmacological relevance at the blood-brain barrier. J. Pharm. Pharmacol. 53, 497-503.

Killian D. M. and Chikhale P. J., 2001. Predominant functional activity of the large amino acid transporter (LAT1) isoform at the cerebrovasculature. Neurosci. Lett. 306, 1-4.

Kitagawa H., Tani E., Ikemoto H., Ozaki I., Nakano A. and Omura S., 1999. Proteasome inhibitors induce mitochondria-independent apoptosis in human glioma cells. FEBS Lett. 443, 181-186.

Kloetzel P. M., 2001. Antigen processing by the proteasome. Nat. Rev. Mol. Cell Biol. 2, 179-187.

Kobayashi K., Ohnishi A., Promsuk J., Shimizu S., Kanai Y., Shiokawa Y., and Nagane M., 2007. Enhanced tumor growth elicited by L-type amino acid transporter 1 in human malignant glioma cells. Neurosurgery 62(2), 493-504.

Krummeich C., Holschbach M. and Stöcklin G., 1994. Direct n.c.a. electrophilic radioiodination of tyrosine analogues; their in vivo stability and brain-uptake in mice. Appl. Radiat. Isot. 45(9), 929-935.

Kuhn D. J., Hunsucker S. A., Chen Q., Voorhees P. M., Orlowski M. and Orlowski R. Z., 2009. Targeted inhibition of the immunoproteasome is a potent strategy against models of multiple myeloma that overcomes resistance to conventional drugs and non specific proteasome inhibitors. Blood 113(19), 4667-4676.

Kuwert T., Probst-Cousin S., Woesler B., Morgenroth C., Lerch H., Matheja P., Palkovic S., Schafers M., Wassmann H, Gullotta F. and Schober O. 1997. Iodine-123-α-methyl tyrosine in gliomas: correlation with cellular density and proliferative activity. J. Nucl. Med. 38, 1551-1555.

Lahoutte T., Caveliers V., Camargo S. M. R., Franca R., Ramadan T., Veljkovic E., Mertens J., Bossuyt A. and Verrey F., 2004. SPECT and PET amino acid tracer influx via system L (h4F2hc-hLAT1) and its transstimulation. J. Nucl. Med. 45, 1591-1596.

Langen K. J., Coenen H. H., Roosen N., Kling P., Muzik O., Herzog H., Kuwert T., Stocklin G. and Feinendegen L. E, 1990. SPECT studies of brain tumors with L-3-[$^{123}$I]iodo-α-methyl tyrosine: comparison with PET, $^{124}$IMT and first clinical results. J. Nucl. Med. 31, 281-286.

Langen K. J., Roosen N., Coenen H. H., Kuikka J. T., Kuwert T., Herzog H., Stocklin G. and Feinendegen L. E. 1991. Brain and brain tumor uptake of L-3-[$^{123}$I]iodo-α-methyl tyrosine: competition with natural L-amino acids. J. Nucl. Med. 32, 1225-1229.

Langen K. J., Clauss R. P., Holschbach M., Miihlensiepen H., Kiwit J. C. W., Zilles K., Coenen H. H. and Müller-Gärtner H. W., 1998. Comparison of iodotyrosines and methionine uptake in a rat glioma model, J. Nucl. Med. 39, 1596-1599.

Langen K. J., Bonnie R., Mühlensiepen H., Jansen P., Broer S., Holschbach M. and Coenen H. H., 2001. 3-[$^{123}$I]iodo-α-methyl-L-tyrosine transport and 4F2 antigen expression in human glioma cells. Nucl. Med. Biol. 28, 5-11.

Langen K. J., Pauleit D. and Coenen H. H., 2002. 3-[$^{123}$I]Iodo-α-methyl-L-tyrosine: uptake mechanisms and clinical applications. Nucl. Med. Biol. 29, 625-631.

Langen K. J., Hamacher K., Weckesser M., Floeth F., Stoffels G., Bauer D., Coenen H. H. and Pauleit D., 2006. O-(2-[$^{18}$F]fluoroethyl)-L-tyrosine: uptake mechanisms and clinical applications. Nucl. Med. Biol. 33, 287-294.

Laurencin C., Domb A., Morris C., Brown V., Chasin M., McConnell R., Lange N. and Langer R., 1990. Poly (anhydride) administration in high doses in vivo: studies of biocompatibility and toxicology. J. Biomed. Mater. Res. 24(11), 1463-1481.

Legnani F. G., Pradilla G., Thai Q. A., Fiorindi A., Recinos P. F., Tyler B. M., Gaini S. M., DiMeco F., Brem H. and Olivi A., 2006. Lactacystin exhibits potent anti-tumor activity in an animal model of malignant glioma when administered via controlled-release polymers. *J. Neurooncol.* 77(3), 225-232.

Manam R. R., Macherla V. R. and Potts B. C. M., 2007. Stereoselective enzymatic reduction of keto-salinosporamide to (−)-salinosporamide A (NPI-0052). *Tetrahedron Lett.* 48, 2537-2540.

Masdehors P., Omura S., Merle-Beral H., Mentz F., Cosset J. M., Dumont J., Magdelenat H. and Delic J., 1999. Increased sensitivity of CLL-derived lymphocytes to apoptotic death activation by the proteasome-specific inhibitor lactacystin. *Br. J. Haematol.* 105(3), 752-757.

Masdehors P., Merle-Beral H., Maloum K., Omura S., Magdelenat H. and Delic J., 2000. Deregulation of the ubiquitin system and p53 proteolysis modify the apoptotic response in B-CLL lymphocytes. *Blood* 96(1), 269-274.

Matsuo H., Tsukada S., Nakata T., Chairoungdua A., Kim D. K., Cha S. H., Inatomi J., Yorifuji H., Fukuda J., Endow H. and Kanai Y., 2000. Expression of a system L neutral amino acid transporter at the blood-brain barrier. *Neuroreport* 11(16), 3507-3511.

Mishto M., Bellavista E., Santoro A., Stolzing A., Ligorio C., Nacmias B., Spazzafumo L., Chiapelli M., Licastro F., Sorbi S., Pession A., Ohm T., Grune T. and Franceschi C., 2006. Immunoproteasome and LMP2 polymorphism in aged and Alzheimer's disease brains. *Neurobiol. Aging* 27, 54-66.

Nawashiro H., Otani N., Uozumi Y. Ooigawa H., Toyooka T., Suzuki T., Katoh H., Tsuzuki N., Ohnuki A., Shima K., Shinomiya N., Matsuo H. and Kanai Y., 2005. High expression of L-type amino acid transporter 1 in infiltrating glioma cells. *Brain Tumor Pathol.* 22, 89-91.

Obin M., Mesco E., Gong X., Haas A. L., Joseph J. and Taylor A., 1999. Neurite outgrowth in PC12 cells: distinguishing the roles of ubiquitylation and ubiquitin-dependent proteolysis. *J. Biol. Chem.* 274(17), 11789-11795.

Oikawa T., Sasaki T., Nakamura M., Shimamura M., Tanahashi N., Omura S. and Tanaka K., 1998. The proteasome is involved in angiogenesis. *Biochem. Biophys. Res. Commun.* 246(1), 243-248.

Omura S., Fujimoto T., Otoguro K., Matsuzaki K., Moriguchi R., Tanaka H. and Sasaki Y., 1991a. Lactacystin, a novel microbial metabolite, induces neuritogenesis of neuroblastoma cells. *J. Antibiot.* 44, 113-116.

Omura S., Matsuzaki K., Fujimoto T., Kosuge K., Furuya T., Fujita S. and Nakagawa A. J., 1991b. Structure of lactacystin, a new microbial metabolite which induces differentiation of neuroblastoma cells. *J. Antibiot.* 44, 117-118.

Palombella V. J., Rando O. J., Goldberg A. L. and Maniatis T., 1994. The ubiquitin-proteasome pathway is required for processing the NF-κB1 precursor protein and the activation of NF-κB. *Cell* 78, 773-785.

Pasquini L. A., Paez P. M., Besio-Moreno M. A. N., Pasquini J. M. and Soto E. F., 2003. Inhibition of the proteasome by lactacystin enhances oligodendroglial cell differentiation. *J. Neurosci.* 23(11), 4635-4644.

Pavan B., Dalpiaz A., Ciliberti N., Biondi C., Manfredini S. and Vertuani S., 2008. Progress in drug delivery to the central nervous system by the prodrug approach. *Molecules* 13, 1035-1065.

Phillips J. B., Williams A. J., Adams J., Elliott P. J., and Tortella F. C., 2000. Proteasome inhibitor PS-519 reduces infarction and attenuates leukocyte infiltration in a rat model of focal cerebral ischemia. *Stroke* 31, 1686-1693.

Piccinini M., Mostert M., Croce S., Baldovino S., Papotti M. and Rinaudo M. T., 2003. Interferon-γ-inducible subunits are incorporated in human brain 20S proteasome. *J. Neuroimmunol.* 135, 135-140.

Pineda M., Fernandez E., Torrents D., Estevez R., Lopez C., Camps M., Lloberas J., Zorzano A. and Palacin M., 1999. Identification of a membrane protein, LAT-2, that coexpresses with 4F2 heavy chain, an L-type amino acid transport activity with broad specificity for small and large zwitterionic amino acids. *J. Biol. Chem.* 274 (28), 19738-19744.

Prudhomme J., McDaniel E., Ponts N., Bertani S., Fenical W., Jensen P. and Le Roch K., 2008. Marine actinomycetes: a new source of compounds against the human malaria parasite. *PLoS ONE* 3(6), e2335 (1-8).

Rautio J., Kumpulainen H., Heimbach T., Oliyai R., Oh D., Jarvinen T. and Savolainen J., 2008. Prodrugs: design and clinical applications. *Nature Rev.* 7, 255-270.

Reddy L. R., Saravanan P. and Corey E. J., 2004. A simple stereocontrolled synthesis of salinosporamide A. *J. Am. Chem. Soc.* 126(20), 6230-6231.

Reddy L. R., Fournier J. F., Reddy B. V. S. and Corey E. J., 2005. An efficient, stereocontrolled synthesis of a potent omuralide-salinosporin hybrid for selective proteasome inhibition. *J. Am. Chem. Soc.* 127(25), 8974-8976.

Ren X. F., Konaklieva M. I., Shi H., Dickey S., Lim D. V., Gonzalez J. and Turos E., 1998, Studies on nonconventionally fused bicyclic β-lactams. *J. Org. Chem.* 63, 8898-8917.

Riemann B., Kopka K., Stogbauer F., Halfter H., Ketteler S., T. Q. Phan, Franzius C., Weckesser M., Ringelstein E. B. and Schober O., 2001. Kinetic parameters of 3-[$^{123}$I] iodo-L-α-methyl tyrosine ([$^{123}$I]IMT) transport in human GOS3 glioma cells. *Nucl. Med. Biol.* 28, 293-297.

Rock K. L. and Goldberg A. L., 1999. Degradation of cell proteins and the generation of MHC class I-presented peptides. *Annu. Rev. Immunol.* 17, 739-779.

Roberts L. M., Black D. S., Raman C., Woodford K., Zhou M., Haggerty J. E., Yan A. T., Cwirla S. E. and Grindstaff K. K., 2008. Subcellular localization of transporters along the rat blood-brain barrier and blood-cerebral-spinal fluid barrier by in vivo biotinylation. *Neurosci.* 155, 423-438.

Schroter F. and Adjaye J., 2014. The proteasome complex and the maintenance of pluripotency: sustain the fate by mopping up? *Stem Cell Res. Ther.* 5(1), 24.

Segawa H., Fukasawa Y., Miyamoto K., Takeda E., Endou H. and Kanai Y., 1999. Identification and functional characterization of a Na$^+$-independent neutral amino acid transporter with broad substrate selectivity. *J. Biol. Chem.* 274(28), 19745-19751.

Shah I. M., Lees K. R., Pien C. P. and Elliott P. J., 2002. Early clinical experience with the novel proteasome inhibitor PS-519. *Br. J. Clin. Pharmacol.* 54, 269-276.

Shah I. M. and Di Napoli M., 2007. The ubiquitin-proteasome system and proteasome inhibitors in central nervous system diseases. *Cardiovasc. Hematol. Disord. Drug Targets* 7(4), 250-273.

Shikano N., Kanai Y., Kawai K., Inatomi J., Kim D. K., Ishikawa N. and Endou H., 2003a. Isoform selectivity of 3-$^{125}$I-iodo-α-methyl-L-tyrosine membrane transport in human L-type amino acid transporters. *J. Nucl. Med.* 44, 244-246.

Shikano N., Kanai Y., Kawai K., Ishikawa N. and Endo H., 2003b. Characterization of 3-[$^{125}$I]iodo-alpha-methyl-L-tyrosine transport via human L-type amino acid transporter 1. *Nucl. Med. Biol.* 30, 31-37.

Shikano N., Kawai K., Flores L. G., Nishii R., Kubota N., Ishikawa N. and Kubodera A., 2003c. An artificial amino acid, 4-iodo-L-meta-tyrosine: biodistribution and excretion via kidney. *J. Nucl. Med.* 44, 625-631.

Simmons-Willis T. A., Koh A. S., Clarkson T. W. and Ballatori N., 2002. Transport of a neurotoxicant by molecular mimicry: the methylmercury-L-cysteine complex is a substrate for human L-type large neutral amino acid transporter (LAT) 1 and LAT2. *Biochem. J.* 367, 239-246.

Simplicio A. L., Clancy J. M. and Gilmer J. F., 2008. Prodrugs for amines. *Molecules* 13, 519-547.

Stadler M., Seip S., Müller H., Mayer-Bartschmid A., Briining M. A., Benet-Buchholz J., Togame H., Dodo R., Reinemer P., Bacon K., Fuchikawi K., Matsukawa S. and Urbhans K., 2004. Substituted heterocycles. Patent WO 2004/071382.

Tani E., Kitagawa H., Ikemoto H. and Matsumoto T., 2001. Proteasome inhibitors induce Fas-mediated apoptosis by c-Myc accumulation and subsequent induction of FasL message in human glioma cells. *FEBS Lett.* 504, 53-58.

Tomoda H. and Omura S., 2000. Lactacystin, a proteasome inhibitor: discovery and its application in cell biology. *Yakugaku Zasshi* 120(10), 935-949.

Uchino H., Kanai Y., Kim D. K., Wempe M. F., Chairoungdua A., Morimoto E., Anders M. W. and Endo H., 2002. Transport of amino acid-related compounds mediated by L-type amino acid transporter 1 (LAT1): insights into the mechanisms of substrate recognition. *Mol. Pharmacol.* 61(4), 729-737.

Vanderlugt C. L., Rahbe S. M., Elliott P. J., Dal Canto M. C. and Miller S. D., 2000. Treatment of established relapsing experimental autoimmune encephalomyelitis with the proteasome inhibitor PS-519. *J. Autoimmun.* 14, 205-211.

Wang C. Y., Cusack J. C., Liu R. and Baldwin A. S., 1999. Control of inducible chemoresistance: Enhanced anti-tumor therapy through increased apoptosis by inhibition of NF-κB. *Nat. Med.* 5, 412-417.

Williams A. J., Hale S. L., Moffet J. R., Dave J. R., Elliott P. J., Adams J. and Tortella F. C., 2003. Delayed treatment with MLN-519 reduces infarction and associated neurologic deficit caused by focal ischemic brain injury in rats via antiinflammatory mechanisms involving nuclear factor-κB activation, gliosis, and leukocyte infiltration. *J. Cereb. Blood Flow Metab.* 23(1), 75-87.

Williams A. J., Berti R., Dave J. R., Elliot P. J., Adams J. and Tortella F. C., 2004. Delayed treatment of ischemia/reperfusion brain injury: extended therapeutic window with proteasome inhibitor MLN-519. *Stroke* 35, 1186-1191.

Williams P. G., Buchanan G. O., Feling R. H., Kauffman C. A., Jensen P. R. and Fenical W., 2005a. New cytotoxic salinosporamides from the marine actinomycete *Salinospora tropica*. *J. Org Chem.* 70, 6196-6203.

Williams A. J., Myers T. M., Cohn S. I., Sharrow K. M., Lu X. C., and Tortella F. C., 2005b. Recovery from ischemic brain injury in the rat following a 10 h delayed injection with MLN519. *Pharmacol. Biochem. Behav.* 81(1), 182-189.

Williams A. J., Dave J. R. and Tortella F. C., 2006. Neuroprotection with the proteasome inhibitor MLN519 in focal ischemic brain injury: relation to nuclear factor kappaB (NF-kappaB), inflammatory gene expression, and leukocyte infiltration. *Neurochem. Int.* 49(2), 106-112.

Williamson M. J., Blank J. L., Bruzzese F. J., Cao Y., Daniels J. S., Dick L. R., Labutti J., Mazzola A. M., Patil A. D., Reimer C. L., Solomon M. S., Stirling M., Tian Y., Tsu C. A., Weatherhead G. S., Zhang J. X. and Rolfe M., 2006. Comparison of biochemical and biological effects of ML858 (Salinosporamide A) and bortezomib. *Mol. Cancer Ther.* 5(12), 3052-3061.

Wojcik C. and Di Napoli M., 2004. Ubiquitin-proteasome system and proteasome inhibition: new strategies in stroke therapy. *Stroke* 35, 1506-1518.

Yanagida O., Kanai Y., Chairoungdua A., Kim D. K., Segawa H., Nii T., Cha S. H., Matsuo H., Fukushima J., Fukasawa Y., Tani Y., Taketani Y., Uchino H., Kim J. Y., Inatomi J., Okayasu I., Miyamoto K., Takeda E., Goya T. and Endou H., 2001. Human L-type amino acid transporter 1 (LAT1): characterization of function and expression in tumor cell lines. *Biochim. Biophys. Acta* 1514, 291-302.

Zhai Q., Wang J., Kim A., Liu Q., Watts R., Hoopfer E., Mitchison T., Luo L. and He Z., 2003. Involvement of the ubiquitin-proteasome system in the early stages of Wallerian degeneration. *Neuron* 39, 217-225.

Zhang L., Zhang Z. G., Zhang R. L., Lu M., Adams J. Elliot P. J. and Chopp M., 2001. Postischemic (6-hour) treatment with recombinant human tissue plasminogen activator and proteasome inhibitor PS-519 reduces infarction in a rat model of embolic focal cerebral ischemia. *Stroke* 32(12), 2926-2931.

EXPERIMENTAL SECTION

1. General Methods

1.A. In Silico Analysis Methods

C=O stretching frequency calculations and global electrophilicity analyses have been performed with the Gaussian 09 revision D.01 suites of program [Frisch et al., 2013], using the B3LYP/DZP-DKH method. Throughout the calculations, the B3LYP representative density functional has been employed (B3LYP model: Becke's density functional (B3) using Lee, Yang and Parr electron correlation (LYP)) [Becke, 1988, 1993; Lee et al., 1988]. The combined DZP-DKH basis set has been used [Barros et al., 2010; Jorge et al., 2009]. The performance of the DZP-DKH basis set is assessed for both atomic (ionisation energy) and molecular (spectroscopy constants) properties.

REFERENCES

Barros C. L., de Oliveira P. J. P., Jorge F. E., Canal Neto A. and Campos M., 2010. Gaussian basis set of double zeta quality for atoms Rb through Xe: Application in non-relativistic and relativistic calculations of atomic and molecular properties. Mol. Phys. 108, 1965-1972.

Becke A. D., 1988. Density-functional exchange-energy approximation with correct asymptotic behavior. Phys Rev A Gen Phys. 38(6), 3098-3100.

Becke A. D., 1993. Density functional thermochemistry. III. The role of exact exchange. J. Chem. Phys. 98(7) 5648-5652.

Corey E. J. and Hogan P. C., 2007. Proteasome inhibiting β-lactam compounds. Patent WO 2007/033039.

Frisch M. J., Trucks G. W., Schlegel H. B., Scuseria G. E., Robb M. A. et al., 2013, Gaussian 09, Revision D.01. Gaussian Inc., Wallingford Conn.

Hogan P. C. and Corey E. J., 2005. Proteasome inhibition by a totally synthetic β-lactam related to salinosporamide A and omuralide. J. Am. Chem. Soc. 127(44), 15386-15387.

Jorge F. E., Canal Neto A., Camiletti G. G. and Machado S. F., 2009. Contracted Gaussian basis sets for Douglas- Kroll-Hess calculations: Estimating scalar relativistic effects of some atomic and molecular properties. J. Chem. Phys. 130(6), 064108.

Lee C., Yang W. and Parr R. G., 1988. Development of the Colle-Salvetti correlation-energy formula into a functional of the electron density. Phys Rev B Condens Matter. 37(2), 785-789.

Ren X. F., Konaklieva M. I., Shi H., Dickey S., Lim D. V., Gonzalez J. and Turos E., 1998. Studies on nonconventionally fused bicyclic lactams. J. Org. Chem. 63, 8898-8917.

Example 1: C=O Stretching Frequency Calculations and Global Electrophilicity Analyses The results of the in silico analyses are summarized in the table below. The calculated infrared C=O stretching frequency ($v_{calc.}$, expressed in cm$^{-1}$) is a spectroscopic parameter characterizing the β-lactam carbonyl reactivity. The higher the stretching frequency, the higher is the electrophilicity of the carbonyl carbon and, consequently the reactivity of the carbonyl group towards nucleophiles. In order to estimate the fair value of the infrared C=O stretching frequency and correct the calculated results, a linear regression analysis of similar published experimental data [Ren et al., 1998; Hogan & Corey, 2005] has been used. Based on this analysis, a scaled factor of 0.95 [$r^2$=0.86] has been applied to the calculated data set ($v_{scaled}$, expressed in cm$^{-1}$). The mean absolute deviation (MAD) is about 4 cm$^{-1}$. In comparison, the experimental and scaled calculated frequencies for the initial β-lactam are 1756 and 1765 cm$^{-1}$, respectively [Hogan & Corey, 2005; Corey & Hogan, 2007].

The calculated electrophilicity index ($\varepsilon_{calc.}$, expressed in Hartree (H)) is a global molecular parameter measuring the capacity of the molecule to undergo a nucleophilic attack. The higher the electrophilicity index, the easier is the attack of the threonine OH group by the C=O group of ligand (assuming a nucleophilic threonine residue be involved in the covalent binding of the ligand to the active site).

As anticipated, the electron-withdrawing influence of the sulfo-, seleno- and telluro-sulfone groups on the β-lactam carbonyl induces a shift in the C=O stretching frequency and the global electrophilicity.

Calculated Infrared C=O stretching frequency (in cm$^{-1}$) and electrophilicity (in Hartree (H)) for β-lactams.

| Structure | Id. | X | R | $v_{calc.}$ (cm$^{-1}$) | $v_{scaled}$ (cm$^{-1}$) (SF = 0.95) | $\varepsilon_{calc.}$ (H) |
|---|---|---|---|---|---|---|
| (6) | 6a | S | H | 1878 | 1784 | 0.0810 |
| | 6b | S | CH$_3$ | 1860 | 1767 | 0.0793 |
| | 6c | Se | H | 1860 | 1767 | 0.0835 |
| | 6d | Se | CH$_3$ | 1859 | 1766 | 0.0799 |
| | 6e | Te | H | 1858 | 1765 | 0.1188 |
| | 6f | Te | CH$_3$ | 1857 | 1764 | 0.1151 |
| | 6g$_R$ | S | =O | 1888 | 1794 | 0.1070 |
| | 6g$_S$ | S | =O | 1890 | 1796 | 0.1096 |
| | 6h$_R$ | Se | =O | 1886 | 1792 | 0.1077 |
| | 6h$_S$ | Se | =O | 1888 | 1794 | 0.1102 |
| | 6i$_R$ | Te | =O | 1885 | 1791 | 0.1266 |
| | 6i$_S$ | Te | =O | 1887 | 1793 | 0.1303 |
| | 6j$_R$ | NMe | =O | 1877 | 1783 | 0.0776 |
| | 6j$_S$ | NMe | =O | 1877 | 1783 | 0.0765 |
| (7) | 7a | S | H | 1879 | 1785 | 0.0803 |
| | 7b | S | CH$_3$ | 1855 | 1762 | 0.0818 |
| | 7c | Se | H | 1855 | 1762 | 0.0862 |
| | 7d | Se | CH$_3$ | 1853 | 1760 | 0.0818 |
| | 7e | Te | H | 1852 | 1759 | 0.1201 |
| | 7f | Te | CH$_3$ | 1851 | 1758 | 0.1165 |
| | 7g$_R$ | S | =O | 1866 | 1773 | 0.1146 |
| | 7g$_S$ | S | =O | 1866 | 1773 | 0.1168 |
| | 7h$_R$ | Se | =O | 1862 | 1769 | 0.1152 |
| | 7h$_S$ | Se | =O | 1863 | 1770 | 0.1173 |
| | 7i$_R$ | Te | =O | 1860 | 1767 | 0.1341 |
| | 7i$_S$ | Te | =O | 1860 | 1767 | 0.1357 |
| | 7j$_R$ | NMe | =O | 1854 | 1761 | 0.0722 |
| | 7j$_S$ | NMe | =O | 1855 | 1762 | 0.0702 |
| (8) | 8a | S | H | 1859 | 1766 | 0.0651 |
| | 8b | S | CH$_3$ | 1857 | 1764 | 0.0598 |
| | 8c | Se | H | 1857 | 1764 | 0.0728 |
| | 8d | Se | CH$_3$ | 1855 | 1762 | 0.0705 |
| | 8e | Te | H | 1855 | 1762 | 0.1067 |
| | 8f | Te | CH$_3$ | 1854 | 1761 | 0.1032 |
| | 8g$_R$ | S | =O | 1885 | 1791 | 0.0972 |
| | 8g$_S$ | S | =O | 1888 | 1794 | 0.0965 |
| | 8h$_R$ | Se | =O | 1883 | 1789 | 0.0982 |
| | 8h$_S$ | Se | =O | 1886 | 1792 | 0.0970 |
| | 8i$_R$ | Te | =O | 1883 | 1789 | 0.1169 |
| | 8i$_S$ | Te | =O | 1885 | 1791 | 0.1168 |
| | 8j$_R$ | NMe | =O | 1870 | 1777 | 0.0608 |
| | 8j$_S$ | NMe | =O | 1872 | 1778 | 0.0611 |

-continued

| Structure | Compound Id. | X | R | $\nu_{calc.}$ (cm$^{-1}$) | $\nu_{scaled}$ (cm$^{-1}$) (SF = 0.95) | $\varepsilon_{calc.}$ (H) |
|---|---|---|---|---|---|---|
| (9) 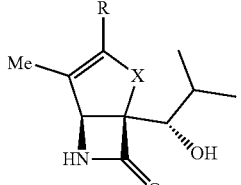 | 9a | S | H | 1877 | 1783 | 0.0595 |
| | 9b | S | CH$_3$ | 1852 | 1759 | 0.0609 |
| | 9c | Se | H | 1851 | 1758 | 0.0737 |
| | 9d | Se | CH$_3$ | 1850 | 1758 | 0.0714 |
| | 9e | Te | H | 1850 | 1758 | 0.1070 |
| | 9f | Te | CH$_3$ | 1848 | 1756 | 0.1037 |
| | 9g$_R$ | S | =O | 1862 | 1769 | 0.1049 |
| | 9g$_S$ | S | =O | 1863 | 1770 | 0.1030 |
| | 9h$_R$ | Se | =O | 1859 | 1766 | 0.1055 |
| | 9h$_S$ | Se | =O | 1860 | 1767 | 0.1030 |
| | 9i$_R$ | Te | =O | 1856 | 1763 | 0.1239 |
| | 9i$_S$ | Te | =O | 1857 | 1764 | 0.1212 |
| | 9j$_R$ | NMe | =O | 1850 | 1758 | 0.0649 |
| | 9j$_S$ | NMe | =O | 1852 | 1759 | 0.0615 |
| (10) 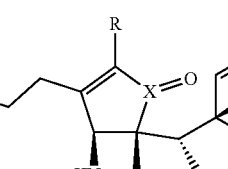 | 10a | S | H | 1886 | 1792 | 0.1290 |
| | 10b | S | CH$_3$ | 1864 | 1771 | 0.1188 |
| | 10c | Se | H | 1865 | 1772 | 0.1391 |
| | 10d | Se | CH$_3$ | 1862 | 1769 | 0.1254 |
| | 10e | Te | H | 1862 | 1769 | 0.1506 |
| | 10f | Te | CH$_3$ | 1860 | 1767 | 0.1434 |
| | 10g$_R$ | S | =O | 1888 | 1794 | 0.1581 |
| | 10g$_S$ | S | =O | 1888 | 1794 | 0.1693 |
| | 10h$_R$ | Se | =O | 1885 | 1791 | 0.1621 |
| | 10h$_S$ | Se | =O | 1865 | 1772 | 0.1799 |
| | 10i$_R$ | Te | =O | 1880 | 1786 | 0.1719 |
| | 10i$_S$ | Te | =O | 1881 | 1787 | 0.1828 |
| (11) 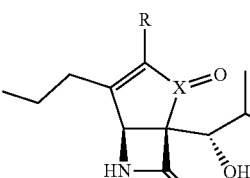 | 11a | S | H | 1884 | 1790 | 0.1277 |
| | 11b | S | CH$_3$ | 1863 | 1770 | 0.1185 |
| | 11c | Se | H | 1864 | 1771 | 0.1384 |
| | 11d | Se | CH$_3$ | 1862 | 1769 | 0.1248 |
| | 11e | Te | H | 1861 | 1768 | 0.1495 |
| | 11f | Te | CH$_3$ | 1859 | 1766 | 0.1424 |
| | 11g$_R$ | S | =O | 1867 | 1774 | 0.1631 |
| | 11g$_S$ | S | =O | 1872 | 1778 | 0.1682 |
| | 11h$_R$ | Se | =O | 1864 | 1771 | 0.1665 |
| | 11h$_S$ | Se | =O | 1869 | 1776 | 0.1752 |
| | 11i$_R$ | Te | =O | 1861 | 1768 | 0.1767 |
| | 11i$_S$ | Te | =O | 1861 | 1768 | 0.1867 |
| (12) 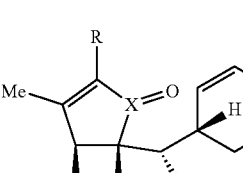 | 12a | S | H | 1884 | 1790 | 0.1070 |
| | 12b | S | CH$_3$ | 1862 | 1769 | 0.0988 |
| | 12c | Se | H | 1862 | 1769 | 0.1192 |
| | 12d | Se | CH$_3$ | 1861 | 1768 | 0.1079 |
| | 12e | Te | H | 1859 | 1766 | 0.1336 |
| | 12f | Te | CH$_3$ | 1857 | 1764 | 0.1288 |
| | 12g$_{/R}$ | S | =O | 1885 | 1791 | 0.1449 |
| | 12g$_{/S}$ | S | =O | 1887 | 1793 | 0.1518 |
| | 12h$_{/R}$ | Se | =O | 1883 | 1789 | 0.1492 |
| | 12h$_{/S}$ | Se | =O | 1880 | 1786 | 0.1611 |
| | 12i$_{/R}$ | Te | =O | 1879 | 1785 | 0.1612 |
| | 12i$_{/S}$ | Te | =O | 1879 | 1785 | 0.1656 |
| (13) 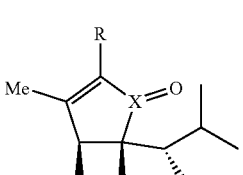 | 13a | S | H | 1882 | 1788 | 0.1058 |
| | 13b | S | CH$_3$ | 1861 | 1768 | 0.0986 |
| | 13c | Se | H | 1861 | 1768 | 0.1183 |
| | 13d | Se | CH$_3$ | 1860 | 1767 | 0.1074 |
| | 13e | Te | H | 1858 | 1765 | 0.1319 |
| | 13f | Te | CH$_3$ | 1857 | 1764 | 0.1265 |
| | 13g$_{/R}$ | S | =O | 1864 | 1771 | 0.1499 |
| | 13g$_{/S}$ | S | =O | 1868 | 1775 | 0.1508 |
| | 13h$_{/R}$ | Se | =O | 1861 | 1768 | 0.1532 |
| | 13h$_{/S}$ | Se | =O | 1866 | 1773 | 0.1577 |
| | 13i$_{/R}$ | Te | =O | 1858 | 1765 | 0.1621 |
| | 13i$_{/S}$ | Te | =O | 1859 | 1766 | 0.1685 |

-continued

| Structure | Compound Id. | X | R | $\nu_{calc.}$ (cm$^{-1}$) | $\nu_{scaled}$ (cm$^{-1}$) (SF = 0.95) | $\varepsilon_{calc.}$ (H) |
|---|---|---|---|---|---|---|
| (14) | 14a | S | H | 1880 | 1786 | 0.1408 |
| | 14b | S | CH$_3$ | 1878 | 1784 | 0.1244 |
| | 14c | Se | H | 1884 | 1790 | 0.1582 |
| | 14d | Se | CH$_3$ | 1882 | 1788 | 0.1385 |
| | 14e | Te | H | 1882 | 1788 | 0.1726 |
| | 14f | Te | CH$_3$ | 1880 | 1786 | 0.1661 |
| | 14g$_{/R}$ | S | =O | 1904 | 1809 | 0.1747 |
| | 14g$_{/S}$ | S | =O | 1906 | 1811 | 0.1846 |
| | 14h$_{/R}$ | Se | =O | 1915 | 1819 | 0.2023 |
| | 14h$_{/S}$ | Se | =O | 1906 | 1811 | 0.2223 |
| | 14i$_{/R}$ | Te | =O | 1909 | 1814 | 0.2134 |
| | 14i$_{/S}$ | Te | =O | 1910 | 1815 | 0.2232 |
| (15) | 15a | S | H | 1879 | 1785 | 0.1439 |
| | 15b | S | CH$_3$ | 1876 | 1782 | 0.1324 |
| | 15c | Se | H | 1881 | 1787 | 0.1646 |
| | 15d | Se | CH$_3$ | 1879 | 1785 | 0.1459 |
| | 15e | Te | H | 1878 | 1784 | 0.1742 |
| | 15f | Te | CH$_3$ | 1876 | 1782 | 0.1672 |
| | 15g$_{/R}$ | S | =O | 1879 | 1785 | 0.1904 |
| | 15g$_{/S}$ | S | =O | 1883 | 1789 | 0.1946 |
| | 15h$_{/R}$ | Se | =O | 1882 | 1788 | 0.2190 |
| | 15h$_{/S}$ | Se | =O | 1884 | 1790 | 0.2167 |
| | 15i$_{/R}$ | Te | =O | 1879 | 1785 | 0.2302 |
| | 15i$_{/S}$ | Te | =O | 1880 | 1786 | 0.2191 |
| (16) | 16a | S | H | 1878 | 1784 | 0.1180 |
| | 16b | S | CH$_3$ | 1874 | 1780 | 0.1034 |
| | 16c | Se | H | 1882 | 1788 | 0.1348 |
| | 16d | Se | CH$_3$ | 1880 | 1786 | 0.1172 |
| | 16e | Te | H | 1880 | 1786 | 0.1592 |
| | 16f | Te | CH$_3$ | 1877 | 1783 | 0.1539 |
| | 16g$_{/R}$ | S | =O | 1902 | 1807 | 0.1619 |
| | 16g$_{/S}$ | S | =O | 1904 | 1809 | 0.1664 |
| | 16h$_{/R}$ | Se | =O | 1916 | 1820 | 0.1894 |
| | 16h$_{/S}$ | Se | =O | 1917 | 1821 | 0.2023 |
| | 16i$_{/R}$ | Te | =O | 1910 | 1815 | 0.2016 |
| | 16i$_{/S}$ | Te | =O | 1921 | 1825 | 0.2063 |
| (17) | 17a | S | H | 1877 | 1783 | 0.1225 |
| | 17b | S | CH$_3$ | 1874 | 1780 | 0.1113 |
| | 17c | Se | H | 1879 | 1785 | 0.1421 |
| | 17d | Se | CH$_3$ | 1877 | 1783 | 0.1250 |
| | 17e | Te | H | 1876 | 1782 | 0.1601 |
| | 17f | Te | CH$_3$ | 1874 | 1780 | 0.1546 |
| | 17g$_{/R}$ | S | =O | 1877 | 1783 | 0.1771 |
| | 17g$_{/S}$ | S | =O | 1878 | 1784 | 0.1772 |
| | 17h$_{/R}$ | Se | =O | 1879 | 1785 | 0.2050 |
| | 17h$_{/S}$ | Se | =O | 1882 | 1788 | 0.1992 |
| | 17i$_{/R}$ | Te | =O | 1876 | 1782 | 0.2173 |
| | 17i$_{/S}$ | Te | =O | 1878 | 1784 | 0.2025 |
| (14j) | 14j | — | — | 1918 | 1822 | 0.2097 |

| Structure | Compound Id. | X | R | $\nu_{calc.}$ (cm$^{-1}$) | $\nu_{scaled}$ (cm$^{-1}$) (SF = 0.95) | $\varepsilon_{calc.}$ (H) |
|---|---|---|---|---|---|---|
| (14k) | 14k | — | — | 1916 | 1820 | 0.2569 |
| (16j) | 16j | — | — | 1917 | 1821 | 0.1965 |
| (16k) | 16k | — | — | 1903 | 1808 | 0.2531 |

1.B. Chemical Syntheses

Unless otherwise noted, chemicals can be obtained from commercial suppliers and used without further purification. All air- or moisture-sensitive reactions were performed under an atmosphere of argon (Ar) using oven-dried glassware.

$^1$H nuclear magnetic resonance (NMR) spectra (400 or 500 MHz) and $^{13}$C NMR spectra (100 or 125 MHz) were registered on a NMR spectrometer using deuterochloroform (CDCl$_3$) as deuterated solvent for the samples. Chemical shifts are relative to tetramethylsilane (TMS-Si(CH$_3$)$_4$) as internal reference. $^{15}$N NMR spectra were registered on a spectrometer using deuterochloroform (CDCl$_3$) as deuterated solvent for the samples. Chemical shifts are relative to nitromethane (CH$_3$NO$_2$) as internal reference. Splitting patterns are described as singlet (s), doublet (d), triplet (t), quartet (q) or multiplet (m). Coupling constants J are reported in hertz (Hz).

Infrared (IR) spectra were obtained using an infrared Fourier transform (IR-FT) spectrophotometer. The resonances are reported in wave numbers (cm$^{-1}$).

High-performance liquid chromatography (HPLC) analyses were carried out with an HPLC/DAD/MS chromatograph equipped with a binary HPLC pump, an autosampler, a vacuum degasser system, a thermo-stated column compartment and a diode array detector. Mass spectroscopic (MS) and high-resolution mass spectroscopic (HRMS) analyses were performed with a mass spectrometer equipped with a triple quad and trap system.

Gas chromatography (GC) analyses were carried out with a GC/FID chromatograph equipped with a capillary column and a FID detector.

Example 1: Synthesis of Compounds (6a)-(6d), (7a)-(7d), (8a)-(8d), (9a)-(9d), (10a)-(10d), (11a)-(11d), (12a)-(12d), (13a)-(13d), (14a)-(14d), (15a)-(15d), (16a)-(16d), (17a)-(17d)

A) Staudinger Ketene-Imine Cycloaddition Reaction

A.1) Preparation of 2-(benzylthio)-3-butenoic Acid

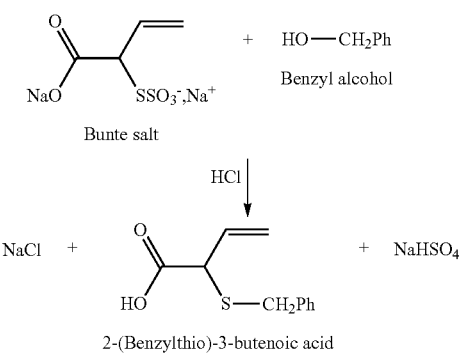

2-(Benzylthio)-3-butenoic acid 2-(benzylthio)-3-butenoic acid (C$_{11}$H$_{12}$O$_2$S) is prepared from 2-chloro-3-butenoic acid and benzyl alcohol ($C_6H_5CH_2OH$) through a Bunte salt prepared with sodium thiosulfate ($Na_2S_2O_3$), as described previously in Stoner et al., 1941, *J. Am. Chem. Soc.* 63(5), 1481.

2-Chloro-3-butenoic acid (241.06 g, 2 mol) is neutralized by sodium carbonate ($Na_2CO_3$) in water (500 ml). An aqueous solution of sodium thiosulfate ($Na_2S_2O_3$, 1 equivalent, 800 ml, 316.22 g, 2 mol, 2.5 M solution in $H_2O$) is added, and the resulting solution is kept at 100° C. for 1 hour. After cooling, concentrated hydrochloric acid (37% HCl in water, 1000 ml, ~12 mol) is added. Sodium chloride (NaCl, ~20 g) is filtered off. The above solution is refluxed for 20 hours with benzyl alcohol (1 equivalent, 216.28 g, 2 mol). The oily layer is neutralized with a sodium carbonate solution and washed with diethyl ether ($Et_2O$). Concentrated hydrochloric acid (182 ml, ~2.2 mol) is then added. The reaction mixture is cooled at 5° C. for 1 day. The reaction gives 2-(benzylthio)-3-butenoic acid (229.11 g, 1.1 mol, 55%).

A.2) Preparation of 2-(benzylthio)-3-butenoic Acid Chloride

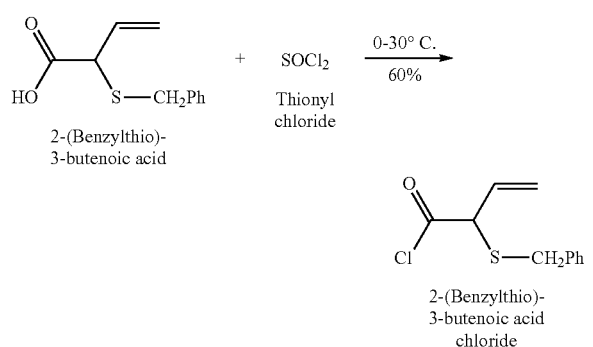

2-(benzylthio)-3-butenoic acid chloride is prepared by reacting 2-(benzylthio)-3-butenoic acid with thionyl chloride, as described previously in Ren et al., 1998, *J. Org. Chem.* 63, 8898-8917.

To a 1000 ml flame dried round bottom flask containing anhydrous 2-(benzyl-thio)-3-butenoic acid (208.28 g, 1 mol) is added thionyl chloride ($SOCl_2$, 118.97 g, 1 mol) dropwise while stirring for 30 minutes at 0° C. The ice bath is removed and the reaction mixture is warmed to 30° C. for 12 hours. The crude mixture is purified by column chromatography to give 2-(benzylthio)-3-butenoic acid chloride (136.03 g, 0.6 mol, 60%).

A.3) Preparation of Sodium Selenosulfate

Sodium selenosulfate ($Na_2SeSO_3$) is prepared from sodium sulfite and selenium, as described in Gao et al., 2009, *Mater. Chem. Phys.* 115, 724-727.

Sodium sulfite ($Na_2SO_3$, 252.08 g, 2 mol) is dissolved in distilled water (800 ml, 25-30° C.) until the appearance of a clear solution. The stirred solution is then warmed to 70° C. Elemental selenium (Se, ~100 mesh, ~99.5%, 1 equivalent, 157.92 g, 2 mol) is slowly added at 70° C. during a period of 2 hours. The mixture is then stirred at 70° C. and 1100 rpm for at least 12 hours. During this process, the selenium powder reacts gradually with sodium sulfite to form a sodium selenosulfate transparent solution. The solution is filtered to obtain a clear, yellowish sodium selenosulfate solution ($Na_2SeSO_3$, 800 ml, 410.02 g, 2 mol, 2.5 M solution in $H_2O$). Upon filtration, the solution is sealed under nitrogen and stored in the dark at 70° C.

A.4) Preparation of 2-(benzylseleno)-3-butenoic Acid

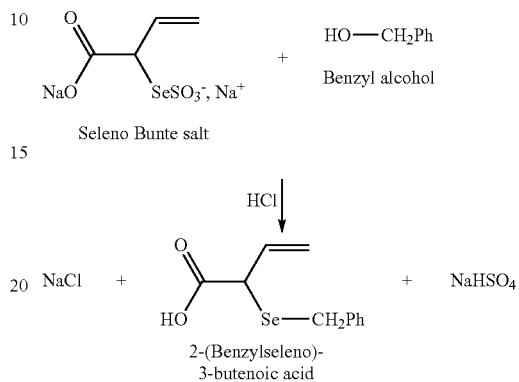

2-(benzylseleno)-3-butenoic acid is prepared from 2-chloro-3-butenoic acid and benzyl alcohol through a seleno Bunte salt prepared with sodium selenosulfate.

2-Chloro-3-butenoic acid (241.06 g, 2 mol) is neutralized by sodium carbonate ($Na_2CO_3$) in water (500 ml). An aqueous solution of freshly prepared sodium selenosulfate (1 equivalent, 800 ml, 410.02 g, 2 mol, 2.5 M solution in $H_2O$) is added, and the resulting solution is kept at 100° C. for 1 hour. After cooling, concentrated hydrochloric acid (37% HCl in water, 1000 ml, ~12 mol) is added. Sodium chloride (NaCl, ~20 g) is filtered off. The above solution is refluxed for 20 hours with benzyl alcohol (1 equivalent, 216.28 g, 2 mol). The oily layer is neutralized with a sodium carbonate solution and washed with diethyl ether ($Et_2O$). Concentrated hydrochloric acid (182 ml, ~2.2 mol) is then added. The reaction mixture is cooled at 5° C. for 1 day. The reaction gives 2-(benzylseleno)-3-butenoic acid (280.70 g, 1.1 mol, 55%).

A.5) Preparation of 2-(benzylseleno)-3-butenoic Acid Chloride

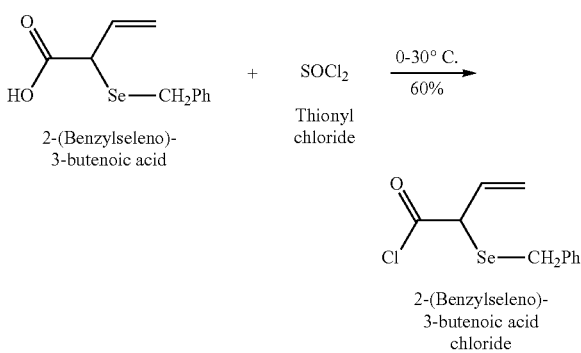

2-(benzylseleno)-3-butenoic acid chloride is prepared by reacting 2-(benzylseleno)-3-butenoic acid with thionyl chloride.

To a 1000 ml flame dried round bottom flask containing anhydrous 2-(benzylseleno)-3-butenoic acid (255.18 g, 1 mol) is added thionyl chloride (SOCl$_2$, 118.97 g, 1 mol) dropwise while stirring for 30 minutes at 0° C. The ice bath is removed and the reaction mixture is warmed to 30° C. for 12 hours. The crude mixture is purified by column chromatography to give 2-(benzylseleno)-3-butenoic acid chloride (164.17 g, 0.6 mol, 60%).

A.6) Preparation of N-(4-Methoxyphenyl)imines

N-(4-Methoxyphenyl)imines are prepared from the condensation of aldehydes and p-anisidine (CH$_3$OC$_6$H$_4$NH$_2$), as described in Long T. E., 2003. N-Thiolated β-lactams. *PhD Thesis*, University of South Florida.

Prior to the reaction, the crude p-anisidine is recrystallized in water at 60° C. and dried in vacuo. If necessary, the acid contaminants are removed by washing with 10% sodium bicarbonate (NaHCO$_3$) or distilling at atmospheric pressure.

A.6.1) Preparation of N-(4-methoxyphenyl)-prop-2-yn-1-imine

N-(4-methoxyphenyl)-prop-2-yn-1-imine is obtained in two steps.

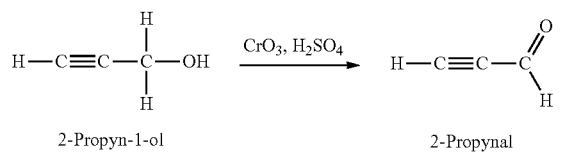

2-Propyn-1-ol          2-Propynal

First, 2-propynal is obtained from 2-propyn-1-ol as described in Veliev et al., 1980, *Synthesis* 6, 461.

2-propyn-1-ol is dissolved in 2-butanone (C$_2$H$_5$COCH$_3$) and oxidized by an aqueous solution of chromium trioxide (CrO$_3$) and sulfuric acid (H$_2$SO$_4$) at ambient temperature and atmospheric pressure. A solution of chromium trioxide (60 g) in sulfuric acid (40 ml) and water (120 ml) is added dropwise with stirring over 1 hour to a solution of 2-propyn-1-ol (35.88 g, 37.26 ml, 640 mmol) in 2-butanone (100 ml). The temperature is maintained at 20-25° C. by cooling. The reaction mixture is stirred for 4 hours and diluted with water (30 ml). The organic layer is separated. The aqueous layer is extracted with diethyl ether (Et$_2$O, 120 ml). The combined organic layers are dried over anhydrous magnesium sulfate (MgSO$_4$). The solvents are removed in vacuo. Distillation of the residual liquid gives 2-propynal (31.13 g, 34.98 ml, 576 mmol, 90%).

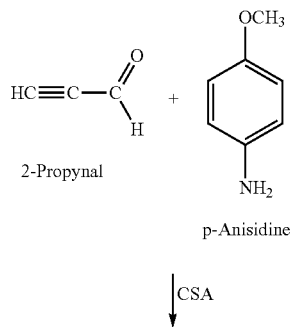

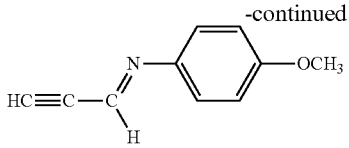

N-(4-Methoxyphenyl)-prop-2-yn-1-imine

Second, N-(4-methoxyphenyl)-prop-2-yn-1-imine is prepared from the condensation of 2-propynal and p-anisidine in the presence of a catalytic amount of camphorsulfonic acid (CSA), as described in Long T. E., 2003. N-Thiolated β-lactams. *PhD Thesis*, University of South Florida.

2-Propynal (29.73 g, 32.46 ml, 550 mmol), p-anisidine (67.73 g, 550 mmol) and camphorsulfonic acid (CSA, 550 mg) are dissolved in dichloromethane (CH$_2$Cl$_2$) and stirred at ambient temperature for 1-2 hours. The progress of the reaction is monitored until all the starting aldehyde is consumed. Conversion to the imine is completed within 1 hour. The reaction mixture is dried over anhydrous magnesium sulfate (MgSO$_4$) and filtered. The solvent is removed in vacuo. The crude product is further purified by column chromatography (silica gel) to give N-(4-methoxyphenyl)-prop-2-yn-1-imine (70.04 g, 440 mmol, 80%).

A.6.2) Preparation of N-(4-methoxyphenyl)-but-2-yn-1-imine

N-(4-methoxyphenyl)-but-2-yn-1-imine is obtained in two steps.

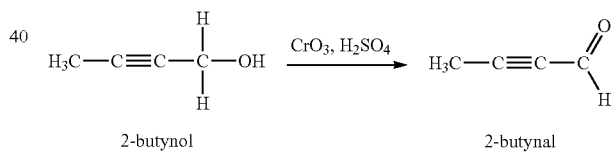

2-butynol          2-butynal

First, 2-butynal is prepared by the oxidation of 2-butynol.

2-butynol is dissolved in 2-butanone (C$_2$H$_5$COCH$_3$) and oxidized by an aqueous solution of chromium trioxide (CrO$_3$) and sulfuric acid (H$_2$SO$_4$) at ambient temperature and atmospheric pressure. A solution of chromium trioxide (60 g) in sulfuric acid (40 ml) and water (120 ml) is added dropwise with stirring over 1 hour to a solution of 2-butynol (44.86 g, 47.87 ml, 640 mmol) in 2-butanone (100 ml). The temperature is maintained at 20-25° C. by cooling. The reaction mixture is stirred for 4 hours and diluted with water (30 ml). The organic layer is separated. The aqueous layer is extracted with diethyl ether (Et$_2$O, 120 ml). The combined organic layers are dried over anhydrous magnesium sulfate (MgSO$_4$). The solvents are removed in vacuo. Distillation of the residual liquid gives 2-butynal (39.21 g, 43.33 ml, 576 mmol, 90%).

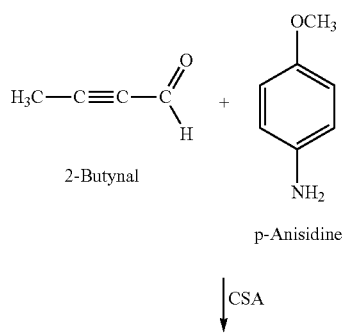

2-Butynal p-Anisidine

↓ CSA

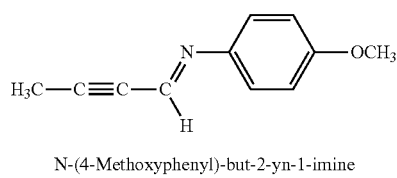

N-(4-Methoxyphenyl)-but-2-yn-1-imine

Second, N-(4-methoxyphenyl)-but-2-yn-1-imine is prepared from the condensation of 2-butynal and p-anisidine in the presence of a catalytic amount of camphorsulfonic acid (CSA), as described in Long T. E., 2003. N-Thiolated β-lactams. *PhD Thesis*, University of South Florida.

2-Butynal (37.44 g, 550 mmol), p-anisidine (67.73 g, 550 mmol) and camphorsulfonic acid (CSA, 550 mg) are dissolved in dichloromethane ($CH_2Cl_2$) and stirred at ambient temperature for 1-2 hours. The progress of the reaction is monitored until all the starting aldehyde is consumed. Conversion to the imine is completed within 1 hour. The reaction mixture is dried over anhydrous magnesium sulfate ($MgSO_4$) and filtered. The solvent is removed in vacuo. The crude product is further purified by column chromatography (silica gel) to give N-(4-methoxyphenyl)-but-2-yn-1-imine (76.21 g, 440 mmol, 80%).

A.7) Preparation of Alkenyl Azetidinones by Staudinger Reaction

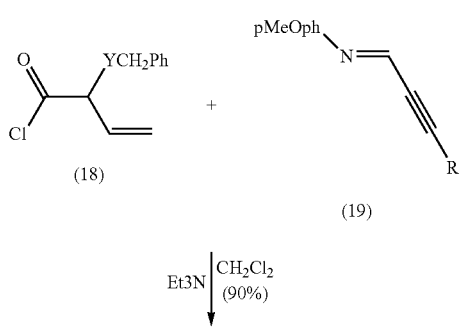

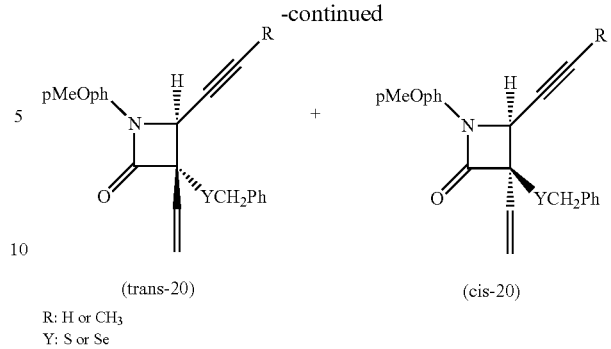

(trans-20)        (cis-20)

R: H or $CH_3$
Y: S or Se

Alkenyl azetidinones (compound 20) are prepared by reaction between 2-(benzylthio)-3-butenoic acid chloride or selenium equivalent (compound 18) and unsaturated N-(4-methoxyphenyl)-prop-2-yn-1-imine or N-(4-methoxy-phenyl)-but-2-yn-1-imine (compound 19), as previously described in Ren et al., 1995, *J. Org. Chem.* 60, 4980-4981, in Ren et al., 1998, *J. Org. Chem.* 63, 8898-8917 and in Long T. E., 2003, N-Thiolated β-lactams. *PhD Thesis*, University of South Florida.

The mechanism of β-lactam formation does not entail a direct acylation of the imine with an acide chloride, but rather a ketene cycloaddition. The ketene forms by deprotonation of an activated acid with a Lewis base such as triethylamine or ethyldiisopropyl-amine. If a base is absent or added after the imine and acid are combined, the ketene does not form and the cycloaddition generally results in a β-lactam with a trans configuration.

General Procedure:

To a stirred solution of triethylamine ($Et_3N$, 22.77 g; 31.36 ml, 225.0 mmol) and imine 19 (200 mmol) in dichloromethane ($CH_2Cl_2$, 1875 ml) at ambient temperature is added via canula a solution of acid chloride 18 (1.25 equivalent, 250 mmol) in dichloromethane ($CH_2Cl_2$, 500 ml). The reaction mixture is stirred at ambient temperature for at least 30 minutes, poured into an aqueous HCl solution (HCl, 5% in $H_2O$, 1875 ml) and extracted with dichloromethane ($CH_2Cl_2$, 3×1250 ml). The combined organic layers are dried over anhydrous magnesium sulfate ($MgSO_4$) and evaporated. The residue is purified by column chromatography (silica gel, dichloromethane:hexanes, 2:1 and then dichloromethane) to give the desired cis β-lactam 20 (90%, 180.0 mmol).

Amounts of Starting Material and Yield:

19a-b (200 mmol): 31.838 g for 19a wherein R is H (N-(4-methoxyphenyl)-prop-2-yn-1-imine)
   34.642 g for 19b wherein R is $CH_3$ (N-(4-methoxyphenyl)-but-2-yn-1-imine)

18a-b (250 mmol): 56.680 g for 18a wherein Y is S (2-(benzylthio)-3-butenoic acid chloride)
   68.405 g for 18b wherein Y is Se (2-(Benzylseleno)-3-butenoic acid chloride)

20a-d (180 mmol): 62.901 g for 20a wherein Y is S and R is H
   65.426 g for 20b wherein Y is S and R is $CH_3$
   71.342 g for 20c wherein Y is Se and R is H
   73.867 g for 20d wherein Y is Se and R is $CH_3$

B. Iodine-Promoted Cyclization Reaction

The previously prepared azetidinones are converted in to 4,5-fused bicyclic ring compounds upon iodination at ambient temperature.

The cis isomer cyclizes easily, while the trans stereoisomer is unreactive and is recovered unchanged. The iodocyclization reaction involving the cis-trans mixture leads to cyclization of only the cis compound. As such, to increase the yield of the cyclization product, the trans compound is first converted to the cis compound.

B.1) Trans-to-Cis Conversion

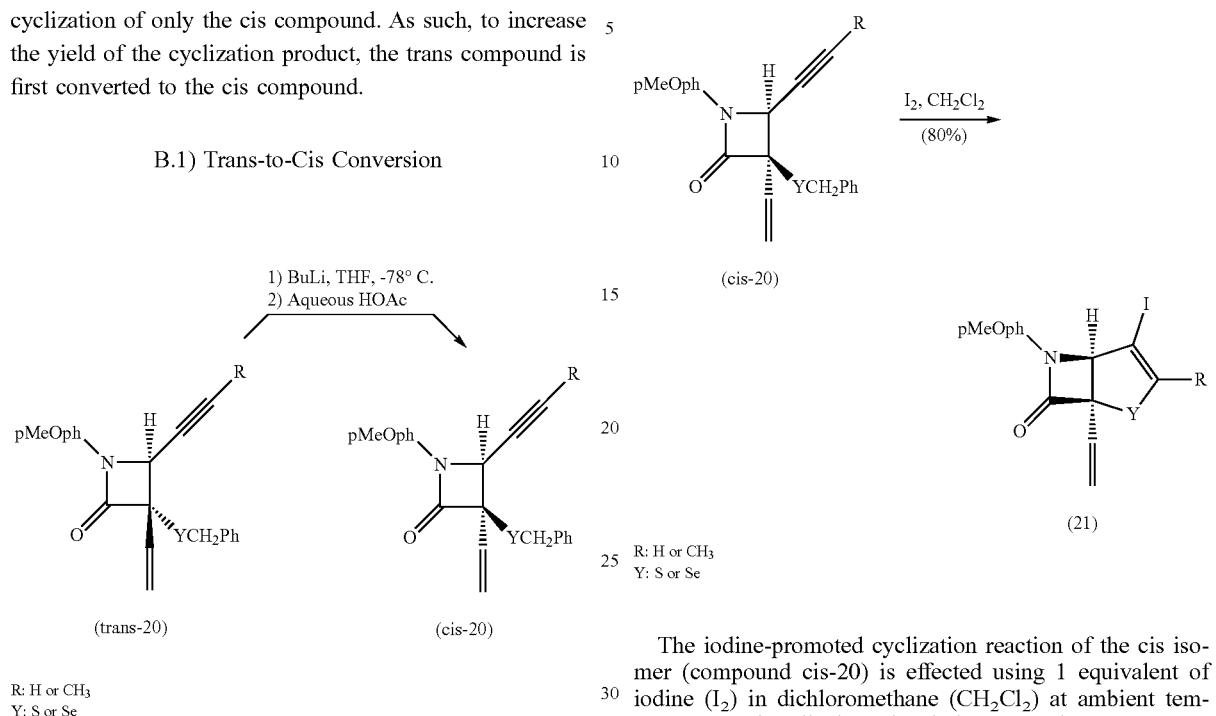

R: H or CH$_3$
Y: S or Se

A trans-to-cis conversion can be carried out by treating the unpurified β-lactam product with n-butyllithium at −78° C. followed by aqueous acetic acid (HOAc), as described in Ren et al., 1998, *J. Org. Chem.* 63, 8898-8917.

General Procedure:

To a stirred solution of the above crude product mixture 20 (180.0 mmol) in tetrahydrofuran (THF, 1800 ml) at −78° C. is added n-butullithium (1.1 equivalent, 80 ml, 2.5 M solution in hexanes, 200.0 mmol). The reaction mixture is stirred for 15 minutes, poured into an aqueous acetic acid solution (HOAc, 5% in H$_2$O, 1800 ml) and extracted with dichloromethane (CH$_2$Cl$_2$, 3×450 ml). The combined organic layers are dried over anhydrous magnesium sulfate (MgSO$_4$), filtered and then evaporated. The crude mixture is purified by column chromatography (80% overall, 144.0 mmol) (compounds cis-20 and trans-20). The diastereoisomers can be separated at this stage. However, it is more convenient to carry the unpurified mixture on to the iodination step, at which point the unreacted trans isomer can be easily retrieved.

Yield:

20a-d (144.0 mmol): 50.321 g for 20a wherein Y is S and R is H 52.341 g for 20b wherein Y is S and R is Me 57.074 g for 20c wherein Y is Se and R is H 59.094 g for 20d wherein Y is Se and R is Me B.2) Iodine-Promoted Cyclization Reaction

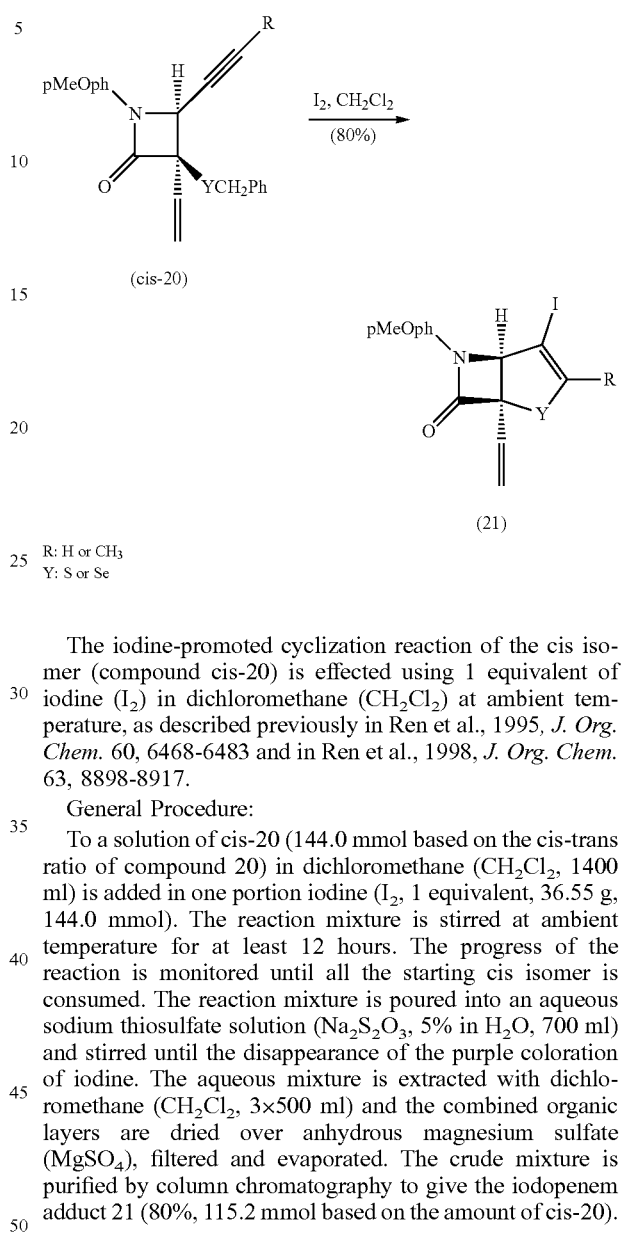

R: H or CH$_3$
Y: S or Se

The iodine-promoted cyclization reaction of the cis isomer (compound cis-20) is effected using 1 equivalent of iodine (I$_2$) in dichloromethane (CH$_2$Cl$_2$) at ambient temperature, as described previously in Ren et al., 1995, *J. Org. Chem.* 60, 6468-6483 and in Ren et al., 1998, *J. Org. Chem.* 63, 8898-8917.

General Procedure:

To a solution of cis-20 (144.0 mmol based on the cis-trans ratio of compound 20) in dichloromethane (CH$_2$Cl$_2$, 1400 ml) is added in one portion iodine (I$_2$, 1 equivalent, 36.55 g, 144.0 mmol). The reaction mixture is stirred at ambient temperature for at least 12 hours. The progress of the reaction is monitored until all the starting cis isomer is consumed. The reaction mixture is poured into an aqueous sodium thiosulfate solution (Na$_2$S$_2$O$_3$, 5% in H$_2$O, 700 ml) and stirred until the disappearance of the purple coloration of iodine. The aqueous mixture is extracted with dichloromethane (CH$_2$Cl$_2$, 3×500 ml) and the combined organic layers are dried over anhydrous magnesium sulfate (MgSO$_4$), filtered and evaporated. The crude mixture is purified by column chromatography to give the iodopenem adduct 21 (80%, 115.2 mmol based on the amount of cis-20).

Yield:

21a-d (115.2 mmol): 44.378 g for 21a wherein Y is S and R is H 45.994 g for 21b wherein Y is S and R is Me 49.780 g for 21c wherein Y is Se and R is H 51.396 g for 21d wherein Y is Se and R is Me C. Sulfur or Selenium Oxidation for Compounds (10a)-(10d), (11a)-(11d), (12a)-(12d), (13a)-(13d), (14a)-(14d), (15a)-(15d), (16a)-(16d), (17a)-(17d)

The formation of mono- or disulfone derivatives or selenium equivalents is achieved by using meta-chloroperoxybenzoic acid (mCPBA), as described in Ren et al., 1998, *J. Org. Chem.* 63, 8898-8917, and in Coantic et al., 2007, *Tetrahedron* 63, 3205-3216.

C.1) Mono-Oxidation

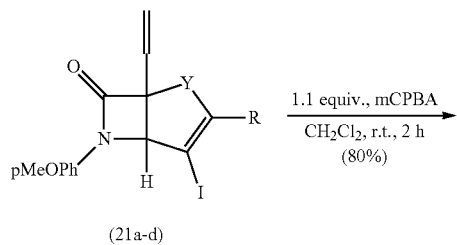

(21a-d)

(21e-h)

The mono-oxidation of the iodopenem adduct is conducted in dichloromethane ($CH_2Cl_2$), at ambient temperature, by using 1.1 equivalent of meta-chloro-peroxybenzoic acid (mCPBA).

General Procedure:

To a stirred suspension of iodopenem adduct 21a-d (9.4 mmol) in dichloromethane ($CH_2Cl_2$, 125 ml) is added in one portion meta-chloroperoxybenzoic acid (mCPBA, 1.1 equivalent, 2.32 g, 10.34 mmol based on 77% purity). The mixture is stirred at room temperature for at least 2 hours. The progress of the reaction is monitored until all the starting β-lactam is consumed. The resulting mixture is washed with a saturated aqueous sodium bicarbonate solution ($NaHCO_3$, 9.60 g, 100 ml) and then with a saturated aqueous sodium chloride solution (NaCl, 36.00 g, 100 ml). The organic layer is dried over anhydrous magnesium sulfate ($MgSO_4$) and then filtered. The solvent is evaporated under reduced pressure to give the crude adduct. The product is further purified by column chromatography (silica gel) to give the monosulfone derivative or selenium equivalent 21e-h (80%, 7.5 mmol).

Amounts of Starting Material and Yields:

21a-d (9.4 mmol): 3.621 g for 21a wherein Y is S; R is H and n is 0

3.753 g for 21b wherein Y is S; R is Me and n is 0

4.062 g for 21c wherein Y is Se; R is H and n is 0

4.194 g for 21d wherein Y is Se; R is Me and n is 0

21e-h (7.5 mmol): 3.009 g for 21e wherein Y is S; R is H and n is 1

3.114 g for 21f wherein Y is S; R is Me and n is 1

3.361 g for 21g wherein Y is Se; R is H and n is 1

3.466 g for 21h wherein Y is Se; R is Me and n is 1

C.2) Di-Oxidation

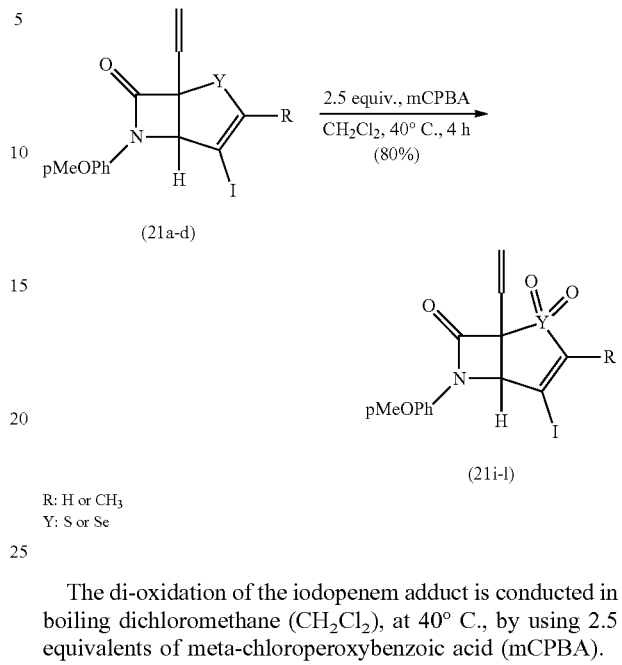

R: H or $CH_3$
Y: S or Se

The di-oxidation of the iodopenem adduct is conducted in boiling dichloromethane ($CH_2Cl_2$), at 40° C., by using 2.5 equivalents of meta-chloroperoxybenzoic acid (mCPBA).

General Procedure:

To a stirred suspension of iodopenem adduct 21a-d (9.4 mmol) in dichloromethane ($CH_2Cl_2$, 125 ml) is added in one portion meta-chloroperoxybenzoic acid (mCPBA, 2.5 equivalent, 5.27 g, 23.5 mmol based on 77% purity). The mixture is stirred at 40° C. for at least 4 hours. The progress of the reaction is monitored until all the starting β-lactam is consumed. The resulting mixture is washed with a saturated aqueous sodium bicarbonate solution ($NaHCO_3$, 9.60 g, 100 ml) and then with a saturated aqueous sodium chloride solution (NaCl, 36.00 g, 100 ml). The organic layer is dried over anhydrous magnesium sulfate ($MgSO_4$) and then filtered. The solvent is evaporated under reduced pressure to give the crude adduct. The product is further purified by column chromatography (silica gel) to give the disulfone derivative or selenium equivalent 21i-l (80%, 7.5 mmol).

Amounts of Starting Material and Yields:

21a-d (9.4 mmol): 3.621 g for 21a wherein Y is S; R is H and n is 0

3.753 g for 21b wherein Y is S; R is Me and n is 0

4.062 g for 21c wherein Y is Se; R is H and n is 0

4.194 g for 21d wherein Y is Se; R is Me and n is 0

21i-l (7.5 mmol): 3.129 g for 21i wherein Y is S; R is H and n is 2

3.234 g for 21j wherein Y is S; R is Me and n is 2

3.481 g for 21k wherein Y is Se; R is H and n is 2

3.586 g for 21l wherein Y is Se; R is Me and n is 2

D. Palladium-Catalyzed Stille Coupling Reactions

The iodopenem adduct is converted to chloroethyl and methyl substituted derivatives via a palladium-catalyzed Stille coupling reaction.

D.1) Preparation of 2-chloroethyltributyltin

The preparation of 2-chloroethyltributyltin is carried out in two steps.

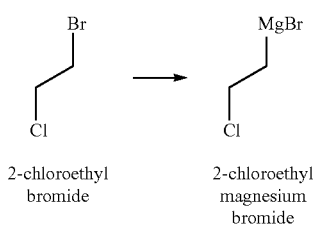

2-chloroethyl bromide → 2-chloroethyl magnesium bromide

First, 2-chloroethyl bromide is reacted with magnesium (Mg, 1 equivalent) in tetrahydrofuran (THF) to form 2-chloro-ethylmagnesium bromide, as described in Kenmore E. J. P., 1965, U.S. Pat. No. 3,180,901 and in Stille et al., 1993, *Org. Synth.* 71, 97-106.

In a dry, three-necked, round-bottomed flask equipped with a reflux condenser, a magnetic stirring bar, a thermometer and a dropping funnel is placed clean magnesium turnings (12.15 g, 500 mmol). The entire system is dried under argon atmosphere to remove all traces of moisture. On cooling, anhydrous tetrahydrofuran (THF, 200 ml) is added to the flask. The dropping funnel is charged with anhydrous 2-chloroethyl bromide (71.70 g, 500 mmol) containing dissolved therein a crystal of iodine (~0.03 g). A minor amount (~2 ml) of 2-chloroethyl bromide is run into the flask. The reaction is initiated by heating the flask to a temperature of from 25° C. to 35° C., causing the ether solvent to reflux (5-15 minutes reflux). When reaction became vigourous, the flask is cooled in order to maintain a reaction temperature below 25° C., while adding an additional amount of 2-chloroethyl bromide. Stirring is continued until all the starting magnesium is consumed and the reaction mixture become clear (up to 2 hours at 15-25° C.). The reaction mixture is then decanted and purified by standard procedures.

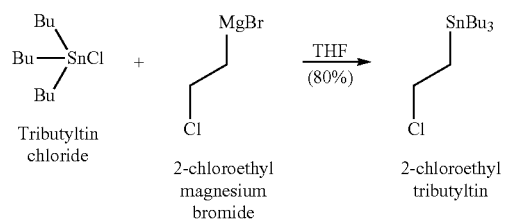

Tributyltin chloride + 2-chloroethyl magnesium bromide → THF (80%) → 2-chloroethyl tributyltin Then, tributyltin chloride (162.75 g; 500 mmol) in tetrahydrofuran (THF, 200 ml) is slowly added to the 2-chloroethylmagnesium bromide solution. The reaction is heated at reflux for at least 12 hours until complete conversion of the chlorotributyltin. Upon cooling to ambient temperature, the reaction is quenched with a saturated aqueous ammonium chloride solution ($NH_4Cl$, 372 g, 1000 ml). The resulting mixture is poured into a separatory funnel and extracted with diethyl ether (1000 ml). The organic fraction is washed with water (2×250 ml), dried over anhydrous magnesium sulfate ($MgSO_4$), filtered and concentrated under reduced pressure. After removal of the solvent, the crude product is purified by distillation to give 2-chloroethyl-tributyltin (80%, 400 mmol).

D.2) Cross-coupling reaction with 2-chloroethyltributyltin

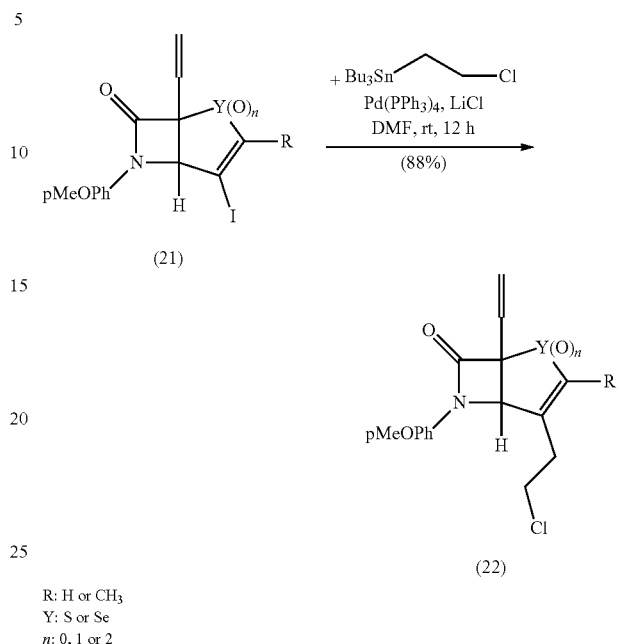

R: H or $CH_3$
Y: S or Se
n: 0, 1 or 2

The attachment of the 2-chloroethyl group is accomplished by treatment of the iodopenem adduct or selenium equivalent 21 with 2-chloroethyltributyltin (1.2 equivalent) in the presence of tetrakis(triphenylphosphine)palladium ($Pd(PPh_3)_4$, 5 mol %) and lithium chloride (LiCl, 1.2 equivalent) in anhydrous N,N-dimethylformamide (DMF) at ambient temperature, as described previously in Konaklieva et al., 1997, *Tetrahedron Lett.* 38(50), 8647-8650, in Ren et al., 1998, *J. Org. Chem.* 63, 8898-8917 and in Huang et al., 2003, *Tetrahedron* 59, 3635-3641.

General Procedure:

The iodopenem adduct or selenium equivalent 21a-l (7.5 mmol) and 2-chloroethyltributyltin (1.2 equivalent, 3.18 g, 9.0 mmol) is added to a round-bottom flask containing tetrakis(triphenylphosphine)-palladium ($Pd(PPh_3)_4$, 0.43 g, 0.375 mmol, 5 mol %) and lithium chloride (LiCl, 1.2 equivalent, 0.38 g, 9.0 mmol) in anhydrous N,N-dimethylformamide (DMF, 25 ml) under nitrogen gas ($N_2$). The reaction mixture is stirred at ambient temperature for at least 12 hours and then treated with a saturated aqueous potassium fluoride solution (KF, 69.22 g, 75 ml). After an additional 30 minutes stirring at ambient temperature, the reaction mixture is filtered through Celite and silica gel and eluted with diethylether ($Et_2O$, 375 ml). The organic layer is washed with water, dried over anhydrous magnesium sulfate ($MgSO_4$) and concentrated in vacuo. The residue is further purified by column chromatography (silica gel, n-pentane) to give the corresponding chloroethyl substituted derivative 22a-l (88%, 6.6 mmol).

Amounts of Starting Material and Yields:

21a-l (7.5 mmol): 2.889 g for 21a wherein Y is S; R is H and n is 0

2.994 g for 21b wherein Y is S; R is Me and n is 0
3.241 g for 21c wherein Y is Se; R is H and n is 0
3.346 g for 21d wherein Y is Se; R is Me and n is 0
3.009 g for 21e wherein Y is S; R is H and n is 1
3.114 g for 21f wherein Y is S; R is Me and n is 1

3.361 g for 21g wherein Y is Se; R is H and n is 1
3.466 g for 21h wherein Y is Se; R is Me and n is 1
3.129 g for 21i wherein Y is S; R is H and n is 2
3.234 g for 21j wherein Y is S; R is Me and n is 2
3.481 g for 21k wherein Y is Se; R is H and n is 2
3.586 g for 21l wherein Y is Se; R is Me and n is 2
22a-l (6.6 mmol): 2.124 g for 22a wherein Y is S; R is H and n is 0
2.217 g for 22b wherein Y is S; R is Me and n is 0
2.434 g for 22c wherein Y is Se; R is H and n is 0
2.526 g for 22d wherein Y is Se; R is Me and n is 0
2.230 g for 22e wherein Y is S; R is H and n is 1
2.322 g for 22f wherein Y is S; R is Me and n is 1
2.539 g for 22g wherein Y is Se; R is H and n is 1
2.632 g for 22h wherein Y is Se; R is Me and n is 1
2.335 g for 22i wherein Y is S; R is H and n is 2
2.428 g for 22j wherein Y is S; R is Me and n is 2
2.645 g for 22k wherein Y is Se; R is H and n is 2
2.737 g for 22l wherein Y is Se; R is Me and n is 2

D.3) Cross-Coupling Reaction with Methyltributyltin

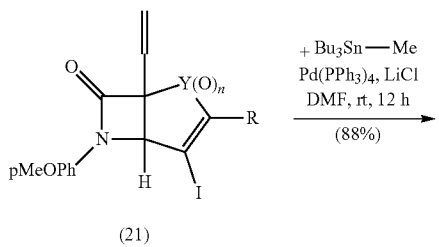

(21)

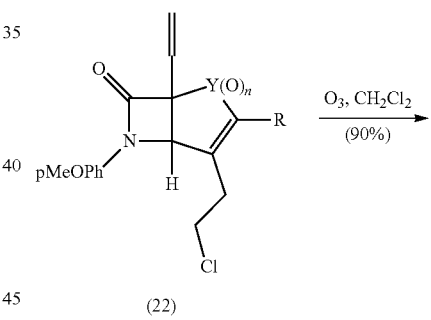

(23)

R: H or CH$_3$
Y: S or Se
n: 0, 1 or 2

The attachment of the methyl group is accomplished in one step by treatment of the iodopenem adduct or selenium equivalent 21 with methyltributyltin (1.2 equivalent) in the presence of tetrakis(triphenylphosphine)palladium (Pd(PPh$_3$)$_4$, 5 mol %) and lithium chloride (LiCl, 1.2 equivalent) in anhydrous N,N-dimethylformamide (DMF) at ambient temperature, as described previously in Konaklieva et al., 1997, *Tetrahedron Lett.* 38(50), 8647-8650, in Ren et al., 1998, *J. Org. Chem.* 63, 8898-8917 and in Huang et al., 2003, *Tetrahedron* 59, 3635-3641.

General Procedure:

The iodopenem adduct or selenium equivalent 21a-l (7.5 mmol) and methyltributyltin (1.2 equivalent, 2.75 g, 9.0 mmol) is added to a round-bottom flask containing tetrakis(tri-phenylphosphine)palladium (Pd(PPh$_3$)$_4$, 0.43 g, 0.375 mmol, 5 mol %) and lithium chloride (LiCl, 1.2 equivalent, 0.38 g, 9.0 mmol) in anhydrous N,N-dimethylformamide (DMF, 25 ml) under nitrogen gas (N$_2$). The reaction mixture is stirred at ambient temperature for at least 12 hours and then treated with a saturated aqueous potassium fluoride solution (KF, 69.2 g, 75 ml). After an additional 30 minutes stirring at ambient temperature, the reaction mixture is filtered through Celite and silica gel and eluted with diethylether (Et$_2$O, 375 ml). The organic layer is washed with water, dried over anhydrous magnesium sulfate (MgSO$_4$) and concentrated in vacuo. The residue is further purified by column chromatography (silica gel, n-pentane) to give the corresponding methyl substituted derivative 23a-l (88%, 6.6 mmol).

Amounts of Starting Material and Yields:

21a-l (7.5 mmol) same as for cross-coupling with 2-chloroethyltributyltin in D.2)

23a-l (6.6 mmol): 1.804 g for 23a wherein Y is S; R is H and n is 0
1.897 g for 23b wherein Y is S; R is Me and n is 0
2.114 g for 23c wherein Y is Se; R is H and n is 0
2.206 g for 23d wherein Y is Se; R is Me and n is 0
1.910 g for 23e wherein Y is S; R is H and n is 1
2.002 g for 23f wherein Y is S; R is Me and n is 1
2.219 g for 23g wherein Y is Se; R is H and n is 1
2.312 g for 23h wherein Y is Se; R is Me and n is 1
2.015 g for 23i wherein Y is S; R is H and n is 2
2.108 g for 23j wherein Y is S; R is Me and n is 2
2.325 g for 23k wherein Y is Se; R is H and n is 2
2.417 g for 23l wherein Y is Se; R is Me and n is 2

E. Ozonolysis of the Vinyl Moiety (22)

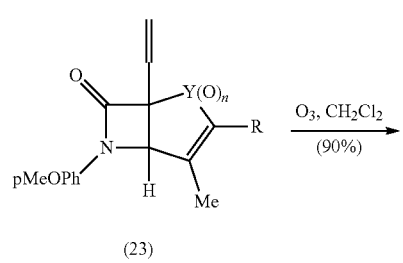

(24)

(23)

-continued

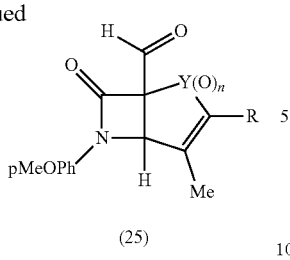

R: H or CH₃
Y: S or Se
n: 0, 1 or 2

Ozonolysis of the vinyl moiety at −78° C. affords the corresponding aldehyde derivatives 24 and 25 in about 90% yields. The reaction proceeds quickly upon bubbling a dilute stream of ozone (O₂/O₃) through a dichloromethane solution, as reported in Ren et al., 1998, *J. Org. Chem.* 63, 8898-8917.

General Procedure:

A solution of β-lactam 22a-l or 23a-l (6.0 mmol) in dichloromethane (CH₂Cl₂, 60 ml) is cooled to −78° C. A slow stream of ozone (O₂/O₃) is then bubbled through the solution. The progress of the reaction is monitored until all the starting β-lactam is consumed. After eliminating the residual ozone by bubbling Argon (Ar) through the solution, the reaction mixture is then poured into water and extracted with dichloromethane (CH₂Cl₂, 4×20 ml). The combined organic layers are dried over anhydrous magnesium sulfate (MgSO₄), filtered, and evaporated. The crude mixture is purified by column chromatography (silica gel, hexanes/ethyl acetate, 8:2) to give the corresponding aldehyde derivatives 24a-l or 25a-l (90%, 5.4 mmol).

Amount of Starting Materials and Yields:

22a-l (6.0 mmol): 1.931 g for 22a wherein Y is S; R is H and n is 0
  2.015 g for 22b wherein Y is S; R is Me and n is 0
  2.212 g for 22c wherein Y is Se; R is H and n is 0
  2.296 g for 22d wherein Y is Se; R is Me and n is 0
  2.027 g for 22e wherein Y is S; R is H and n is 1
  2.111 g for 22f wherein Y is S; R is Me and n is 1
  2.308 g for 22g wherein Y is Se; R is H and n is 1
  2.392 g for 22h wherein Y is Se; R is Me and n is 1
  2.123 g for 22i wherein Y is S; R is H and n is 2
  2.207 g for 22j wherein Y is S; R is Me and n is 2
  2.404 g for 22k wherein Y is Se; R is H and n is 2
  2.488 g for 22l wherein Y is Se; R is Me and n is 2

23a-l (6.0 mmol): 1.640 g for 23a wherein Y is S; R is H and n is 0
  1.724 g for 23b wherein Y is S; R is Me and n is 0
  1.921 g for 23c wherein Y is Se; R is H and n is 0
  2.006 g for 23d wherein Y is Se; R is Me and n is 0
  1.736 g for 23e wherein Y is S; R is H and n is 1
  1.820 g for 23f wherein Y is S; R is Me and n is 1
  2.017 g for 23g wherein Y is Se; R is H and n is 1
  2.102 g for 23h wherein Y is Se; R is Me and n is 1
  1.832 g for 23i wherein Y is S; R is H and n is 2
  1.916 g for 23j wherein Y is S; R is Me and n is 2
  2.113 g for 23k wherein Y is Se; R is H and n is 2
  2.198 g for 23l wherein Y is Se; R is Me and n is 2

24a-l (5.4 mmol): 1.749 g for 24a wherein Y is S; R is H and n is 0
  1.824 g for 24b wherein Y is S; R is Me and n is 0
  2.002 g for 24c wherein Y is Se; R is H and n is 0
  2.077 g for 24d wherein Y is Se; R is Me and n is 0
  1.835 g for 24e wherein Y is S; R is H and n is 1
  1.911 g for 24f wherein Y is S; R is Me and n is 1
  2.088 g for 24g wherein Y is Se; R is H and n is 1
  2.164 g for 24h wherein Y is Se; R is Me and n is 1
  1.921 g for 24i wherein Y is S; R is H and n is 2
  1.997 g for 24j wherein Y is S; R is Me and n is 2
  2.175 g for 24k wherein Y is Se; R is H and n is 2
  2.250 g for 24l wherein Y is Se; R is Me and n is 2

25a-l (5.4 mmol): 1.487 g for 25a wherein Y is S; R is H and n is 0
  1.563 g for 25b wherein Y is S; R is Me and n is 0
  1.740 g for 25c wherein Y is Se; R is H and n is 0
  1.816 g for 25d wherein Y is Se; R is Me and n is 0
  1.573 g for 25e wherein Y is S; R is H and n is 1
  1.649 g for 25f wherein Y is S; R is Me and n is 1
  1.826 g for 25g wherein Y is Se; R is H and n is 1
  1.902 g for 25h wherein Y is Se; R is Me and n is 1
  1.660 g for 25i wherein Y is S; R is H and n is 2
  1.735 g for 25j wherein Y is S; R is Me and n is 2
  1.913 g for 25k wherein Y is Se; R is H and n is 2
  1.989 g for 25l wherein Y is Se; R is Me and n is 2

F. Attachment of a 2-Cyclohexenyl Group on the Formyl Carbon

The attachment of the 2-cyclohexenyl group on the formyl carbon is accomplished in two steps.

F.1) Preparation of 2-cyclohexenylzinc Chloride

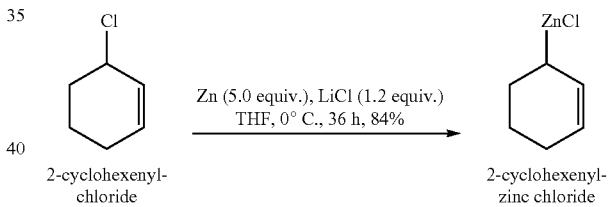

2-cyclohexenyl-chloride    2-cyclohexenyl-zinc chloride 2-cyclohexenylzinc chloride is prepared from 2-cyclohexenyl chloride by a lithium chloride (LiCl)-mediated insertion of zinc dust as described in Ren et al., 2007, *J. Am. Chem. Soc.* 129, 5376-5377.

The dropwise addition of 2-cyclohexenyl chloride (1.0 equivalent) to a suspension of zinc dust (Zn, 5.0 equivalent) and dry lithium chloride (LiCl, 1.2 equivalent) in tetrahydrofuran (THF) provides 2-cyclohexenylzinc chloride. Zinc dust (Zn, granulometry <10 μm, 5.0 equivalent, 81.74 g, 1.250 mol) and dry lithium chloride (LiCl, 1.2 equivalent, 12.72 g, 300 mmol) are covered with dry tetrahydrofuran (THF, 125 ml) and activated by the addition of a few dozen drops of 1,2-dibromoethane and chlorotrimethylsilane (TMSCl). After stirring for 10 minutes, a solution of 2-cyclohexenyl chloride (1.0 equivalent, 29.15 g, 250 mmol) in tetrahydrofuran (THF, 250 ml) is added dropwise at 0° C. within 2 hours. The resulting mixture is stirred under nitrogen at 0° C. for 36 hours and centrifuged. The reaction gives a 2-cyclohexenylzinc chloride solution (400 ml, 0.5 M solution in THF, 0.2 mol, 80% yield determined by iodinolysis).

2-Cyclohexenylzinc chloride can also be synthesized by an indirect route according to the scheme below.

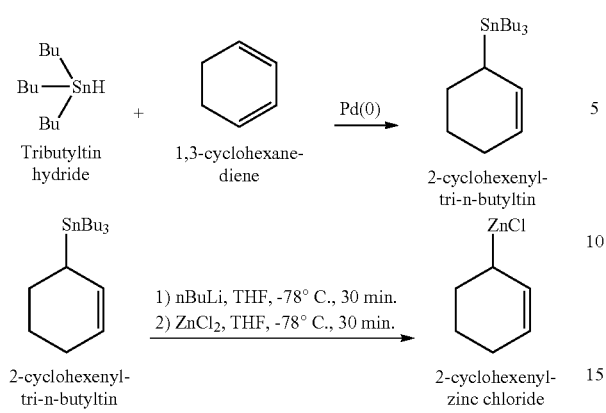

2-cyclohexenyl-tri-n-butyltin is first prepared from a palladium(0)-catalyzed 1,4-addition of tributyltin hydride to 1,3-cyclohexanediene, as described previously in Miyake and Yamamura, 1992, *Chem. Lett.* 3, 507-508.

To a solution a 1,3-cyclohexanediene (72.12 g, 85.75 ml, 0.9 mol) and tetrakis(triphenylphosphine)-palladium(0) (Pd (PPh$_3$)$_4$, 34.67 g, 30 mmol) in benzene (1.5 l) under nitrogen atmosphere, is added tributyltin hydride (Bu$_3$SnH, 87.32 g, 300 mmol) in benzene (750 ml) dropwise at ambient temperature and stirred for 10 minutes. The solvent is then removed under reduced pressure. The product is purified by silica gel chromatography to give 2-cyclohexenyl-tri-n-butyltin (86.86 g, 234 mmol) in 78% yield based on the amount of tributyltin hydride.

2-Cyclohexenyl-tri-n-butyltin is sequentially transmetalated by treatment with 1 equivalent of n-butyllithium (n-BuLi) and 1 equivalent of zinc chloride (ZnCl$_2$) to form 2-cyclohexenylzinc chloride in tetrahydrofuran (THF) solution as described in Reddy et al., 2004, *J. Am. Chem. Soc.* 126(20), 6230-6231.

To a solution of 2-cyclohexenyl-tri-n-butyltin (74.24 g, 200 mmol) in tetrahydrofuran (THF, 200 ml) at −78° C. under nitrogen is added a butyllithium solution (nBuLi, 80 ml, 2.5 M solution in hexane, 200 mmol). After an additional 30 minutes stirring, a zinc chloride solution (ZnCl$_2$, 200 ml, 1 M solution in THF, 27.26 g, 200 mmol) is added and stirring is continued for 30 minutes at −78° C. to give a 2-cyclohexenylzinc chloride solution (400 ml, 0.5 M solution in THF, 0.2 mol).

F.2) Addition of 2-cyclohexenylzinc Chloride to the Formyl Carbon

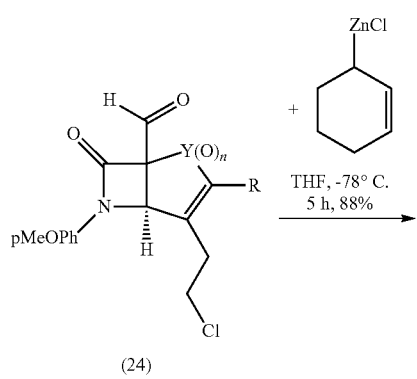

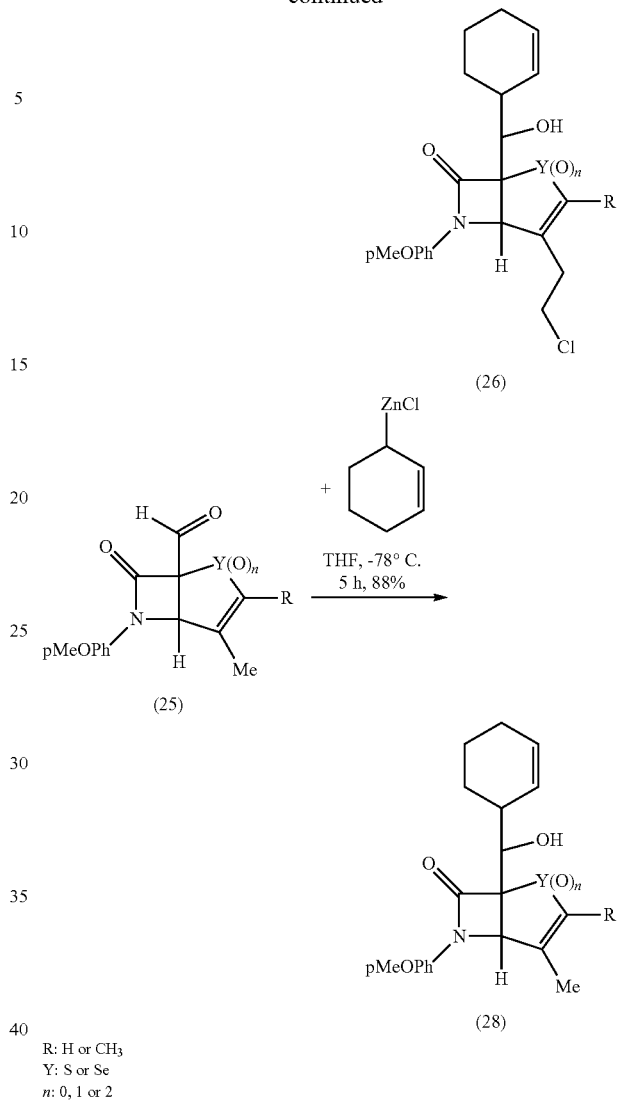

R: H or CH$_3$
Y: S or Se
n: 0, 1 or 2

The attachment of the 2-cyclohexenyl group to the formyl carbon of 24 and 25 is accomplished with high selectivity by reaction of 2 equivalents of 2-cyclohexenylzinc chloride with 1 equivalent of the aldehyde in tetrahydrofuran (THF) as described in Reddy et al., 2004, *J. Am. Chem. Soc.* 126(20), 6230-6231.

General Procedure:

To a solution of freshly prepared 2-cyclohexenylzinc chloride (10 ml, 0.5 M solution in THF, 5 mmol) at −78° C. under nitrogen is added a −78° C. solution of aldehyde 24a-l or 25a-l (2.5 mmol in 3 ml of THF). After stirring for 5 h at −78° C., the reaction mixture is quenched with water (10 ml) then extracted with ethyl acetate (3×10 ml). The combined organic layers are dried over anhydrous sodium sulfate (Na$_2$SO$_4$) and solvent is removed in vacuo to give the crude product 26a-l or 28a-l (88%, 2.2 mmol). The crude product is purified by column chromatography (silica gel, ethylacetate/hexanes, 1:10 to 1:2) to give a pure major diastereomer (83%, 2.0 mmol) and a minor diastereomer (5%, 0.1 mmol) (20:1 ratio).

Amount of Starting Materials and Yields:

24a-l (2.5 mmol): 0.809 g for 24a wherein Y is S; R is H and n is 0

0.845 g for 24b wherein Y is S; R is Me and n is 0
0.927 g for 24c wherein Y is Se; R is H and n is 0
0.962 g for 24d wherein Y is Se; R is Me and n is 0
0.849 g for 24e wherein Y is S; R is H and n is 1
0.885 g for 24f wherein Y is S; R is Me and n is 1
0.967 g for 24g wherein Y is Se; R is H and n is 1
1.002 g for 24h wherein Y is Se; R is Me and n is 1
0.889 g for 24i wherein Y is S; R is H and n is 2
0.925 g for 24j wherein Y is S; R is Me and n is 2
1.007 g for 24k wherein Y is Se; R is H and n is 2
1.042 g for 24l wherein Y is Se; R is Me and n is 2
25a-l (2.5 mmol): 0.688 g for 25a wherein Y is S; R is H and n is 0
0.723 g for 25b wherein Y is S; R is Me and n is 0
0.806 g for 25c wherein Y is Se; R is H and n is 0
0.841 g for 25d wherein Y is Se; R is Me and n is 0
0.728 g for 25e wherein Y is S; R is H and n is 1
0.763 g for 25f wherein Y is S; R is Me and n is 1
0.846 g for 25g wherein Y is Se; R is H and n is 1
0.881 g for 25h wherein Y is Se; R is Me and n is 1
0.768 g for 25i wherein Y is S; R is H and n is 2
0.803 g for 25j wherein Y is S; R is Me and n is 2
0.886 g for 25k wherein Y is Se; R is H and n is 2
0.921 g for 25l wherein Y is Se; R is Me and n is 2
26a-l (2.2 mmol): 0.893 g for 26a wherein Y is S; R is H and n is 0
0.924 g for 26b wherein Y is S; R is Me and n is 0
0.996 g for 26c wherein Y is Se; R is H and n is 0
1.027 g for 26d wherein Y is Se; R is Me and n is 0
0.928 g for 26e wherein Y is S; R is H and n is 1
0.959 g for 26f wherein Y is S; R is Me and n is 1
1.031 g for 26g wherein Y is Se; R is H and n is 1
1.062 g for 26h wherein Y is Se; R is Me and n is 1
0.963 g for 26i wherein Y is S; R is H and n is 2
0.994 g for 26j wherein Y is S; R is Me and n is 2
1.067 g for 26k wherein Y is Se; R is H and n is 2
1.097 g for 26l wherein Y is Se; R is Me and n is 2
28a-l (2.2 mmol): 0.786 g for 28a wherein Y is S; R is H and n is 0
0.817 g for 28b wherein Y is S; R is Me and n is 0
0.890 g for 28c wherein Y is Se; R is H and n is 0
0.920 g for 28d wherein Y is Se; R is Me and n is 0
0.822 g for 28e wherein Y is S; R is H and n is 1
0.852 g for 28f wherein Y is S; R is Me and n is 1
0.925 g for 28g wherein Y is Se; R is H and n is 1
0.956 g for 28h wherein Y is Se; R is Me and n is 1
0.857 g for 28i wherein Y is S; R is H and n is 2
0.888 g for 28j wherein Y is S; R is Me and n is 2
0.960 g for 28k wherein Y is Se; R is H and n is 2
0.991 g for 28l wherein Y is Se; R is Me and n is 2

G. Attachment of an Isopropyl Group on the Formyl Carbon

The attachment of the isopropyl group on the formyl carbon is accomplished in two steps.

G.1) Preparation of 2-propylzinc Chloride

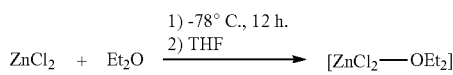

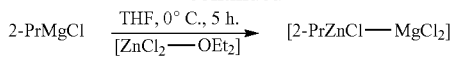

2-propylzinc chloride (2-PrZnCl) is obtained from 2-propylmagnesium chloride (2-PrMgCl) by transmetallation using zinc chloride etherate (ZnCl$_2$—OEt$_2$) in tetrahydrofuran (THF).

Zinc chloride (ZnCl$_2$, 27.26 g, 0.2 mol) is dissolved in dry diethyl ether (Et$_2$O, 21 ml, 0.2 mol) at −78° C. The mixture is stirred up to 12 hours at −78° C. and then diluted with tetrahydrofuran (THF, 279 ml). A solution of 2-propylmagnesium chloride (100 ml, 2 M solution in THF) is added to the zinc chloride etherate solution (ZnCl$_2$—OEt$_2$ in THF, 300 ml, 0.2 mol). The mixture is stirred up to 5 hours at 0° C. to give a 2-propylzinc chloride solution (400 ml, 0.5 M solution in THF, 0.2 mol).

G.2) Addition of 2-propylzinc Chloride to the Formyl Carbon

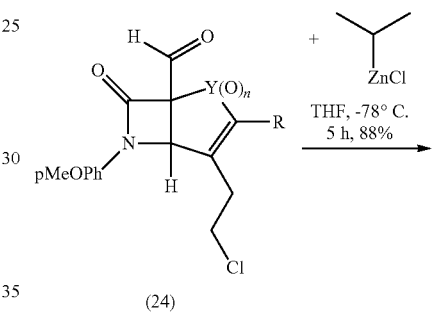

(24)

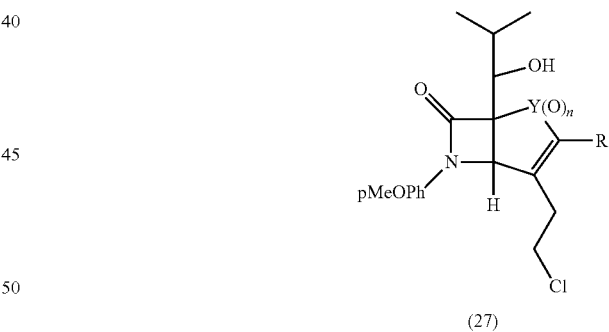

(27)

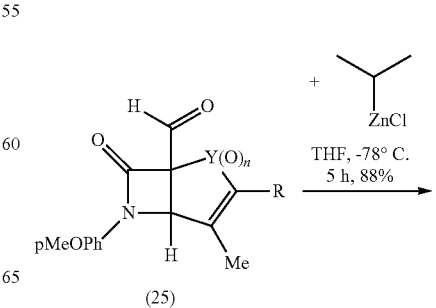

(25)

-continued

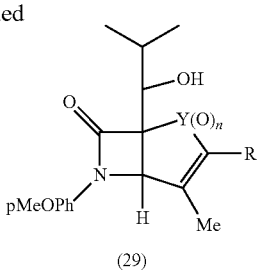

(29)

R: H or CH₃
Y: S or Se
n: 0, 1 or 2

The attachment of the 2-propyl group to the formyl carbon of 24 and 25 is accomplished with high selectivity by reaction of 2 equivalents of 2-propylzinc chloride with 1 equivalent of the aldehyde in tetrahydrofuran (THF).

General Procedure:

To a freshly prepared solution of 2-propylzinc chloride (10 ml, 0.5 M solution in THF, 5 mmol) at −78° C. under nitrogen is added a −78° C. solution of aldehyde 24a-l or 25a-l (2.5 mmol in 3 ml of THF). After stirring for 5 hours at −78° C., the reaction mixture is quenched with water (10 ml) and then extracted with ethyl acetate (EtOAc, 3×10 ml). The combined organic layers are dried over anhydrous sodium sulfate ($Na_2SO_4$) and solvent is removed in vacuo. The crude mixture is purified by column chromatography (silica gel, ethyl acetate/hexanes, 1:10 to 1:2) to give the corresponding 2-propyl derivatives 27a-l or 29a-l (88%, 2.2 mmol).

Amount of Starting Materials and Yields:

24a-l (2.5 mmol): same as for addition of 2-cyclohex-enylzinc chloride to the formyl carbon in F.2)

25a-l (2.5 mmol): same as for addition of 2-cyclohex-enylzinc chloride to the formyl carbon in F.2)

27a-l (2.2 mmol): 0.809 g for 27a wherein Y is S; R is H and n is 0
0.840 g for 27b wherein Y is S; R is Me and n is 0
0.913 g for 27c wherein Y is Se; R is H and n is 0
0.943 g for 27d wherein Y is Se; R is Me and n is 0
0.845 g for 27e wherein Y is S; R is H and n is 1
0.875 g for 27f wherein Y is S; R is Me and n is 1
0.948 g for 27g wherein Y is Se; R is H and n is 1
0.979 g for 27h wherein Y is Se; R is Me and n is 1
0.880 g for 27i wherein Y is S; R is H and n is 2
0.911 g for 27j wherein Y is S; R is Me and n is 2
0.983 g for 27k wherein Y is Se; R is H and n is 2
1.014 g for 27l wherein Y is Se; R is Me and n is 2

29a-l (2.2 mmol): 0.703 g for 29a wherein Y is S; R is H and n is 0
0.734 g for 29b wherein Y is S; R is Me and n is 0
0.806 g for 29c wherein Y is Se; R is H and n is 0
0.837 g for 29d wherein Y is Se; R is Me and n is 0
0.738 g for 29e wherein Y is S; R is H and n is 1
0.769 g for 29f wherein Y is S; R is Me and n is 1
0.841 g for 29g wherein Y is Se; R is H and n is 1
0.872 g for 29h wherein Y is Se; R is Me and n is 1
0.773 g for 29i wherein Y is S; R is H and n is 2
0.804 g for 29j wherein Y is S; R is Me and n is 2
0.876 g for 29k wherein Y is Se; R is H and n is 2
0.907 g for 29l wherein Y is Se; R is Me and n is 2

H. Nitrogen Deprotection

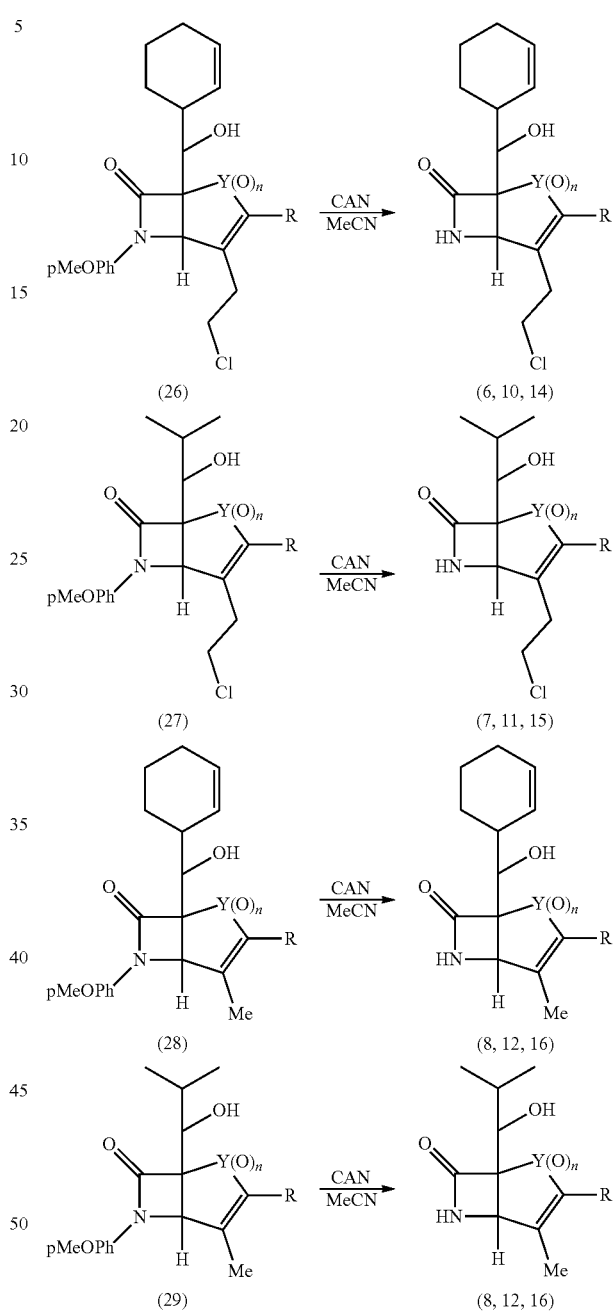

The p-methoxyphenyl N-protecting group (p-anisyl moiety) of protected β-lactams 26-29 is oxidatively cleaved using ceric ammonium nitrate (CAN) in aqueous acetonitrile (MeCN), to afford the corresponding N-unsubstituted β-lactams as described in Kronenthal et al., 1982, *J. Org. Chem.* 47(14), 2765-2768, in Konaklieva et al., 1997, *Tetrahedron Lett.* 38(50), 8647-8650 and in Ren et al., 1998, *J. Org. Chem.* 63, 8898-8917.

General Procedure:

To a solution of N-p-methoxy-phenyl β-lactam 26a-l, 27a-l, 28a-l or 29a-l (1 equivalent, 2.0 mmol) in acetonitrile (MeCN, 30 ml) at 0° C. is added a pre-cooled solution of ceric ammonium nitrate (CAN, 3 equivalents, 3.29 g, 6.0 mmol in 30 ml $H_2O$). After stirring for 1 hour at 0° C., the reaction mixture is poured into an aqueous sodium bisulfite solution ($NaHSO_3$, 5% in $H_2O$, 30 ml). The aqueous mixture is extracted with diethylether ($Et_2O$, 3×15 ml). The combined organic layers are treated with an aqueous sodium bicarbonate solution ($NaHCO_3$, 5% in $H_2O$, 30 ml) and the aqueous layer is back-washed with one portion of diethylether ($Et_2O$, 15 ml). The recombined organic layers are dried over anhydrous magnesium sulfate ($MgSO_4$) and filtered. The solvent is removed in vacuo to give the crude product which is purified on a silica gel column using ethylacetate (EtOAc) as eluent to give the pure N-unsubstituted β-lactams (6a)-(6d), (7a)-(7d), (8a)-(8d), (9a)-(9d), (10a)-(10d), (11a)-(11d), (12a)-(12d), (13a)-(13d), (14a)-(14d), (15a)-(15d), (16a)-(16d), (17a)-(17d) (90%, 1.8 mmol).

Amount of Starting Materials and Yields:

26a-l (2.0 mmol): 0.812 g for 26a wherein Y is S; R is H and n is 0
   0.840 g for 26b wherein Y is S; R is Me and n is 0
   0.906 g for 26c wherein Y is Se; R is H and n is 0
   0.934 g for 26d wherein Y is Se; R is Me and n is 0
   0.844 g for 26e wherein Y is S; R is H and n is 1
   0.872 g for 26f wherein Y is S; R is Me and n is 1
   0.938 g for 26g wherein Y is Se; R is H and n is 1
   0.966 g for 26h wherein Y is Se; R is Me and n is 1
   0.876 g for 26i wherein Y is S; R is H and n is 2
   0.904 g for 26j wherein Y is S; R is Me and n is 2
   0.970 g for 26k wherein Y is Se; R is H and n is 2
   0.998 g for 26l wherein Y is Se; R is Me and n is 2
27a-l (2.0 mmol): 0.735 g for 27a wherein Y is S; R is H and n is 0
   0.764 g for 27b wherein Y is S; R is Me and n is 0
   0.830 g for 27c wherein Y is Se; R is H and n is 0
   0.857 g for 27d wherein Y is Se; R is Me and n is 0
   0.768 g for 27e wherein Y is S; R is H and n is 1
   0.795 g for 27f wherein Y is S; R is Me and n is 1
   0.862 g for 27g wherein Y is Se; R is H and n is 1
   0.890 g for 27h wherein Y is Se; R is Me and n is 1
   0.800 g for 27i wherein Y is S; R is H and n is 2
   0.828 g for 27j wherein Y is S; R is Me and n is 2
   0.894 g for 27k wherein Y is Se; R is H and n is 2
   0.922 g for 27l wherein Y is Se; R is Me and n is 2
28a-l (2.0 mmol): 0.715 g for 28a wherein Y is S; R is H and n is 0
   0.743 g for 28b wherein Y is S; R is Me and n is 0
   0.809 g for 28c wherein Y is Se; R is H and n is 0
   0.837 g for 28d wherein Y is Se; R is Me and n is 0
   0.747 g for 28e wherein Y is S; R is H and n is 1
   0.775 g for 28f wherein Y is S; R is Me and n is 1
   0.841 g for 28g wherein Y is Se; R is H and n is 1
   0.869 g for 28h wherein Y is Se; R is Me and n is 1
   0.779 g for 28i wherein Y is S; R is H and n is 2
   0.807 g for 28j wherein Y is S; R is Me and n is 2
   0.873 g for 28k wherein Y is Se; R is H and n is 2
   0.901 g for 28l wherein Y is Se; R is Me and n is 2
29a-l (2.0 mmol): 0.639 g for 29a wherein Y is S; R is H and n is 0
   0.667 g for 29b wherein Y is S; R is Me and n is 0
   0.733 g for 29c wherein Y is Se; R is H and n is 0
   0.761 g for 29d wherein Y is Se; R is Me and n is 0
   0.671 g for 29e wherein Y is S; R is H and n is 1
   0.699 g for 29f wherein Y is S; R is Me and n is 1
   0.764 g for 29g wherein Y is Se; R is H and n is 1
   0.793 g for 29h wherein Y is Se; R is Me and n is 1
   0.703 g for 29i wherein Y is S; R is H and n is 2
   0.731 g for 29j wherein Y is S; R is Me and n is 2
   0.796 g for 29k wherein Y is Se; R is H and n is 2
   0.824 g for 29l wherein Y is Se; R is Me and n is 2
6a-d (1.8 mmol): 0.540 g for 6a wherein Y is S; R is H
   0.565 g for 6b wherein Y is S; R is Me
   0.624 g for 6c wherein Y is Se; R is H
   0.649 g for 6d wherein Y is Se; R is Me
7a-d (1.8 mmol): 0.471 g for 7a wherein Y is S; R is H
   0.496 g for 7b wherein Y is S; R is Me
   0.556 g for 7c wherein Y is Se; R is H
   0.581 g for 7d wherein Y is Se; R is Me
8a-d (1.8 mmol): 0.452 g for 8a wherein Y is S; R is H
   0.478 g for 8b wherein Y is S; R is Me
   0.537 g for 8c wherein Y is Se; R is H
   0.562 g for 8d wherein Y is Se; R is Me
9a-d (1.8 mmol): 0.384 g for 9a wherein Y is S; R is H
   0.409 g for 9b wherein Y is S; R is Me
   0.468 g for 9c wherein Y is Se; R is H
   0.494 g for 9d wherein Y is Se; R is Me
10a-d (1.8 mmol): 0.568 g for 10a wherein Y is S; R is H
   0.594 g for 10b wherein Y is S; R is Me
   0.653 g for 10c wherein Y is Se; R is H
   0.678 g for 10d wherein Y is Se; R is Me
11a-d (1.8 mmol): 0.500 g for 11a wherein Y is S; R is H
   0.525 g for 11b wherein Y is S; R is Me
   0.584 g for 11c wherein Y is Se; R is H
   0.610 g for 11d wherein Y is Se; R is Me
12a-d (1.8 mmol): 0.481 g for 12a wherein Y is S; R is H
   0.506 g for 12b wherein Y is S; R is Me
   0.566 g for 12c wherein Y is Se; R is H
   0.591 g for 12d wherein Y is Se; R is Me
13a-d (1.8 mmol): 0.413 g for 13a wherein Y is S; R is H
   0.438 g for 13b wherein Y is S; R is Me
   0.497 g for 13c wherein Y is Se; R is H
   0.522 g for 13d wherein Y is Se; R is Me
14a-d (1.8 mmol): 0.597 g for 14a wherein Y is S; R is H
   0.623 g for 14b wherein Y is S; R is Me
   0.682 g for 14c wherein Y is Se; R is H
   0.707 g for 14d wherein Y is Se; R is Me
15a-d (1.8 mmol): 0.529 g for 15a wherein Y is S; R is H
   0.554 g for 15b wherein Y is S; R is Me
   0.613 g for 15c wherein Y is Se; R is H
   0.638 g for 15d wherein Y is Se; R is Me
16a-d (1.8 mmol): 0.510 g for 16a wherein Y is S; R is H
   0.535 g for 16b wherein Y is S; R is Me
   0.594 g for 16c wherein Y is Se; R is H
   0.620 g for 16d wherein Y is Se; R is Me
17a-d (1.8 mmol): 0.442 g for 17a wherein Y is S; R is H
   0.467 g for 17b wherein Y is S; R is Me
   0.526 g for 17c wherein Y is Se; R is H
   0.551 g for 17d wherein Y is Se; R is Me

I. Carbamylation

I.1 Preparation of Carboxylic-Carbonic Anhydride Derivatives

The preparation of carboxylic-carbonic anhydride derivatives can be carried out by reacting methyl chlorothiolformate with carboxylic acids (e.g., acetic, propionic, n-butanoic, n-pentanoic, n-hexanoic, n-octanoic, n-decanoic, lauric, myristic, palmitic, stearic, oleic, linoleic, linolenic and arachidonic acids) and coupling the resultant compounds with N-hydroxysuccinimide as described in the following example.

I.1.1) Preparation of [(isobutanoyloxy)carbonyloxy] Succinimide

The preparation of [(isobutanoyloxy)carbonyloxy] succinimide is carried out in two steps.

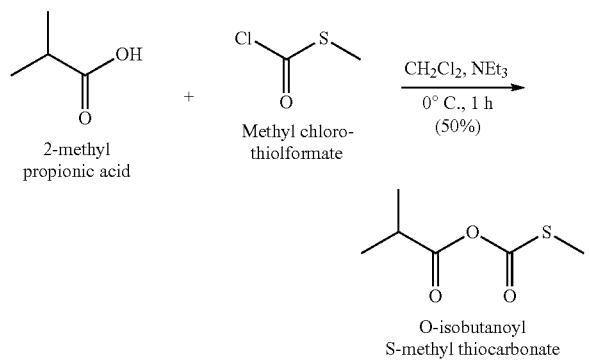

First, O-isobutanoyl S-methyl thiocarbonate is prepared from 2-methyl propionic acid and methyl-chlorothiolformate in the presence of trietylamine (NEt₃), as described in Khan et al., 1999. *J. Agric. Food Chem.* 47, 3269-3273 with modifications.

2-methyl propionic acid (($CH_3)_2CHCOOH$, 1.02 ml, 0.97 g, 11 mmol) is dissolved in dry dichloromethane ($CH_2Cl_2$, 50 ml) containing dry triethylamine ($NEt_3$, 1.84 ml, 1.34 g, 13.24 mmol) with stirring under dry nitrogen. The solution is cooled to 0° C. and methylchloroformate (1.04 ml, 1.34 g, 12.12 mmol), dissolved in dry dichloromethane ($CH_2Cl_2$, 20 ml), is added dropwise over 20 min. The solution is stirred at 0° C. for 1 hour and incubated at room temperature overnight. The reaction mixture is then washed with ice-cold 5% aqueous sodium bicarbonate ($NaHCO_3$, 50 ml) and 5% aqueous citric acid ($HOC(COOH)(CH_2COOH)_2$, 50 ml). The organic layer is dried over anhydrous sodium sulfate ($Na_2SO_4$), filtered, and concentrated in vacuo (10 mm Hg) at 0° C. to give O-isobutanoyl S-methyl thiocarbonate (0.89 g, 5.5 mmol, 50%).

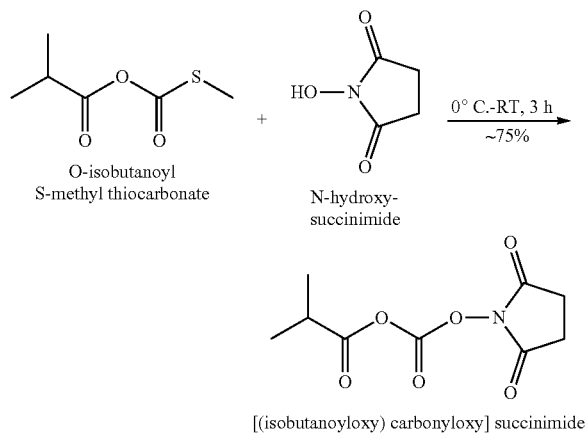

Second, [(isobutanoyloxy)carbonyloxy] succinimide is prepared from O-isobutanoyl S-methyl thiocarbonate and N-hydroxysuccinimide, as described in Gallop et al., 2004. PCT US04-043823.

To a solution of O-isobutanoyl S-methyl thiocarbonate (0.39 g, 2.4 mmol) in dichloromethane ($CH_2Cl_2$, 5 ml) is added N-hydroxysuccinimide (0.55 g, 4.75 mmol). The reaction mixture is cooled to 0° C. A solution of 32% (v/v) peracetic acid in acetic acid (1.7 ml, 0.55 g, 7 mmol) is added dropwise over 10 min. The solution is stirred at room temperature for 3 h, diluted with diethyl ether ($Et_2O$, 25 ml), washed with water (2×5 ml), saturated sodium bicarbonate solution ($NaHCO_3$, 5 ml) and brine (5 ml), and dried over anhydrous sodium sulfate ($Na_2SO_4$), filtered and concentrated in vacuo to give [(isobutanoyloxy)carbonyloxy] succinimide (0.41 g, 1.8 mmol, 75%).

I.1.2) Anhydride-Drug Linkage

Anhydride-drug linkage is carried out in one step, as described in Gallop et al., 2004. PCT US04-043823.

To a solution of the drug (1.8 mmol) and sodium bicarbonate ($NaHCO_3$, 0.30 g, 3.6 mmol) in water (7.2 ml) is added a solution of [(isobutanoyloxy)carbonyloxy] succinimide (0.41 g, 1.8 mmol) in acetonitrile (MeCN, 3.6 ml) over 1 min. The reaction mixture is stirred at ambient temperature for 16 hours, diluted with diethyl ether ($Et_2O$, 18 ml) and washed with 0.1 M aqueous potassium hydrogen sulphate ($KHSO_4$, 3×18 ml). The organic phase is separated, dried over anhydrous magnesium sulfate ($MgSO_4$), filtered, and concentrated in vacuo to afford the corresponding anhydride prodrug (1.7 mmol, 95%).

I.2 Preparation of N-acyloxy-alkoxycarbonyl Derivatives

The preparation of N-acyloxy-alkoxycarbonyl derivatives can be carried out by reacting O-(1-chloroalkyl)S-alkyl thiocarbonate with carboxylic acids (e.g., acetic, propionic, n-butanoic, n-pentanoic, n-hexanoic, n-octanoic, n-decanoic, lauric, myristic, palmitic, stearic, oleic, linoleic, linolenic and arachidonic acids) and coupling the resultant compounds with N-hydroxysuccinimide as described in the following example.

I.2.1) Preparation of [(1-isobutanoyloxyethoxy)carbonyloxy] Succinimide

The preparation of [(1-isobutanoyloxyethoxy)carbonyloxy] succinimide is carried out in three steps, as described in Gallop et al., 2004. PCT US04-043823.

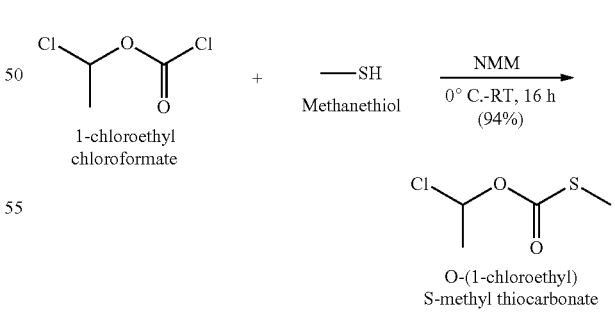

First, O-(1-chloroethyl)S-methyl thiocarbonate is prepared from 1-chloroethyl chloroformate and methanethiol in the presence of 4-methylmorpholine (NMM).

A solution of 1-chloroethyl chloroformate (10.80 ml, 14.30 g, 100 mmol) and methanethiol (4.81 g, 100 mmol) in dichloromethane ($CH_2Cl_2$, 30 ml) is cooled to 0° C. in an ice-water bath. 4-methylmorpholine (10.99 ml, 10.11 g, 100 mmol) is added dropwise over 1 hour. The reaction mixture is stirred at room temperature for 16 hours, diluted with dichloromethane (CH$_2$Cl$_2$, 60 ml), washed with water (30 ml), saturated bicarbonate solution (NaHCO$_3$, 30 ml) and brine (30 ml), dried over anhydrous sodium sulfate (Na$_2$SO$_4$), filtered and concentrated in vacuo. The residue is purified by vacuum distillation (95° C., 20 Torr) to provide O-(1-chloroethyl)S-methyl thiocarbonate as colorless liquid (14.47 g, 94 mmol, 94%).

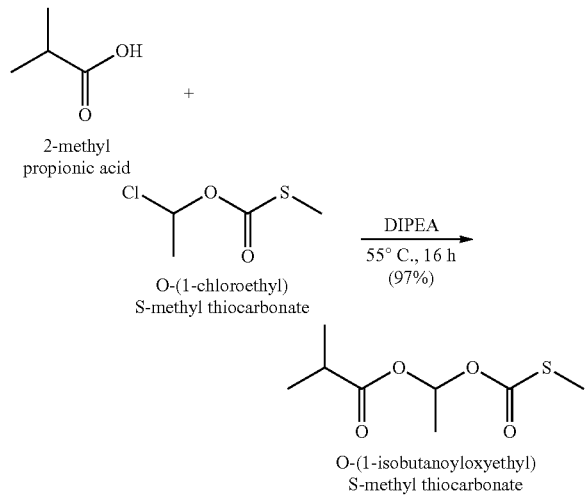

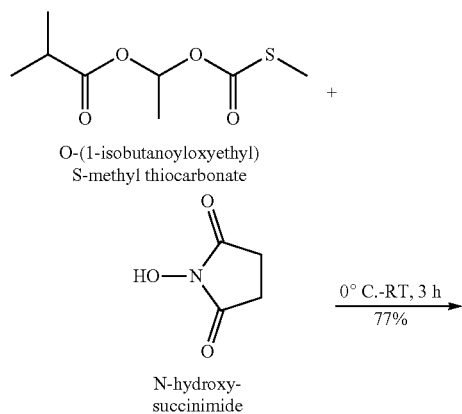

Second, O-(1-isobutanoyloxyethyl)S-methyl thiocarbonate is prepared from 2-methyl propionic acid and 0-(1-chloroethyl)S-methyl thiocarbonate in the presence of N,N-diisopropylethylamine (DIPEA).

O-(1-chloroethyl)S-methyl thiocarbonate (0.39 g, 2.5 mmol) is dissolved in 2-methyl propionic acid ((CH$_3$)$_2$CH$_2$COOH, 0.33 g, 0.35 ml, 3.8 mmol). The mixture is slowly added to a pre-mixed solution of 2-methyl propionic acid ((CH$_3$)$_2$CHCOOH, 0.33 g, 0.35 ml, 3.8 mmol) and N,N-diisopropylethylamine (DIPEA, [(CH$_3$)$_2$CH]$_2$NC$_2$H$_5$, 0.49 g, 3.8 mmol). The reaction mixture is heated to 55° C. for 16 hours, diluted with diethyl ether (Et$_2$O, 62.5 ml), washed with water (2×12.5 ml), saturated bicarbonate solution (NaHCO$_3$, 2×12.5 ml), and brine (12.5 ml), dried over anhydrous sodium sulfate (Na$_2$SO$_4$), filtered and concentrated in vacuo to give O-(1-isobutanoyloxyethyl)S-methyl thiocarbonate as colourless liquid (0.50 g, 2.4 mmol, 97%).

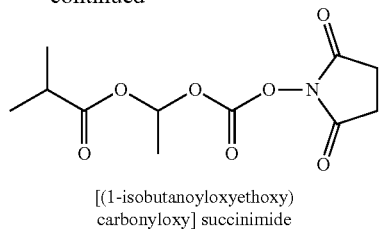

[(1-isobutanoyloxyethoxy) carbonyloxy] succinimide

Third, [(1-isobutanoyloxyethoxy)carbonyloxy] succinimide is prepared from 0-(1-isobutanoyloxyethyl)S-methyl thiocarbonate and N-hydroxysuccinimide.

To a solution of O-(1-isobutanoyloxyethyl)S-methyl thiocarbonate (0.50 g, 2.4 mmol) in dichloromethane (CH$_2$Cl$_2$, 5 ml) is added N-hydroxysuccinimide (0.55 g, 4.75 mmol). The reaction mixture is cooled to 0° C. A solution of 32% (v/v) peracetic acid in acetic acid (1.7 ml, 0.55 g, 7 mmol) is added dropwise over 10 min. The solution is stirred at room temperature for 3 h, diluted with diethyl ether (Et$_2$O, 25 ml), washed with water (2×5 ml), saturated sodium bicarbonate solution (NaHCO$_3$, 5 ml) and brine (5 ml), and dried over anhydrous sodium sulfate (Na$_2$SO$_4$), filtered and concentrated in vacuo to give [(1-isobutanoyloxyethoxy) carbonyloxy] succinimide as colorless oil (0.50 g, 1.8 mmol, 77%).

I.2.2) Carbamate-Drug Linkage

Carbamate-drug linkage is carried out in one step, as described in Gallop et al., 2004. PCT US04-043823.

To a solution of the drug (1.8 mmol) and sodium bicarbonate (NaHCO$_3$, 0.30 g, 3.6 mmol) in water (7.2 ml) is added a solution of [(1-isobutanoyloxyethoxy)carbonyloxy] succinimide (0.49 g, 1.8 mmol) in acetonitrile (MeCN, 3.6 ml) over 1 min. The reaction mixture is stirred at ambient temperature for 16 hours, diluted with diethyl ether (Et$_2$O, 18 ml) and washed with 0.1 M aqueous potassium hydrogen sulphate (KHSO$_4$, 3×18 ml). The organic phase is separated, dried over anhydrous magnesium sulfate (MgSO$_4$), filtered, and concentrated in vacuo to afford the corresponding carbamate prodrug (1.7 mmol, 96%).

I.3 Preparation of N-α-aminoacyl/peptidyl derivatives

The preparation of N-α-aminoacyl/peptidyl derivatives can be carried out by successively reacting 9-fluorenylmethoxycarbonyl (Fmoc) N-protected α-amino acids/peptide acids with thionyl chloride (SOCl$_2$) and methanethiol (CH$_3$SH), and coupling the resultant compounds with N-hydroxysuccinimide as described in the following example. The method utilizes esterification of the α-amino acid/peptide C-terminal, and this in turn demands that all auxiliary α-amino acid/peptide carboxylates and amines be protected.

I.3.1) Preparation of Fmoc-N-(α-aminoacyl/peptidyl)oxy Succinimide

The preparation of Fmoc-N-(α-aminoacyl/peptidyl)oxy succinimide is carried out in three steps.

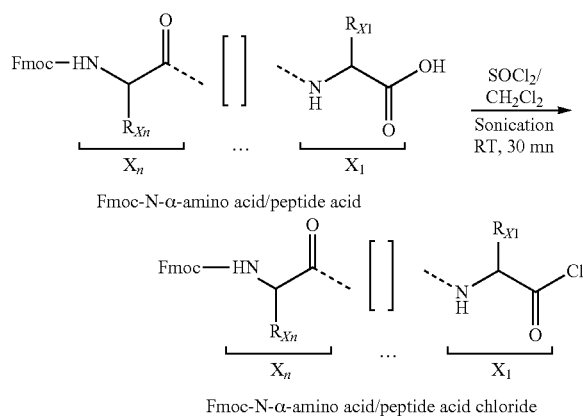

Fmoc-N-α-amino acid/peptide acid

Fmoc-N-α-amino acid/peptide acid chloride

First, Fmoc-N-α-amino acid/peptide acid chloride is prepared from suitably protected Fmoc-N-α-amino acid/peptide acid in the presence of thionyl chloride ($SOCl_2$), as described in Sureshbabu & Hemantha, 2008. *Arkivoc* ii, 243-249.

To a solution of Fmoc-N-α-amino acid/peptide acid (15 mmol) in dichloromethane ($CH_2Cl_2$, 75 ml) is added thionyl chloride ($SOCl_2$, 5.35 g, 45 mmol). The reaction is carried out under ultrasonication (30 min) and monitored by thin layer chromatography and/or gas chromatography analysis until complete conversion of the substrate. The reaction mixture is then concentrated in vacuo and triturated with hexane. The resulting precipitate is filtered and dried in vacuo (70-90%).

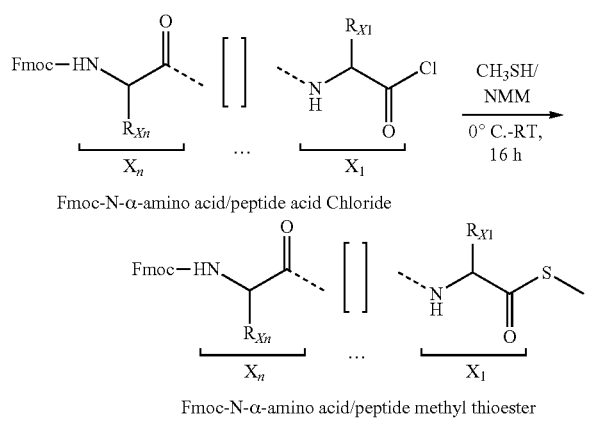

Fmoc-N-α-amino acid/peptide acid Chloride

Fmoc-N-α-amino acid/peptide methyl thioester

Second, Fmoc-N-α-amino acid/peptide methyl thioester is prepared from Fmoc-N-α-amino acid/peptide acid chloride and methanethiol ($CH_3SH$) in the presence of 4-methylmorpholine (NMM), as previously described in 1.2.1) (Step 1).

A solution of Fmoc-N-α-amino acid/peptide acid chloride (10 mmol) and methanethiol (0.48 g, 10 mmol) in dichloromethane ($CH_2Cl_2$, 3 ml) is cooled to 0° C. in an ice-water bath. 4-methylmorpholine (1.10 ml, 1.01 g, 10 mmol) is added dropwise over 1 hour. The reaction mixture is stirred at room temperature for 16 hours, diluted with dichloromethane ($CH_2Cl_2$, 6 ml), washed with water (3 ml), saturated bicarbonate solution ($NaHCO_3$, 3 ml) and brine (3 ml), dried over anhydrous sodium sulfate ($Na_2SO_4$), filtered and concentrated in vacuo. The residue is purified by vacuum distillation (95° C., 20 Torr) to provide Fmoc-N-α-amino acid/peptide methyl thioester (70-90%).

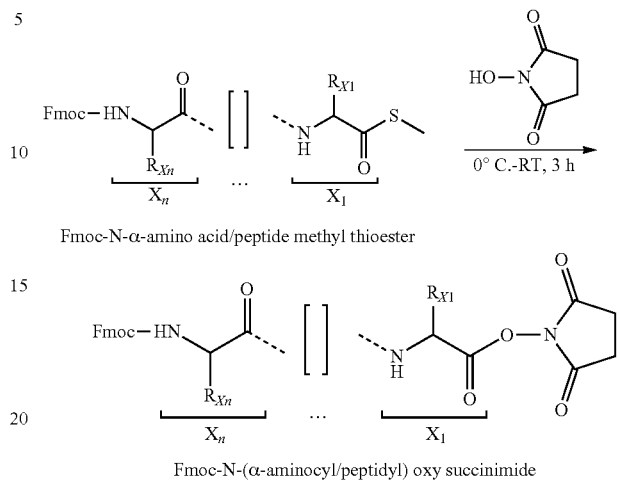

Fmoc-N-α-amino acid/peptide methyl thioester

Fmoc-N-(α-aminocyl/peptidyl) oxy succinimide

Third, Fmoc-N-(α-aminoacyl/peptidyl)oxy succinimide is prepared from Fmoc-N-α-amino acid/peptide methyl thioester and N-hydroxysuccinimide, as previously described in 1.2.1) (Step 3).

To a solution of Fmoc-N-α-amino acid/peptide methyl thioester (2.4 mmol) in dichloromethane ($CH_2Cl_2$, 5 ml) is added N-hydroxysuccinimide (0.55 g, 4.75 mmol). The reaction mixture is cooled to 0° C. A solution of 32% (v/v) peracetic acid in acetic acid (1.7 ml, 0.55 g, 7 mmol) is added dropwise over 10 min. The solution is stirred at room temperature for 3 h, diluted with diethyl ether ($Et_2O$, 25 ml), washed with water (2×5 ml), saturated sodium bicarbonate solution ($NaHCO_3$, 5 ml) and brine (5 ml), and dried over anhydrous sodium sulfate ($Na_2SO_4$), filtered and concentrated in vacuo to give [Fmoc-N-(α-aminoacyl/peptidyl) oxy] succinimide (75-80%).

I.3.2) N-α-amino acid/Peptide-Drug Linkage

N-α-amino acid/peptide-drug linkage is carried out in one step, as previously described in 1.2.2).

To a solution of the drug (1.8 mmol) and sodium bicarbonate ($NaHCO_3$, 0.30 g, 3.6 mmol) in water (7.2 ml) is added a solution of [Fmoc-N-(α-aminoacyl/peptidyl)oxy] succinimide (1.8 mmol) in acetonitrile (MeCN, 3.6 ml) over 1 min. The reaction mixture is stirred at ambient temperature for 16 hours, diluted with diethyl ether ($Et_2O$, 18 ml) and washed with 0.1 M aqueous potassium hydrogen sulphate ($KHSO_4$, 3×18 ml). The organic phase is separated, dried over anhydrous magnesium sulfate ($MgSO_4$), filtered, and concentrated in vacuo to afford the corresponding carbamate prodrug (85-95%).

I.3.3) Fmoc-Group Removal

The deprotection of Fmoc-N-α-aminoacyl/peptidyl derivatives is achieved by using tris(2-aminoethyl)amine (TAEA), as described in Tantry et al., 2006. *Arkivoc* (i), 21-30.

Tris(2-aminoethyl)amine (TAEA, 5 ml, 4.88 g, 33.4 mmol) is added to a solution of Fmoc-N-α-aminoacyl/peptidyl derivative (1 mmol) in dichloromethane ($CH_2Cl_2$, 5 ml) and stirred for 20 min. After completion of the reaction, the solution is further diluted with dichloromethane ($CH_2Cl_2$, 30 ml), washed with phosphate buffer (3×5 ml)

and water (3×5 ml). The organic layer is dried over anhydrous sodium sulfate (Na$_2$SO$_4$) and concentrated in vacuo to afford the corresponding Fmoc-deprotected derivative.

I.4 Preparation of (N-(α-aminoacyl/peptidyl)oxy)carbonyl Derivatives

The preparation of (N-(α-aminoacyl/peptidyl)oxy)carbonyl derivatives can be carried out by reacting 9-fluorenylmethoxycarbonyl (Fmoc) N-protected α-amino acids/peptide acids with methylchloro thiolformatate, and coupling the resultant compounds with N-hydroxysuccinimide as described in the following example. As noted above, the method requires that all auxiliary α-amino acid/peptide carboxylates and amines be protected.

I.4.1) Preparation of [(Fmoc-N-(α-aminoacyl/peptidyl)oxy)carbonyloxy] Succinimide The preparation of [(Fmoc-N-(α-aminoacyl/peptidyl)oxy)carbonyloxy] succinimide is carried out in two steps.

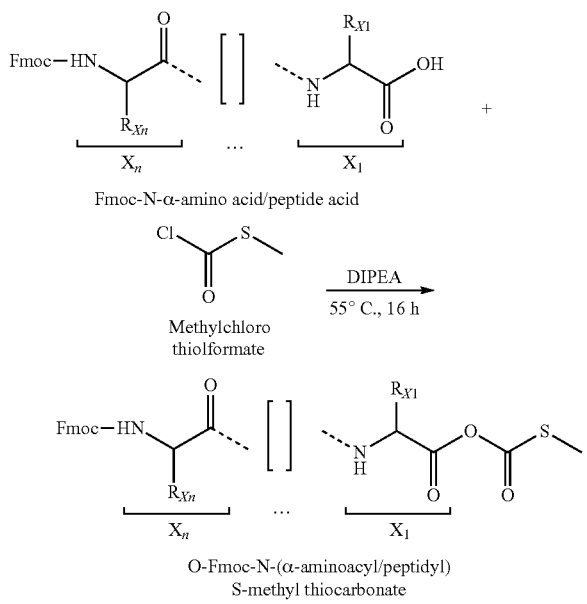

First, O-Fmoc-N-(α-aminoacyl/peptidyl)S-methyl thiocarbonate is prepared from Fmoc-N-α-amino acid/peptide acid and methylchlorothiolformate in the presence of N,N-diisopropylethylamine (DIPEA).

Fmoc-N-α-amino acid/peptide acid (7.6 mmol) is dissolved in dry dichloromethane (CH$_2$Cl$_2$, 35 ml) containing N,N-diisopropylethylamine (DIPEA, [(CH$_3$)$_2$CH]$_2$NC$_2$H$_5$, 0.49 g, 3.8 mmol) with stirring under dry nitrogen. Methylchlorothiolformate (ClCOSCH$_3$, 0.72 ml, 0.93 g, 8.4 mmol), dissolved in dry dichloromethane (CH$_2$Cl$_2$, 15 ml), is added dropwise over 20 min. The reaction mixture is heated to 55° C. for 16 hours, washed with water (2×12.5 ml), saturated bicarbonate solution (NaHCO$_3$, 2×12.5 ml), and brine (12.5 ml), dried over anhydrous sodium sulfate (Na$_2$SO$_4$), filtered and concentrated in vacuo to give O-Fmoc-N-(α-aminoacyl/peptidyl)S-methyl thiocarbonate.

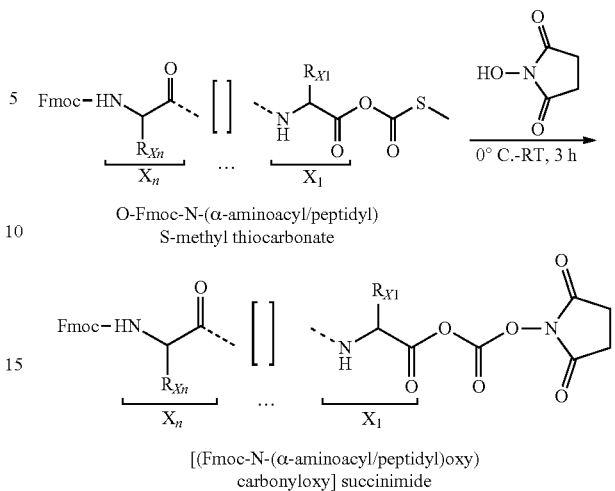

Second, [(Fmoc-N-(α-aminoacyl/peptidyl)oxy)carbonyloxy] succinimide is prepared from O-Fmoc-N-(α-aminoacyl/peptidyl)S-methyl thiocarbonate and N-hydroxysuccinimide, as previously described in 1.2.1) (Step 3).

To a solution of O-Fmoc-N-(α-aminoacyl/peptidyl)S-methyl thiocarbonate (2.4 mmol) in dichloromethane (CH$_2$Cl$_2$, 5 ml) is added N-hydroxysuccinimide (0.55 g, 4.75 mmol). The reaction mixture is cooled to 0° C. A solution of 32% (v/v) peracetic acid in acetic acid (1.7 ml, 0.55 g, 7 mmol) is added dropwise over 10 min. The solution is stirred at room temperature for 3 h, diluted with diethyl ether (Et$_2$O, 25 ml), washed with water (2×5 ml), saturated sodium bicarbonate solution (NaHCO$_3$, 5 ml) and brine (5 ml), and dried over anhydrous sodium sulfate (Na$_2$SO$_4$), filtered and concentrated in vacuo to give [Fmoc-N-(α-aminoacyl/peptidyl)carbonyloxy] succinimide (75-80%).

1.4.2) (Fmoc-N-(α-aminoacyl/peptidyl)oxy)carbonyl-drug Linkage (Fmoc-N-(α-aminoacyl/peptidyl)oxy)carbonyl-drug linkage is carried out in one step, as previously described in 1.2.2).

To a solution of the drug (1.8 mmol) and sodium bicarbonate (NaHCO$_3$, 0.30 g, 3.6 mmol) in water (7.2 ml) is added a solution of [(Fmoc-N-(α-aminoacyl/peptidyl)oxy)carbonyloxy] succinimide (1.8 mmol) in acetonitrile (MeCN, 3.6 ml) over 1 min. The reaction mixture is stirred at ambient temperature for 16 hours, diluted with diethyl ether (Et$_2$O, 18 ml) and washed with 0.1 M aqueous potassium hydrogen sulphate (KHSO$_4$, 3×18 ml). The organic phase is separated, dried over anhydrous magnesium sulfate (MgSO$_4$), filtered, and concentrated in vacuo to afford the corresponding carbamate prodrug (85-95%).

1.4.3) Fmoc-Group Removal

The deprotection of (Fmoc-N-(α-aminoacyl/peptidyl)oxy)carbonyl derivatives is achieved by using tris(2-aminoethyl)amine (TAEA), as previously described in 1.3.3).

Tris(2-aminoethyl)amine (TAEA, 5 ml, 4.88 g, 33.4 mmol) is added to a solution of (Fmoc-N-(α-aminoacyl/peptidyl)oxy)carbonyl derivative (1 mmol) in dichloromethane (CH$_2$Cl$_2$, 5 ml) and stirred for 20 min. After completion of the reaction, the solution is further diluted with dichloromethane (CH$_2$Cl$_2$, 30 ml), washed with phosphate buffer (3×5 ml) and water (3×5 ml). The organic layer is dried over anhydrous sodium sulfate (Na$_2$SO$_4$) and concentrated in vacuo to afford the corresponding Fmoc-deprotected derivative.

I.5 Preparation of (N-(α-aminoacyl/peptidyl)oxyethoxy)carbonyl Derivatives

The preparation of (N-(α-aminoacyl/peptidyl)oxyethoxy)carbonyl derivatives can be carried out by reacting 9-fluorenylmethoxycarbonyl (Fmoc) N-protected α-amino acids/peptide acids with 0-(1-chloroethyl)S-methyl thiocarbonate, and coupling the resultant compounds with N-hydroxysuccinimide as described in the following example. As noted above, the method requires that all auxiliary α-amino acid/peptide carboxylates and amines be protected.

1.5.1) Preparation of [(Fmoc-N-(α-aminoacyl/peptidyl)oxyethoxy)carbonyloxy] Succinimide The preparation of [(Fmoc-N-(α-aminoacyl/peptidyl)oxyethoxy)carbonyloxy] succinimide is carried out in three steps.

First, O-(1-chloroethyl)S-methyl thiocarbonate is prepared from 1-chloroethyl chloroformate and methanethiol in the presence of 4-methylmorpholine (NMM), as previously described in 1.2.1).

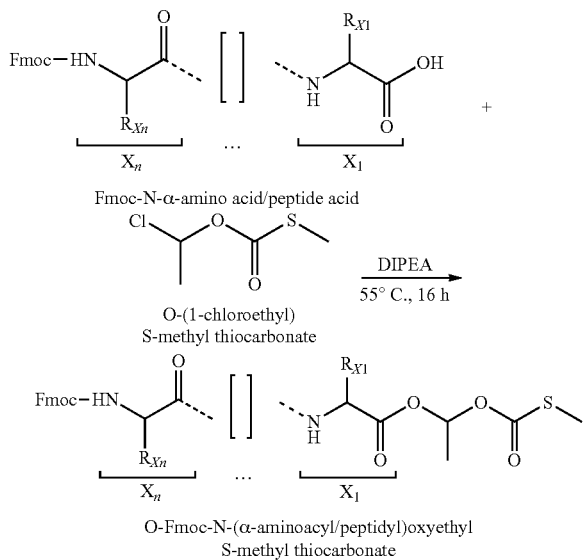

Second, O-Fmoc-N-(α-aminoacyl/peptidyl)oxyethyl S-methyl thiocarbonate is prepared from Fmoc-N-α-amino acid/peptide acid and O-(1-chloroethyl)S-methyl thiocarbonate in the presence of N,N-diisopropylethylamine (DIPEA).

Fmoc-N-α-amino acid/peptide acid (7.6 mmol) is dissolved in dry dichloromethane (CH$_2$Cl$_2$, 35 ml) containing N,N-diisopropylethylamine (DIPEA, [(CH$_3$)$_2$CH]$_2$NC$_2$H$_5$, 0.49 g, 3.8 mmol) with stirring under dry nitrogen. O-(1-chloroethyl)S-methyl thiocarbonate (1.31 g, 8.4 mmol), dissolved in dry dichloromethane (CH$_2$Cl$_2$, 15 ml), is added dropwise over 20 min. The reaction mixture is heated to 55° C. for 16 hours, washed with water (2×12.5 ml), saturated bicarbonate solution (NaHCO$_3$, 2×12.5 ml), and brine (12.5 ml), dried over anhydrous sodium sulfate (Na$_2$SO$_4$), filtered and concentrated in vacuo to give O-Fmoc-N-(α-aminoacyl/peptidypoxyethyl S-methyl thiocarbonate.

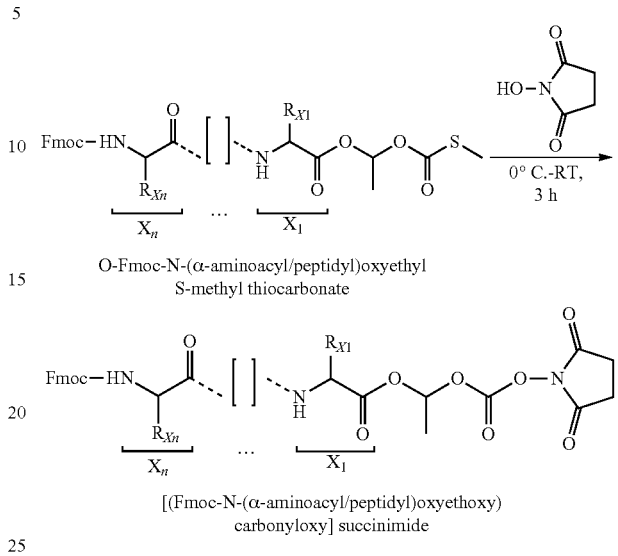

Third, [(Fmoc-N-(α-aminoacyl/peptidyl)oxyethoxy)carbonyloxy] succinimide is prepared from O-Fmoc-N-(α-aminoacyl/peptidyl)oxyethyl S-methyl thiocarbonate and N-hydroxysuccinimide, as previously described in 1.2.1) (Step 3).

To a solution of O-Fmoc-N-(α-aminoacyl/peptidyl)oxyethyl S-methyl thiocarbonate (2.4 mmol) in dichloromethane (CH$_2$Cl$_2$, 5 ml) is added N-hydroxysuccinimide (0.55 g, 4.75 mmol). The reaction mixture is cooled to 0° C. A solution of 32% (v/v) peracetic acid in acetic acid (1.7 ml, 0.55 g, 7 mmol) is added dropwise over 10 min. The solution is stirred at room temperature for 3 h, diluted with diethyl ether (Et$_2$O, 25 ml), washed with water (2×5 ml), saturated sodium bicarbonate solution (NaHCO$_3$, 5 ml) and brine (5 ml), and dried over anhydrous sodium sulfate (Na$_2$SO$_4$), filtered and concentrated in vacuo to give [(Fmoc-N-(α-aminoacyl/peptidyl)oxyethoxy)carbonyloxy] succinimide (75-80%).

1.5.2) (Fmoc-N-(α-aminoacyl/peptidyl)oxyethoxy)carbonyl-drug Linkage (Fmoc-N-(α-aminoacyl/peptidyl)oxyethoxy)carbonyl-drug linkage is carried out in one step, as previously described in 1.2.2).

To a solution of the drug (1.8 mmol) and sodium bicarbonate (NaHCO$_3$, 0.30 g, 3.6 mmol) in water (7.2 ml) is added a solution of [(Fmoc-N-(α-aminoacyl/peptidyl)oxyethoxy)carbonyloxy] succinimide (1.8 mmol) in acetonitrile (MeCN, 3.6 ml) over 1 min. The reaction mixture is stirred at ambient temperature for 16 hours, diluted with diethyl ether (Et$_2$O, 18 ml) and washed with 0.1 M aqueous potassium hydrogen sulphate (KHSO$_4$, 3×18 ml). The organic phase is separated, dried over anhydrous magnesium sulfate (MgSO$_4$), filtered, and concentrated in vacuo to afford the corresponding carbamate prodrug (85-95%).

1.5.3) Fmoc-Group Removal

The deprotection of (Fmoc-N-(α-aminoacyl/peptidyl)oxyethoxy)carbonyl derivatives is achieved by using tris(2-aminoethyl)amine (TAEA), as previously described in 1.3.3).

Tris(2-aminoethyl)amine (TAEA, 5 ml, 4.88 g, 33.4 mmol) is added to a solution of (Fmoc-N-(α-aminoacyl/peptidyl)oxyethoxy)carbonyl derivative (1 mmol) in dichloromethane (CH$_2$Cl$_2$, 5 ml) and stirred for 20 min. After completion of the reaction, the solution is further diluted with dichloromethane (CH$_2$Cl$_2$, 30 ml), washed with phosphate buffer (3×5 ml) and water (3×5 ml). The organic layer is dried over anhydrous sodium sulfate (Na$_2$SO$_4$) and concentrated in vacuo to afford the corresponding Fmoc-deprotected derivative.

Example 2: Synthesis of Tellurium-Containing Compounds

The previously described synthesis methods are used, except as regards the obtention of sodium tellurosulfate and its synthesis and storage conditions.

Preparation of Sodium Tellurosulfate

Sodium tellurosulfate (Na$_2$TeSO$_3$) is prepared from sodium sulfite and tellurium, as described in Arbad et al., 2011, Arch. Appl. Sci. Res. 3(2), 422-430, with modifications.

Sodium sulfite (Na$_2$SO$_3$, 252.08 g, 2 mol) is dissolved in distilled water (800 ml, 25-30° C.) until the appearance of a clear solution. The stirred solution is then warmed to 90° C. under reflux. Elemental tellurium (Te, ~100 mesh, ~99.5%, 1.75 equivalent, 446.61 g, 3.5 mol) is slowly added at 90° C. during a period of 2 hours. The mixture is then stirred at 90° C. and 1100 rpm for at least 12 hours. During this process, the tellurian powder reacts gradually with sodium sulfite to form a sodium tellurosulfate solution. The solution is filtered to obtain a clear sodium tellurosulfate solution (Na$_2$TeSO$_3$, 800 ml, 507.29 g, 2 mol, 2.5 M solution in H$_2$O). Upon filtration, the solution is sealed under nitrogen and stored at 70° C. The metastable sodium tellurosulfate is formed only in hot condition. In cold condition, atmospheric air oxidize tellurium ion to metallic tellurium.

Example 3: Synthesis (141), (14a), (14c), (14e), (15a), (15c) and (15e)

A) Staudinger Ketene-Imine Cycloaddition Reaction and Iodine-Promoted Cyclization A.1) Preparation of 2,2-bis(ethylthio)acetyl Chloride

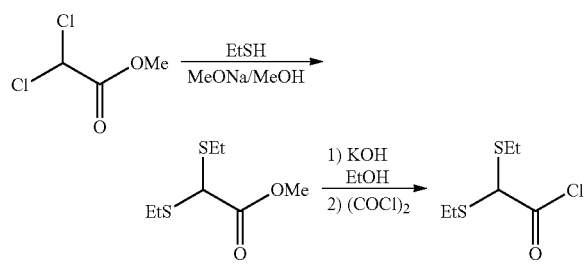

2,2-bis(ethylthio)acetyl chloride was prepared in three steps. First, 2,2-dichloroacetate and ethanethiol were reacted to obtain methyl 2,2-bis(ethylthio)acetate which was subsequently saponified with KOH and then transformed in the corresponding acyl chloride as described previously in Lerner M. L., Alkylation of the carbanion from methyl bis(ethylthio)acetate with alkyl and aralkyl halides, *J. Org. Chem.*, 1976, 41, 2228-2229; and Belluš D., Incorporation of Sulfur Dioxide into the Products of Reaction of Schiff Bases with Halo- or Alkylthio-ketenes in Liquid SO$_2$., *Helv. Chim. Acta*, 1975, 58, 2509-2511.

MeOH (100 mL) was added slowly at 0° C. to Sodium (5 g, 217 mmol). After a total dissolution of Na, ethanethiol (16 mL, 217 mmol), was added dropwise at the same temperature, then methyl 2,2-dichloroacetate (11.2 mL, 108 mmol). The resulting mixture was stirred at room temperature for 2 days. After this time, the reaction was quenched with a saturated solution of NaHCO$_3$ (100 mL) and MeOH was evaporated. The aqueous phase was then extracted with Et$_2$O (2×100 mL). The organic layers were combined, washed with brine (50 mL), dried (MgSO$_4$), filtered and the solvent was removed in vacuum. The remaining colorless liquid (15.7 g, 81.0 mmol, 75%) was pure by NMR and used without further purification.

A solution of KOH (9.1 g, 162 mmol) in MeOH (100 mL) and H$_2$O (50 mL) was added to a solution of methyl 2,2-bis(ethylthio)acetate (15.7 g, 81.0 mmol) in MeOH (60 mL) and the mixture was stirred for 2 h at ambient temperature. After this time, MeOH was removed under reduced pressure, the remaining aqueous phase was acidified with 1M HCl and extracted with CH$_2$Cl$_2$ (3×20 mL). The combined organic layers were dried (MgSO$_4$), filtered and the solvent was removed in vacuum to yield 2,2-bis(ethylthio) acetic acid (13.2 g, 73.7 mmol, 91%). Then oxalyl chloride (14.0 g, 110.6 mmol) was added dropwise and after addition, the mixture was stirred for 12h at room temperature. After this time the solvent was removed in vacuum to yield the title compound (14.0 g, 70.7 mmol, 96%) as a yellow oil. The 2,2-bis(ethylthio)acetyl chloride was pure by NMR and used without further purification.

A.2) Preparation of ethyl 2-chlorobut-3-enoate

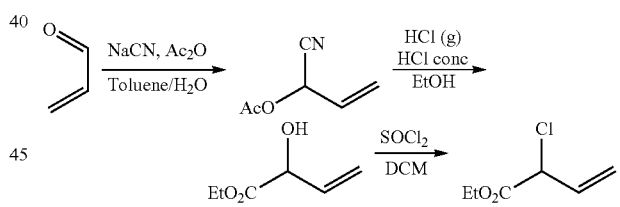

Ethyl 2-chlorobut-3-enoate was obtained in three steps. Acrolein was reacted with anhydride acetic and sodium cyanide to obtain 1-cyanoallyl acetate which was susbsequently transformed to ethyl 2-hydroxybut-3-enoate with ethanol and hydrochloric acid which was then chlorinated with thionyl chloride as described in Stach H., Huggenberg W., Hesse M., Synthese von 2-Hydroxy-3-methyl-2-hexen-4-olid, *Helv. Chim. Acta*, 1987, 70, 369-374; and Rambaud M. R., *CR Acad. Sci.*, 1933.

Acrolein (14 g, 200 mmol) was added to a solution at 0° C. of toluene (50 mL) and anhydride acetic (22.8 g, 200 mmol). Then a solution of NaCN (14.7 g, 300 mmol) in water (150 mL) was added dropwise and the mixture was stirred for 3 h at 0° C. After this time, the aqueous phase was then extracted with toluene (3×50 mL). The organic layers were combined, washed with brine (50 mL), dried (MgSO$_4$), filtered and the solvent was removed in vacuum. The 1-cyanoallyl acetate was pure by NMR and used without further purification (23.8 g, 86%).

The cyano compound (3 g, 24.0 mmol) was dissolved in a solution of saturated HCl (g) in EtOH (100 mL)/HCl concentrated (1.5 mL). And the reaction was stirred at reflux for 3h. Then, EtOH was evaporated in vacuo and the residue was purified by column chromatography (SiO$_2$, petroleum ether/ethyl acetate) to yield the ethyl 2-hydroxybut-3-enoate (2.4 g, 76%) as a yellow oil.

SOCl$_2$ (2.7 mL, 36.8 mmol) was added dropwise to ethyl 2-hydroxybut-3-enoate (2.4 g, 18.4 mmol) in DCM and heated at 35° C. After 6 h, SOCl$_2$ was evaporated in vacuo to yield ethyl 2-chlorobut-3-enoate (629 mg, 4.2 mmol, 23%).

A.3) Preparation of 2-(benzylthio)but-3-enoyl Chloride (18)

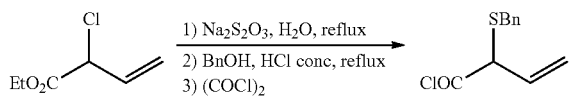

Na$_2$S$_2$O$_3$ in H$_2$O was added and the mixture was stirred at reflux for 2 h.

After cooling to ambient temperature, concentrated HCl (10 mL) and benzylic alcohol were subsequently added and the mixture was reflux for 16 h. After cooling to ambient temperature, the organic layer was separated and the aqueous layer was extracted with Et$_2$O. The combined organic layers were dried (MgSO$_4$), filtered and the solvent was removed. A solution of NaOH in H$_2$O was added and the mixture was vigorously stirred at ambient temperature for 3 h. The mixture was washed with Et$_2$O, and the Et$_2$O was discorded, the aqueous layer was acidified with 1 M HCl, extracted with Et$_2$O. The combined organic extracts were washed with brine, dried (MgSO$_4$), filtered and the solvent was removed in vacuo to yield 2-(benzylthio)but-3-enoic acid.

Then, oxalyl chloride was added to 2-(benzylthio)but-3-enoic acid and the mixture was stirred for 12 h at room temperature. Excess of oxalyl chloride was evaporated in vacuo to yield 2-(benzylthio)but-3-enoyl chloride.

A.4) General Procedure for Staudinger Reaction and Iodine-Promoted Cyclization

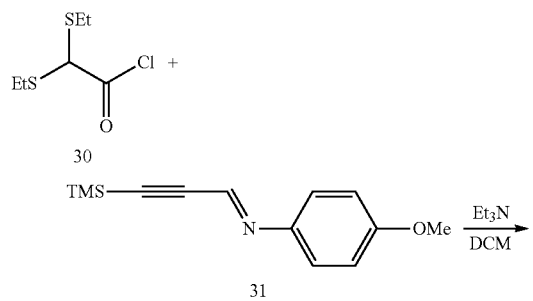

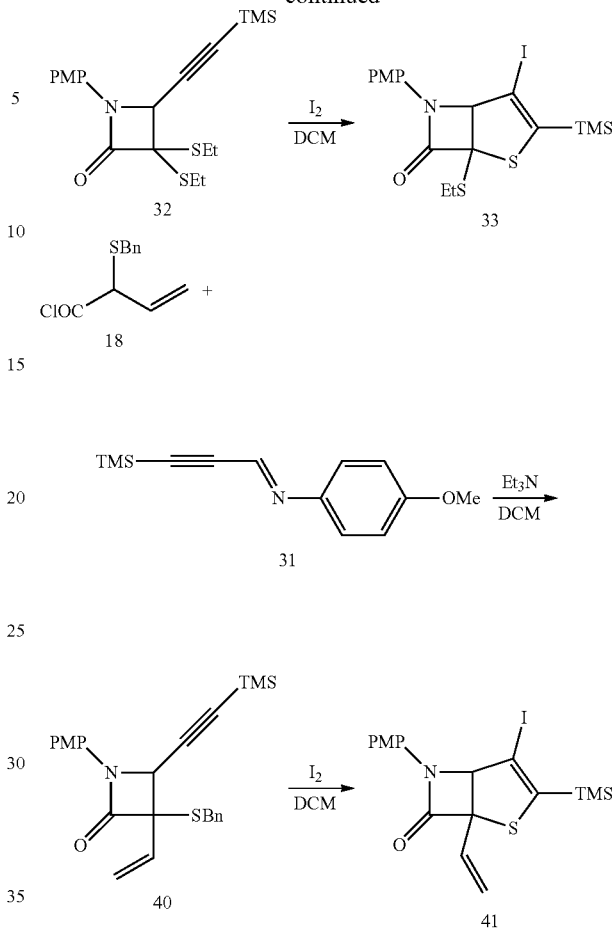

Azetidinones 32 and 40 are prepared by Staudinger reaction between acyl chlorides 30 and 18 and imine 31 and are subsequently transformed in iodo-penem adducts 33 and 41 by iodine-promoted cyclization as previously described in Ren et al., 1998, *J. Org. Chem.* 63, 8898-8917 and in Long T. E., 2003, N-Thiolated β-lactams. *PhD Thesis*, University of South Florida.

Acid chloride 30 or 18 (1.2 eq.) in CH$_2$Cl$_2$ was added by cannulation to a stirred solution of imine 31 (1 eq) and NEt$_3$ (1.5 eq) in CH$_2$Cl$_2$ at ambient temperature. After stirring for 30 min, the mixture was quenched with 1 M HCl, extracted with CH$_2$Cl$_2$, the combined organic layers were dried (MgSO$_4$), filtered, the solvent was removed in vacuum and the residue was purified by column chromatography to yield azetidinone 32 or 40.

Iodine was added to a solution of azetidinone 32 or 40 in CH$_2$Cl$_2$ and the solution stirred for 2 h at ambient temperature. The reaction was quenched with a saturated solution of Na$_2$S$_2$O$_3$ and extracted with CH$_2$Cl$_2$. The combined organic layers were washed with brine, dried (MgSO$_4$), filtered and the solvent was removed in vacuo. The residue was purified by column chromatography to yield iodo-penem adducts 33 or 41.

B) Procedure for Ozonolysis of Vinyl Moiety and Attachment of 2-cyclohexenyl or Isopropyl Group on the Formyl Carbon

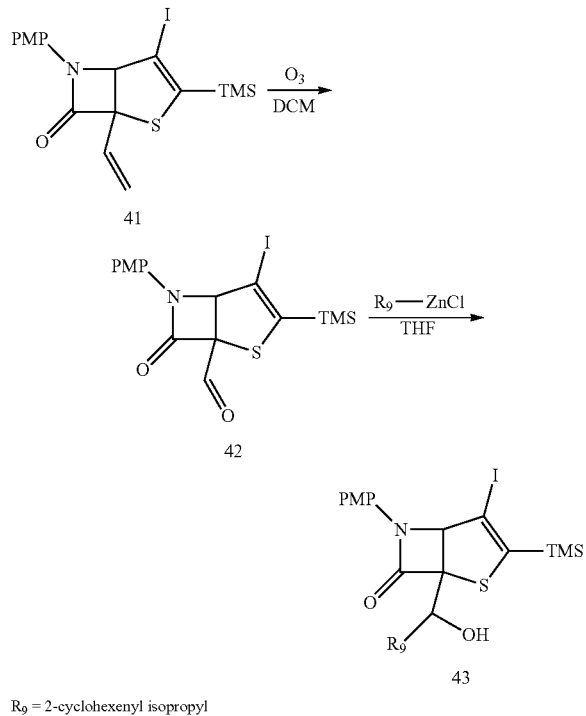

R9 = 2-cyclohexenyl isopropyl

The ozonolysis of the vinyl moiety of compound 41 to obtain the corresponding aldehyde derivatives 42 is carried out according to example 1, section E.

The attachment of the 2-cyclohexenyl group to the formyl carbon of 42 is accomplished with 2-cyclohexenylzinc chloride to obtain compound 43 as disclosed in example 1, section F.

The attachment of the isopropyl group to the formyl carbon of 42 is accomplished with isopropylzinc chloride to obtain compound 43 as disclosed in example 1, section G.

C) General Procedure for Palladium-Catalyzed Stille Cross-Coupling Reaction

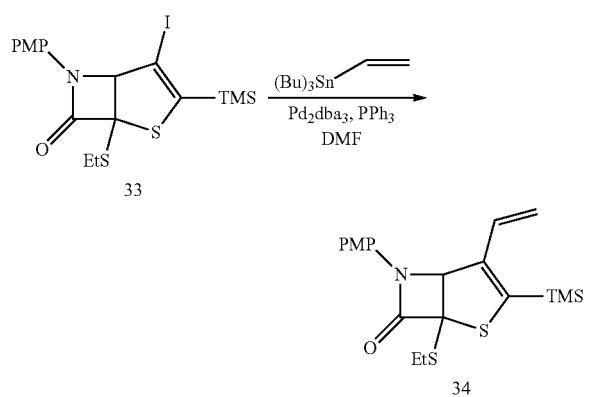

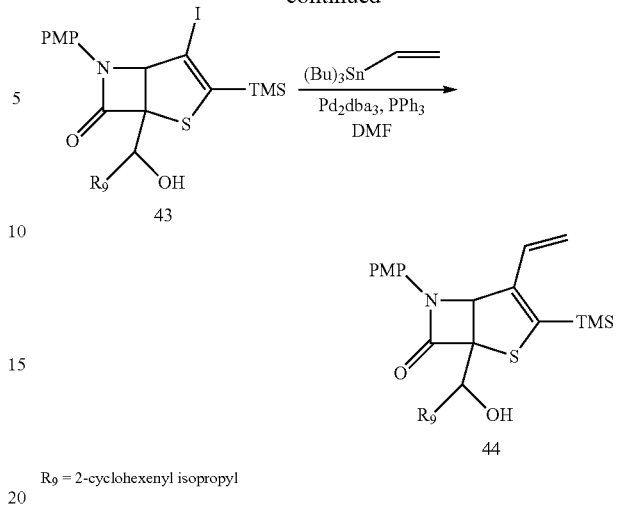

R9 = 2-cyclohexenyl isopropyl

The iodide adducts 33 and 43 are reacted with tributyl (vinyl)tin via a palladium-catalyzed Stille cross-coupling reaction to yield vinyl compounds 34 and 44 as disclosed in Ren X. F., Konaklieva M. I., Shi H., Dickey S., Lim D. V., Gonzalez J. and Turos E., Studies on nonconventionally fused bicyclic β-lactams. *J. Org. Chem.*, 1998, 63, 8898-8917.

Iodo compound 33 or 43 (1 eq.) was dissolved in DMF, then $Pd_2dba_3$ (0.05 eq.) and $PPh_3$ (0.07 eq.) were added and finally tributylvinyltin (1.1 eq.). The reaction mixture was stirred at room temperature for 12 h and quenched with water. The aqueous layer was extract with $Et_2O$, and the combined organic layers were washed with brine, dried ($MgSO_4$), filtered and the solvent was removed in vacuo. The residue was purified by column chromatography to yield vinyl-β-Lactam 34 or 44.

D) General Procedure of Reverse Wacker Oxidation and Reduction of Aldehyde

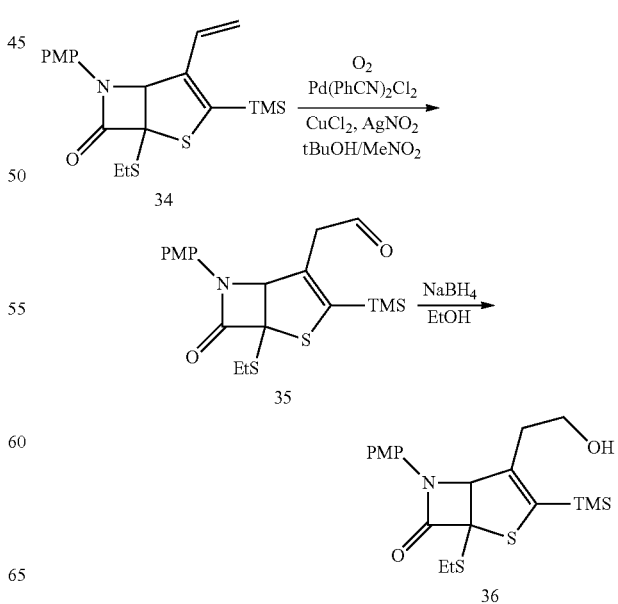

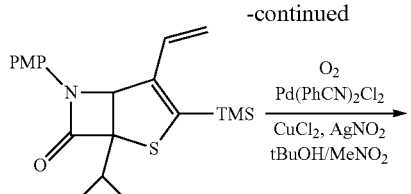

44

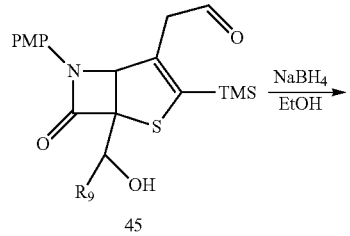

45

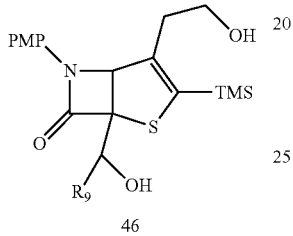

46

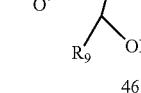

$R_9$ = 2-cyclohexenyl isopropyl

The carbon-carbon double bond of compounds 34 and 44 is oxidized by a reverse Wacker reaction to form aldehydes 35 and 45 which are subsequently reduced to the corresponding alcohols 36 and 46 as described previsouly in Wickens Z. K., Morandi B., Grubbs R. H. Aldehyde-Selective Wacker-Type Oxidation of Unbiased Alkenes Enabled by a Nitrite Co-Catalyst, *Angew. Chem. Int. Ed.*, 2013, 52, 11257-11260; and Weiner B., Baeza A., Jerphagnon T., Feringa B. L., Aldehyde Selective Wacker Oxidations of Phthalimide Protected Allylic Amines: A New Catalytic Route to $\beta^3$-Amino Acids, *J. Am. Chem. Soc.*, 2009, 131, 9473-9474; and Xiao-Shan N., Mei-Mei W., Chuan-Zhi Y., Xian-Min C., Yan-Biao K., tert-Butyl Nitrite: Organic Redox Cocatalyst for Aerobic Aldehyde-Selective Wacker-Tsuji Oxidation, *Org. Lett.* 2016, 18, 2700-2703.

$PdCl_2(PhCN)_2$ (0.12 eq.) $CuCl_2 \cdot 2H_2O$ (0.12 eq.) and $AgNO_2$ (0.6 eq.) were weighed into a 20 mL vial charged with a stir bar. The vial was sparged for 2 minutes with oxygen (1 atm, balloon). Premixed and oxygen saturated tBuOH (7.5 mL) and $MeNO_2$ (0.5 mL) was added followed by the alkene 34 or 44 (1 eq.) were added in that order via syringe. The solution was saturated with oxygen by an additional 45 seconds of sparging. The reaction was then allowed to stir at room temperature for 6 hours. Then, the reaction was quenched by addition to water (50 mL) and extracted three times with dichloromethane (25 mL). The combined organic layers were subsequently washed with a saturated solution of $NaHCO_3$ and dried over $Na_2SO_4$. The solvent was removed under reduced pressure and the desired aldehyde product was purified using flash chromatography to yield the title compound aldehyde-β-Lactam 35 or 45.

Aldehyde-β-Lactam 35 or 45 was dissolved in EtOH and $NaBH_4$ (3 eq.) was added by small portion at 0° C. After 3 h, the reaction was quenched with brine, EtOH was evaporated at reduced pressure, and the aqueous phase was extracted with DCM. The combined organic layers were dried ($MgSO_4$), filtered and the solvent was removed in vacuo. The residue was purified by column chromatography to yield alcohol-β-Lactam 36 or 46.

E) General Procedure of Sulfonylation and Deprotection

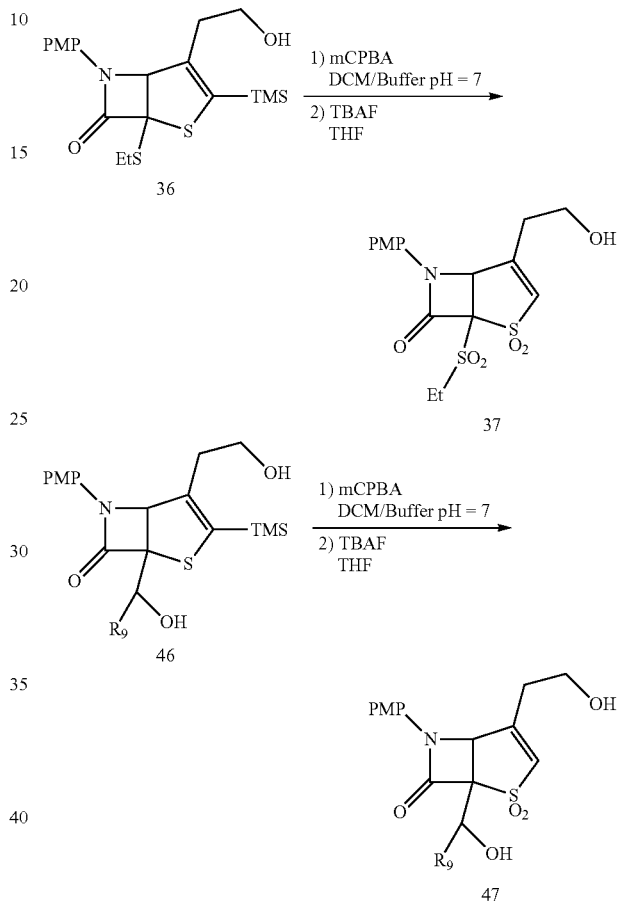

$R_9$ = 2-cyclohexenyl isopropyl

The sulfur atoms of compounds 36 and 46 were oxidized to the corresponding sulfones and the trimethylsilyl group was then removed with tetrabutylammonium chloride to yields sulfones 37 and 47 as described previously in Ren X. F., Konaklieva M. I., Shi H., Dickey S., Lim D. V., Gonzalez J. and Turos E., Studies on nonconventionally fused bicyclic β-lactams. *J. Org. Chem.*, 1998, 63, 8898-8917.

m-CPBA (5 eq.) was added to a solution of thioether 36 or 46 (1 eq.) in $CH_2Cl_2$/buffer (pH=7) and the mixture was stirred at ambient temperature for 16 h. After removal of the solvent in vacuum, the residue was dissolved in EtOAc and washed with sat. $NaHCO_3$ solution (3×20 mL). The organic layer was dried ($MgSO_4$), filtered and the solvent was removed in vacuo to yield the corresponding TMS protected sulfone.

A solution of TBAF in THF (1 M, 1.2 eq.) was added to a solution of said TMS protected sulfone (1 eq.) in THF and the mixture was stirred at ambient temperature for 2 h. After removing the solvent in vacuum, the residue was dissolved in EtOAc and washed with $H_2O$ and brine. The organic layer was dried ($MgSO_4$), filtered and the solvent was removed in vacuum. The residue was purified by column chromatography to yield deprotected sulfone compound 37 or 47.

F) General Procedure of Chlorination and PMP Deprotection

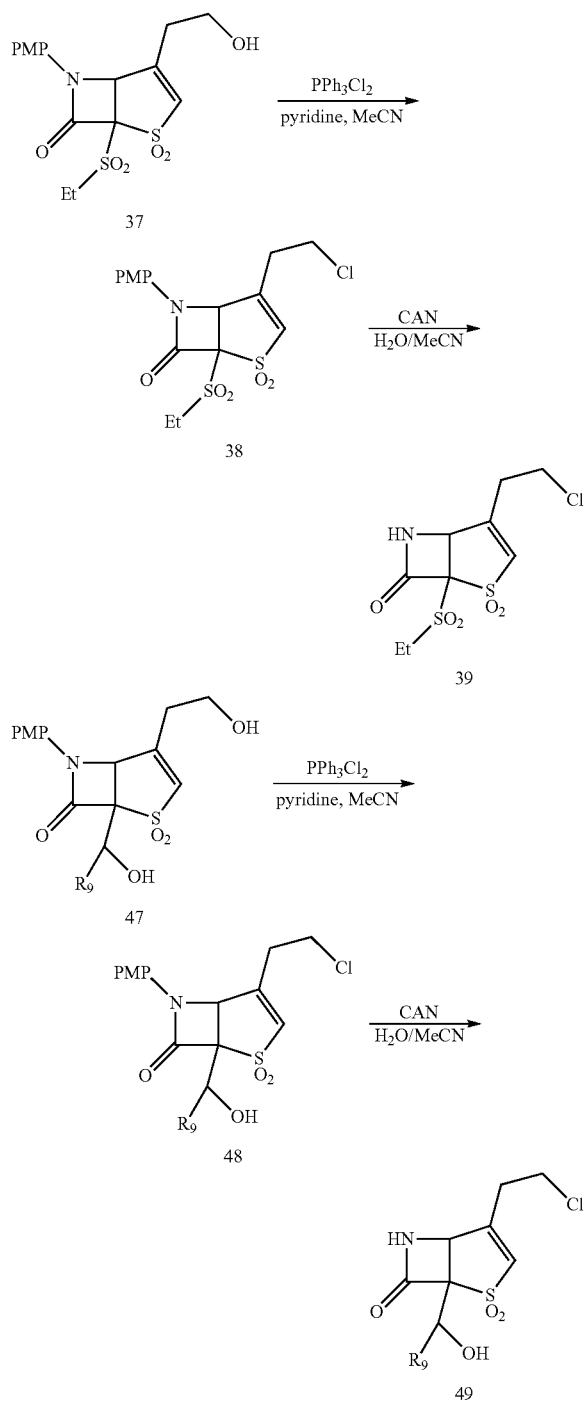

The alcohol group of sulfones 37 and 47 was substituted with a chloride to afford compounds 38 and 48 and the p-methoxyphenyl N-protecting group (p-anisyl moiety) was then oxidatively cleaved using ceric ammonium nitrate, to afford the corresponding N-unsubstituted β-lactams 39 and 49 as described in Corey E. J. and Hogan P. C., 2007, Proteasome inhibiting β-lactam compounds, PCT patent application published under n° 2007/033039.

To a solution of alcohol 37 or 47 (1 eq.) in $CH_3CN$, was added pyridine (3 eq.) and dichlorotriphenylphosphorane (1.5 eq.). The reaction mixture was stirred at ambient temperature for 4 h. Then, the reaction was quenched with brine, and the aqueous phase was extracted with EtOAc. The combined organic layers were washed with HCl 1M and brine, dried ($MgSO_4$), filtered and the solvent was removed in vacuo. The residue was purified by column chromatography to yield chloro-β-Lactam 38 or 48.

A solution of CAN (4 eq.) in $H_2O$ (5 mL) was added dropwise to a solution of substituted amide 38 or 48 (1 eq.) in MeCN (5 mL) at 0° C. in a way that the red color of the drop disappeared before the addition of the next drop. After addition, the mixture was stirred for 3 h at 0° C. $Et_2O$ (40 mL) was added and the solution washed with $NaHCO_3$ (20 ml) and $H_2O$ (2×20 mL). The organic phase was dried ($MgSO_4$), filtered and the solvent removed in vacuum. The residue was purified by column chromatography to yield the target N-unsubstituted β-lactam 39 or 49.

G) Carbamylation

The β-lactams 39 or 49 can be carbamylated as described in example 1, section I.

Example 4: Synthesis of N-methylated Compounds (6j), (7j), (8j), and (9j)

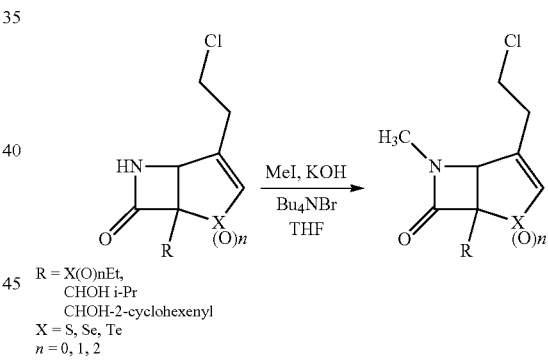

R = X(O)nEt,
CHOH i-Pr
CHOH-2-cyclohexenyl
X = S, Se, Te
n = 0, 1, 2

Compounds (6j), (7j), (8j), and (9j) are obtained by N-methylation of the corresponding NH-β-lactam with methyl iodide as described in Degennaro L., Zenzola M., Laurino A., Cavalluzzi M. M., Franchini C., Habtemariam S., Matucci R., Luisi R., Lentini G. 2-Arylazetidines as ligands for nicotinic acetylcholine receptors, *Chemistry of Heterocyclic Compounds*, 2017, 53, 329-334; Sammes P. G., Smith S., Preparation of Azetidines from 1.3-Aminopropanols, *J. Chem. Soc., Perkin Trans.* 1, 1984, 2415-2419; Reuschling D., Pietsch H., Linkies A., *Tetrahedron Lett.*, 1978, 7, 615-618; and Kaluza Z., Park S. H., 4-Substituted Azetidin-2-ones, New Building Blocks for the Synthesis of β-lactams, *Synlett*, 1996, 9, 895-896.

The NH-β-lactam was dissolved in anhydrous THF (20 ml), then tetrabutylammonium bromide (0.128 g, 0.4 mmol, 0.1 equiv), KOH (0.246 g, 4.4 mmol, 1.0 equiv), and MeI (0.852 g, 6.0 mmol, 1.4 equiv) were added and the solution was stirred for 8 h at 25° C. The reaction mixture was filtered, the filtrate was poured into water and extracted with Et$_2$O. The combined organic layers were dried over anhydrous Na$_2$SO$_4$ and evaporated under reduced pressure to yield N-methyl-β-lactam (6j), (7j), (8j), or (9j).

Example 5: Molecular Docking of Compound 14h in the Human Proteasome

Figure 9:
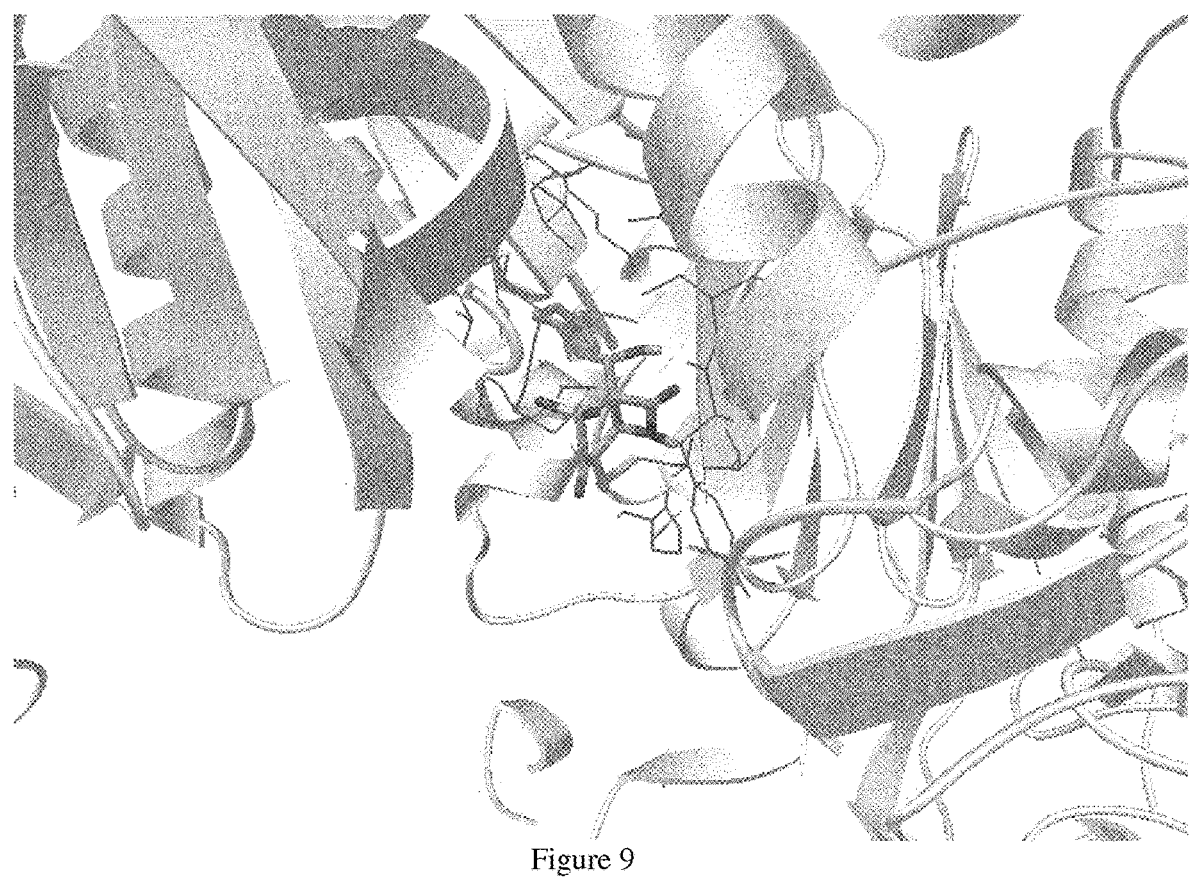
FIG. 9 shows molecular docking of compound 14h in the β subunit of the human proteasome.

FIG. 9 shows the molecular docking of compound 14h in the human proteasome.

Preliminary docking calculations were performed with Autodock 4.2.6 software according to Morris, G. M., Huey, R., Lindstrom, W., Sanner, M. F., Belew, R. K., Goodsell, D. S. and Olson, A. J. Autodock4 and AutoDockTools4: automated docking with selective receptor flexiblity. *J. Computational Chemistry* 2009, 16, 2785-91.

Molecule 14h was used as ligand and the target was an X-Ray structure of human proteasome complex with Delanzomib from Protein Data Bank (PDB ID: 5LF4) according to Schrader, J., Henneberg, F., Mata, R. A., Tittmann, K., Schneider, T. R., Stark, H., Bourenkov, G. and Charo, A. The inhibition mechanism of human 20S proteasomes enables next-generation inhibitor design. *Science* 2016, 353, 594-598.

FIG. 9 shows the best position of 14h in the binding pocket of the β5 subunit of the human proteasome. The binding energy value was −4.9 kcal·mol$^{-1}$ (affinity constant: 263 μM). In the figure, 14h is displayed with sticks and aminoacids of the binding pocket are displayed with wireframe.

The invention claimed is:
1. A simonorealide compound of general formula (1a) or (1b):

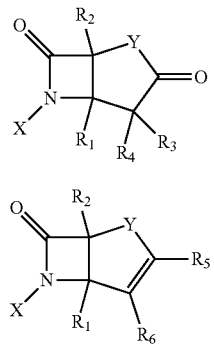

wherein
X is H or —CO—O—R$_7$;
Y is NR$_8$, S(O)$_n$, Se(O)$_n$ or Te(O)$_n$;
R$_1$ is selected from hydrogen, alkyl, alkenyl, alkynyl, aryl, arylalkyl, arylalkenyl, arylalkynyl, cycloalkyl, cycloalkenyl, cycloalkynyl, and substituted derivatives thereof;
R$_2$ is —CH(OH)R$_9$, —SO$_2$—R, —SeO$_2$—R or —TeO$_2$—R with R is an alkyl, and substituted derivatives thereof;
R$_3$ and R$_4$ are independently selected from hydrogen, alkyl, halogen, haloalkyl, haloalkenyl, haloalkynyl, hydroxyalkyl, alkyl substituted by group selected from —O—SO$_2$—R', —O—SeO$_2$—R' or —O—TeO$_2$—R' with R' is an alkyl, or an aryl, and substituted derivatives thereof;
R$_5$ is selected from hydrogen, hydroxyl, sulfhydryl, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof;
R$_6$ is selected from hydrogen, alkyl, halogen, haloalkyl, haloalkenyl, haloalkynyl, hydroxyalkyl, alkyl substituted by group selected from —O—SO$_2$—R', —O—SeO$_2$—R' or —O—TeO$_2$—R' with R' is an alkyl, or an aryl, and substituted derivatives thereof;
R$_7$ is —[C(R$_{10}$)(R$_{11}$)—O—CO]$_m$—R$_{12}$;
R$_8$ is hydrogen, alkyl, and substituted derivatives thereof;
R$_9$ is selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof;
R$_{10}$ and R$_{11}$ are independently selected from hydrogen, alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, alkoxy, alkoxycarbonyl, carbamoyl, and substituted derivatives thereof;
R$_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof; or R$_{12}$ is transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or R$_{12}$ is a transport substrate of GLUT1, MCT1, CAT1, CNT2 or SVCT2; or R$_{12}$ is a peptide substrate; or R$_{12}$ is a peptide vector;
n is 0, 1 or 2;
m is 0 or 1;
with the proviso that when Y is NH then X is not H.

2. A compound according to claim 1, wherein
X is —CO—O—R$_{12}$ or CO—O—C(R$_{10}$)(R$_{11}$)—O—CO—R$_{12}$;
R$_{10}$ and R$_{11}$ are independently selected from hydrogen and alkyl; and
R$_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl, heteroarylalkyl, heteroarylalkenyl, heteroarylalkynyl, cycloheteroalkyl, cycloheteroalkenyl, cycloheteroalkynyl, acyl, and substituted derivatives thereof, or R$_{12}$ is transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or R$_{12}$ is a transport substrate of GLUT1, MCT1, CAT1, CNT2 or SVCT2; or R$_{12}$ is a peptide substrate; or R$_{12}$ is a peptide vector.

3. A compound according to claim 1, wherein said compound corresponds to a general formula (2c), (2d), (3c), (3d), (4c), (4d), (5c) or (5d)

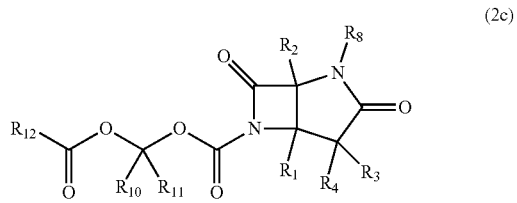

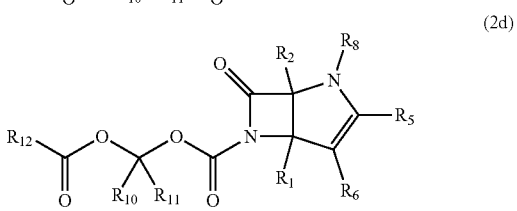

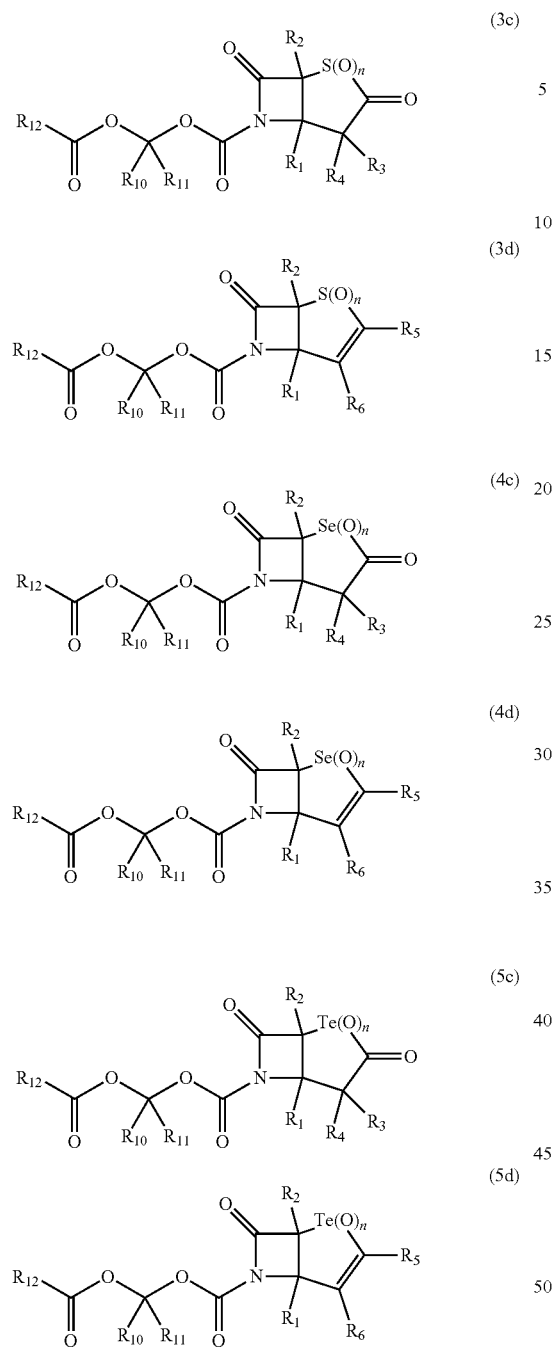

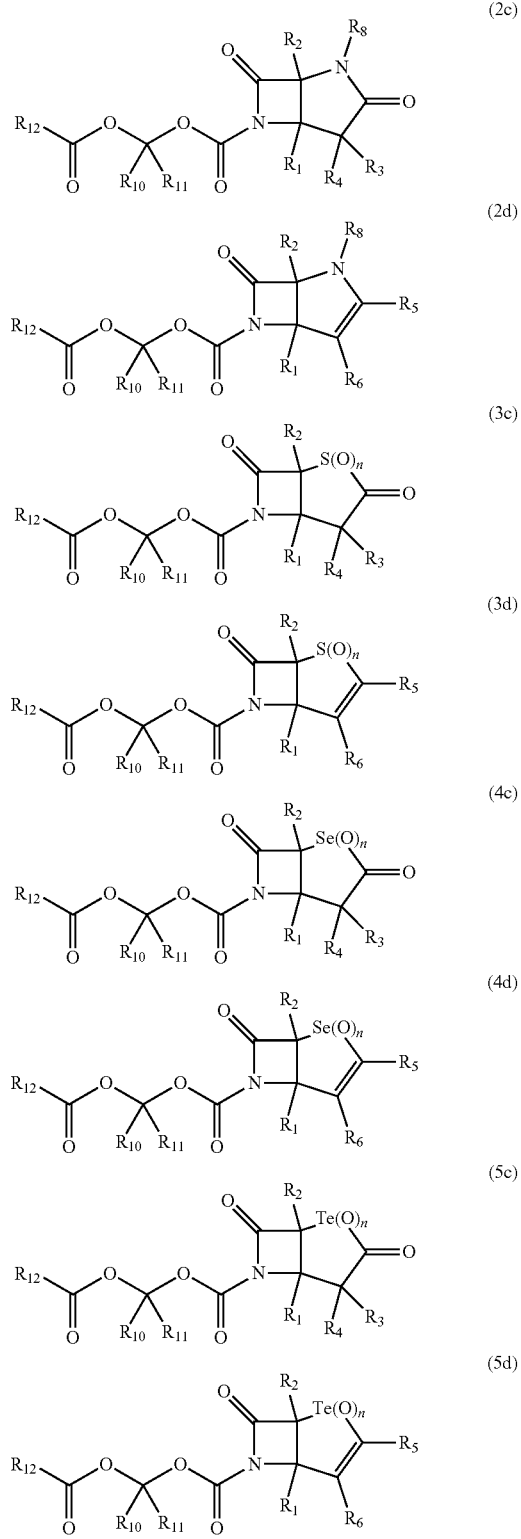

wherein $R_1$, $R_2$, $R_3$, $R_4$, $R_5$, $R_6$, $R_8$, $R_9$, $R_{10}$, $R_{11}$, and n are as defined in claim 1; and $R_{12}$ is selected from alkyl, alkenyl, alkynyl, aryl, arylalkyl, arylalkenyl, arylalkynyl, cycloalkyl, cycloalkenyl, cycloalkynyl, heteroalkyl, heteroalkenyl, heteroalkynyl, heteroaryl heteroarylalkyl, heteroarylalkenyl, heteroarylalkynyl, cycloheteroalkyl, cycloheteroalkenyl, cycloheteroalkynyl, acyl, and substituted derivatives thereof.

4. A compound according to claim 1, wherein said compound corresponds to a general formula (2c), (2d), (3c), (3d), (4c), (4d), (5c) or (5d)

wherein $R_1$, $R_2$, $R_3$, $R_4$, $R_5$, $R_6$, $R_8$, $R_9$, $R_{10}$, $R_{11}$, and n are as defined herein; and $R_{12}$ is a transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyldopa, gabapentin, 3-iodo-α-methyl-L-tyrosine, 3-fluoro-α-methyl-L-tyrosine, 3-iodo-O-methyl-L-tyrosine, 3-iodo-O-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector.

5. A compound according to claim 1, wherein said compound corresponds to a general formula (2e), (2f), (3e), (3f), (4e), (4f), (5e) or (5f)

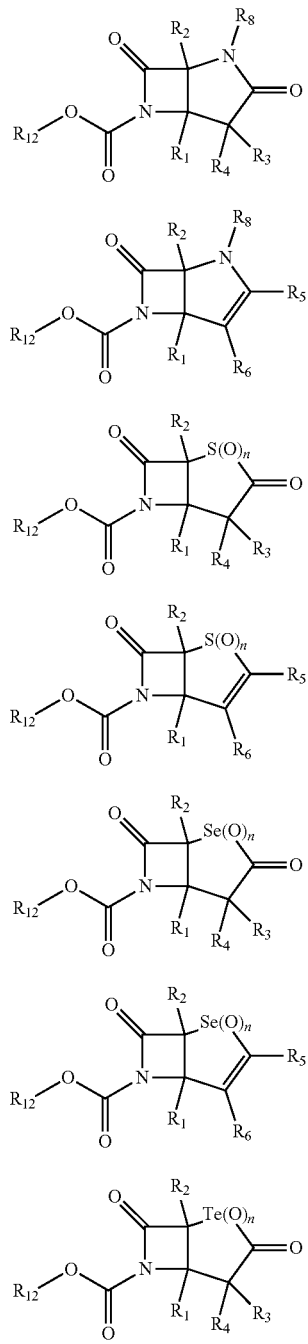

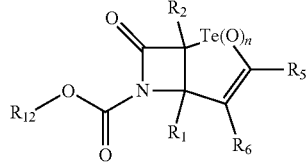

wherein $R_1$, $R_2$, $R_3$, $R_4$, $R_5$, $R_6$, $R_8$, $R_9$, and n are as defined in claim 1; and $R_{12}$ is a transport substrate of LAT1 selected from leucine, isoleucine, valine, phenylalanine, tyrosine, tryptophan, histidine, methionine, L-dopa, 3-O-methyldopa, α-methyl-phenylalanine, α-methyl-tyrosine, α-methyl-dopa, gabapentin, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa, 2-iodo-L-tyrosine, 2-fluoro-L-tyrosine, and substituted derivatives thereof; or $R_{12}$ is a transport substrate of GLUT1, MCT1, CAT1, CNT2 or SVCT2; or $R_{12}$ is a peptide substrate; or $R_{12}$ is a peptide vector.

6. A compound according to claim 1 wherein $R_1$ is H.

7. A compound according claim 1, wherein
$R_2$ is —CH(OH)$R_9$, —SO$_2$—R, —SeO$_2$—R or —TeO$_2$—R;
R is an alkyl and substituted derivatives thereof;
$R_9$ is selected from alkyl and cycloalkenyl.

8. A compound according to claim 1, wherein
$R_3$ and $R_4$ are independently selected from hydrogen, alkyl and haloalkyl;
$R_5$ is selected from H or alkyl; and
$R_6$ is selected from alkyl or haloalkyl.

9. A compound according to claim 1, wherein $R_8$ is H.

10. A compound according to claim 1, wherein $R_{12}$ is selected from alkyl, tyrosine, 3-iodo-α-methyl-L-tyrosine, 3-fluoro-α-methyl-L-tyrosine, 3-iodo-O-methyl-L-tyrosine, 3-iodo-O-methyl-α-methyl-L-tyrosine, 4-iodo-L-meta-tyrosine, 6-iodo-L-meta-tyrosine, O-(2-fluoroethyl)-L-tyrosine, 3-O-methyl-6-fluoro-L-dopa or 2-iodo-L-tyrosine, 2-fluoro-L-tyrosine.

11. A compound according to claim 1, wherein
$R_1$ is H;
$R_3$ and $R_4$ are independently selected from hydrogen, alkyl and haloalkyl;
$R_5$ is selected from hydrogen or alkyl;
$R_6$ is selected from alkyl or haloalkyl;
$R_8$ is hydrogen;
$R_9$ is selected from alkyl and cycloalkenyl;
$R_{10}$ and $R_{11}$ are independently selected from hydrogen and alkyl.

12. A compound according to claim 11, wherein
$R_1$ is H;
$R_3$ is H;
$R_4$ is methyl or 2-chloroethyl;
$R_5$ is selected from hydrogen or methyl;
$R_6$ is selected from methyl or 2-chloroethyl;
$R_8$ is hydrogen;
$R_9$ is selected from isopropyl and cyclohex-2-enyl;
$R_{10}$ and $R_{11}$ are independently selected from hydrogen and methyl.

13. A composition comprising a therapeutically effective amount of a compound as defined in claim 1, and a pharmaceutically acceptable vehicle, carrier or diluent.

14. A process of preparation of compounds of general formula (1b) of claim 1, wherein in general formula (1b) $R_2$ is —$SO_2$—R, —$SeO_2$—R or —$TeO_2$—R with R is an alkyl; $R_6$ is chloroethyl, and X is H; comprising the following steps:
the formation of alkenyl azetidinone by a Staudinger reaction between acyl chloride and imine;
the iodine-promoted cyclization of to form iodopenem adduct;
the Stille cross-coupling between and tributyl(vinyl)tin to form compound;
the reverse Wacker oxidation of the carbon-carbon double bond of compound to form aldehyde;
the reduction of aldehyde to form alcohol;
optionally the oxidation of alcohol to form the corresponding sulfoxyde, sulfone, selenoxide, selenone, telluroxide or tellurone;
the desilylation to form compound;
the chlorination of compound to form chloride; and
the deprotection of the nitrogen of the β-lactam ring of compound to form proteasome inhibitor;

15. A process of preparation of compounds of general formula (1b) of claim 1, wherein in general formula (1b) $R_2$ is —CH(OH)$R_9$; $R_6$ is chloroethyl; Y is $S(O)_n$, $Se(O)_n$ or $Te(O)_n$ and n is 0, 1 or 2; and X is H; comprising the following steps:
the formation of alkenyl azetidinone by a Staudinger reaction between acyl chloride and imine;
the iodine-promoted cyclization of to form iodopenem adduct;
the ozonolysis of the carbon-carbon double bond of compound to form aldehyde;
the addition of $R_9$—ZnCl on the aldehyde to form alcohol;
the Stille cross-coupling between and tributyl(vinyl)tin to form compound;
the reverse Wacker oxidation of the carbon-carbon double bond of compound to form aldehyde;
the reduction of aldehyde to form alcohol;

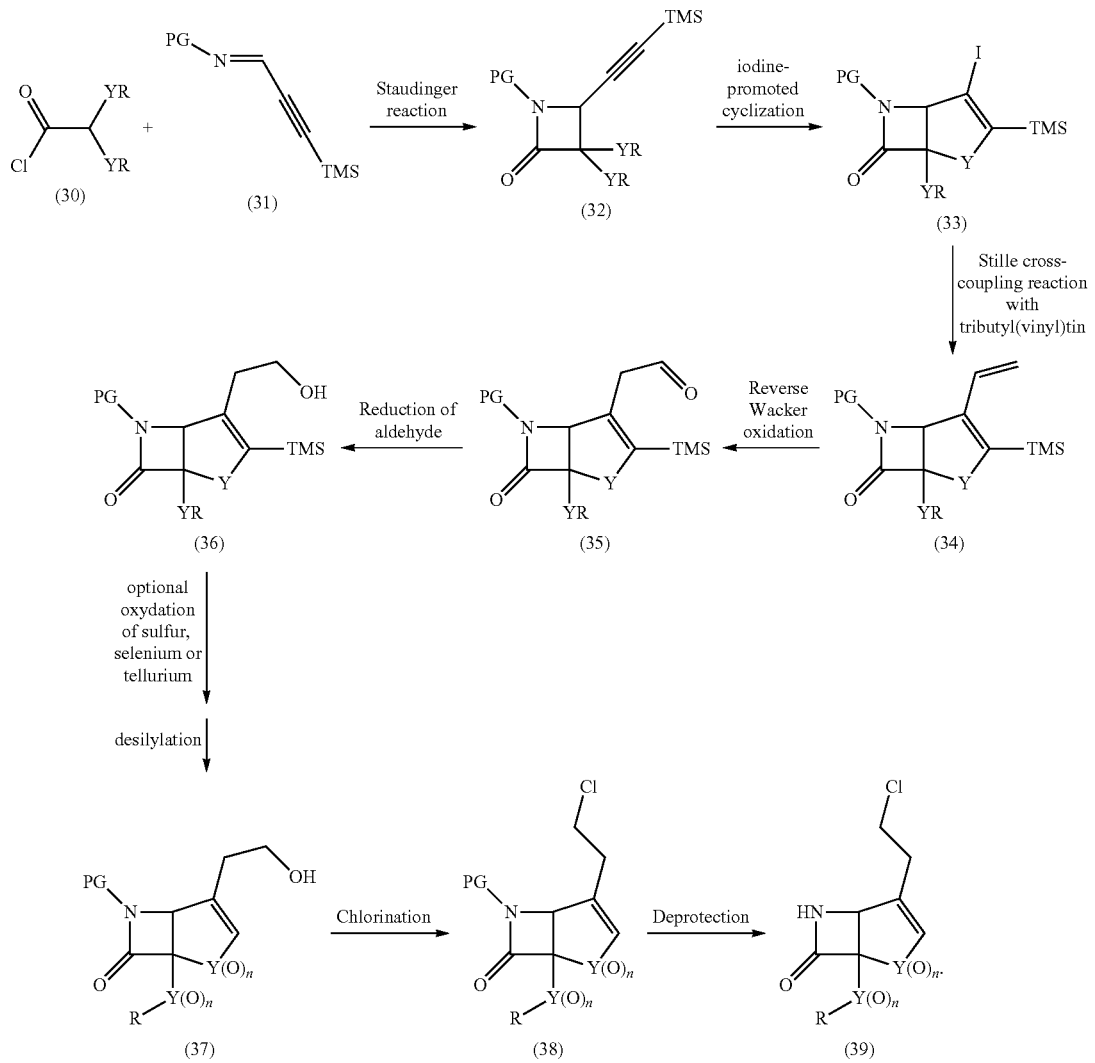

optionally the oxidation of alcohol to form the corresponding sulfoxide, sulfone, selenoxide, selenone, telluroxide or tellurone;
the desilylation to form compound;
the chlorination of compound to form chloride; and
the deprotection of the nitrogen of the β-lactam ring of compound to form proteasome inhibitor;

16. A process of preparation of compounds of general formula (1b) of claim 1, wherein in general formula (1b) $R_2$ is —$SO_2$—R, —$SeO_2$—R or —$TeO_2$—R with R is an alkyl; $R_6$ is methyl; and X is H; comprising the following steps:
the formation of alkenyl azetidinone by a Staudinger reaction between acyl chloride and imine;

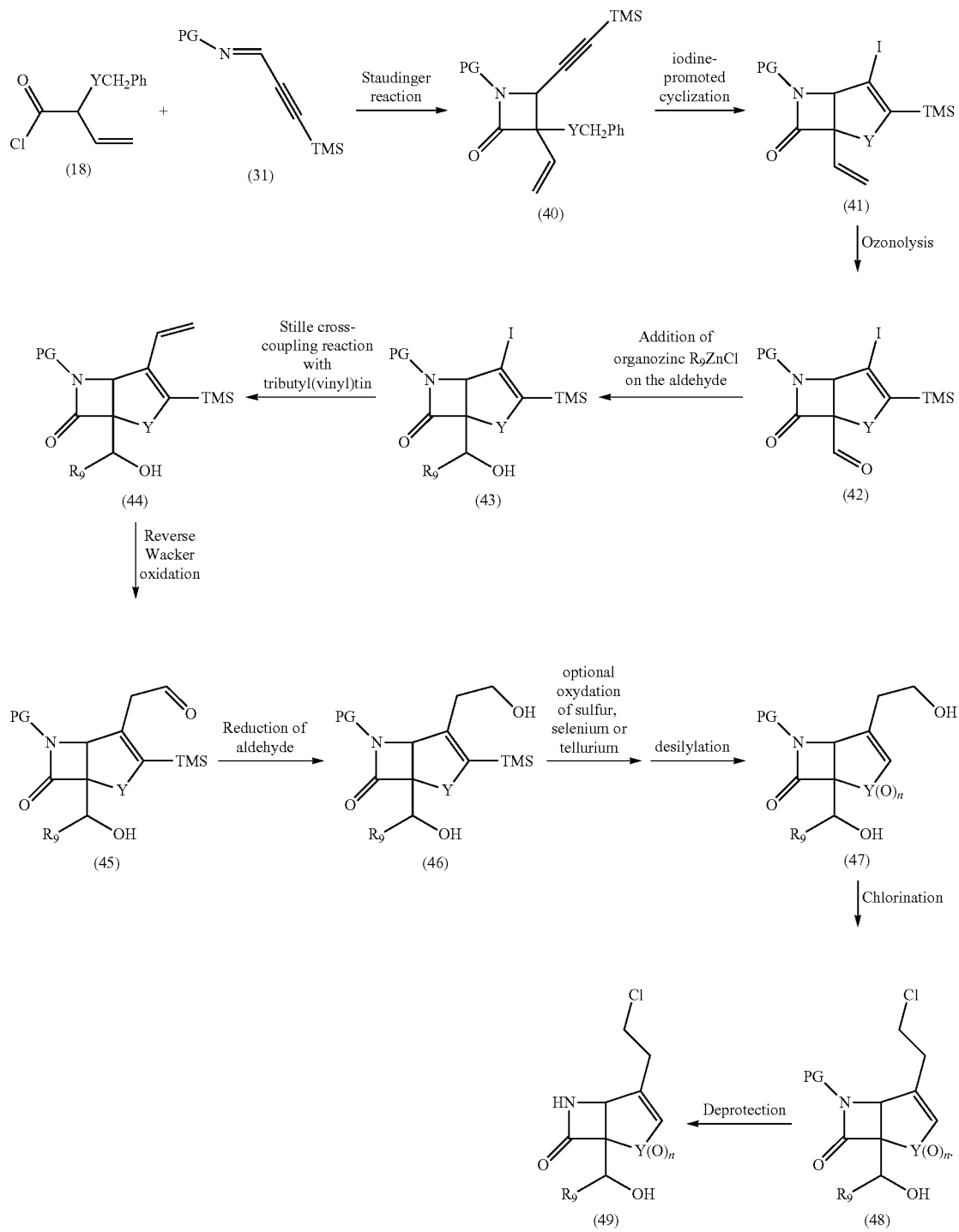

Y is S, Se or Te
PG is an amino-protecting group
$n$ is 0, 1 or 2 the iodine-promoted cyclization of to form iodopenem adduct;
the cross-coupling between and methylmagnesium bromide to form compound;
optionally the oxidation of alcohol to form the corresponding sulfoxyde, sulfone, selenoxide, selenone, telluroxide or tellurone;
the desilylation to form compound; and
the deprotection of the nitrogen of the β-lactam ring of compound to form proteasome inhibitor;

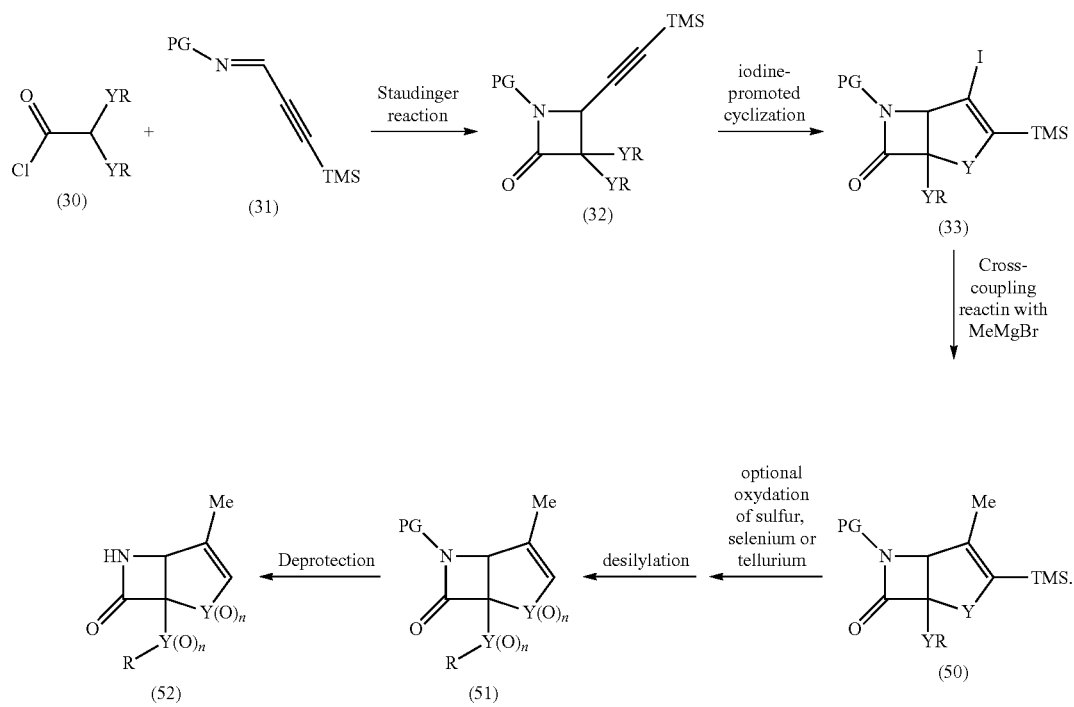

Y is independently S, Se or Te
R is alkyl
PG is an amino-protecting group
n is 2

17. A process of preparation of compounds of general formula (1b) of claim 1, wherein in general formula (1b) $R_2$ is —CH(OH)$R_9$; $R_6$ is methyl; Y is S(O)$_n$, Se(O)$_n$ or Te(O)$_n$ and n is 0, 1 or 2; and X is H; comprising the following steps:
the formation of alkenyl azetidinone by a Staudinger reaction between acyl chloride and imine;
the iodine-promoted cyclization of to form iodopenem adduct;
the ozonolysis of the carbon-carbon double bond of compound to form aldehyde;
the addition of $R_9$—ZnCl on the aldehyde to form alcohol;
the cross-coupling between and methylmagnesium bromide to form compound;
optionally the oxidation of alcohol to form the corresponding sulfoxide, sulfone, selenoxide, selenone, telluroxide or tellurone;
the desilylation to form compound; and
the deprotection of the nitrogen of the β-lactam ring of compound to form proteasome inhibitor;

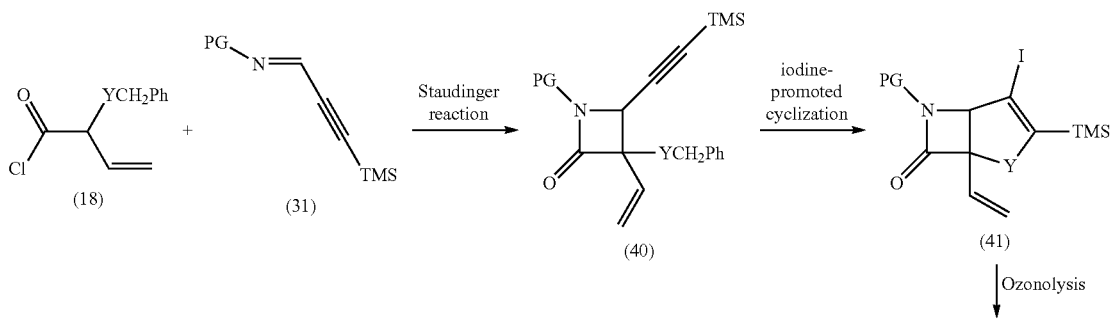

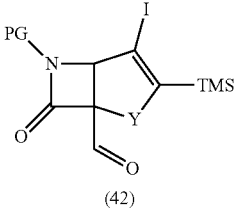
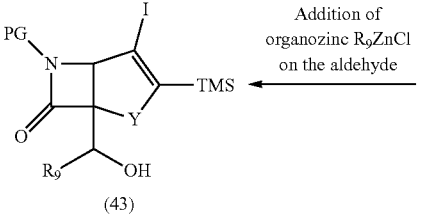
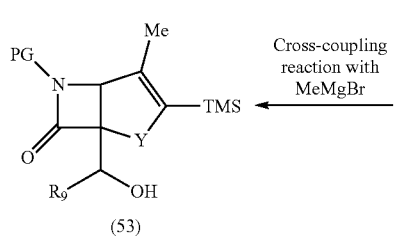
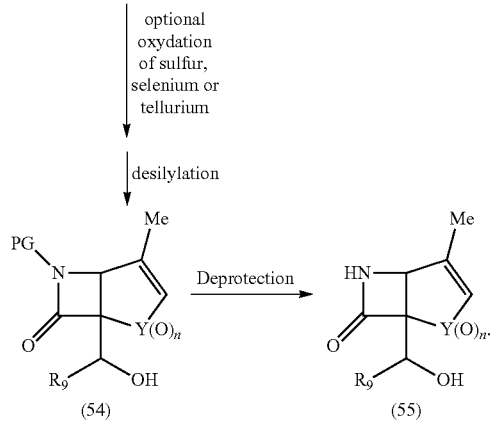
Y is S, Se or Te
PG is an amino-protecting group
n is 0, 1 or 2
18. The method of claim 15, wherein n is 0.
19. The method of claim 17, wherein n is 0.
\* \* \* \* \*

SEQUENCE LISTING

```
<160> NUMBER OF SEQ ID NOS: 23

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 4
<212> TYPE: PRT
<213> ORGANISM: Artificial Sequence
<220> FEATURE:
<223> OTHER INFORMATION: Peptide substrate

<400> SEQUENCE: 4

Leu Leu Val Tyr
1

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8
```

-continued

```
<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 18
<212> TYPE: PRT
<213> ORGANISM: Artificial Sequence
<220> FEATURE:
<223> OTHER INFORMATION: Peptide vector
<220> FEATURE:
<221> NAME/KEY: MISC_FEATURE
<222> LOCATION: (2)..(2)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (3)..(3)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (5)..(5)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (6)..(6)
<223> OTHER INFORMATION: Xaa is Ser or Thr
<220> FEATURE:
<221> NAME/KEY: MISC_FEATURE
<222> LOCATION: (7)..(7)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (8)..(8)
<223> OTHER INFORMATION: Xaa is Ser or Thr
<220> FEATURE:
<221> NAME/KEY: MISC_FEATURE
<222> LOCATION: (12)..(12)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (13)..(13)
<223> OTHER INFORMATION: Xaa is Ser or Thr
<220> FEATURE:
<221> NAME/KEY: MISC_FEATURE
<222> LOCATION: (14)..(14)
<223> OTHER INFORMATION: Xaa represents natural or non-natural
      (including D-configuration) aliphatic or aromatic amino acids
<220> FEATURE:
<221> NAME/KEY: MISC_FEATURE
<222> LOCATION: (15)..(15)
<223> OTHER INFORMATION: Xaa is Ser or Thr
<220> FEATURE:
<221> NAME/KEY: MISC_FEATURE
<222> LOCATION: (16)..(16)
<223> OTHER INFORMATION: Xaa represents natural or non-natural
      (including D-configuration) aliphatic or aromatic amino acids
<220> FEATURE:
<221> NAME/KEY: MISC_FEATURE
```

```
<222> LOCATION: (17)..(17)
<223> OTHER INFORMATION: Xaa represents natural or non-natural
      (including D-configuration) aliphatic or aromatic amino acids

<400> SEQUENCE: 11

Arg Xaa Xaa Arg Xaa Xaa Xaa Xaa Arg Arg Arg Xaa Xaa Xaa Xaa Xaa
1               5                   10                  15

Xaa Arg

<210> SEQ ID NO 12
<211> LENGTH: 17
<212> TYPE: PRT
<213> ORGANISM: Artificial Sequence
<220> FEATURE:
<223> OTHER INFORMATION: Peptide vector
<220> FEATURE:
<221> NAME/KEY: MISC_FEATURE
<222> LOCATION: (2)..(2)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (3)..(3)
<223> OTHER INFORMATION: Xaa is Ser or Thr.
<220> FEATURE:
<221> NAME/KEY: MISC_FEATURE
<222> LOCATION: (4)..(4)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (6)..(6)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (7)..(7)
<223> OTHER INFORMATION: Xaa is Ser or Thr.
<220> FEATURE:
<221> NAME/KEY: MISC_FEATURE
<222> LOCATION: (8)..(8)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (10)..(10)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (11)..(11)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (12)..(12)
<223> OTHER INFORMATION: Xaa is Ser or Thr.
<220> FEATURE:
<221> NAME/KEY: MISC_FEATURE
<222> LOCATION: (13)..(13)
<223> OTHER INFORMATION: Xaa represents natural or non-natural
      (including D-configuration) aliphatic or aromatic amino acids.
<220> FEATURE:
<221> NAME/KEY: MISC_FEATURE
<222> LOCATION: (16)..(16)
<223> OTHER INFORMATION: Xaa is Ser or Thr.

<400> SEQUENCE: 12

Arg Xaa Xaa Xaa Arg Xaa Xaa Xaa Arg Xaa Xaa Xaa Xaa Arg Arg Xaa
1               5                   10                  15

Arg

<210> SEQ ID NO 13
```

```
<211> LENGTH: 18
<212> TYPE: PRT
<213> ORGANISM: Artificial Sequence
<220> FEATURE:
<223> OTHER INFORMATION: Peptide vector

<400> SEQUENCE: 13

Arg Gly Gly Arg Leu Ser Tyr Ser Arg Arg Phe Ser Thr Ser Thr
1               5                   10                  15
Gly Arg

<210> SEQ ID NO 14
<211> LENGTH: 10
<212> TYPE: PRT
<213> ORGANISM: Artificial Sequence
<220> FEATURE:
<223> OTHER INFORMATION: Peptide vector

<400> SEQUENCE: 14

Arg Arg Leu Ser Tyr Ser Arg Arg Arg Phe
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Peptide vector

<400> SEQUENCE: 15

Arg Gly Gly Arg Leu Ala Tyr Leu Arg Arg Trp Ala Val Leu Gly
1               5                   10                  15
Arg

<210> SEQ ID NO 16
<211> LENGTH: 17
<212> TYPE: PRT
<213> ORGANISM: Artificial Sequence
<220> FEATURE:
<223> OTHER INFORMATION: Peptide vector

<400> SEQUENCE: 16

Ala Trp Ser Phe Arg Val Ser Tyr Arg Gly Ile Ser Tyr Arg Arg Ser
1               5                   10                  15
Arg

<210> SEQ ID NO 17
<211> LENGTH: 18
<212> TYPE: PRT
<213> ORGANISM: Artificial Sequence
<220> FEATURE:
<223> OTHER INFORMATION: Peptide vector

<400> SEQUENCE: 17

Arg Gly Thr Ser Thr Ser Phe Arg Arg Ser Tyr Ser Leu Arg Gly
1               5                   10                  15
Gly Arg

<210> SEQ ID NO 18
<211> LENGTH: 10
<212> TYPE: PRT
<213> ORGANISM: Artificial Sequence
<220> FEATURE:
<223> OTHER INFORMATION: Peptide vector
```

```
<400> SEQUENCE: 18

Phe Arg Arg Arg Ser Tyr Ser Leu Arg Arg
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Peptide vector

<400> SEQUENCE: 19

Arg Gly Leu Val Ala Trp Arg Arg Arg Leu Tyr Ala Leu Arg Gly Gly
1               5                   10                  15

Arg

<210> SEQ ID NO 20
<211> LENGTH: 17
<212> TYPE: PRT
<213> ORGANISM: Artificial Sequence
<220> FEATURE:
<223> OTHER INFORMATION: Peptide vector

<400> SEQUENCE: 20

Arg Ser Arg Arg Tyr Ser Ile Gly Arg Tyr Ser Val Arg Phe Ser Trp
1               5                   10                  15

Ala

<210> SEQ ID NO 21
<211> LENGTH: 18
<212> TYPE: PRT
<213> ORGANISM: Artificial Sequence
<220> FEATURE:
<223> OTHER INFORMATION: Peptide vector

<400> SEQUENCE: 21

Arg Gly Gly Arg Leu Ser Tyr Ser Arg Arg Arg Phe Ser Thr Ser Thr
1               5                   10                  15

Gly Arg

<210> SEQ ID NO 22
<211> LENGTH: 10
<212> TYPE: PRT
<213> ORGANISM: Artificial Sequence
<220> FEATURE:
<223> OTHER INFORMATION: Peptide vector

<400> SEQUENCE: 22

Arg Arg Leu Ser Tyr Ser Arg Arg Arg Phe
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Peptide vector

<400> SEQUENCE: 23

Arg Gly Gly Arg Leu Ala Tyr Leu Arg Arg Arg Trp Ala Val Leu Gly
1               5                   10                  15

Arg
```